US008968886B2

(12) United States Patent
Rybtchinski et al.

(10) Patent No.: US 8,968,886 B2
(45) Date of Patent: Mar. 3, 2015

(54) DOUBLY REDUCED PERYLENE-DIIMIDES AND SUPRAMOLECULAR POLYMERS DERIVED FROM PERYLENE-DIIMIDES

(75) Inventors: Boris Rybtchinski, Tel Aviv (IL); Elijah Shirman, Rehovot (IL); Alona Ustinov, Rehovot (IL); Netanel Ben-Shitrit, Rehovot (IL); Haim Weissman, Rehovot (IL); Elisha M. Krieg, Rehovot (IL); Galina Golubkov, Rehovot (IL); Jonathan Baram, Rehovot (IL)

(73) Assignee: Yeda Research and Development Co., Ltd., Rehovot (IL)

( * ) Notice: Subject to any disclaimer, the term of this patent is extended or adjusted under 35 U.S.C. 154(b) by 632 days.

(21) Appl. No.: 12/933,685

(22) PCT Filed: Mar. 26, 2009

(86) PCT No.: PCT/IL2009/000348
§ 371 (c)(1),
(2), (4) Date: Nov. 18, 2010

(87) PCT Pub. No.: WO2009/118742
PCT Pub. Date: Oct. 1, 2009

(65) Prior Publication Data
US 2011/0101276 A1    May 5, 2011

Related U.S. Application Data

(60) Provisional application No. 61/064,778, filed on Mar. 26, 2008.

(51) Int. Cl.
| | | |
|---|---|---|
| H01L 51/54 | (2006.01) |
| C09K 11/06 | (2006.01) |
| C08F 138/02 | (2006.01) |
| C08F 26/06 | (2006.01) |
| C07F 1/10 | (2006.01) |
| B82Y 30/00 | (2011.01) |
| C07D 471/06 | (2006.01) |

(52) U.S. Cl.
CPC ........... *C07D 471/06* (2013.01); *Y10S 428/917* (2013.01); *Y10S 977/773* (2013.01); *Y10S 977/81* (2013.01)
USPC ........ 428/690; 428/917; 257/40; 252/301.16; 977/773; 977/810; 546/37; 526/241

(58) Field of Classification Search
None
See application file for complete search history.

(56) References Cited

U.S. PATENT DOCUMENTS

2007/0202353 A1 *   8/2007   Inagaki et al. ................ 428/690

FOREIGN PATENT DOCUMENTS

| CN | 101 157 757 A | 4/2008 |
| EP | 0 422 535 A1 | 4/1991 |
| WO | WO 02/14318 A1 | 2/2002 |
| WO | WO 02/14414 A3 | 2/2002 |
| WO | WO 2005097944 A1 * | 10/2005 |
| WO | WO 2005124453 A2 * | 12/2005 |
| WO | WO 2008/139452 A3 | 11/2008 |
| WO | WO 2008139452 A2 * | 11/2008 | ........... C07D 471/06 |

OTHER PUBLICATIONS

Golubkov et al. "Economical Design in Noncolvalent Nanoscale Synthesis: Diverse Photofunctional Nanostructures Based on a Single Covalent Building Block" Angew. Chem. Int. Ed. 2009, 48, 926-930. Date of on-line publication: Jan. 7, 2009.*
Ford et al. "Photochemistry of 3,4,9,10-perylenetetracarboxylic dianhydride dyes. 4. Spectroscopic and redox properties of oxidized and reduced forms of the bis(2,5-di-tert-butylphenyl)imide derivative" *J. Phys. Chem.*, 93 (18), pp. 6692-6696, (1989).
Katz, T. J., *J. Am. Chem. Soc.* 1960, 82, 3784-3785.
Holy, N. L., *Chem. Rev.* 1974, 74, 243-277.
Ichikawa, M.; Tamaru, K., *J. Am. Chem. Soc.* 1971, 93, 2079-2080.
Müllen, K.; Oth, J. F. M.; Engels, H. W.; Vogel, E., *Angew. Chem. Int. Ed.* 1979, 18, 229-231.
Müllen, K., *Helv. Chim. Acta* 1978, 61, 2307-2317.
Müllen, K., *Helv. Chim. Acta* 1978, 61, 1296-1304.
Müllen, K.; Huber, W.; Meul, T.; Nakagawa, M.; Iyoda, M., *J. Am. Chem. Soc.* 1982, 104, 5403-5411.
Müllen, K., *Chem. Rev.* 1984, 84, 603-646.
Huber, W.; Müllen, K., *Acc. Chem. Res.* 1986, 19, 300-306.
Rabinovitz, M.; Ayalon, A., *Pure Appl. Chem.* 1993, 65, 111-118.
Frim, R.; Mannschreck, A.; Rabinovitz, M., *Angew. Chem. Int. Ed.* 1990, 29, 919-921.
Cohen, Y.; Klein, J.; Rabinovitz, M., *J. Am. Chem. Soc.* 1988, 110, 4634-4640.

(Continued)

*Primary Examiner* — Andrew K Bohaty
(74) *Attorney, Agent, or Firm* — Pearl Cohen Zedek Latzer Baratz LLP; Mark S. Cohen

(57) ABSTRACT

This invention is directed to perylene-diimide aromatic dianion compounds, process of preparation and uses thereof. The perylene-diimide aromatic dianion compounds of this invention are stable in aqueous solution and can be used for photofunctional and electron transfer systems in aqueous phase. This invention is also directed to supramolecular polymers derived from perylene-diimide compounds and to uses thereof. (1) wherein said compound is a dianion; wherein, X is —NR$_1$; Y is —NR$_2$;

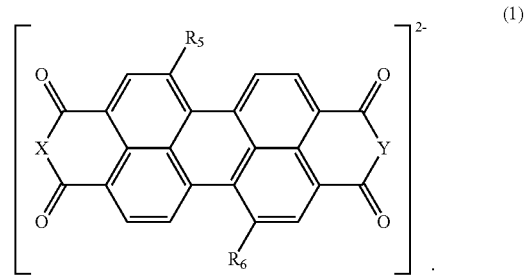

25 Claims, 37 Drawing Sheets

(56) References Cited

OTHER PUBLICATIONS

Rabinovitz, M.; Willner, I.; Minsky, A., *Acc. Chem. Res.* 1983, 16, 298-304.

Willner, I.; Becker, J. Y.; Rabinovitz, M., *J. Am. Chem. Soc.* 1979, 101, 395-401.

Aprahamian, I.; Wegner, H. A.; Sternfeld, T.; Rauch, K.; De Meijere, A.; Sheradsky, T.; Scott, L. T.;Rabinovitz, M., *Chem. Asian J.* 2006, 1, 678-685.

Fox, M. A., *Chem. Rev.* 1979, 79, 253-273.

Schmidt-Mende, L.; Fechtenkotter, A.; Müllen, K.; Moons, E.; Friend, R. H.; MacKenzie, J. D., *Science* 2001, 293, 1119-1122.

Wasielewski, M. R., *J. Org. Chem.* 2006, 71, 5051-5066.

Würthner, F., *Chem. Commun.* 2004, 1564-1579.

Gosztola, D.; Niemczyk, M. P.; Svec, W.; Lukas, A. S.; Wasielewski, M. R., *J. Phys. Chem. A* 2000, 104, 6545-6551.

Lu, W.; Gao, J. P.; Wang, Z. Y.; Qi, Y.; Sacripante, G. G.; Duff, J. D.; Sundararajan, P. R., Macromolecules 1999, 32, 8880-8885.

J.-H. Ryu, D.-J. Hong, M. Lee, *Chem. Commun.* 2008, 1043-1054.

J. Baram, E. Shirman, N. Ben-Shitrit, A. Ustinov, H. Weissman, I. Pinkas, S. G. Wolf, B. Rybtchinski, J. Am. Chem. Soc. 2008, 130, 14966-14967.

X. Zhang, Z. J. Chen, F. Würthner, J. Am. Chem. Soc. 2007, 129, 4886-4887.

Y. K. Che, A. Datar, K. Balakrishnan, L. Zang, *J. Am. Chem. Soc.* 2007, 129, 7234-7235.

Z. B. K. Li, Y. E.; Talmon, M. A. Hillmyer, T. P. Lodge, *Science* 2004, 306, 98-101.

S. Binsilong, J. D. Kildea, W. C. Patalinghug, B. W. Skelton, A. H. White, *Aust. J. Chem.* 1994, 47, 1545-1551.

M. Vanburgel, D. A. Wiersma, K. Duppen, J. Chem. Phys. 1995, 102, 20-33.

M. J. Ahrens, L. E. Sinks, B. Rybtchinski, W. H. Liu, B. A. Jones, J. M. Giaimo, A. V. Gusev, A. J. Goshe, D. M. Tiede, M. R. Wasielewski, J. Am. Chem. Soc. 2004, 126, 8284-8294.

Shirman, E.; Ustinov, A.; Ben-Shitrit, N.; Weissman, H.; Iron, M. A.; Cohen, R.; Rybtchinski, B. J. Phys. Chem. B 2008, 112, 8855-8858.

Cui, H. G.; Chen, Z. Y.; Zhong, S.; Wooley, K. L.; Pochan, D. J. Science 2007, 317, 647-650.

Dreiss, C. A. Soft Matter 2007, 3, 956-970.

Jain, S.; Bates, F. S. Macromolecules 2004, 37, 1511-1523.

Rajasingh et a.; "Selective Bromination of Perylene Diimides under Mild Conditions", J. Org. Chem. 2007, 72, 5973-5979.

\* cited by examiner

PDI  PDI$^{2-}$  PDI  PDI$^{2-}$

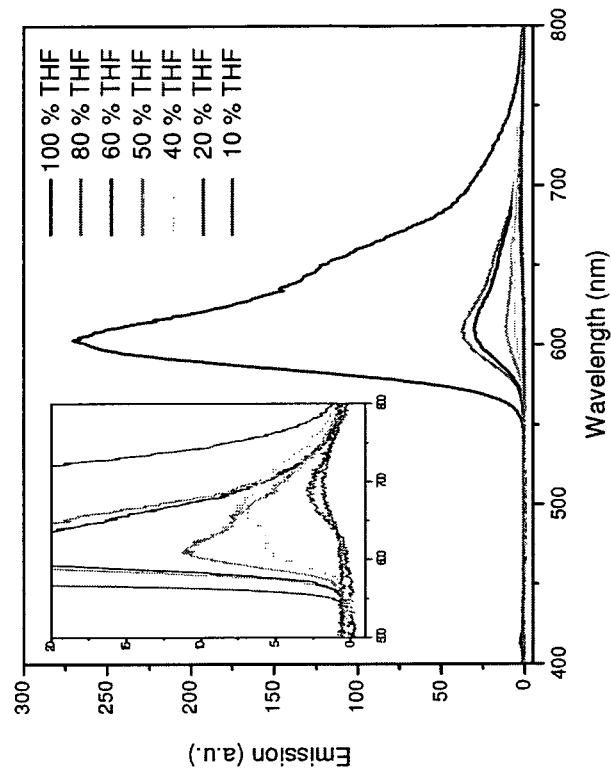
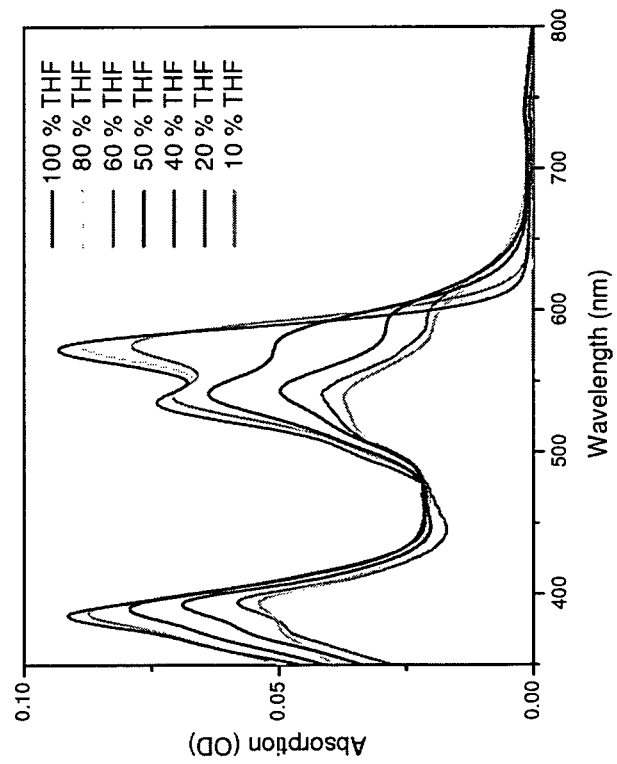
Fig. 22B
Fig. 22A

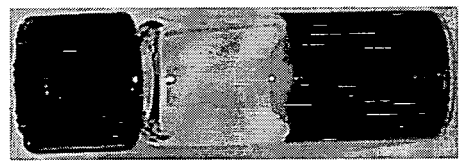
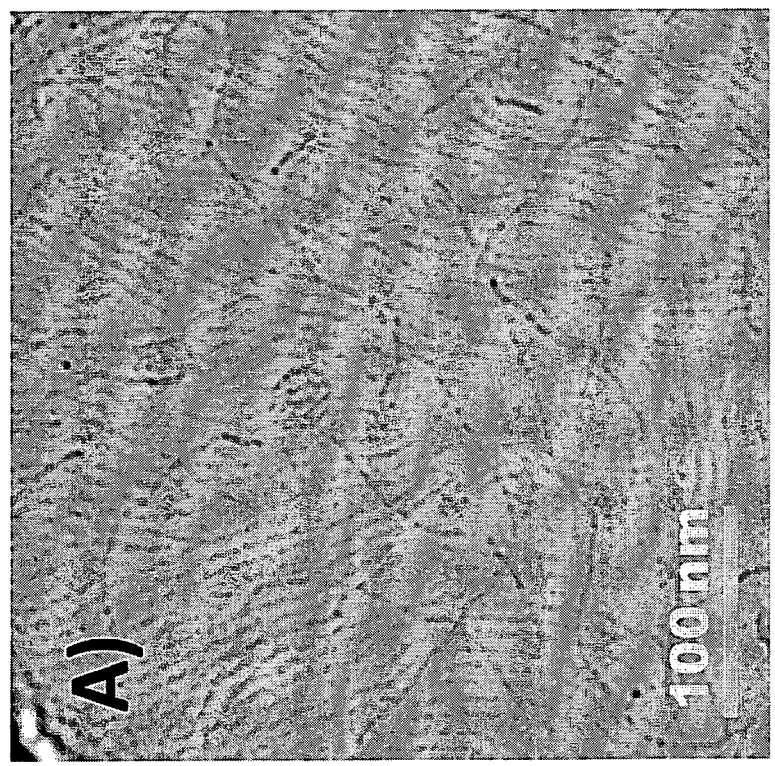
Fig. 23B
Fig. 23A single molecules → small rodlike aggregates → segmented fibers → bundles of fibers → 3D-network

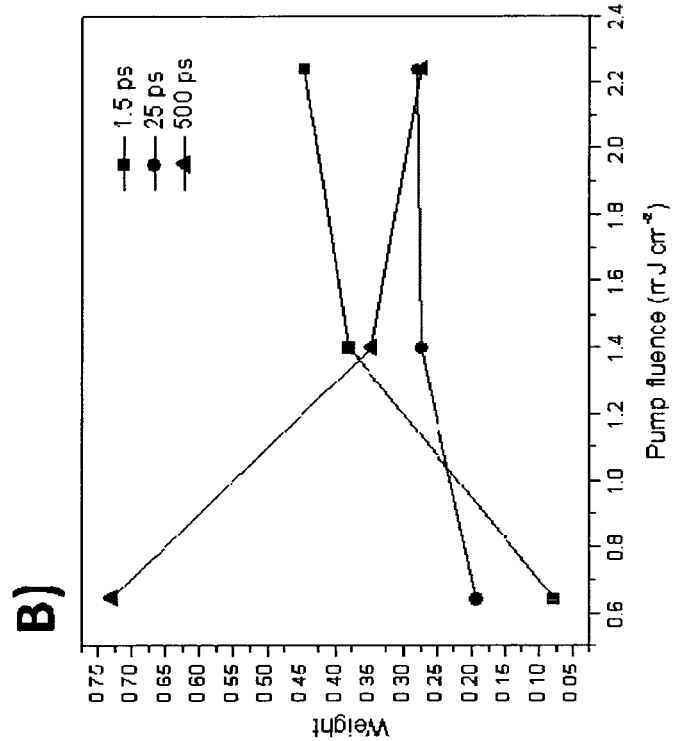
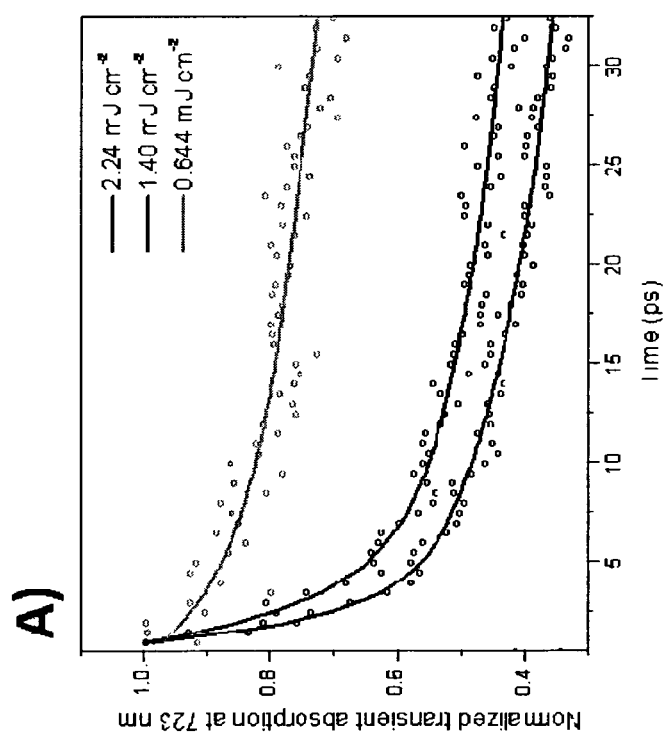
Fig. 30A
Fig. 30B

Compound XV – top row
Compound X – bottom row

DOUBLY REDUCED PERYLENE-DIIMIDES AND SUPRAMOLECULAR POLYMERS DERIVED FROM PERYLENE-DIIMIDES

CROSS-REFERENCE TO RELATED APPLICATIONS

This application is a National Phase Application of PCT International Application No. PCT/IL2009/000348, International Filing Date Mar. 26, 2009, claiming priority of U.S. Provisional Application Ser. No. 61/064,778 filed Mar. 26, 2008.

FIELD OF THE INVENTION

This invention is directed to perylene-diimide aromatic dianion compounds, process of preparation and uses thereof. The perylene-diimide aromatic dianion compounds of this invention are stable in aqueous solution and can be used for photofunctional and electron transfer systems in aqueous phase. This invention is also directed to supramolecular polymers derived from perylene-diimide compounds and to uses thereof.

BACKGROUND OF THE INVENTION

Perylene-diimides (PDIs) are outstanding versatile organic chromophores. They demonstrate exceptional thermal and photochemical stability, strongly absorb visible light, and show high fluorescence quantum yields. PDIs have been utilized as industrial dyes, electronic materials, sensors, photovoltaics, and building blocks for light-harvesting and artificial photosynthetic systems. Importantly, photophysical and redox properties of PDIs can be conveniently modified through substitution in the aromatic core at the positions 1, 6, 7, and 12 (bay region). Substitutions at bay positions and expansion of the PDI core are usually carried out starting from the halogenated derivatives, particularly brominated PDIs.

Doubly reduced aromatic compounds, aromatic dianions, have been extensively studied due to their fundamental importance in understanding aromaticity, n-delocalization, and electron transfer. Most aromatic dianions strongly absorb visible light to reach highly energetic excited states, allowing access to high energy electron transfer reactions. The excess charge on aromatic dianions makes them very reactive toward oxidants and protic solvents, especially water.

There is a need in the art to develop compounds having new electronic properties for use as industrial dyes, electronic materials, sensors, photovoltaics, supercapacitors and building blocks for light-harvesting and artificial photosynthetic systems.

SUMMARY OF THE INVENTION

This invention is directed to perylene-diimide aromatic dianion compounds, process of preparation and uses thereof. This invention is also directed to supramolecular polymers derived from perylene-diimide compounds and to uses thereof.

In one embodiment, the present invention provides a doubly reduced perylene-diimide compound represented by the structure of formula (1):

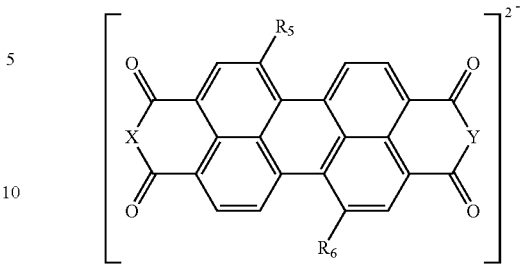

(1)

wherein said compound is a dianion;
wherein:
X is —NR$_1$;
Y is —NR$_2$;
R$_1$ is [(CH$_2$)$_n$O]$_o$CH$_3$, [(CH$_2$)$_n$C(O)O]$_o$CH$_3$, [(CH$_2$)$_n$C(O)NH]$_o$CH$_3$, [(CH$_2$)$_n$CH=CH$_2$]$_o$CH$_3$, [(CH$_2$)$_n$CH=CH]$_o$CH$_3$, [(CH$_2$)$_n$NH]$_o$CH$_3$, (C$_1$-C$_{32}$)alkyl, (C$_3$-C$_8$)cycloalkyl, aryl, heteroaryl, (C$_1$-C$_{32}$)alkyl-COOH, (C$_1$-C$_{32}$)alkyl-Si-A, or [C(O)CHR$_3$NH]$_p$H wherein said aryl or heteroaryl groups are optionally substituted by 1-3 groups comprising halide, CN, CO$_2$H, OH, SH, NH$_2$, CO$_2$—(C$_1$-C$_6$ alkyl) or O—(C$_1$-C$_6$ alkyl); wherein A comprises three same or different of the following substituents Cl, Br, I, O(C$_1$-C$_8$)alkyl or (C$_1$-C$_8$) alkyl; and wherein R$_3$ in said [C(O)CHR$_3$NH]$_p$H is independently the same or different when p is larger than 1;
R$_2$ is [(CH$_2$)$_q$O]$_r$CH$_3$, [(CH$_2$)$_q$C(O)O]$_r$CH$_3$, [(CH$_2$)$_q$C(O)NH]$_r$CH$_3$, [(CH$_2$)$_q$CH=CH$_2$]$_r$CH$_3$, [(CH$_2$)$_q$CH=CH]$_r$CH$_3$, [(CH$_2$)$_q$NH]$_r$CH$_3$, (C$_1$-C$_{32}$)alkyl, (C$_3$-C$_8$)cycloalkyl, aryl, heteroaryl, (C$_1$-C$_{32}$)alkyl-COOH, (C$_1$-C$_{32}$)alkyl-Si-A, or [C(O)CHR$_4$NH]$_s$H wherein said aryl or heteroaryl groups are optionally substituted by 1-3 groups comprising halide, CN, CO$_2$H, OH, SH, NH$_2$, CO$_2$—(C$_1$-C$_6$ alkyl) or O—(C$_1$-C$_6$ alkyl); wherein A comprises three same or different of the following substituents Cl, Br, I, O(C$_1$-C$_8$)alkyl or (C$_1$-C$_8$) alkyl; and wherein R$_4$ in said [C(O)CHR$_4$NH]$_s$H is independently the same or different when s is larger than 1;
R$_3$ is H, (C$_1$-C$_6$)alkyl, (C$_1$-C$_6$)hydroxyalkyl, (C$_1$-C$_6$)mercaptoalkyl, (C$_1$-C$_6$)aminoalkyl, (C$_1$-C$_6$)carboxyalkyl, (C$_1$-C$_6$)carb oxamidoalkyl, (C$_1$-C$_6$)guanidinoalkyl, aryl, (aryl)alkyl, heteroaryl or (heteroaryl)alkyl wherein the aromatic ring of said aryl, (aryl)alkyl, heteroaryl or (heteroaryl)alkyl groups are optionally substituted by 1-3 groups comprising halide, CN, CO$_2$H, OH, SH, NH$_2$, CO$_2$—(C$_1$-C$_6$ alkyl) or O—(C$_1$-C$_6$ alkyl);
R$_4$ is H, (C$_1$-C$_6$)alkyl, (C$_1$-C$_6$)hydroxyallyl, (C$_1$-C$_6$)mercaptoalkyl, (C$_1$-C$_6$)aminoalkyl, (C$_1$-C$_6$)carb oxyalkyl, (C$_1$-C$_6$)carboxamidoalkyl, (C$_1$-C$_6$)guanidinoalkyl, aryl, (aryl)alkyl, heteroaryl or (heteroaryl)alkyl wherein the aromatic ring of said aryl, (aryl)alkyl, heteroaryl or (heteroaryl)alkyl groups are optionally substituted by 1-3 groups comprising halide, CN, CO$_2$H, OH, SH, NH$_2$, CO$_2$—(C$_1$-C$_6$ alkyl) or O—(C$_1$-C$_6$ alkyl);
R$_5$ and R$_6$ are independently H, —OR$_x$ where R$_x$ is (C$_1$-C$_6$) alkyl or [(CH$_2$)$_n$O]$_o$CH$_3$, aryl, heteroaryl, C≡C—R$_7$, CH=CR$_8$R$_9$, NR$_{10}$R$_{11}$ or a saturated carbocyclic or heterocyclic ring wherein said saturated heterocyclic ring or heteroaryl contains at least one nitrogen atom and R$_5$ or R$_6$ are connected via the nitrogen atom and wherein said saturated carbocyclic ring, heterocyclic ring, aryl and heteroaryl groups are optionally substituted by 1-3 groups comprising halide, aryl, heteroaryl, CN, CO$_2$H, OH, SH, NH$_2$, CO$_2$—(C$_1$-C$_6$ alkyl) or O—(C$_1$-C$_6$ alkyl);
R$_7$ is H, halo, (C$_1$-C$_{32}$)alkyl, aryl, heteroaryl, Si(H)$_3$ or Si[(C$_1$-C$_8$)alkyl]$_3$ wherein said aryl or heteroaryl groups are optionally substituted by 1-3 groups comprising halide, CN, $CO_2H$, OH, SH, $NH_2$, $CO_2$—($C_1$-$C_6$ alkyl) or O—($C_1$-$C_6$ alkyl);

$R_8$, $R_9$, $R_{10}$ and $R_{11}$ are independently H, ($C_1$-$C_{32}$)alkyl, aryl or heteroaryl wherein said aryl or heteroaryl groups are optionally substituted by 1-3 groups comprising halide, CN, $CO_2H$, OH, SH, $NH_2$, $CO_2$—($C_1$-$C_6$ alkyl) or O—($C_1$-$C_6$ alkyl);

n is an integer from 1-5;
o is an integer from 1-100;
p is an integer from 1-100;
q is an integer from 2-5;
r is an integer from 1-100; and
s is an integer from 1-100.

In one embodiment, the present invention provides a doubly reduced perylene-diimide compound represented by the structure of formula 7a or 7b:

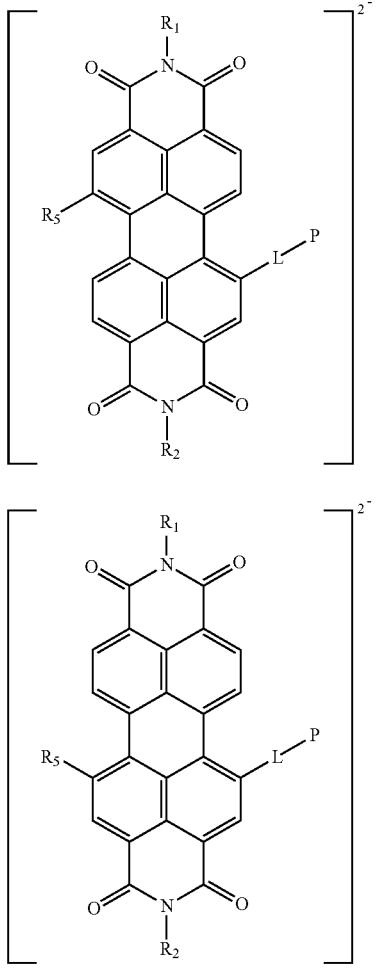

wherein said compound is a dianion;
wherein
$R_1$ is $[(CH_2)_nO]_oCH_3$, $[(CH_2)_nC(O)O]_oCH_3$, $[(CH_2)_nC(O)NH]_oCH_3$, $[(CH_2)_nCH_2$=$CH_2]_oCH_3$, $[(CH_2)_nCH$=$CH]_oCH_3$, $[(CH_2)_nNH]_oCH_3$, ($C_1$-$C_{32}$)alkyl, ($C_3$-$C_8$)cycloalkyl, aryl, heteroaryl, ($C_1$-$C_{32}$)alkyl-COOH, ($C_1$-$C_{32}$)alkyl-Si-A, or $[C(O)CHR_3NH]_pH$ wherein said aryl or heteroaryl groups are optionally substituted by 1-3 groups comprising halide, CN, $CO_2H$, OH, SH, $NH_2$, $CO_2$—($C_1$-$C_6$ alkyl) or O—($C_1$-$C_6$ alkyl); wherein A comprises three same or different of the following substituents Cl, Br, I, O($C_1$-$C_8$)alkyl or ($C_1$-$C_8$) alkyl; and wherein $R_3$ in said $[C(O)CHR_3NH]_pH$ is independently the same or different when p is larger than 1;

$R_2$ is $[(CH_2)_qO]_rCH_3$, $[(CH_2)_qC(O)O]_rCH_3$, $[(CH_2)_qC(O)NH]_rCH_3$, $[(CH_2)_qCH_2$=$CH_2]_rCH_3$, $[(CH_2)_qCH$=$CH]_rCH_3$, $[(CH_2)_qNH]_rCH_3$, ($C_1$-$C_{32}$)alkyl, ($C_3$-$C_8$)cycloalkyl, aryl, heteroaryl, ($C_1$-$C_{32}$)alkyl-COOH, ($C_1$-$C_{32}$)alkyl-Si-A, or $[C(O)CHR_4NH]_sH$ wherein said aryl or heteroaryl groups are optionally substituted by 1-3 groups comprising halide, CN, $CO_2H$, OH, SH, $NH_2$, $CO_2$—($C_1$-$C_6$ alkyl) or O—($C_1$-$C_6$ alkyl); wherein A comprises three same or different of the following substituents Cl, Br, I, O($C_1$-$C_8$)alkyl or ($C_1$-$C_8$) alkyl; and wherein $R_4$ in said $[C(O)CHR_4NH]_sH$ is independently the same or different when s is larger than 1;

$R_5$ is H, —$OR_x$ where $R_x$ is $C_1$-$C_6$ alkyl or $[(CH_2)_nO]_oCH_3$, aryl, heteroaryl, C≡C—$R_7$; CH=$CR_8R_9$, $NR_{10}R_{11}$ or a saturated carbocyclic or heterocyclic ring wherein said saturated heterocyclic ring or heteroaryl contains at least one nitrogen atom and $R_5$ or $R_6$ are connected via the nitrogen atom and wherein said saturated carbocyclic ring, heterocyclic ring, aryl and heteroaryl groups are optionally substituted by 1-3 groups comprising halide, aryl, heteroaryl, CN, $CO_2H$, OH, SH, $NH_2$, $CO_2$—($C_1$-$C_6$ alkyl) or O—($C_1$-$C_6$ alkyl);

$R_7$ is H, halo, ($C_1$-$C_{32}$)alkyl, aryl, heteroaryl, Si(H)$_3$ or Si[($C_1$-$C_8$)alkyl]$_3$ wherein said aryl or heteroaryl groups are optionally substituted by 1-3 groups comprising halide, aryl, heteroaryl, CN, $CO_2H$, OH, SH, $NH_2$, $CO_2$—($C_1$-$C_6$ alkyl) or O—($C_1$-$C_6$ alkyl);

$R_8$, $R_9$, $R_{10}$ and $R_{11}$ are independently H, ($C_1$-$C_{32}$)alkyl, aryl or heteroaryl wherein said aryl or heteroaryl groups are optionally substituted by 1-3 groups comprising halide, CN, $CO_2H$, OH, SH, $NH_2$, $CO_2$—($C_1$-$C_6$ alkyl) or O—($C_1$-$C_6$ alkyl);

L is an unsaturated linker;
P is a perylene-diimide group, aryl or heteroaryl, wherein said aryl and heteroaryl groups are optionally substituted by 1-3 groups comprising halide, aryl, heteroaryl, CN, $CO_2H$, OH, SH, $NH_2$, $CO_2$—($C_1$-$C_6$ alkyl) or O—($C_1$-$C_6$ alkyl);

n is an integer from 1-5;
o is an integer from 1-100;
p is an integer from 1-100;
q is an integer from 2-5;
r is an integer from 1-100; and
s is an integer from 1-100;
or a metal complex thereof.

In one embodiment, the present invention provides a supramolecular polymer, comprising a monomer unit represented by formula VIa or VIb:

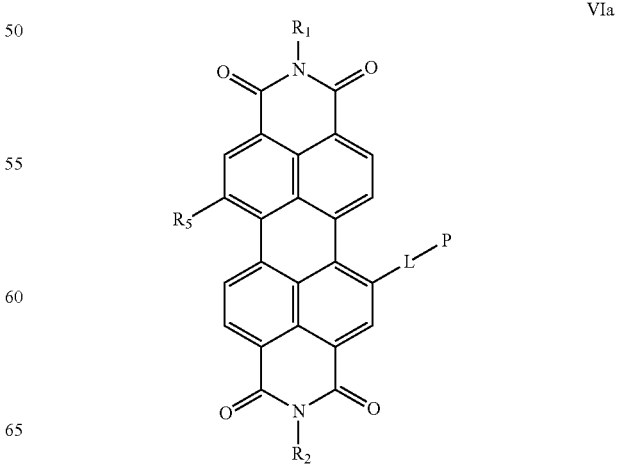

VIa

-continued

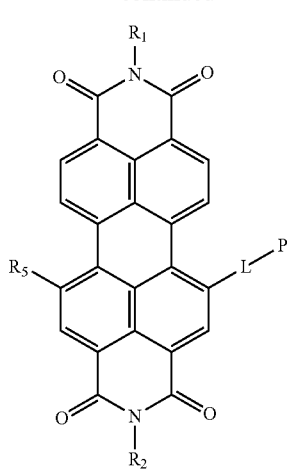

wherein
$R_1$ is $[(CH_2)_nO]_oCH_3$, $[(CH_2)_nC(O)O]_oCH_3$, $[(CH_2)_nC(O)NH]_oCH_3$, $[(CH_2)_nCH=CH_2]_oCH_3$, $[(CH_2)_nCH=CH]_oCH_3$, $[(CH_2)_nNH]_oCH_3$, $(C_1-C_{32})$alkyl, $(C_3-C_8)$cycloalkyl, aryl, heteroaryl, $(C_1-C_{32})$alkyl-COOH, $(C_1-C_{32})$alkyl-Si-A, or $[C(O)CHR_3NH]_pH$ wherein said aryl or heteroaryl groups are optionally substituted by 1-3 groups comprising halide, CN, $CO_2H$, OH, SH, $NH_2$, $CO_2$—$(C_1-C_6$ alkyl) or O—$(C_1$-$C_6$ alkyl); wherein A comprises three same or different of the following substituents Cl, Br, I, O$(C_1-C_8)$alkyl or $(C_1-C_8)$ alkyl; and wherein $R_3$ in said $[C(O)CHR_3NH]_pH$ is independently the same or different when p is larger than 1;
$R_2$ is $[(CH_2)_qO]_rCH_3$, $[(CH_2)_qC(O)O]_rCH_3$, $[(CH_2)_qC(O)NH]_rCH_3$, $[(CH_2)_qCH=CH_2]_rCH_3$, $[(CH_2)_qCH=CH]_rCH_3$, $[(CH_2)_qNH]_rCH_3$, $(C_1-C_{32})$alkyl, $(C_3-C_8)$cycloalkyl, aryl, heteroaryl, $(C_1-C_{32})$alkyl-COOH, $(C_1-C_{32})$alkyl-Si-A, or $[C(O)CHR_4NH]_sH$ wherein said aryl or heteroaryl groups are optionally substituted by 1-3 groups comprising halide, CN, $CO_2H$, OH, SH, $NH_2$, $CO_2$—$(C_1-C_6$ alkyl) or O—$(C_1$-$C_6$ alkyl); wherein A comprises three same or different of the following substituents Cl, Br, I, O$(C_1-C_8)$alkyl or $(C_1-C_8)$ alkyl; and wherein $R_4$ in said $[C(O)CHR_4NH]_sH$ is independently the same or different when s is larger than 1;
$R_5$ is H, —$OR_x$ where $R_x$ is $(C_1-C_6)$alkyl or $[(CH_2)_nO]_oCH_3$, aryl, heteroaryl, CH=$CR_8R_9$, $NR_{10}R_{11}$ or a saturated carbocyclic or heterocyclic ring wherein said saturated heterocyclic ring or heteroaryl contains at least one nitrogen atom and $R_5$ or $R_6$ are connected via the nitrogen atom and wherein said saturated carbocyclic ring, heterocyclic ring, aryl and heteroaryl groups are optionally substituted by 1-3 groups comprising halide, aryl, heteroaryl, CN, $CO_2H$, OH, SH, $NH_2$, $CO_2$—$(C_1-C_6$ alkyl) or O—$(C_1-C_6$ alkyl);
$R_7$ is H, halo, $(C_1-C_{32})$alkyl, aryl, heteroaryl, $Si(H)_3$ or $Si[(C_1-C_8)$alkyl$]_3$ wherein said aryl or heteroaryl groups are optionally substituted by 1-3 groups comprising halide, aryl, heteroaryl, CN, $CO_2H$, OH, SH, $NH_2$, $CO_2$—$(C_1-C_6$ alkyl) or O—$(C_1-C_6$ alkyl);
$R_8$, $R_9$, $R_{10}$ and $R_{11}$ are independently H, $(C_1-C_{32})$alkyl, aryl or heteroaryl wherein said aryl or heteroaryl groups are optionally substituted by 1-3 groups comprising halide, CN, $CO_2H$, OH, SH, $NH_2$, $CO_2$—$(C_1-C_6$ alkyl) or O—$(C_1-C_6$ alkyl);
L is an unsaturated linker;
P is a perylene-diimide group, aryl or heteroaryl, wherein said aryl and heteroaryl groups are optionally substituted by 1-3 groups comprising halide, aryl, heteroaryl, CN, $CO_2H$, OH, SH, $NH_2$, $CO_2$—$(C_1-C_6$ alkyl) or O—$(C_1-C_6$ alkyl);
n is an integer from 1-5;
o is an integer from 1-100;
p is an integer from 1-100;
q is an integer from 2-5;
r is an integer from 1-100; and
s is an integer from 1-100;
or a metal complex thereof.

In one embodiment, the present invention provides a process for preparing a doubly reduced perylene-diimide compound represented by the structure of formula (1):

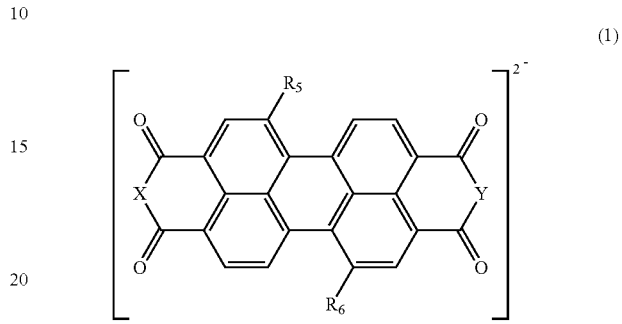

(1)

wherein said compound is a dianion;
wherein:
X is —$NR_1$;
Y is —$NR_2$;
$R_1$ is $[(CH_2)_nO]_oCH_3$, $[(CH_2)_nC(O)O]_oCH_3$, $[(CH_2)_nC(O)NH]_oCH_3$, $[(CH_2)_nCH=CH_2]_oCH_3$, $[(CH_2)_nCH=CH]_oCH_3$, $[(CH_2)_nNH]_oCH_3$, $(C_1-C_{32})$alkyl, $(C_3-C_8)$cycloalkyl, aryl, heteroaryl, $(C_1-C_{32})$alkyl-COOH, $(C_1-C_{32})$alkyl-Si-A, or $[C(O)CHR_3NH]_pH$ wherein said aryl or heteroaryl groups are optionally substituted by 1-3 groups comprising halide, CN, $CO_2H$, OH, SH, $NH_2$, $CO_2$—$(C_1-C_6$ alkyl) or O—$(C_1$-$C_6$ alkyl); wherein A comprises three same or different of the following substituents Cl, Br, I, O$(C_1-C_8)$alkyl or $(C_1-C_8)$ alkyl; and wherein $R_3$ in said $[C(O)CHR_3NH]_pH$ is independently the same or different when p is larger than 1;
$R_2$ is $[(CH_2)_qO]_rCH_3$, $[(CH_2)_qC(O)O]_rCH_3$, $[(CH_2)_qC(O)NH]_rCH_3$, $[(CH_2)_qCH=CH_2]_rCH_3$, $[(CH_2)_qCH=CH]_rCH_3$, $[(CH_2)_qNH]_rCH_3$, $(C_1-C_{32})$alkyl, $(C_3-C_8)$cycloalkyl, aryl, heteroaryl, $(C_1-C_{32})$alkyl-COOH, $(C_1-C_{32})$alkyl-Si-A, or $[C(O)CHR_4NH]_sH$ wherein said aryl or heteroaryl groups are optionally substituted by 1-3 groups comprising halide, CN, $CO_2H$, OH, SH, $NH_2$, $CO_2$—$(C_1-C_6$ alkyl) or O—$(C_1$-$C_6$ alkyl); wherein A comprises three same or different of the following substituents Cl, Br, I, O$(C_1-C_8)$alkyl or $(C_1-C_8)$ alkyl; and wherein $R_4$ in said $[C(O)CHR_4NH]_sH$ is independently the same or different when s is larger than 1;
$R_3$ is H, $(C_1-C_6)$alkyl, $(C_1-C_6)$hydroxyalkyl, $(C_1-C_6)$mercaptoalkyl, $(C_1-C_6)$aminoalkyl, $(C_1-C_6)$carboxyalkyl, $(C_1-C_6)$ carboxamidoalkyl, $(C_1-C_6)$guanidino alkyl, aryl, (aryl)alkyl, heteroaryl or (heteroaryl)alkyl wherein the aromatic ring of said aryl, (aryl)alkyl, heteroaryl or (heteroaryl)alkyl groups are optionally substituted by 1-3 groups comprising halide, CN, $CO_2H$, OH, SH, $NH_2$, $CO_2$—$(C_1-C_6$ alkyl) or O—$(C_1$-$C_6$ alkyl);
$R_4$ is H, $(C_1-C_6)$alkyl, $(C_1-C_6)$hydroxyalkyl, $(C_1-C_6)$mercaptoalkyl, $(C_1-C_6)$amino alkyl, $(C_1-C_6)$carboxyalkyl, $(C_1-C_6)$ carboxamido alkyl, $(C_1-C_6)$guanidino alkyl, aryl, (aryl)alkyl, heteroaryl or (heteroaryl)alkyl wherein the aromatic ring of said aryl, (aryl)alkyl, heteroaryl or (heteroaryl)alkyl groups are optionally substituted by 1-3 groups comprising halide, CN, $CO_2H$, OH, SH, $NH_2$, $CO_2$—$(C_1-C_6$ alkyl) or O—$(C_1$-$C_6$ alkyl);
$R_5$ and $R_6$ are independently H, —$OR_x$ where $R_x$ is $C_1-C_6$ alkyl or $[(CH_2)_nO]_oCH_3$, aryl, heteroaryl, C≡C—$R_7$, CH=$CR_8R_9$, $NR_{10}R_{11}$ or a saturated carbocyclic or heterocyclic ring wherein said saturated heterocyclic ring or heteroaryl contains at least one nitrogen atom and $R_5$ or $R_6$ are connected via the nitrogen atom and wherein said saturated carbocyclic ring, heterocyclic ring, aryl and heteroaryl groups are optionally substituted by 1-3 groups comprising halide, aryl, heteroaryl, CN, $CO_2H$, OH, SH, $NH_2$, $CO_2$—($C_1$-$C_6$ alkyl) or O—($C_1$-$C_6$ alkyl);

$R_7$ is H, halo, ($C_1$-$C_{32}$)alkyl, aryl, heteroaryl, $Si(H)_3$ or $Si[(C_1$-$C_8)alkyl]_3$ wherein said aryl or heteroaryl groups are optionally substituted by 1-3 groups comprising halide, CN, $CO_2H$, OH, SH, $NH_2$, $CO_2$—($C_1$-$C_6$ alkyl) or O—($C_1$-$C_6$ alkyl);

$R_8$, $R_9$, $R_{10}$ and $R_{11}$ are independently H, ($C_1$-$C_{32}$)alkyl, aryl or heteroaryl wherein said aryl or heteroaryl groups are optionally substituted by 1-3 groups comprising halide, CN, $CO_2H$, OH, SH, $NH_2$, $CO_2$—($C_1$-$C_6$ alkyl) or O—($C_1$-$C_6$ alkyl);

n is an integer from 1-5;
o is an integer from 1-100;
p is an integer from 1-100;
q is an integer from 2-5;
r is an integer from 1-100; and
s is an integer from 1-100;

comprising the steps of:
a) brominating a compound of formula (II)

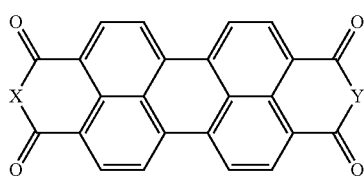

wherein X and Y are as defined above;
in the presence of bromine and a chlorinated solvent at reflux for a period of time sufficient to obtain a mixture comprising compounds of formula 1,6-(IV) and 1,7-(IV);

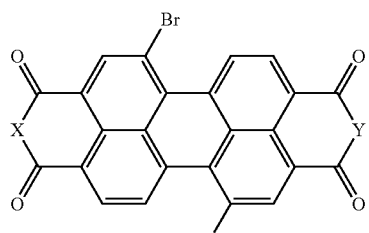

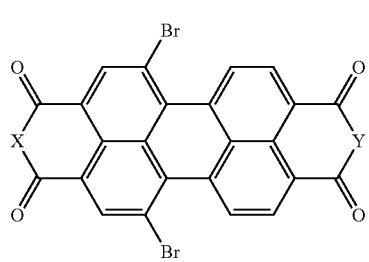

b) separating the 1,6-(IV) and 1,7-(IV) regioisomer compounds;
c) coupling a compound of formula 1,7-(IV) with a terminal acetylene, vinylstannane, vinylsilane, arylstannane, arylsilane, heteroarylstannane, heteroarylsilane, alcohol or amines reagent wherein coupling of a said compound of formula 1,7-(IV) with said reagents is optionally catalyzed using a transition metal catalyst, to obtain a compound of formula (I)

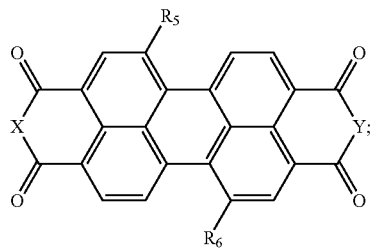

and
d) forming a dianion compound of formula 1.

In one embodiment, the present invention provides a process for preparing a doubly reduced perylene-diimide compound represented by the structure of formula (1):

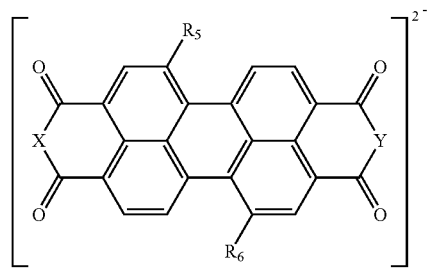

comprising the steps of
a) dissolving a compound of formula (I) in a protic solvent;

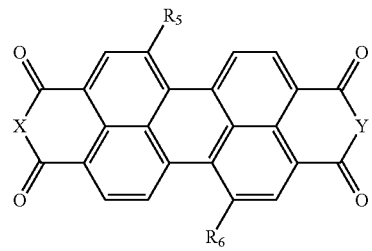

b) forming a dianion compound of formula (1), wherein X, Y, $R_5$ and $R_6$ are as described above for compound (1).

In one embodiment, the present invention provides a process for preparing a doubly reduced perylene-diimide compound represented by the structure of formula (2):

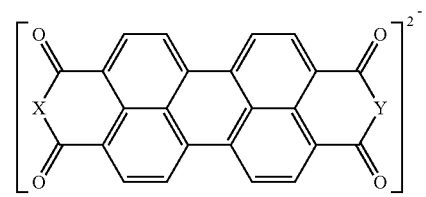

wherein said compound is a dianion;
wherein:
X is —$NR_1$;
Y is —$NR_2$;
$R_1$ is $[(CH_2)_nO]_oCH_3$, $[(CH_2)_nC(O)O]_oCH_3$, $[(CH_2)_nC(O)NH]_oCH_3$, $[(CH_2)_nCH_2$=$CH_2]_oCH_3$, $[(CH_2)_nCH$≡$CH]_o$ CH₃, [(CH₂)ₙNH]ₒCH₃, (C₁-C₃₂)alkyl, (C₃-C₈)cycloalkyl, aryl, heteroaryl, (C₁-C₃₂)alkyl-COOH, (C₁-C₃₂)alkyl-Si-A, or [C(O)CHR₃NH]ₚH wherein said aryl or heteroaryl groups are optionally substituted by 1-3 groups comprising halide, CN, CO₂H, OH, SH, NH₂, CO₂—(C₁-C₆ alkyl) or O—(C₁-C₆ alkyl); wherein A comprises three same or different of the following substituents Cl, Br, I, O(C₁-C₈)alkyl or (C₁-C₈)alkyl; and wherein R₃ in said [C(O)CHR₃NH]ₚH is independently the same or different when p is larger than 1;

R₂ is [(CH₂)_q O]_r CH₃, [(CH₂)_q C(O)O]_r CH₃, [(CH₂)_q C(O)NH]_r CH₃, [(CH₂)_q CH₂═CH₂]_r CH₃, [(CH₂)_q CH═CH]_r CH₃, [(CH₂)_q NH]_r CH₃, (C₁-C₃₂)alkyl, (C₃-C₈)cycloalkyl, aryl, heteroaryl, (C₁-C₃₂)alkyl-COOH, (C₁-C₃₂)alkyl-Si-A, or [C(O)CHR₄NH]_s H wherein said aryl or heteroaryl groups are optionally substituted by 1-3 groups comprising halide, CN, CO₂H, OH, SH, NH₂, CO₂—(C₁-C₆ alkyl) or O—(C₁-C₆ alkyl); wherein A comprises three same or different SH, NH₂, CO₂—(C₁-C₆ alkyl) or O—(C₁-C₆ alkyl); wherein A comprises three same or different of the following substituents Cl, Br, I, O(C₁-C₈)alkyl or (C₁-C₈)alkyl; and wherein R₄ in said [C(O)CHR₄NH]_s H is independently the same or different when s is larger than 1;

R₃ is H, (C₁-C₆)alkyl, (C₁-C₆)hydroxyalkyl, (C₁-C₆)mercaptoalkyl, (C₁-C₆)aminoalkyl, (C₁-C₆)carboxyalkyl, (C₁-C₆)carboxamidoalkyl, (C₁-C₆)guanidinoalkyl, aryl, (aryl)alkyl, heteroaryl or (heteroaryl)alkyl wherein the aromatic ring of said aryl, (aryl)alkyl, heteroaryl or (heteroaryl)alkyl groups are optionally substituted by 1-3 groups comprising halide, CN, CO₂H, OH, SH, NH₂, CO₂—(C₁-C₆ alkyl) or O—(C₁-C₆ alkyl);

R₄ is H, (C₁-C₆)alkyl, (C₁-C₆)hydroxyalkyl, (C₁-C₆)mercaptoalkyl, (C₁-C₆)aminoalkyl, (C₁-C₆)carboxyalkyl, (C₁-C₆)carboxamidoalkyl, (C₁-C₆)guanidinoalkyl, aryl, (aryl)alkyl, heteroaryl or (heteroaryl)alkyl wherein the aromatic ring of said aryl, (aryl)alkyl, heteroaryl or (heteroaryl)alkyl groups are optionally substituted by 1-3 groups comprising halide, CN, CO₂H, OH, SH, NH₂, CO₂—(C₁-C₆ alkyl) or O—(C₁-C₆ alkyl);

n is an integer from 1-5;
o is an integer from 1-100;
p is an integer from 1-100;
q is an integer from 2-5;
r is an integer from 1-100; and
s is an integer from 1-100;
comprising the steps of:
a) dissolving a compound of formula (II) in a protic solvent

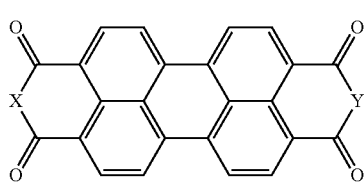
(II)

wherein X and Y are as defined above; and
b) forming a dianion compound of formula (2), wherein X and Y are as described above for compound (2).

In one embodiment, the present invention provides a process for preparing a doubly reduced perylene-diimide compound represented by the structure of formula 7a or 7b:

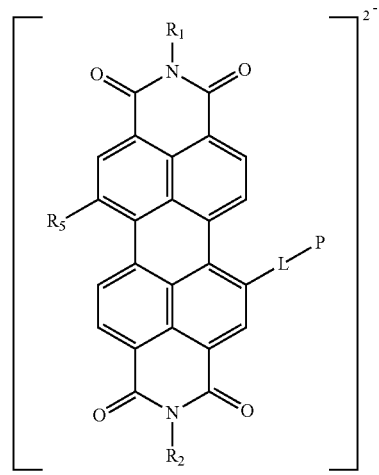
7a

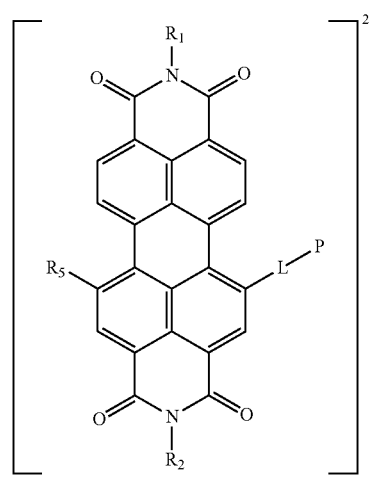
7b wherein
R₁ is [(CH₂)ₙO]ₒCH₃, [(CH₂)ₙC(O)O]ₒCH₃, [(CH₂)ₙC(O)NH]ₒCH₃, [(CH₂)ₙCH₂═CH₂]ₒCH₃, [(CH₂)ₙCH═CH]ₒCH₃, (CH₂)ₙNH]ₒCH₃, (C₁-C₃₂)alkyl, (C₃-C₈)cycloalkyl, aryl, heteroaryl, (C₁-C₃₂)alkyl-COOH, (C₁-C₃₂)alkyl-Si-A, or [C(O)CHR₃NH]ₚH wherein said aryl or heteroaryl groups are optionally substituted by 1-3 groups comprising halide, CN, CO₂H, OH, SH, NH₂, CO₂—(C₁-C₆ alkyl) or O—(C₁-C₆ alkyl); wherein A comprises three same or different of the following substituents Cl, Br, I, O(C₁-C₈)alkyl or (C₁-C₈)alkyl; and wherein R₃ in said [C(O)CHR₃NH]ₚH is independently the same or different when p is larger than 1;

R₂ is [(CH₂)_q O]_r CH₃, [(CH₂)_q C(O)O]_r CH₃, [(CH₂)_q C(O)NH]_r CH₃, [(CH₂)_q CH₂═CH₂]_r CH₃, [(CH₂)_q CH═CH]_r CH₃, [(CH₂)_q NH]_r CH₃, (C₁-C₃₂)alkyl, (C₃-C₈)cycloalkyl, aryl, heteroaryl, (C₁-C₃₂)alkyl-COOH, (C₁-C₃₂)alkyl-Si-A, or [C(O)CHR₄NH]_s H wherein said aryl or heteroaryl groups are optionally substituted by 1-3 groups comprising halide, CN, CO₂H, OH, SH, NH₂, CO₂—(C₁-C₆ alkyl) or O—(C₁-C₆ alkyl); wherein A comprises three same or different of the following substituents Cl, Br, I, O(C₁-C₈)alkyl or (C₁-C₈)alkyl; and wherein R₄ in said [C(O)CHR₄NH]_s H is independently the same or different when s is larger than 1;

R₅ is H, —ORₓ where Rₓ is (C₁-C₆)alkyl or [(CH₂)ₙO]ₒCH₃, aryl, heteroaryl, C≡C—R₇, CH═CR₈R₉, NR₁₀R₁₁ or a saturated carbocyclic or heterocyclic ring wherein said saturated heterocyclic ring or heteroaryl contains at least one nitrogen atom and R₅ or R₆ are connected via the nitrogen atom and wherein said saturated carbocyclic ring, heterocyclic ring, aryl and heteroaryl groups are optionally substituted by 1-3 groups comprising halide, aryl, heteroaryl, CN, $CO_2H$, OH, SH, $NH_2$, $CO_2$—($C_1$-$C_6$ alkyl) or O—($C_1$-$C_6$ alkyl);

$R_7$ is H, halo, ($C_1$-$C_{32}$)alkyl, aryl, heteroaryl, $Si(H)_3$ or $Si[(C_1$-$C_8)alkyl]_3$ wherein said aryl or heteroaryl groups are optionally substituted by 1-3 groups comprising halide, aryl, heteroaryl, CN, $CO_2H$, OH, SH, $NH_2$, $CO_2$—($C_1$-$C_6$ alkyl) or O—($C_1$-$C_6$ alkyl);

$R_8$, $R_9$, $R_{10}$ and $R_{11}$ are independently H, ($C_1$-$C_{32}$)alkyl, aryl or heteroaryl wherein said aryl or heteroaryl groups are optionally substituted by 1-3 groups comprising halide, CN, $CO_2H$, OH, SH, $NH_2$, $CO_2$—($C_1$-$C_6$ alkyl) or O—($C_1$-$C_6$ alkyl);

L is an unsaturated linker;

P is a perylene-diimide group, aryl or heteroaryl, wherein said aryl and heteroaryl groups are optionally substituted by 1-3 groups comprising halide, aryl, heteroaryl, CN, $CO_2H$, OH, SH, $NH_2$, $CO_2$—($C_1$-$C_6$ alkyl) or O—($C_1$-$C_6$ alkyl);

n is an integer from 1-5;
o is an integer from 1-100;
p is an integer from 1-100;
q is an integer from 2-5;
r is an integer from 1-100; and
s is an integer from 1-100;
or a metal complex thereof;
comprising the steps of
  a) dissolving a compound of formula VIa or VIb in a protic solvent

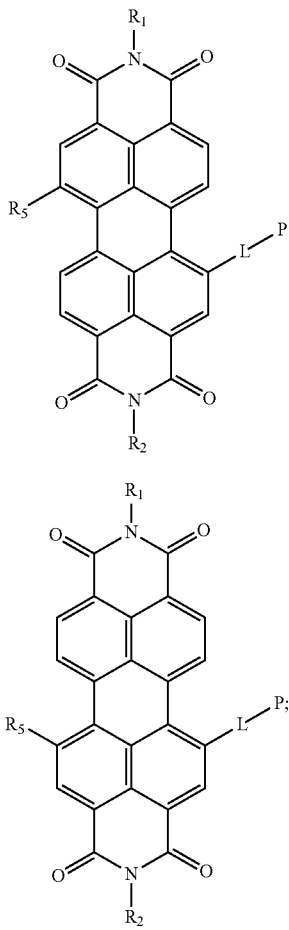

and
  b) forming a dianion compound of formula 7a or 7b.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

FIG. 22 depicts UV-vis absorption (A) and fluorescence (B) spectra of a solution of Compound X in THF and different THF/water mixtures.

FIG. 23 depicts a Cryo-TEM image of a $10^{-4}$ M colloid solution of Compound X in water/THF (80:20, v/v) displaying partially ordered supramolecular fibers (A) and an illustration of a filtration experiment of the same sample showing almost quantitative removal of the fibers by filtration over a 0.20 μm Teflon syringe filter (B).

FIG. 30 depicts (A) the decay of the transient absorption intensity of self-assembled Compound X at 723 nm at different pump powers (circles) and a triexponential fit to the decay with $\tau_1 \sim 1.5$ ps, $\tau_2 \sim 25$ ps, and $\tau_3 \sim 500$ ps (curves), and (B) the dependence of the contribution of the decay time constants on the pump fluence.

Figure 1:
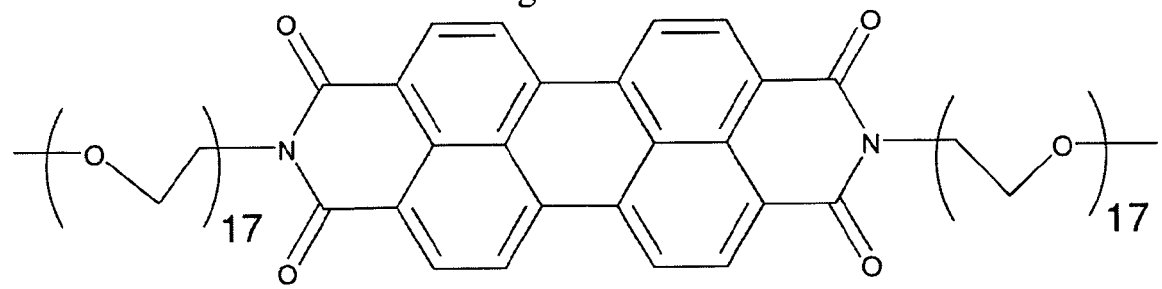
FIG. 1 depicts a representative perylene-diimide compound of formula III.
Figure 2:
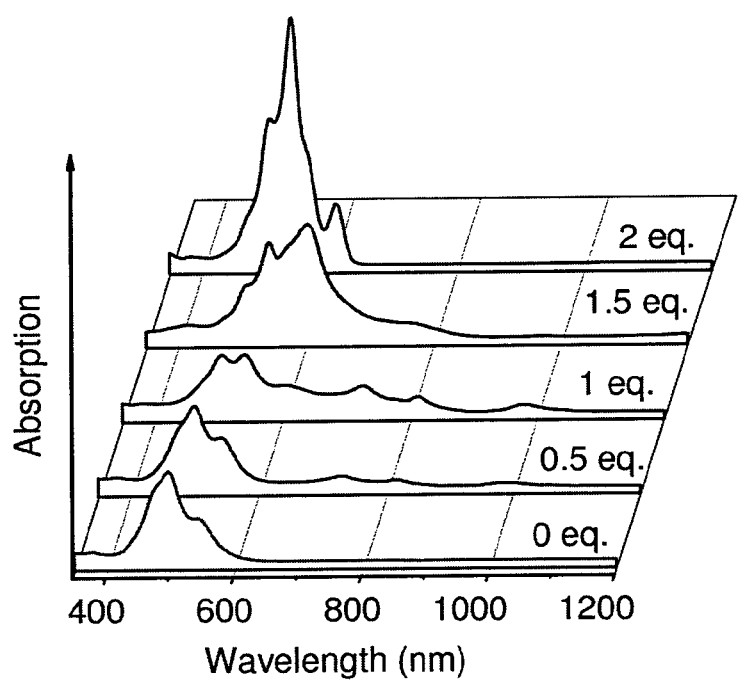
FIG. 2 depicts a UV-VIS spectra for the titration of compound of formula III with $Na_2S_2O_4$.

It will be appreciated that for simplicity and clarity of illustration, elements shown in the Figs. have not necessarily been drawn to scale. For example, the dimensions of some of the elements may be exaggerated relative to other elements for clarity. Further, where considered appropriate, reference numerals may be repeated among the Figs. to indicate corresponding or analogous elements.

DETAILED DESCRIPTION OF THE PRESENT INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

In one embodiment, this invention provides a doubly reduced perylene-diimide compound represented by the structure of formula (1):

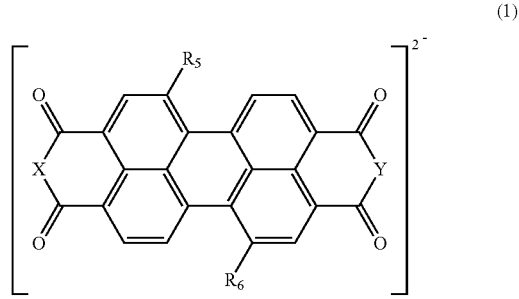

wherein said compound is a dianion;
wherein:
X is O or —$NR_1$;
Y is O or —$NR_2$;

$R_1$ is $[(CH_2)_nO]_oCH_3$, $[(CH_2)_nC(O)O]_oCH_3$, $[(CH_2)_nC(O)NH]_oCH_3$, $[(CH_2)_nCH=CH_2]_oCH_3$, $[(CH_2)_nCH\equiv CH]_oCH_3$, $[(CH_2)_nNH]_oCH_3$, $(C_1\text{-}C_{32})$alkyl, $(C_3\text{-}C_8)$cycloalkyl, aryl, heteroaryl, $(C_1\text{-}C_{32})$alkyl-COOH, $(C_1\text{-}C_{32})$alkyl-Si-A, or $[C(O)CHR_3NH]_pH$ wherein said aryl or heteroaryl groups are optionally substituted by 1-3 groups comprising halide, CN, $CO_2H$, OH, SH, $NH_2$, $CO_2$—$(C_1\text{-}C_6$ alkyl) or O—$(C_1\text{-}C_6$ alkyl); wherein A comprises three same or different of the following substituents Cl, Br, I, $O(C_1\text{-}C_8)$alkyl or $(C_1\text{-}C_8)$alkyl; and wherein $R_3$ in said $[C(O)CHR_3NH]_pH$ is independently the same or different when p is larger than 1;

$R_2$ is $[(CH_2)_qO]_rCH_3$, $[(CH_2)_qC(O)O]_rCH_3$, $[(CH_2)_qC(O)NH]_rCH_3$, $[(CH_2)_qCH=CH_2]_rCH_3$, $[(CH_2)_qCH\equiv CH]_rCH_3$, $[(CH_2)_qNH]_rCH_3$, $(C_1\text{-}C_{32})$alkyl, $(C_3\text{-}C_8)$cycloalkyl, aryl, heteroaryl, $(C_1\text{-}C_{32})$alkyl-COOH, $(C_1\text{-}C_{32})$alkyl-Si-A, or $[C(O)CHR_4NH]_sH$ wherein said aryl or heteroaryl groups are optionally substituted by 1-3 groups comprising halide, CN, $CO_2H$, OH, SH, $NH_2$, $CO_2$—$(C_1\text{-}C_6$ alkyl) or O—$(C_1\text{-}C_6$ alkyl); wherein A comprises three same or different of the following substituents Cl, Br, I, $O(C_1\text{-}C_8)$alkyl or $(C_1\text{-}C_8)$alkyl; and wherein $R_4$ in said $[C(O)CHR_4NH]_sH$ is independently the same or different when s is larger than 1;

$R_3$ is H, $(C_1\text{-}C_6)$alkyl, $(C_1\text{-}C_6)$hydroxyalkyl, $(C_1\text{-}C_6)$mercaptoalkyl, $(C_1\text{-}C_6)$aminoalkyl, $(C_1\text{-}C_6)$carboxyalkyl, $(C_1\text{-}C_6)$carboxamidoalkyl, $(C_1\text{-}C_6)$guanidinoalkyl, aryl, (aryl)alkyl, heteroaryl or (heteroaryl)alkyl wherein the aromatic ring of said aryl, (aryl)alkyl, heteroaryl or (heteroaryl)alkyl groups are optionally substituted by 1-3 groups comprising halide, CN, $CO_2H$, OH, SH, $NH_2$, $CO_2$—$(C_1\text{-}C_6$ alkyl) or O—$(C_1\text{-}C_6$ alkyl);

$R_4$ is H, $(C_1\text{-}C_6)$alkyl, $(C_1\text{-}C_6)$hydroxyalkyl, $(C_1\text{-}C_6)$mercaptoalkyl, $(C_1\text{-}C_6)$aminoalkyl, $(C_1\text{-}C_6)$carboxyalkyl, $(C_1\text{-}C_6)$carboxamidoalkyl, $(C_1\text{-}C_6)$guanidinoalkyl, aryl, (aryl)alkyl, heteroaryl or (heteroaryl)alkyl wherein the aromatic ring of said aryl, (aryl)alkyl, heteroaryl or (heteroaryl)alkyl groups are optionally substituted by 1-3 groups comprising halide, CN, $CO_2H$, OH, SH, $NH_2$, $CO_2$—$(C_1\text{-}C_6$ alkyl) or O—$(C_1\text{-}C_6$ alkyl);

$R_5$ and $R_6$ are independently H, —$OR_x$ where $R_x$ is $C_1\text{-}C_6$ alkyl or $[(CH_2)_nO]_oCH_3$, aryl, heteroaryl, $C\equiv C$—$R_7$, $CH=CR_8R_9$, $NR_{10}R_{11}$ or a saturated carbocyclic or heterocyclic ring wherein said saturated heterocyclic ring or heteroaryl contains at least one nitrogen atom and $R_5$ or $R_6$ are connected via the nitrogen atom and wherein said saturated carbocyclic ring, heterocyclic ring, aryl and heteroaryl groups are optionally substituted by 1-3 groups comprising halide, aryl, heteroaryl, CN, $CO_2H$, OH, SH, $NH_2$, $CO_2$—$(C_1\text{-}C_6$ alkyl) or O—$(C_1\text{-}C_6$ alkyl);

$R_7$ is H, halo, $(C_1\text{-}C_{32})$alkyl, aryl, heteroaryl, $Si(H)_3$ or $Si[(C_1\text{-}C_8)$alkyl$]_3$ wherein said aryl or heteroaryl groups are optionally substituted by 1-3 groups comprising halide, CN, $CO_2H$, OH, SH, $NH_2$, $CO_2$—$(C_1\text{-}C_6$ alkyl) or O—$(C_1\text{-}C_6$ alkyl);

$R_8$, $R_9$, $R_{10}$ and $R_{11}$ are independently H, $(C_1\text{-}C_{32})$alkyl, aryl or heteroaryl wherein said aryl or heteroaryl groups are optionally substituted by 1-3 groups comprising halide, CN, $CO_2H$, OH, SH, $NH_2$, $CO_2$—$(C_1\text{-}C_6$ alkyl) or O—$(C_1\text{-}C_6$ alkyl);

n is an integer from 1-5;
o is an integer from 1-100;
p is an integer from 1-100;
q is an integer from 2-5;
r is an integer from 1-100; and
s is an integer from 1-100.

In one embodiment, the dianion compound of this invention is a compound of formula 1, wherein X is $NR_1$. In one embodiment, the dianion compound of this invention is a compound of formula 1, wherein X is O. In another embodiment, $R_1$ is $[(CH_2)_nO]_oCH_3$, $(C_1\text{-}C_{32})$alkyl or $[C(O)CHR_3NH]_pH$. In another embodiment, $R_1$ is $[(CH_2)_nO]_oCH_3$, and n is 2 or 3. In another embodiment, $R_1$ is $[(CH_2)_nO]_oCH_3$, and n is 2. In another embodiment, $R_1$ is $[(CH_2)_nO]_oCH_3$, and n is 3. In another embodiment, o is an integer from 1-50. In another embodiment, o is an integer from 1-25. In another embodiment, o is 15. In another embodiment, o is 17. In another embodiment, o is 25. In another embodiment, $R_1$ is $[(CH_2)_nO]_oCH_3$, n is 2 and o is 17. In another embodiment, $R_1$ is $(C_1\text{-}C_{32})$alkyl. In another embodiment, $R_1$ is $[C(O)CHR_3NH]_pH$. In another embodiment $R_1$ is $[C(O)CHR_3NH]_pH$ and $R_3$ is $CH_3$. In another embodiment $R_3$ is H. In another embodiment, p is an integer from 1-50. In another embodiment, p is an integer from 1-25. In another embodiment, p is 15. In another embodiment, p is 17. In another embodiment, p is 25. In another embodiment, $R_1$ is $(C_3\text{-}C_{32})$alkyl-COOH. In another embodiment, $R_1$ is $(C_3\text{-}C_{32})$alkyl-$SiCl_3$. In another embodiment, $R_1$ is $(C_3\text{-}C_{32})$alkyl-$Si(OMe)_3$. In another embodiment, $R_1$ is $(C_3\text{-}C_{32})$alkyl-$SiCl(OMe)_2$.

In one embodiment, the dianion compound of this invention is a compound of formula 1, wherein Y is $NR_2$. In one embodiment, the dianion compound of this invention is a compound of formula 1, wherein Y is O. In another embodiment $R_2$ is $[(CH_2)_qO]_rCH_3$, $(C_1\text{-}C_{32})$alkyl or $[C(O)CHR_3NH]_sH$. In another embodiment, $R_2$ is $[(CH_2)_qO]_rCH_3$, and n is 2 or 3. In another embodiment, $R_2$ is $[(CH_2)_qO]_rCH_3$, and n is 2. In another embodiment, $R_2$ is $[(CH_2)_qO]_rCH_3$, and n is 3. In another embodiment, r is an integer from 1-50. In another embodiment, r is an integer from 1-25. In another embodiment, r is 15. In another embodiment, r is 17. In another embodiment, r is 25. In another embodiment, $R_2$ is $[(CH_2)_nO]_oCH_3$, n is 2 and o is 17. In another embodiment, $R_2$ is $(C_1\text{-}C_{32})$alkyl. In another embodiment, $R_2$ is $[C(O)CHR_3NH]_sH$. In another embodiment $R_2$ is $[C(O)CHR_3NH]_pH$ and $R_3$ is $CH_3$. In another embodiment $R_3$ is H. In another embodiment, s is an integer from 1-50. In another embodiment, s is an integer from 1-25. In another embodiment, s is 15. In another embodiment, s is 17. In another embodiment, s is 25. In another embodiment, $R_2$ is $(C_3\text{-}C_{32})$alkyl-COOH. In another embodiment, $R_2$ is $(C_3\text{-}C_{32})$alkyl-$SiCl_3$. In another embodiment, $R_2$ is $(C_3\text{-}C_{32})$alkyl-$Si(OMe)_3$. In another embodiment, $R_2$ is $(C_3\text{-}C_{32})$alkyl-$SiCl(OMe)_2$.

In one embodiment, the dianion compound of this invention is a compound of formula 1, wherein $R_1$ and $R_2$ are the same. In another embodiment, $R_1$ and $R_2$ are different.

In one embodiment, the dianion of this invention is a represented by formula 1, wherein $R_5$ and $R_6$ are independently H, aryl, heteroaryl, $C\equiv C$—$R_7$, $CH=CR_8R_9$, $NR_{10}R_{11}$ or a saturated carbocyclic or heterocyclic ring wherein said saturated heterocyclic ring or heteroaryl contains at least one nitrogen atom and $R_5$ or $R_6$ are connected via the nitrogen atom and wherein said saturated carbocyclic ring, heterocyclic ring, aryl and heteroaryl groups are optionally substituted by 1-3 groups comprising halide, aryl, heteroaryl, CN, $CO_2H$, OH, SH, $NH_2$, $CO_2$—$(C_1\text{-}C_6$ alkyl) or O—$(C_1\text{-}C_6$ alkyl).

In one embodiment, the dianion compound of this invention is represented by formula 1, wherein $R_5$ and $R_6$ are the same. In another embodiment, $R_5$ and $R_6$ are different. In another embodiment $R_5$ and $R_6$ are hydrogen. In another embodiment, one of $R_5$ and $R_6$ is —$OR^x$ where $R_x$ is $[(CH_2)_nO]_oCH_3$, and the other of $R_5$ and $R_6$ is $C\equiv C$—$R_7$. In another embodiment, one or both of $R_5$ and $R_6$ is —$OR^x$ where $R_x$ is $[(CH_2)_nO]_oCH_3$, and n is 2 or 3. In another embodiment, one of $R_5$ and $R_6$ is —$OR^x$ where $R_x$ is $[(CH_2)_nO]_oCH_3$, and n is 2. In another embodiment, one of $R_5$ and $R_6$ is —$OR^x$ where $R_x$ is $[(CH_2)_nO]_oCH_3$, and n is 3. In another embodiment, o is an integer from 1-50. In another embodiment, o is an integer from 1-25. In another embodiment, o is 15. In another embodiment, o is 17. In another embodiment, o is 25. In another embodiment, one of $R_5$ and $R_6$ is —$OR^x$ where $R_x$ is $[(CH_2)_nO]_oCH_3$, n is 2 and o is 17. In one embodiment, one of $R_5$ and/or $R_6$ is C≡C—$R_7$ where $R_7$ is aryl optionally substituted by 1-3 groups comprising halide, aryl, heteroaryl, CN, $CO_2H$, OH, SH, $NH_2$, $CO_2$—($C_1$-$C_6$ alkyl) or O—($C_1$-$C_6$ alkyl). In one embodiment $R_7$ is phenyl, optionally substituted by terpyridyl. In another embodiment, one of $R_5$ and $R_6$ is —$OR^x$ where $R_x$ is $[(CH_2)_nO]_oCH_3$, n is 2 and o is 17 and the other of $R_5$ and $R_6$ is phenyl substituted by terpyridyl. In another embodiment, $R_5$ and $R_6$ are independently a phenyl substituted by bipyridyl. In another embodiment, $R_5$ and $R_6$ are independently a phenyl substituted by terpyridyl.

In one embodiment, this invention provides a doubly reduced compound, wherein said compound is represented by the structure of formula 2:

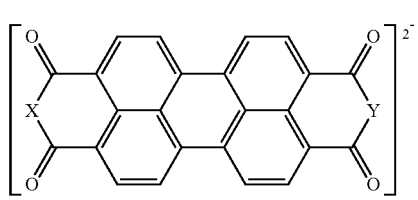

(2)

wherein said compound is a dianion;
wherein X and Y are as described above for compound of formula 1.

In one embodiment, the dianion compound of this invention is a compound of formula 2, wherein X is $NR_1$. In one embodiment, the dianion compound of this invention is a compound of formula 2, wherein X is O. In another embodiment $R_1$ is $[(CH_2)_nO]_oCH_3$, ($C_1$-$C_{32}$)alkyl or $[C(O)CHR_3NH]_pH$. In another embodiment, $R_1$ is $[(CH_2)_nO]_oCH_3$, and n is 2 or 3. In another embodiment, $R_1$ is $[(CH_2)_nO]_oCH_3$, and n is 2. In another embodiment, $R_1$ is $[(CH_2)_nO]_oCH_3$, and n is 3. In another embodiment, o is an integer from 1-50. In another embodiment, o is an integer from 1-25. In another embodiment, o is 15. In another embodiment, o is 17. In another embodiment, o is 25. In another embodiment, $R_1$ is $[(CH_2)_nO]_oCH_3$, n is 2 and o is 17. In another embodiment, $R_1$ is ($C_1$-$C_{32}$)alkyl. In another embodiment, $R_1$ is $[C(O)CHR_3NH]_pH$. In another embodiment $R_1$ is $[C(O)CHR_3NH]_pH$ and $R_3$ is $CH_3$. In another embodiment $R_3$ is H. In another embodiment, p is an integer from 1-50. In another embodiment, p is an integer from 1-25. In another embodiment, p is 15. In another embodiment, p is 17. In another embodiment, p is 25. In another embodiment, $R_1$ is ($C_3$-$C_{32}$)alkyl-COOH. In another embodiment, $R_1$ is ($C_3$-$C_{32}$)alkyl-$SiCl_3$. In another embodiment, $R_1$ is ($C_3$-$C_{32}$)alkyl-$Si(OMe)_3$. In another embodiment, $R_1$ is ($C_3$-$C_{32}$)alkyl-$SiCl(OMe)_2$.

In one embodiment, the dianion compound of this invention is a compound of formula 2, wherein Y is $NR_2$. In one embodiment, the dianion compound of this invention is a compound of formula 2, wherein Y is O. In another embodiment, $R_2$ is $[(CH_2)_qO]_rCH_3$, ($C_1$-$C_{32}$)alkyl or $[C(O)CHR_3NH]_sH$. In another embodiment, $R_1$ is $[(CH_2)_qO]_rCH_3$, and n is 2 or 3. In another embodiment, $R_1$ is $[(CH_2)_qO]_rCH_3$, and n is 2. In another embodiment, $R_1$ is $[(CH_2)_qO]_rCH_3$, and n is 3. In another embodiment, r is an integer from 1-50. In another embodiment, r is an integer from 1-25. In another embodiment, r is 15. In another embodiment, r is 17. In another embodiment, r is 25. In another embodiment, $R_2$ is $[(CH_2)_nO]_oCH_3$, n is 2 and o is 17. In another embodiment, $R_1$ is ($C_1$-$C_{32}$)alkyl. In another embodiment, $R_1$ is $[C(O)CHR_3NH]_sH$. In another embodiment $R_2$ is $[C(O)CHR_3NH]_pH$ and $R_3$ is $CH_3$. In another embodiment $R_3$ is H. In another embodiment, s is an integer from 1-50. In another embodiment, s is an integer from 1-25. In another embodiment, s is 15. In another embodiment, s is 17. In another embodiment, s is 25. In another embodiment, $R_2$ is ($C_3$-$C_{32}$)alkyl-COOH. In another embodiment, $R_2$ is ($C_3$-$C_{32}$)alkyl-$SiCl_3$. In another embodiment, $R_2$ is ($C_3$-$C_{32}$)alkyl-$Si(OMe)_3$. In another embodiment, $R_2$ is ($C_3$-$C_{32}$)alkyl-$SiCl(OMe)_2$.

In one embodiment, the dianion compound of this invention is a compound of formula 2, wherein $R_1$ and $R_2$ are the same. In another embodiment, $R_1$ and $R_2$ are different.

In one embodiment, this invention provides a doubly reduced compound represented by the structure of formula (3):

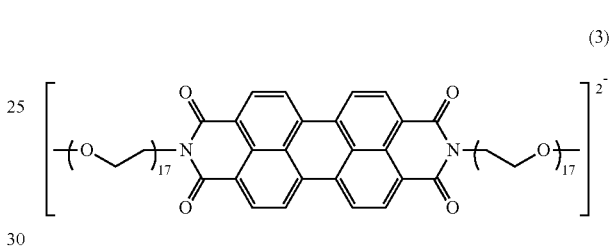

(3)

wherein said compound is a dianion.

In one embodiment, this invention provides a doubly reduced compound represented by the structure of formula (4):

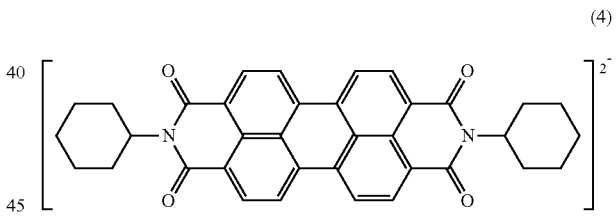

(4)

wherein said compound is a dianion.

In one embodiment, this invention provides a doubly reduced compound represented by the structure of formula (5):

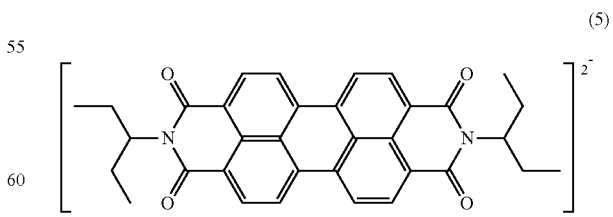

(5)

wherein said compound is a dianion.

In one embodiment, this invention provides a doubly reduced compound represented by the structure of formula (6):

(6)

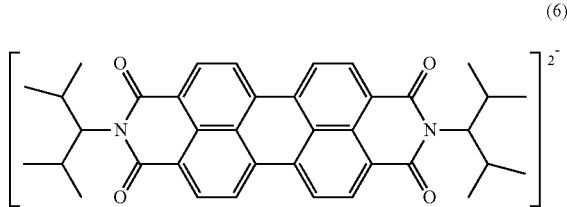

wherein said compound is a dianion.

In one embodiment, the UV-Vis characteristics of the doubly reduced compounds 4-6 are identical to the UV-Vis doubly reduced compound 3.

In another embodiment, this invention provides a doubly reduced perylene-diimide compound represented by the structure of formula 7a or 7b:

7a

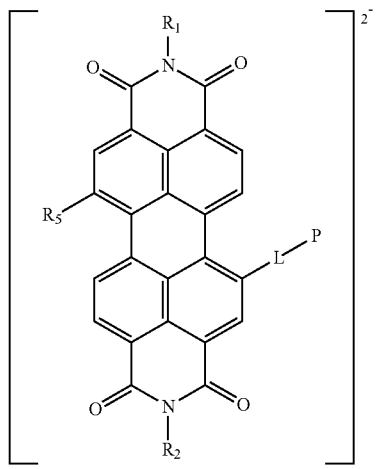

7b

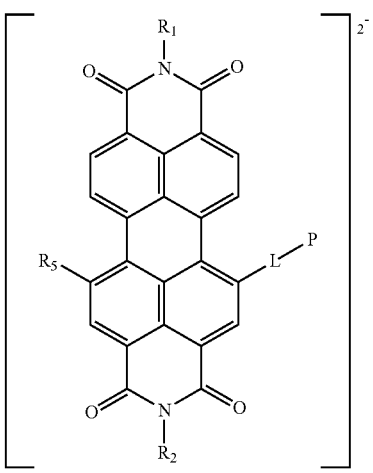

wherein said compound is a dianion;
wherein
$R_1$ is $[(CH_2)_nO]_oCH_3$, $[(CH_2)_nC(O)O]_oCH_3$, $[(CH_2)_nC(O)NH]_oCH_3$, $[(CH_2)_nCH=CH_2]_oCH_3$, $[(CH_2)_nCH=CH]_oCH_3$, $[(CH_2)_nNH]_oCH_3$, $(C_1-C_{32})$alkyl, $(C_3-C_8)$cycloalkyl, aryl, heteroaryl, $(C_1-C_{32})$alkyl-COOH, $(C_1-C_{32})$alkyl-Si-A, or $[C(O)CHR_3NH]_pH$ wherein said aryl or heteroaryl groups are optionally substituted by 1-3 groups comprising halide, CN, $CO_2H$, OH, SH, $NH_2$, $CO_2$—$(C_1-C_6$ alkyl) or O—$(C_1-C_6$ alkyl); wherein A comprises three same or different of the following substituents Cl, Br, I, $O(C_1-C_8)$alkyl or $(C_1-C_8)$ alkyl; and wherein $R_3$ in said $[C(O)CHR_3NH]_pH$ is independently the same or different when p is larger than 1;
$R_2$ is $[(CH_2)_nO]_rCH_3$, $[(CH_2)_qC(O)O]_rCH_3$, $[(CH_2)_qC(O)NH]_rCH_3$, $[(CH_2)_qCH_2=CH_2]_rCH_3$, $[(CH_2)_qCH=CH]_rCH_3$, $[(CH_2)_qNH]_rCH_3$, $(C_1-C_{32})$alkyl, $(C_3-C_8)$cycloalkyl, aryl, heteroaryl, $(C_1-C_{32})$alkyl-COOH, $(C_1-C_{32})$alkyl-Si-A, or $[C(O)CHR_4NH]_sH$ wherein said aryl or heteroaryl groups are optionally substituted by 1-3 groups comprising halide, CN, $CO_2H$, OH, SH, $NH_2$, $CO_2$—$(C_1-C_6$ alkyl) or O—$(C_1-C_6$ alkyl); wherein A comprises three same or different of the following substituents Cl, Br, I, $O(C_1-C_8)$alkyl or $(C_1-C_8)$ alkyl; and wherein $R_4$ in said $[C(O)CHR_4NH]_sH$ is independently the same or different when s is larger than 1;
$R_5$ and $R_6$ are independently H, —$OR_x$ where $R_x$ is $C_1-C_6$ alkyl or $[(CH_2)_nO]_oCH_3$, aryl, heteroaryl, C≡C—$R_7$, CH=$CR_8R_9$, $NR_{10}R_{11}$ or a saturated carbocyclic or heterocyclic ring wherein said saturated heterocyclic ring or heteroaryl contains at least one nitrogen atom and $R_5$ or $R_6$ are connected via the nitrogen atom and wherein said saturated carbocyclic ring, heterocyclic ring, aryl and heteroaryl groups are optionally substituted by 1-3 groups comprising halide, aryl, heteroaryl, CN, $CO_2H$, OH, SH, $NH_2$, $CO_2$—$(C_1-C_6$ alkyl) or O—$(C_1-C_6$ alkyl);
$R_7$ is H, halo, $(C_1-C_{32})$alkyl, aryl, heteroaryl, $Si(H)_3$ or $Si[(C_1-C_8)$alkyl$]_3$ wherein said aryl or heteroaryl groups are optionally substituted by 1-3 groups comprising halide, aryl, heteroaryl, CN, $CO_2H$, OH, SH, $NH_2$, $CO_2$—$(C_1-C_6$ alkyl) or O—$(C_1-C_6$ alkyl);
$R_8$, $R_9$, $R_{10}$ and $R_{11}$ are independently H, $(C_1-C_{32})$alkyl, aryl or heteroaryl wherein said aryl or heteroaryl groups are optionally substituted by 1-3 groups comprising halide, CN, $CO_2H$, OH, SH, $NH_2$, $CO_2$—$(C_1-C_6$ alkyl) or O—$(C_1-C_6$ alkyl);
L is an unsaturated linker; and
P is a perylene-diimide group, aryl or heteroaryl, wherein said aryl and heteroaryl groups are optionally substituted by 1-3 groups comprising halide, aryl, heteroaryl, CN, $CO_2H$, OH, SH, $NH_2$, $CO_2$—$(C_1-C_6$ alkyl) or O—$(C_1-C_6$ alkyl);
n is an integer from 1-5;
o is an integer from 1-100;
p is an integer from 1-100;
q is an integer from 2-5;
r is an integer from 1-100; and
s is an integer from 1-100;
or a metal complex thereof.

In one embodiment, P is aryl or heteroaryl, wherein said aryl and heteroaryl groups are optionally substituted by 1-3 groups comprising halide, aryl, heteroaryl, CN, $CO_2H$, OH, SH, $NH_2$, $CO_2$—$(C_1-C_6$ alkyl) or O—$(C_1-C_6$ alkyl).

In one embodiment, P is aryl wherein said aryl group is optionally substituted by 1-3 groups comprising halide, aryl, heteroaryl, CN, $CO_2H$, OH, SH, $NH_2$, $CO_2$—$(C_1-C_6$ alkyl) or O—$(C_1-C_6$ alkyl).

In one embodiment, P is aryl wherein said aryl group is optionally substituted by 1-3 groups comprising heteroaryl groups. In another embodiment, said substituted heteroaryl group is a metal chelator. In one embodiment, X is an aryl, substituted by 1-3 groups comprising pyridyl groups. In one embodiment, X is phenyl substituted by terpyridyl. In one embodiment, X is phenyl substituted by bipyridyl. In another embodiment, said bipyridyl or terpyridyl binds a metal ion or zero valent metal. In another embodiment the metal ion is Pt(II). In another embodiment the metal ion is Pd(II). In another embodiment the metal ion is Rh(I). In another embodiment, the metal ion is Ag(I). In another embodiment, the metal ion or zero valent metal has a redox potential that does not oxidize the dianion. In another embodiment, the dianion 7a or 7b possess a terpyridyl group which coordinates to a metal ion or zero valent metal.

In one embodiment, P is a perylene-diimide group of formula Va or Vb:

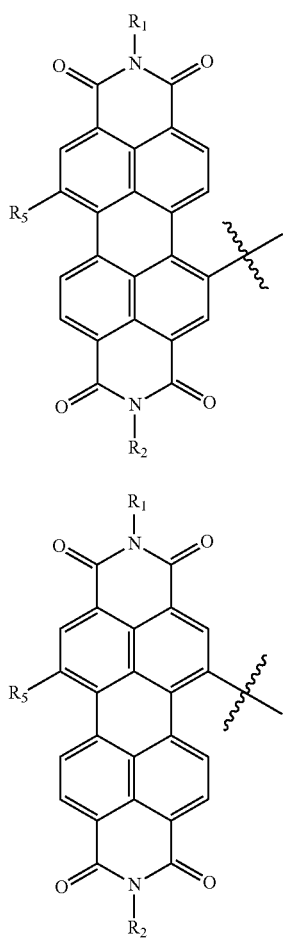

wherein $R_1$, $R_2$ and $R_5$ are as defined above for formulas 7a and 7b.

In one embodiment, L of compound 7a and 7b contains an ethylnyl (—C≡C—) group. In one embodiment, L is an ethynyl group. In another embodiment, L is an diethynylbenzene group. In a further embodiment, L is a diethynyldipyridyl group. In another embodiment L is a bipiridyl group.

In one embodiment, $R^1$ of compound 7a and 7b is alkyl. In another embodiment, $R^1$ is —CH(CH$_2$CH$_3$)$_2$. In one embodiment, $R^2$ is alkyl. In another embodiment, $R^2$ is —CH(CH$_2$CH$_3$)$_2$. In one embodiment $R^1$ and $R^2$ are different. In another embodiment, $R^1$ and $R^2$ are the same. In one embodiment, $R^1$ and $R^2$ are both alkyl. In one embodiment, $R^1$ and $R^2$ are both —CH(CH$_2$CH$_3$)$_2$.

In one embodiment, $R_5$ of compound 7a and 7b is H or —OR$^x$ where R$^x$ is C$_1$-C$_6$ alkyl or [(CH$_2$)$_n$O]$_o$CH$_3$. In another embodiment, $R_5$ is —OR$^x$ where R$^x$ is [(CH$_2$)$_n$O]$_o$CH$_3$, and n is 2 or 3. In another embodiment, $R_1$ is [(CH$_2$)$_n$O]$_o$CH$_3$, and n is 2. In another embodiment, $R_5$ is —OR$^x$ where R$^x$ is [(CH$_2$)$_n$O]$_o$CH$_3$, and n is 3. In another embodiment, o is an integer from 1-50. In another embodiment, o is an integer from 1-25. In another embodiment, o is 15. In another embodiment, o is 17. In another embodiment, o is 25. In another embodiment, $R_5$ is —OR$^x$ where R$^x$ is [(CH$_2$)$_n$O]$_o$CH$_3$, n is 2 and o is 17.

In another embodiment, this invention provides a doubly reduced perylene-diimide compound represented by the structure of formula (8):

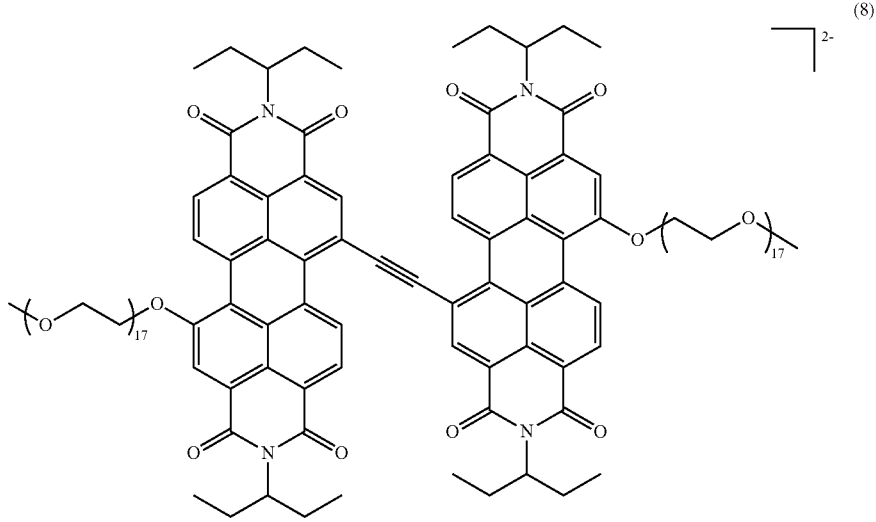

In another embodiment, this invention provides a doubly reduced perylene-diimide compound represented by the structure of formula (9)
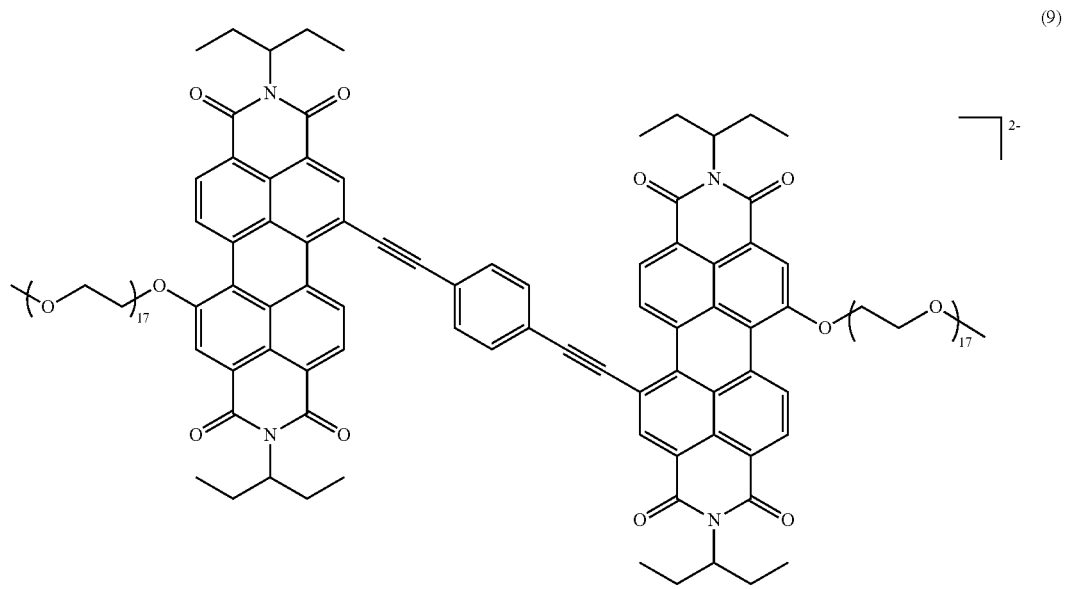
(9)
In another embodiment, this invention provides a doubly reduced perylene-diimide compound represented by the structure of formula (10)
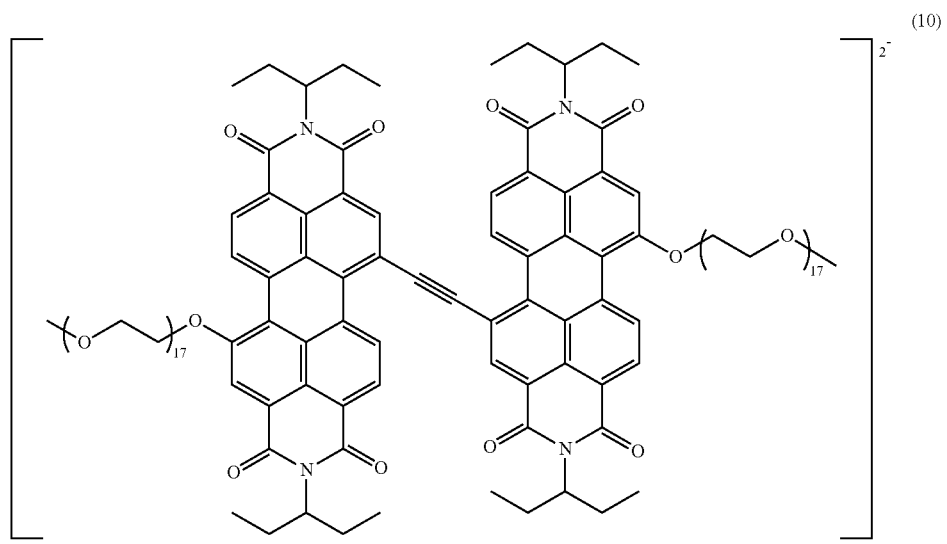
(10)

In another embodiment, this invention provides a doubly reduced perylene-diimide compound represented by the structure of formula (11)

metal ion. In another embodiment, the counter ion of the perylene dianion is a counter ion that would not oxidize the dianion.

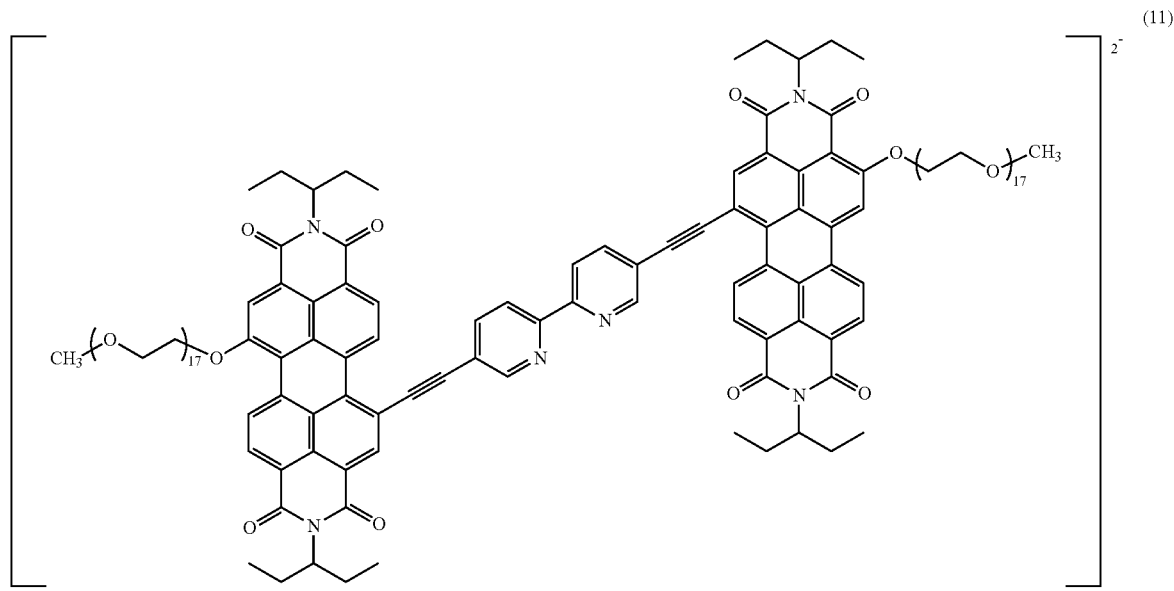

(11)

In another embodiment, this invention provides a doubly reduced perylene-diimide compound represented by the structure of formula (12)

In another embodiment, the perylene dianions of this embodiment comprise an aryl or heteroaryl group. In another embodiment, the aryl or heteroaryl group is a metal chelator.

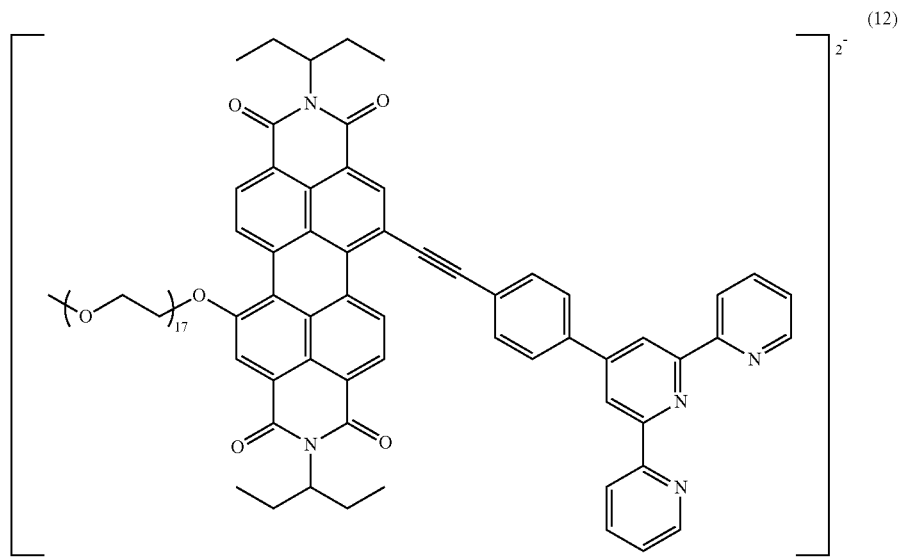

(12)

In one embodiment the counter ion of the perylene dianions of this invention is a sodium ion, magnesium ion, calcium ion, alkali metal ion, potassium ion or alkaline earth In another embodiment, the metal chelator is pyridyl, bipyridyl or terpyridyl. In another embodiment the metal chelator coordinates to a metal ion or zero valent metal that does not oxidize the perylene dianion. In another embodiment the metal ion is Pt(II). In another embodiment the metal ion is Pd(II). In another embodiment the metal ion is Rh(I). In another embodiment, the metal ion is Ag(I).

In another embodiment, this invention is directed to supramolecular polymeric structures, comprising a monomer unit represented by formula VIa or VIb:

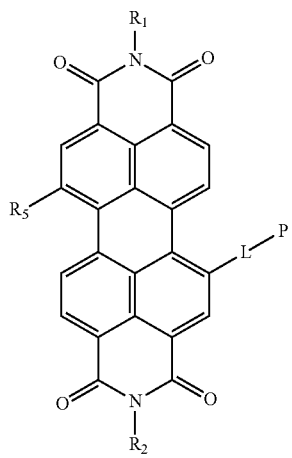

VIa

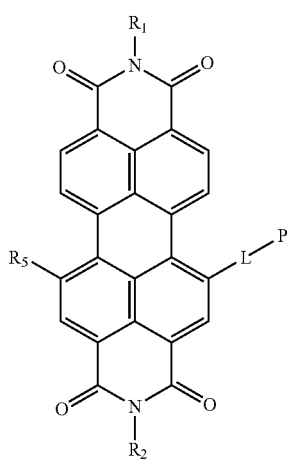

VIb wherein
$R_1$ is $[(CH_2)_nO]_oCH_3$, $[(CH_2)_nC(O)O]_oCH_3$, $[(CH_2)_nC(O)NH]_oCH_3$, $[(CH_2)_6CH_2=CH_2]_oCH_3$, $[(CH_2)_nCH=CH]_oCH_3$, $[(CH_2)_nNH]_oCH_3$, $(C_1-C_{32})$alkyl, $(C_3-C_8)$cycloalkyl, aryl, heteroaryl, $(C_1-C_{32})$alkyl-COOH, $(C_1-C_{32})$alkyl-Si-A, or $[C(O)CHR_3NH]_pH$ wherein said aryl or heteroaryl groups are optionally substituted by 1-3 groups comprising halide, CN, $CO_2H$, OH, SH, $NH_2$, $CO_2-(C_1-C_6$ alkyl) or $O-(C_1-C_6$ alkyl); wherein A comprises three same or different of the following substituents Cl, Br, I, $O(C_1-C_8)$alkyl or $(C_1-C_8)$alkyl; and wherein $R_3$ in said $[C(O)CHR_3NH]_pH$ is independently the same or different when p is larger than 1;
$R_2$ is $[(CH_2)_qO]_rCH_3$, $[(CH_2)_qC(O)O]_rCH_3$, $[(CH_2)_qC(O)NH]_rCH_3$, $[(CH_2)_qCH_2=CH_2]_rCH_3$, $[(CH_2)_qCH=CH]_r$ CH_3$, $[(CH_2)_qNH]_rCH_3$, $(C_1-C_{32})$alkyl, $(C_3-C_8)$cycloalkyl, aryl, heteroaryl, $(C_1-C_{32})$alkyl-COOH, $(C_1-C_{32})$alkyl-Si-A, or $[C(O)CHR_4NH]_sH$ wherein said aryl or heteroaryl groups are optionally substituted by 1-3 groups comprising halide, CN, $CO_2H$, OH, SH, $NH_2$, $CO_2-(C_1-C_6$ alkyl) or $O-(C_1-C_6$ alkyl); wherein A comprises three same or different of the following substituents Cl, Br, I, $O(C_1-C_8)$alkyl or $(C_1-C_8)$ alkyl; and wherein $R_4$ in said $[C(O)CHR_4NH]_sH$ is independently the same or different when s is larger than 1;
$R_5$ and $R_6$ are independently H, $-OR_x$ where $R_x$ is $C_1-C_6$ alkyl or $[(CH_2)_nO]_oCH_3$, aryl, heteroaryl, $C\equiv C-R_7$, $CH=CR_8R_9$, $NR_{10}R_{11}$ or a saturated carbocyclic or heterocyclic ring wherein said saturated heterocyclic ring or heteroaryl contains at least one nitrogen atom and $R_5$ or $R_6$ are connected via the nitrogen atom and wherein said saturated carbocyclic ring, heterocyclic ring, aryl and heteroaryl groups are optionally substituted by 1-3 groups comprising halide, aryl, heteroaryl, CN, $CO_2H$, OH, SH, $NH_2$, $CO_2-(C_1-C_6$ alkyl) or $O-(C_1-C_6$ alkyl);
$R_7$ is H, halo, $(C_1-C_{32})$alkyl, aryl, heteroaryl, $Si(H)_3$ or $Si[(C_1-C_8)alkyl]_3$ wherein said aryl or heteroaryl groups are optionally substituted by 1-3 groups comprising halide, aryl, heteroaryl, CN, $CO_2H$, OH, SH, $NH_2$, $CO_2-(C_1-C_6$ alkyl) or $O-(C_1-C_6$ alkyl);
$R_8$, $R_9$, $R_{10}$ and $R_{11}$ are independently H, $(C_1-C_{32})$alkyl, aryl or heteroaryl wherein said aryl or heteroaryl groups are optionally substituted by 1-3 groups comprising halide, CN, $CO_2H$, OH, SH, $NH_2$, $CO_2-(C_1-C_6$ alkyl) or $O-(C_1-C_6$ alkyl);
L is an unsaturated linker;
P is a perylene-diimide group, aryl or heteroaryl, wherein said aryl and heteroaryl groups are optionally substituted by 1-3 groups comprising halide, aryl, heteroaryl, CN, $CO_2H$, OH, SH, $NH_2$, $CO_2-(C_1-C_6$ alkyl) or $O-(C_1-C_6$ alkyl);
n is an integer from 1-5;
o is an integer from 1-100;
p is an integer from 1-100;
q is an integer from 2-5;
r is an integer from 1-100; and
s is an integer from 1-100;
or a metal complex thereof.

In one embodiment, of the supramolecular structure VIa and VIb is aryl or heteroaryl, wherein said aryl and heteroaryl groups are optionally substituted by 1-3 groups comprising halide, aryl, heteroaryl, CN, $CO_2H$, OH, SH, $NH_2$, $CO_2-(C_1-C_6$ alkyl) or $O-(C_1-C_6$ alkyl).

In one embodiment, P of the supramolecular structure VIa and VIb is aryl wherein said aryl group is optionally substituted by 1-3 groups comprising halide, aryl, heteroaryl, CN, $CO_2H$, OH, SH, $NH_2$, $CO_2-(C_1-C_6$ alkyl) or $O-(C_1-C_6$ alkyl).

In one embodiment, P of the supramolecular structure VIa and VIb is aryl wherein said aryl group is optionally substituted by 1-3 groups comprising heteroaryl groups. In one embodiment, X is aryl, optionally substituted by 1-3 groups comprising pyridyl groups. In one embodiment, X is phenyl substituted by terpyridyl. In one embodiment, X is phenyl substituted by bipyridyl. In another embodiment said pyridyl, bipyridyl or terpyridyl binds a metal ion to yield a metal complex of VIa and/or VIb.

In one embodiment, P is a perylene-diimide group of formula Va or Vb:

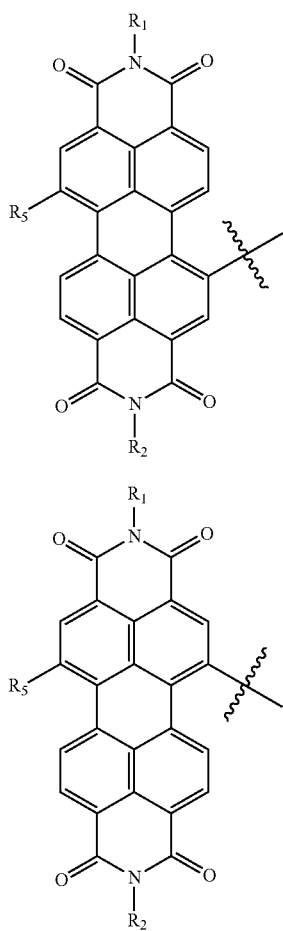

wherein $R_1$, $R_2$ and $R_5$ are as defined above for formulas VIa and VIb.

In one embodiment, L of the supramolecular structure VIa and VIb contains an ethylnyl (—C≡C—) group. In one embodiment, L is an ethynyl group. In another embodiment, L is an diethynylbenzene group. In a further embodiment, L is an diethynyldipyridyl group. In another embodiment, L contains a bipyridyl group.

In one embodiment, $R^1$ of the supramolecular structure VIa and VIb is alkyl. In another embodiment, $R^1$ is —CH(CH$_2$CH$_3$)$_2$. In one embodiment, $R^2$ is alkyl. In another embodiment, $R^2$ is —CH(CH$_2$CH$_3$)$_2$. In one embodiment $R^1$ and $R^2$ are different. In another embodiment, $R^1$ and $R^2$ are the same. In one embodiment, $R^1$ and $R^2$ are both alkyl. In one embodiment, $R^1$ and $R^2$ are both —CH(CH$_2$CH$_3$)$_2$.

In one embodiment, $R_5$ of the supramolecular structure VI and VIb is H or —OR$^x$ where $R^x$ is $C_1$-$C_6$ alkyl or [(CH$_2$)$_n$O]$_o$CH$_3$. In another embodiment, $R_5$ is —OR$^x$ where $R^x$ is [(CH$_2$)$_n$O]$_o$CH$_3$, and n is 2 or 3. In another embodiment, $R_1$ is [(CH$_2$)$_n$O]$_o$CH$_3$, and n is 2. In another embodiment, $R_5$ is —OR$^x$ where $R^x$ is [(CH$_2$)$_n$O]$_o$CH$_3$, and n is 3. In another embodiment, o is an integer from 1-50. In another embodiment, o is an integer from 1-25. In another embodiment, o is 15. In another embodiment, o is 17. In another embodiment, o is 25. In another embodiment, $R_5$ is —OR$^x$ where $R^x$ is [(CH$_2$)$_n$O]$_o$CH$_3$, n is 2 and o is 17.

In one embodiment, this invention is directed to supramolecular polymeric structures, wherein the monomer unit of the polymer comprises multiple covalently attached perylene groups. In another embodiment, the perylene groups are substituted by polyallylene glycol polymer to obtain an amphiphilic monomer. In another embodiment, the perylene groups are substituted by polyethylene glycol polymer to obtain an amphiphilic monomer.

Supramolecular polymers are those in which the monomers are held together by noncovalent interactions such as hydrogen bonds, π-π interactions and/or hydrophoboic interactions. In all condensed molecular materials, either they are liquid glassy, or (liquid) crystalline, noncovalent interactions with little specificity or directionality are present, resulting in many of the mechanical and reological properties that polymers have.

In another embodiment, the monomer unit of the supramolecular polymer comprises of between two to five covalently attached perylene groups of formula I-III. In another embodiment, the monomer unit comprises groups of formula VIa or VIb. In another embodiment, the monomer units comprises two covalently attached perylene groups of formula In another embodiment, this invention provides a supramolecular polymer comprising a monomer unit represented by formula (VII):

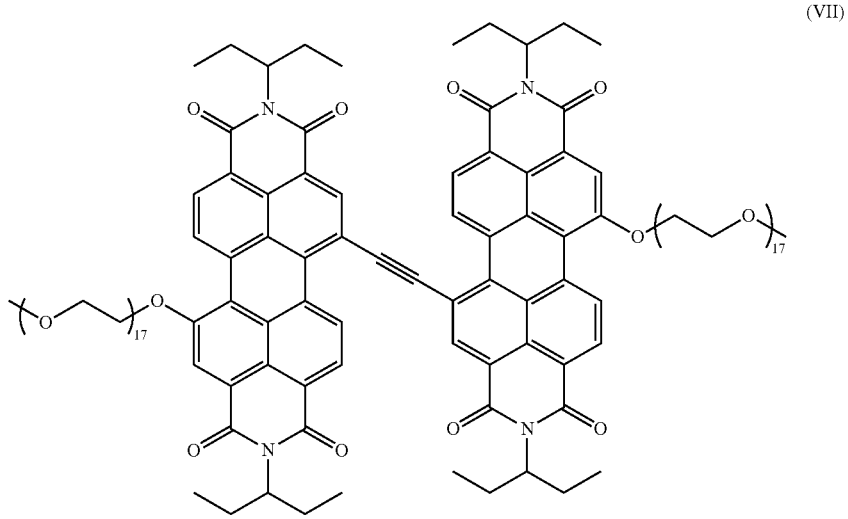

In another embodiment, this invention provides a supramolecular polymer comprising a monomer unit represented by formula (VIII):
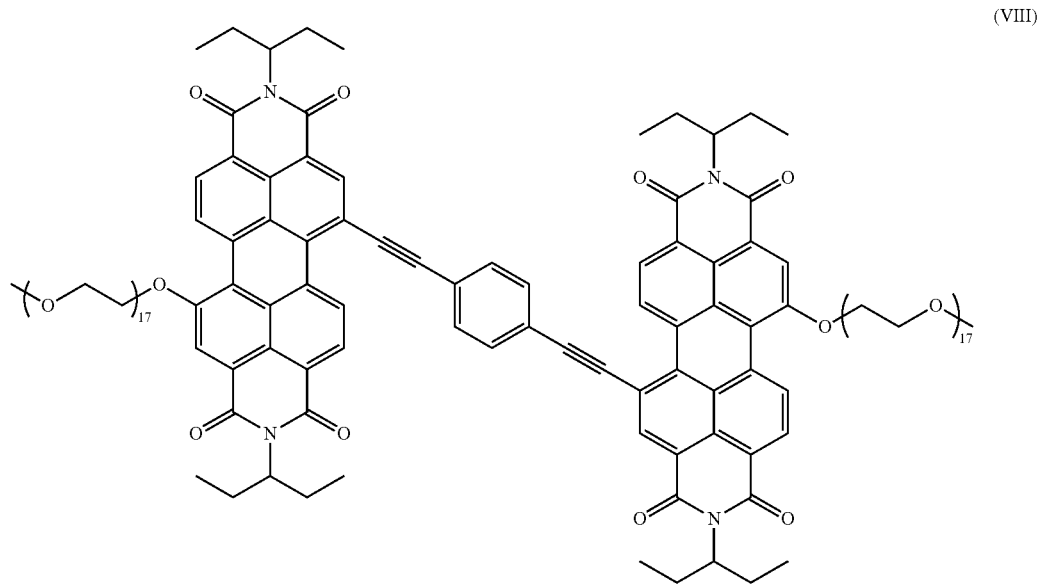
(VIII)
In another embodiment, this invention provides a supramolecular polymer comprising a monomer unit represented by formula (IX):
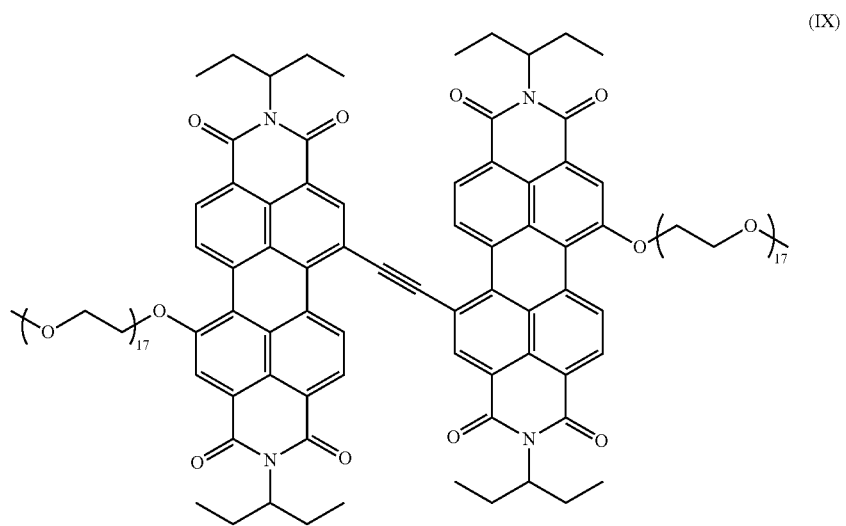
(IX)

In another embodiment, this invention provides a supramolecular polymer comprising a monomer unit represented by formula (X):

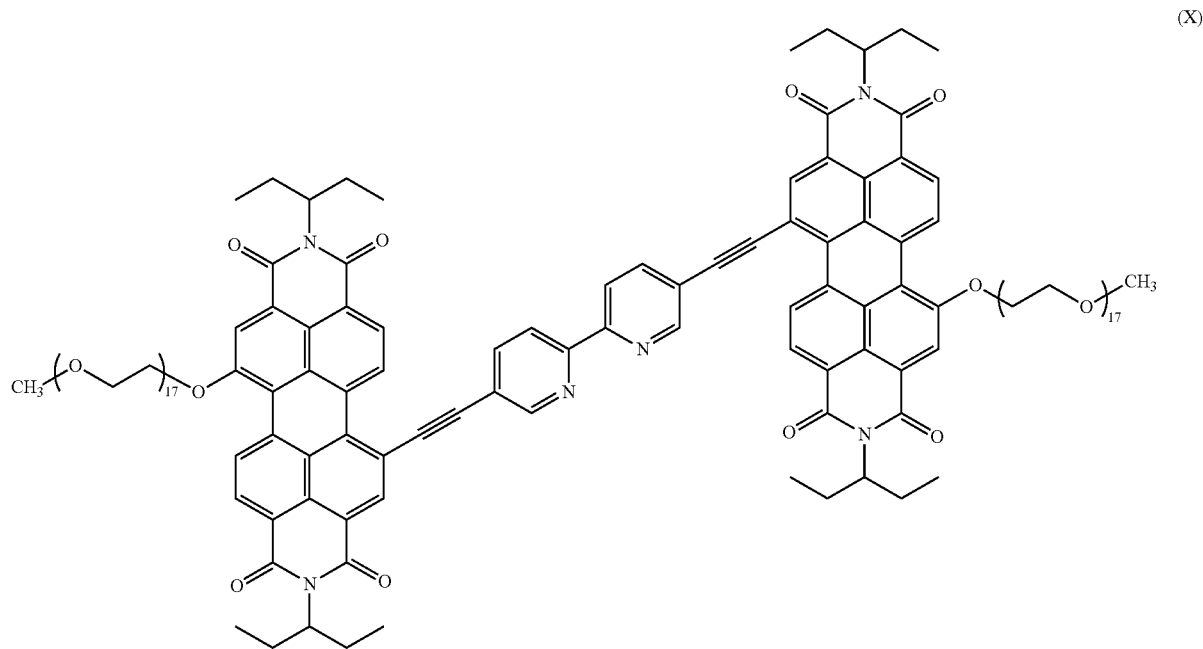

In another embodiment, this invention provides a supramolecular polymer comprising a monomer unit represented by formula XI:

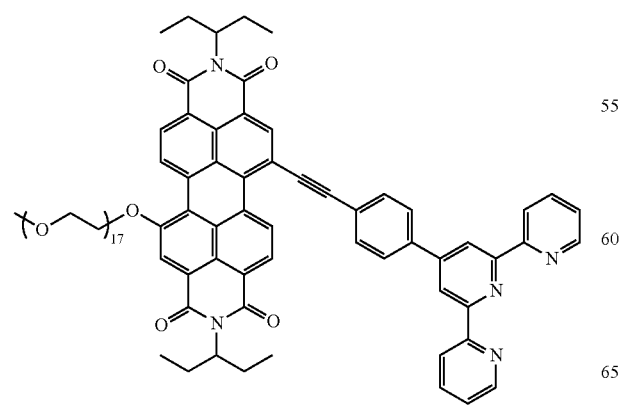

In another embodiment, the supramolecular polymer of formula XI comprises a monomer unit represented by a metal complex of formula VIa or VIb. In one embodiment, the metal complex is a platinum complex. In one embodiment, the metal complex is a palladium complex. In one embodiment, the metal complex is a silver complex.

In another embodiment, this invention provides a supramolecular polymer comprising a monomer unit represented by formula (XII):

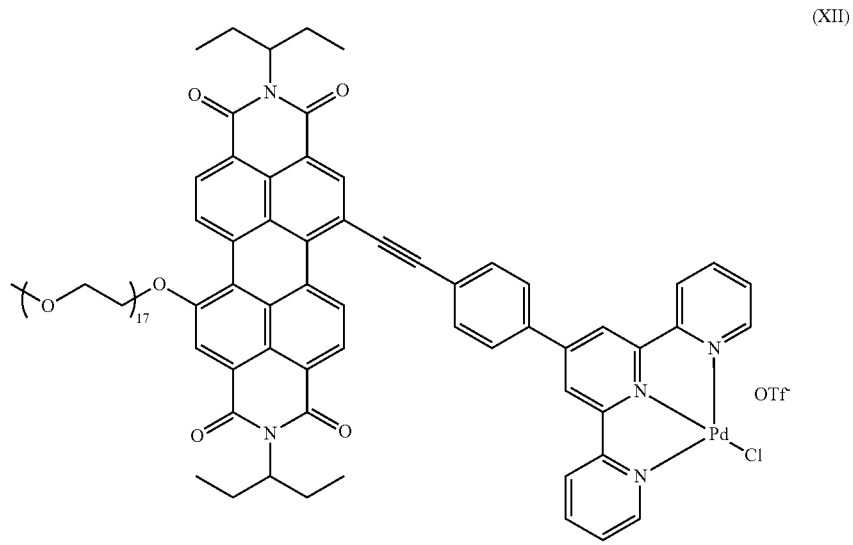
(XII)
In another embodiment, this invention provides a supramolecular polymer comprising a monomer unit represented by formula (XIII):
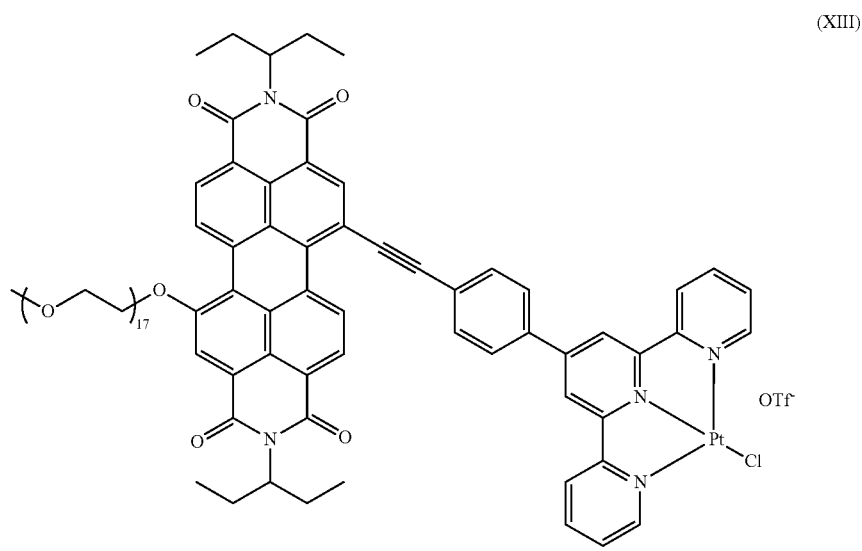
(XIII)

In another embodiment, this invention provides a supramolecular polymer comprising a monomer unit represented by formula (XIV):

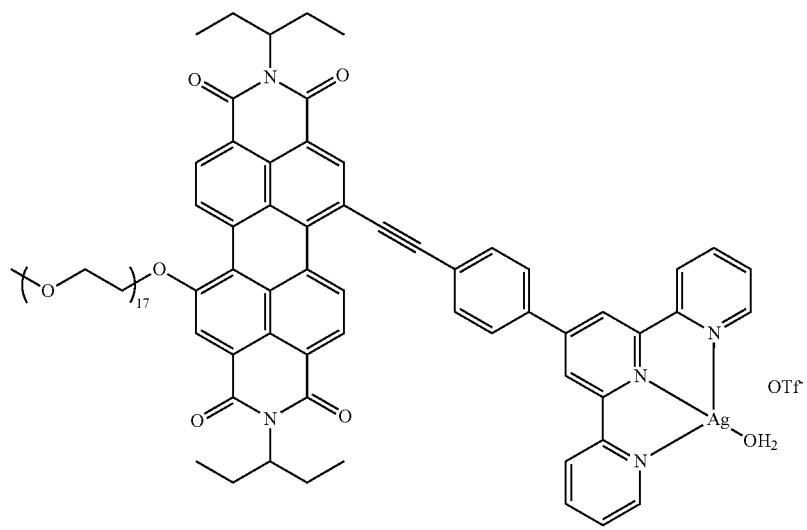

(XIV)

In another embodiment, this invention provides a supramolecular polymer comprising a monomer unit represented by formula (XV):

hydrophobic interactions between perylene diimide cores. In another embodiment, said supramolecular polymers can be separated by filtration.

In one embodiment, the supramolecular polymer is in a form of a gel (three dimensional matrix). In another embodiment, the supramolecular polymer is in a form of a ribbon. In (XV)

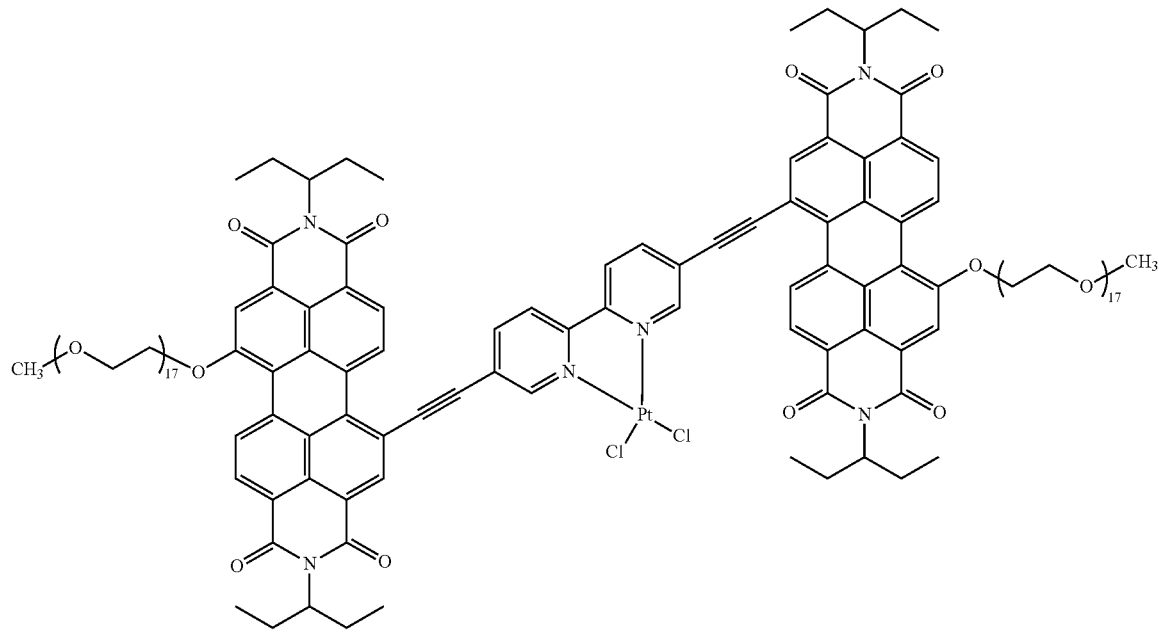

Figure 12:
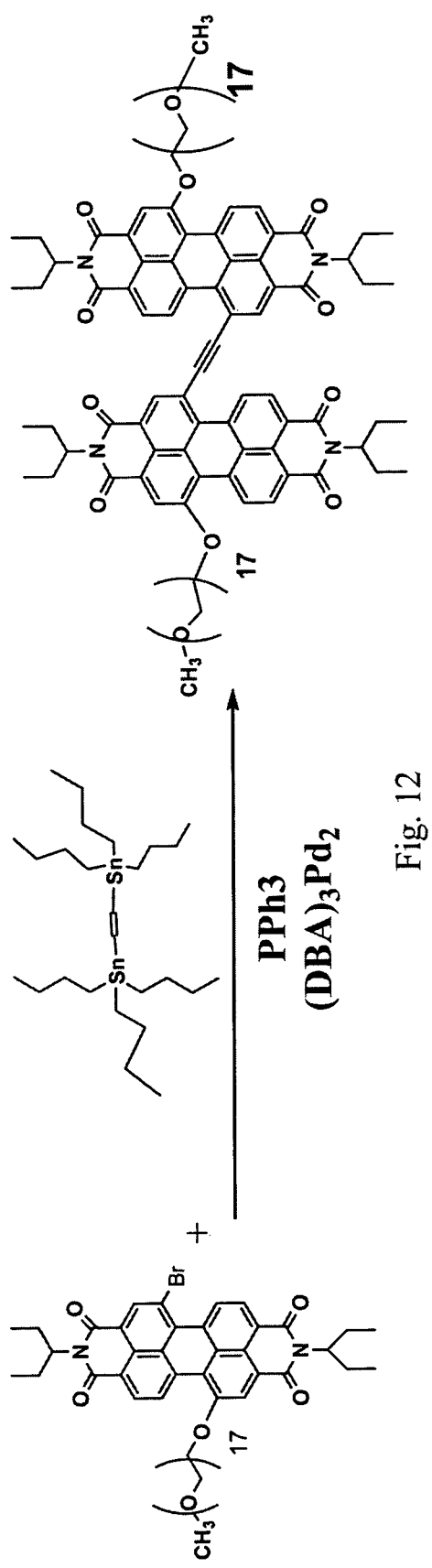
FIG. 12 depicts the synthesis of acetylene-bridged perylene dimers.
Figure 13:
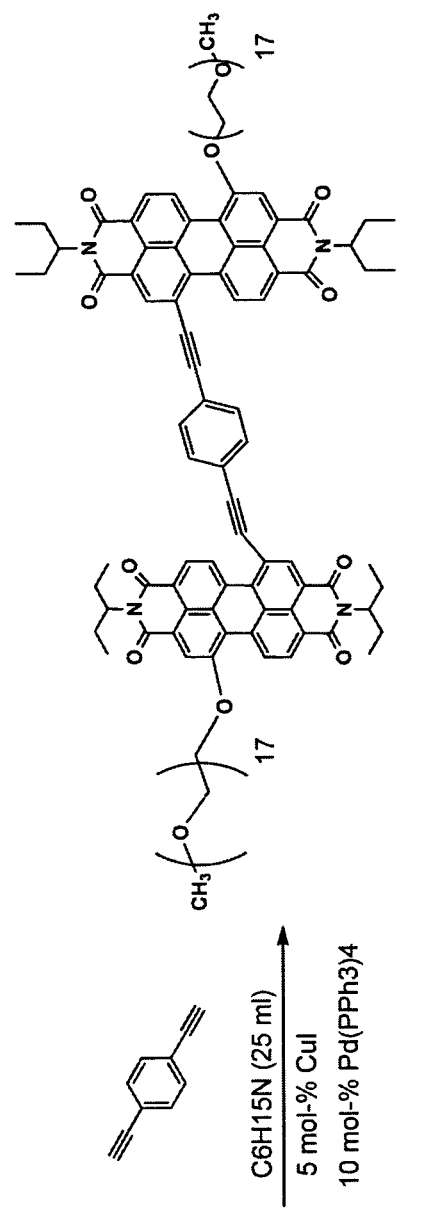
FIG. 13 depicts the synthesis of diethynylbenzene-bridged perylene dimers.
Figure 13:
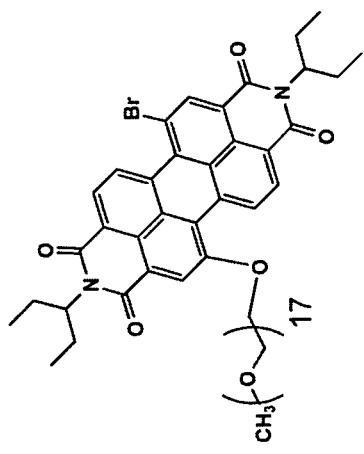
Figure 14:
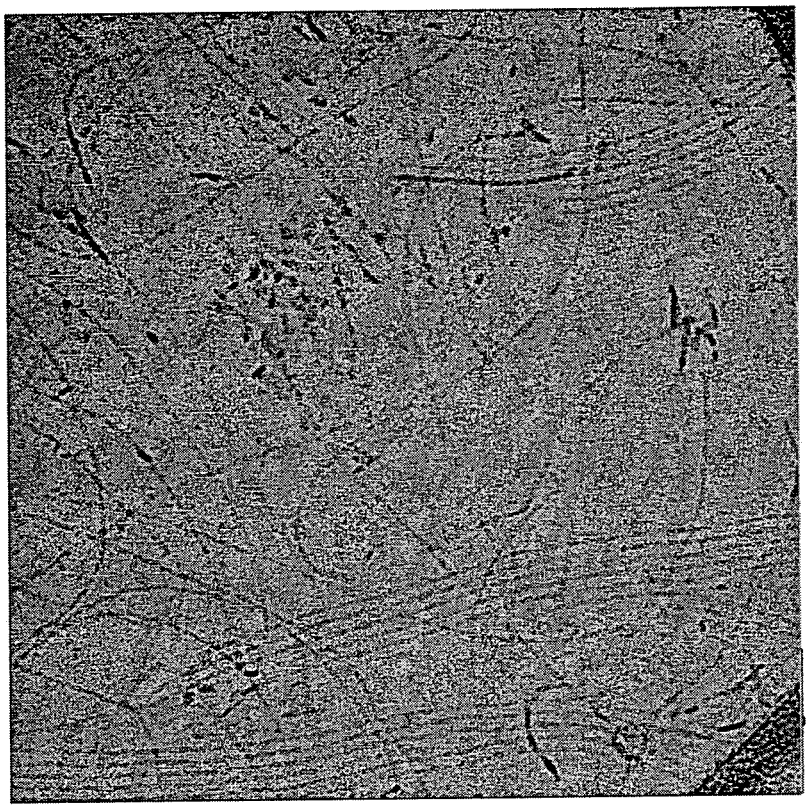
FIG. 14 depicts a cryo-TEM image of supramolecular polymers of perylene dimers of the types illustrated in FIG. 12 and FIG. 13. Polymer width is 4 nm and polymer length is several microns.

In another embodiment, the synthesis of Compounds (VII) and (VIII) of are depicted in FIG. 12 and FIG. 13.

In another embodiment, the monomer units of the supramolecular polymer are perylene groups which are connected through an ethynyl bridge. In another embodiment, the monomer units of the supramolecular polymer are perylene groups which are connected through a diethynylbenzene bridge. In another embodiment, said supramolecular polymers are formed in an aqueous media containing tetrahydrofuran, where the driving forces of formation being strong another embodiment, the supramolecular polymer is in a form of tube. In another embodiment, the supramolecular polymer is in a form of vesicle. In another embodiment, the supramolecular polymer is in the form of a platelet. In another embodiment, the supramolecular polymer is in a form of a spherical micelle. In another embodiment, the supramolecular polymer is in a form of a wormlike. In another embodiment, the supramolecular polymer is in a form of a spherical rod. In another embodiment, the supramolecular polymer is in a form of a spherical toroid. In another embodiment, the supramolecular structure is formed in aqueous conditions.

In another embodiment, said supramolecular polymers are depolymerized by reduction. In one embodiment, the reduction is performed using sodium dithionite. In another embodiment, the reduction is performed using hydrazine in the presence of a catalyst (e.g., platinum). In another embodiment, said supramolecular polymers are reduced to yield mono and/or dianion perylenes. In another embodiment, the reduction of said supramolecular polymers results in formation of short oligomers. In another embodiment, said short oligomers can be separated from said supramolecular polymers by filtration through a 0.2 micron filter.

In another embodiment, oxidation of the reduced perylenes reforms said supramolecular polymers. In one embodiment, the reduced perylene reforms said supramolecular polymer upon contact with air. In another embodiment, the reduction/oxidation cycle may be repeated more than once. In one embodiment, the reduction/oxidation cycle may be repeated twice. In one embodiment, the reduction/oxidation cycle may be repeated three times.

The apparent depolymerization of the fibers upon reduction is due to enhanced solvation of the anionic species and their mutual repulsion. In another embodiment, air can be used to reverse the process. Oxygen-induced supramolecular polymerization bearing potential for a variety of applications. In another embodiment, orthogonal self-assembly propensities of the reduced and neutral perylene diimides (PDIs) make them advantageous building blocks for tunable multifunctional supramolecular systems.

As the fibers can undergo reversible fission, accompanied by a significant change in electronic properties, photofunction switching is possible. In one embodiment, femtosecond transient absorption studies on compound 1 reveal that in the neutral fibers the PDI excited state peak shows multiexponential decay with time constants of 0.3, 4, and 300 ps. The contribution of the fast processes (0.3 and 4 ps) is dependent on the laser power, indicating that exciton annihilation takes place. This is typical of dye aggregates, where a high photon flux of a laser pulse causes multiple excitations enabling annihilation processes. It is a result of good exciton mobility in dye assemblies, creating a basis for light harvesting. Disaggregated 1 (chloroform solution) does not show power-dependent behavior. The fiber exciton dynamics is restored by oxidation with air. Thus, the fiber photofunction can be turned off and on using the reduction/oxidation sequence.

Novel photofunctional supramolecular polymers have been prepared based on hydrophobic interactions. In-situ control over hydrophobic self-assembly and photofunction of aromatic building blocks can be achieved through the reversible charging of aromatic systems. The latter allows for assembly/disassembly sequence akin to reversible depolymerization. This methodology can be useful for creation of adaptive multifunctional supramolecular systems.

In one embodiment, the dianions are delocalized on the aromatic ring(s).

An "alkyl" group refers, in one embodiment, to a saturated aliphatic hydrocarbon, including straight-chain and branched-chain groups. In one embodiment, the alkyl group has 1-12 carbons. In another embodiment, the alkyl group has 1-8 carbons. In another embodiment, the alkyl group has 1-6 carbons. In another embodiment, the alkyl group has 1-4 carbons. The alkyl group may be unsubstituted or substituted by one or more groups selected from halogen, cyano, hydroxy, alkoxy carbonyl, amido, alkylamido, dialkylamido, nitro, amino, alkylamino, dialkylamino, carboxyl, thio and thioalkyl. In one embodiment, the alkyl group is —$CH_3$, —$CH(CH_3)_2$, —$CH_2CH(CH_3)_2$, —$CH(CH_3)CH_2CH_3$, and the like A "cycloalkyl" group refers, in one embodiment, to a saturated aliphatic cyclic hydrocarbon group. In one embodiment, the cycloalkyl group has 3-12 carbons. In another embodiment, the cycloalkyl group has 3-8 carbons. In another embodiment, the cycloalkyl group has 3-6 carbons. In another embodiment, the cycloalkyl group has 3 carbons. The cycloalkyl group may be unsubstituted or substituted by one or more groups selected from halogen, cyano, hydroxy, alkoxy carbonyl, amido, alkylamido, dialkylamido, nitro, amino, alkylamino, dialkylamino, carboxyl, thio and thioalkyl. In one embodiment, the cycloalkyl group is cyclopropyl, cyclobutyl, cyclopentyl, cyclohexyl, and the like.

The term "carbocyclic ring" refers to a saturated or unsaturated ring composed exclusively of carbon atoms. In one embodiment, the carbocyclic ring is a 3-12 membered ring. In another embodiment, the carbocyclic ring is a 3-8 membered ring. In one embodiment, the carbocyclic ring is a five membered ring. In another embodiment, the carbocyclic ring is a six membered ring. In one embodiment the carbocyclic ring may be unsubstituted or substituted by one or more groups selected from halogen, cyano, haloalkyl, hydroxy, alkoxy carbonyl, amido, alkylamido, dialkylamido, nitro, amino, alkylamino, dialkylamino, carboxy or thio or thioalkyl. Nonlimiting examples of carbocyclic ring are benzene, cyclohexane, and the like.

The term "aryl" refers to an aromatic group having at least one carbocyclic aromatic ring, which may be unsubstituted or substituted by one or more groups selected from halogen, cyano, aryl, heteroaryl, haloalkyl, hydroxy, alkoxy carbonyl, amido, alkylamido, dialkylamido, nitro, amino, alkylamino, dialkylamino, carboxy or thio or thioalkyl. Nonlimiting examples of aryl rings are phenyl, naphthyl, and the like. In one embodiment, the aryl group is a 5-12 membered ring. In another embodiment, the aryl group is a 5-8 membered ring. In one embodiment, the aryl group is a five membered ring. In one embodiment, the aryl group is a six membered ring. In another embodiment, the aryl group comprises of 1-4 fused rings.

The term "arylalkyl" refers to an alkyl group as defined above substituted by an aryl group as defined above. Examples of arylalkyl, but not limited to are —$CH_2Ph$ or —$CH_2CH_2Ph$.

The term "heteroaryl" refers to an aromatic group having at least one heterocyclic aromatic ring. In one embodiment, the heteroaryl comprises at least one heteroatom such as sulfur, oxygen, nitrogen, silicon, phosphorous or any combination thereof, as part of the ring. In another embodiment, the heteroaryl may be unsubstituted or substituted by one or more groups selected from halogen, aryl, heteroaryl, cyano, haloalkyl, hydroxy, alkoxy carbonyl, amido, alkylamido, dialkylamido, nitro, amino, alkylamino, dialkylamino, carboxy or thio or thioalkyl. Nonlimiting examples of heteroaryl rings are pyranyl, pyrrolyl, pyrazinyl, pyrimidinyl, pyrazolyl, pyridinyl, furanyl, thiophenyl, thiazolyl, imidazolyl, isoxazolyl, and the like. In one embodiment, the heteroaryl group is a 5-12 membered ring. In one embodiment, the heteroaryl group is a five membered ring. In one embodiment, the heteroaryl group is a six membered ring. In another embodiment, the heteroaryl group is a 5-8 membered ring. In another embodiment, the heteroaryl group comprises of 1-4 fused rings. In another embodiment, the heteroaryl group is 1,2,3-triazole. In one embodiment the heteroaryl is a pyridyl. In one embodiment the heteroaryl is a bipyridyl. In one embodiment the heteroaryl is a terpyridyl.

The terms "halide" and "halogen" refer to in one embodiment to F, in another embodiment to Cl, in another embodiment to Br, in another embodiment to I.

A "heterocyclic" group refers to a heterocycle. In one embodiment, said heterocycle refers to a ring structure comprising in addition to carbon atoms, sulfur, oxygen, nitrogen, silicon or phosphorous or any combination thereof, as part of the ring. In another embodiment the heterocycle is a 3-12 membered ring. In another embodiment the heterocycle is a 6 membered ring. In another embodiment the heterocycle is a 5-7 membered ring. In another embodiment the heterocycle is a 4-8 membered ring. In another embodiment, the heterocycle group may be unsubstituted or substituted by a halide, haloalkyl, hydroxyl, alkoxy, carbonyl, amido, alkylamido, dialkylamido, cyano, nitro, $CO_2H$, amino, alkylamino, dialkylamino, carboxyl, thio and/or thioalkyl. In another embodiment, the heterocycle ring may be fused to another saturated or unsaturated cycloalkyl or heterocyclic 3-8 membered ring. In another embodiment, the heterocyclic ring is a saturated ring. In another embodiment, the heterocyclic ring is an unsaturated ring.

The term "hydroxylalkyl" refers to an alkyl as described above substituted by hydroxyl group. Nonlimiting examples of hydroxyalkyl are —$CH_2OH$, —$CH_2CH_2OH$ and the like.

The term "mercaptoalkyl" refers to an alkyl as described above substituted by sulfur derivative group. Nonlimiting examples of mercaptoalkyl are —$CH_2SH$, —$CH_2CH_2SH$, —$CH_2CH_2SCH_3$, and the like The term "aminoalkyl" refers to an alkyl as described above substituted by an amine group. Nonlimiting examples of aminoalkyl are —$CH_2NH_2$, —$CH_2CH_2N(CH_3)_2$, —$(CH_2)_5 NH_2$ and the like.

The term "carboxyalkyl" refers to an alkyl as described above substituted by a carboxylic acid group, aldehyde or keto group. Nonlimiting examples of carboxyalkyl are —$CH_2COOH$, —$CH_2CH_2COOH$, —$CH_2CH_2C(O)H$, —$CH_2CH_2C(O)CH_3$ and the like.

The term "carboxamidoalkyl" refers to an alkyl as described above substituted by an amide group. Nonlimiting examples of carboxyalkyl are —$CH_2CONH_2$, —$CH_2CH_2CONH_2$, —$CH_2CH_2C(O)NH$—$CH_3$ and the like The term "guanidinoalkyl" refers to an alkyl as described above substituted by a guanidine group. Nonlimiting examples of guanidinoalkyl are —$CH_2CH_2CH_2NHC$(=NH)—$NH_2$, $CH_2CH_2NH$—C=NH—$N(Me)_2$ and the like.

In one embodiment, the present invention provides a process for preparing a doubly reduced perylene-compound represented by the structure of formula (1):

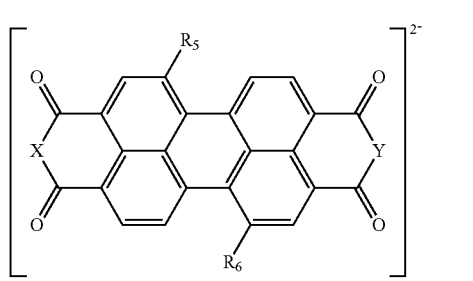

(1)

wherein said compound is a dianion;
wherein:
X is O or —$NR_1$;
Y is O or —$NR_2$;

$R_1$ is $[(CH_2)_nO]_oCH_3$, $[(CH_2)_nC(O)O]_oCH_3$, $[(CH_2)_nC(O)NH]_oCH_3$, $[(CH_2)_nCH_2=CH_2]_oCH_3$, $[(CH_2)_nCH=CH]_oCH_3$, $[(CH_2)_nNH]_oCH_3$, $(C_1-C_{32})$alkyl, $(C_3-C_8)$cycloalkyl, aryl, heteroaryl, $(C_1-C_{32})$alkyl-COOH, $(C_1-C_{32})$alkyl-Si-A, or $[C(O)CHR_3NH]_pH$ wherein said aryl or heteroaryl groups are optionally substituted by 1-3 groups comprising halide, CN, $CO_2H$, OH, SH, $NH_2$, $CO_2$—$(C_1-C_6$ alkyl) or O—$(C_1-C_6$ alkyl); wherein A comprises three same or different of the following substituents Cl, Br, I, $O(C_1-C_8)$alkyl or $(C_1-C_8)$alkyl; and wherein $R_3$ in said $[C(O)CHR_3NH]_pH$ is independently the same or different when p is larger than 1;

$R_2$ is $[(CH_2)_qO]_rCH_3$, $[(CH_2)_qC(O)O]_rCH_3$, $[(CH_2)_qC(O)NH]_rCH_3$, $[(CH_2)_qCH_2=CH_2]_rCH_3$, $[(CH_2)_qCH=CH_3]_rCH_3$, $[(CH_2)_qNH]_rCH_3$, $(C_1-C_{32})$alkyl, $(C_3-C_8)$cycloalkyl, aryl, heteroaryl, $(C_1-C_{32})$alkyl-COOH, $(C_1-C_{32})$alkyl-Si-A, or $[C(O)CHR_4NH]_sH$ wherein said aryl or heteroaryl groups are optionally substituted by 1-3 groups comprising halide, CN, $CO_2H$, OH, SH, $NH_2$, $CO_2$—$(C_1-C_6$ alkyl) or O—$(C_1-C_6$ alkyl); wherein A comprises three same or different of the following substituents Cl, Br, I, $O(C_1-C_8)$alkyl or $(C_1-C_8)$alkyl; and wherein $R_4$ in said $[C(O)CHR_4NH]_sH$ is independently the same or different when s is larger than 1;

$R_3$ is H, $(C_1-C_6)$alkyl, $(C_1-C_6)$hydroxyalkyl, $(C_1-C_6)$mercaptoalkyl, $(C_1-C_6)$amino alkyl, $(C_1-C_6)$carboxyalkyl, $(C_1-C_6)$carboxamidoalkyl, $(C_1-C_6)$guanidino alkyl, aryl, (aryl)alkyl, heteroaryl or (heteroaryl)alkyl wherein the aromatic ring of said aryl, (aryl)alkyl, heteroaryl or (heteroaryl)alkyl groups are optionally substituted by 1-3 groups comprising halide, CN, $CO_2H$, OH, SH, $NH_2$, $CO_2$—$(C_1-C_6$ alkyl) or O—$(C_1-C_6$ alkyl);

$R_4$ is H, $(C_1-C_6)$alkyl, $(C_1-C_6)$hydroxyalkyl, $(C_1-C_6)$mercaptoalkyl, $(C_1-C_6)$aminoalkyl, $(C_1-C_6)$carboxyalkyl, $(C_1-C_6)$carboxamidoalkyl, $(C_1-C_6)$guanidinoalkyl, aryl, (aryl)alkyl, heteroaryl or (heteroaryl)alkyl wherein the aromatic ring of said aryl, (aryl)alkyl, heteroaryl or (heteroaryl)alkyl groups are optionally substituted by 1-3 groups comprising halide, CN, $CO_2H$, OH, SH, $NH_2$, $CO_2$—$(C_1-C_6$ alkyl) or O—$(C_1-C_6$ alkyl);

$R_5$ and $R_6$ are independently H, —$OR^x$ where $R^x$ is $C_1-C_6$ alkyl or $[(CH_2)_nO]_oCH_3$, aryl, heteroaryl, C=C—$R_7$, CH=$CR_8R_9$, $NR_{10}R_{11}$ or a saturated carbocyclic or heterocyclic ring wherein said saturated heterocyclic ring or heteroaryl contains at least one nitrogen atom and $R_5$ or $R_6$ are connected via the nitrogen atom and wherein said saturated carbocyclic ring, heterocyclic ring, aryl and heteroaryl groups are optionally substituted by 1-3 groups comprising halide, aryl, heteroaryl, CN, $CO_2H$, OH, SH, $NH_2$, $CO_2$—$(C_1-C_6$ alkyl) or O—$(C_1-C_6$ alkyl);

$R_7$ is H, halo, $(C_1-C_{32})$alkyl, aryl, heteroaryl, $Si(H)_3$ or $Si[(C_1-C_8)$alkyl$]_3$ wherein said aryl or heteroaryl groups are optionally substituted by 1-3 groups comprising halide, CN, $CO_2H$, OH, SH, $NH_2$, $CO_2$—$(C_1-C_6$ alkyl) or O—$(C_1-C_6$ alkyl);

$R_8$, $R_9$, $R_{10}$ and $R_{11}$ are independently H, $(C_1-C_{32})$alkyl, aryl or heteroaryl wherein said aryl or heteroaryl groups are optionally substituted by 1-3 groups comprising halide, CN, $CO_2H$, OH, SH, $NH_2$, $CO_2$—$(C_1-C_6$ alkyl) or O—$(C_1-C_6$ alkyl);

n is an integer from 1-5;
o is an integer from 1-100;
p is an integer from 1-100;
q is an integer from 2-5;
r is an integer from 1-100; and
s is an integer from 1-100;

comprising the steps of a) dissolving a compound of formula (I) in a protic solvent;

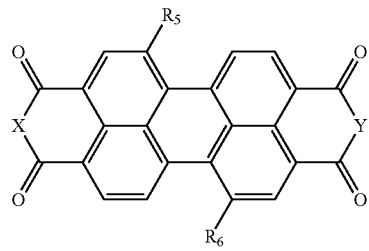
(I)

and b) forming a dianion compound of formula (1).

In one embodiment, step b) comprises reducing a compound of formula (I). In one embodiment, step b) comprises adding dithionite (e.g., sodium dithionite), thereby obtaining the dianion compound of formula (1). In one embodiment, step b) comprises adding dithionite in a protic solvent, thereby obtaining the dianion compound of formula (1).

In another embodiment, the neutral compound of formula (I) refers to the non-charged compound as represented by formula (I), wherein X, Y, $R_5$ and $R_6$ are as described for formula 1.

In one embodiment, the present invention provides a process for preparing a doubly reduced perylene-compound represented by the structure of formula (1):

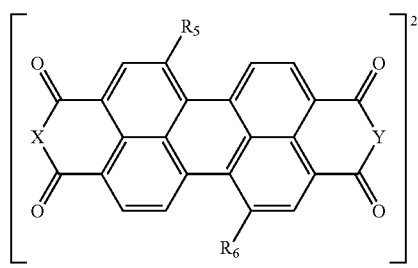
(1)

wherein said compound is a dianion;

wherein $R_5$, $R_6$, X and Y are as described above; comprising the steps of:

a) brominating a compound of formula (II)

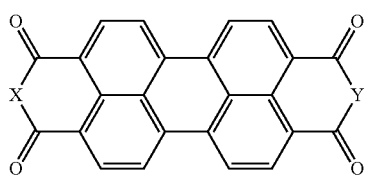
(II)

wherein X and Y are as defined above;

in the presence of bromine and a chlorinated solvent at reflux for a period of time sufficient to obtain a mixture comprising compounds of formula 1,6-(IV) and 1,7-(IV);

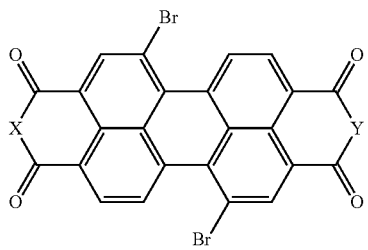
1,7-(IV)

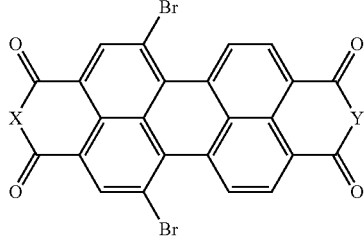
1,6-(IV)

b) separating the 1,6-(IV) and 1,7-(IV) regioisomer compounds;
c) coupling a compound of formula 1,7-(IV) with a terminal acetylene, vinylstannane, vinylsilane, arylstannane, arylsilane, heteroarylstannane, heteroarylsilane, alcohol or amines reagent wherein coupling of a said compound of formula 1,7-(IV) with said reagents is optionally catalyzed using a transition metal catalyst; and
d) forming a dianion compound of formula (1).

In one embodiment, the process for preparation of compound of formula 1 comprises a bromination step using a chlorinated solvent. In another embodiment, said chlorinated solvent is dichloromethane, chloroform, or a chlorinated aliphatic solvent.

In another embodiment, said period of time for the bromination is between 1-4 days. In another embodiment, said period of time for the bromination is between 24-48 h.

In one embodiment, said 1,6-(IV) and 1,7-(IV) regioisomer compounds are separated by a recrystallization step. In one embodiment, the recrystallization yields chemically pure perylene-diimide of formula 1,7-(IV). In another embodiment, said recrystallization is from dichloromethane/hexane mixture (v/v, 1:1).

In one embodiment, step d) comprises reducing a compound of formula (1). In one embodiment, step d) comprises adding dithionite (e.g., sodium dithionite), thereby obtaining the dianion compound of formula (1). In one embodiment, step d) comprises adding adding dithionite in a protic solvent, thereby obtaining the dianion compound of formula (1).

In one embodiment, the present invention provides a process for preparing a doubly reduced perylene-compound represented by the structure of formula (2):

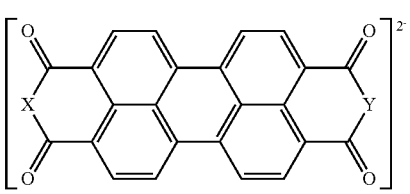
(2)

wherein said compound is a dianion;
wherein X and Y are as defined above for compound (1);
comprising the steps of a) dissolving a compound of formula (II) in a protic solvent

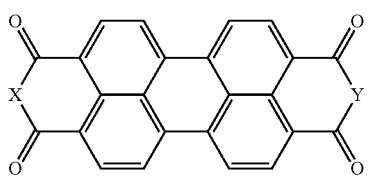

(II)

and b) forming a dianion compound of formula (2).

In one embodiment, step b) comprises reducing a compound of formula (II). In one embodiment, step b) comprises adding dithionite (e.g., sodium dithionite), thereby obtaining the dianion compound of formula (2). In one embodiment, step b) comprises adding adding dithionite in a protic solvent, thereby obtaining the dianion compound of formula (2).

In one embodiment, the present invention provides a process for preparing a doubly reduced perylene-compound represented by the structure of formula (3):

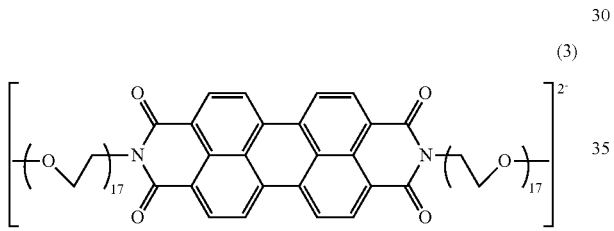

(3)

wherein said compound is a dianion;
comprising the steps of a) dissolving a compound of formula (III) in a protic solvent;

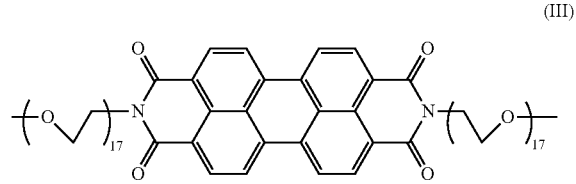

(III)

and b) forming a dianion compound of formula (3).

In one embodiment, step b) comprises reducing a compound of formula (III). In one embodiment, step b) comprises adding dithionite (e.g., sodium dithionite), thereby obtaining the dianion compound of formula (3). In one embodiment, step b) comprises adding adding dithionite in a protic solvent, thereby obtaining the dianion compound of formula (3).

In one embodiment, the present invention provides a process for preparing a doubly reduced perylene-diimide compound represented by the structure of formula 7a or 7b:

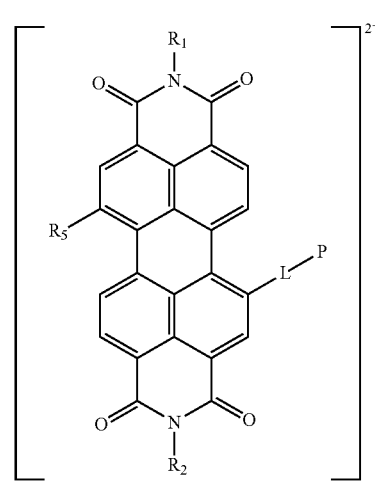

7a

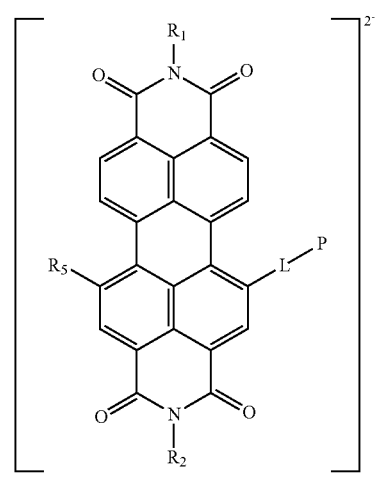

7b wherein said compound is a dianion;
wherein
$R_1$ is $[(CH_2)_nO]_oCH_3$, $[(CH_2)_nC(O)O]_oCH_3$, $[(CH_2)_nC(O)NH]_oCH_3$, $[(CH_2)_nCH=CH_2]_oCH_3$, $[(CH_2)_nCH=CH]_oCH_3$, $[(CH_2)_nNH]_oCH_3$, $(C_1-C_{32})$alkyl, $(C_3-C_8)$cycloalkyl, aryl, heteroaryl, $(C_1-C_{32})$alkyl-COOH, $(C_1-C_{32})$alkyl-Si-A, or $[C(O)CHR_3NH]_pH$ wherein said aryl or heteroaryl groups are optionally substituted by 1-3 groups comprising halide, CN, $CO_2H$, OH, SH, $NH_2$, $CO_2$—$(C_1-C_6$ alkyl) or O—$(C_1-C_6$ alkyl); wherein A comprises three same or different of the following substituents Cl, Br, I, $O(C_1-C_8)$alkyl or $(C_1-C_8)$alkyl; and wherein $R_3$ in said $[C(O)CHR_3NH]_pH$ is independently the same or different when p is larger than 1;
$R_2$ is $[(CH_2)_nO]_rCH_3$, $[(CH_2)_qC(O)O]_rCH_3$, $[(CH_2)_qC(O)NH]_rCH_3$, $[(CH_2)_qCH=CH_2]_rCH_3$, $[(CH_2)_rCH=CH]_rCH_3$, $[(CH_2)_qNH]_rCH_3$, $(C_1-C_{32})$alkyl, $(C_3-C_8)$cycloalkyl, aryl, heteroaryl, $(C_1-C_{32})$alkyl-COOH, $(C_1-C_{32})$alkyl-Si-A, or $[C(O)CHR_4NH]_sH$ wherein said aryl or heteroaryl groups are optionally substituted by 1-3 groups comprising halide, CN, $CO_2H$, OH, SH, $NH_2$, $CO_2$—$(C_1-C_6$ alkyl) or O—$(C_1-C_6$ alkyl); wherein A comprises three same or different of the following substituents Cl, Br, I, $O(C_1-C_8)$alkyl or $(C_1-C_8)$alkyl; and wherein $R_4$ in said $[C(O)CHR_4NH]_sH$ is independently the same or different when s is larger than 1;
$R_5$ and $R_6$ are independently H, —$OR_x$ where $R_x$ is $C_1-C_6$ alkyl or $[(CH_2)_nO]_oCH_3$, aryl, heteroaryl, C≡C—$R_7$, CH=$CR_8R_9$, $NR_{10}R_{11}$ or a saturated carbocyclic or heterocyclic ring wherein said saturated heterocyclic ring or heteroaryl contains at least one nitrogen atom and $R_5$ or $R_6$ are connected via the nitrogen atom and wherein said saturated carbocyclic ring, heterocyclic ring, aryl and heteroaryl groups are optionally substituted by 1-3 groups comprising halide, aryl, heteroaryl, CN, $CO_2H$, OH, SH, $NH_2$, $CO_2$—($C_1$-$C_6$ alkyl) or O—($C_1$-$C_6$ alkyl);

$R_7$ is H, halo, ($C_1$-$C_{32}$)alkyl, aryl, heteroaryl, $Si(H)_3$ or $Si[(C_1$-$C_8)$alkyl$]_3$ wherein said aryl or heteroaryl groups are optionally substituted by 1-3 groups comprising halide, aryl, heteroaryl, CN, $CO_2H$, OH, SH, $NH_2$, $CO_2$—($C_1$-$C_6$ alkyl) or O—($C_1$-$C_6$ alkyl);

$R_8$, $R_9$, $R_{10}$ and $R_{11}$ are independently H, ($C_1$-$C_{32}$)alkyl, aryl or heteroaryl wherein said aryl or heteroaryl groups are optionally substituted by 1-3 groups comprising halide, CN, $CO_2H$, OH, SH, $NH_2$, $CO_2$—($C_1$-$C_6$ alkyl) or O—($C_1$-$C_6$ alkyl);

L is an unsaturated linker;

P is a perylene-diimide group, aryl or heteroaryl, wherein said aryl and heteroaryl groups are optionally substituted by 1-3 groups comprising halide, aryl, heteroaryl, CN, $CO_2H$, OH, SH, $NH_2$, $CO_2$—($C_1$-$C_6$ alkyl) or O—($C_1$-$C_6$ alkyl);

n is an integer from 1-5;
o is an integer from 1-100;
p is an integer from 1-100;
q is an integer from 2-5;
r is an integer from 1-100; and
s is an integer from 1-100;
or metal thereof;
comprising the steps of
a) dissolving a compound of formula VIa or VIb in a protic solvent; and

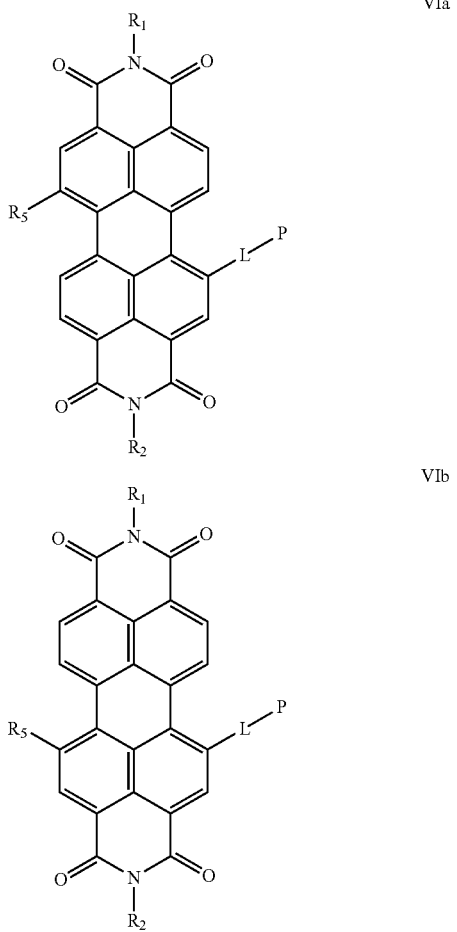

b) optionally complexing compounds VI and VIb with metal ion to obtain a metal complex; and
c) forming a dianion compound of formula 7a or 7b;

In one embodiment, step c) comprises reducing a compound of formula (I). In one embodiment, step c) comprises adding dithionite (e.g., sodium dithionite), thereby obtaining the dianion compound of formula 7a or 7b. In one embodiment, step c) comprises adding dithionite in a protic solvent, thereby obtaining the dianion compound of formula 7a or 7b.

In one embodiment, the metal ion may be first reduced to zero valent metal followed by reduction of the perylene to its dianion form. In another embodiment, the metal does not oxidize the perylene.

In one embodiment, the said process for the preparation of the dianion compounds 1-12 comprises the step of adding dithionite in a protic solvent. In another embodiment, dithionite in a protic solvent is also added to the supramolecular polymer of this invention. In another embodiment, the protic solvent is methanol, ethanol or water. In another embodiment, the protic solvent is methanol. In another embodiment, the protic solvent is ethanol. In another embodiment, the protic solvent is water.

In one embodiment the addition of the dithionite is conducted at room temperature. In another embodiment, this step is conducted at a temperature range from 20-25 degrees Celsius. In another embodiment, this step is conducted at a temperature range from 0-5 degrees Celsius. In another embodiment, this step is conducted at a temperature range from 5-20 degrees Celsius. In another embodiment, this step is conducted at a temperature range from 25-40 degrees Celsius.

In one embodiment, the addition of the dithionite is conducted under an inert atmosphere. In another embodiment, the inert atmosphere is nitrogen, argon or helium. In another embodiment, the inert atmosphere is nitrogen.

In one embodiment, dithionite is titrated into solutions of compounds I-III, VIa or VIb in a protic solvent. In another embodiment, dithionite is titrated into solutions of the supramolecular polymers. In another embodiment, a stoichiometric amount of dithionite is added in a protic solvent. In another embodiment, 1-5 equivalents of dithionite are titrated into solutions of compounds I-III, VIa or VIb in a protic solvent. In another embodiment, 1-5 equivalents of dithionite are added to solutions of compounds I-III, VIa or VIb in a protic solvent. In one embodiment, compounds I-III, VIa or VIb in a protic solvent and dithionite react for 0-6 hours. In another embodiment, compounds I-III, VIa or VIb in a protic solvent and dithionite react for 1-3 hours. In another embodiment, compounds I-III, VIa or VIb in a protic solvent and dithionite react for 1 hour. In another embodiment, compounds I-III, VIa or VIb in a protic solvent and dithionite react for 2 hours. In another embodiment, compounds I-III, VIa or VIb in a protic solvent and dithionite react at basic pH for 0-6 hours. In another embodiment, compounds I-III, VIa or VIb in a protic solvent and dithionite react with sonication for 0-6 hours. In another embodiment, compounds I-III, VIa or VIb in a protic solvent and dithionite react with sonication for 1 hour.

In one embodiment, compounds I-III, VIa or VIb in a protic solvent and dithionite react at basic pH. In another embodiment, the pH is adjusted using a carbonate or bicarbonate salt. In another embodiment, the pH is adjusted using sodium bicarbonate. In another embodiment, the pH is adjusted to a range from 8-12.

In one embodiment, the said process for the preparation of the dianion compounds 1-12 comprises the step of adding excess hydrazine and a platinum catalyst in a protic solvent to their corresponding neutral structures. In another embodiment, the protic solvent is methanol, ethanol or water. In another embodiment, the protic solvent is methanol. In another embodiment, the protic solvent is ethanol. In another embodiment, the protic solvent is water. In another embodiment, 50-200 equivalents of hydrazine are used. In another embodiment, 100 equivalents of hydrazine are used.

In another embodiment, the platinum catalyst is metallic platinum nanoparticles. In another embodiment, the platinum is Pt(0). In another embodiment, the platinum nanoparticles are 4-7 nanometers.

In one embodiment, the compounds of this invention are adsorbed on solid surfaces. In another embodiment, the solid surface is silica, glass, CdSe, CdS, ZnS, GaAs, metal oxide, semiconductor or titania. In another embodiment, the solid surfaces are nanoparticles. In another embodiment, the surface is CdSe, CdS, ZnS, silica or titania nanoparticles. In another embodiment, the surface is silica nanoparticles. In another embodiment, the surface is titania nanoparticles.

Figure 11:
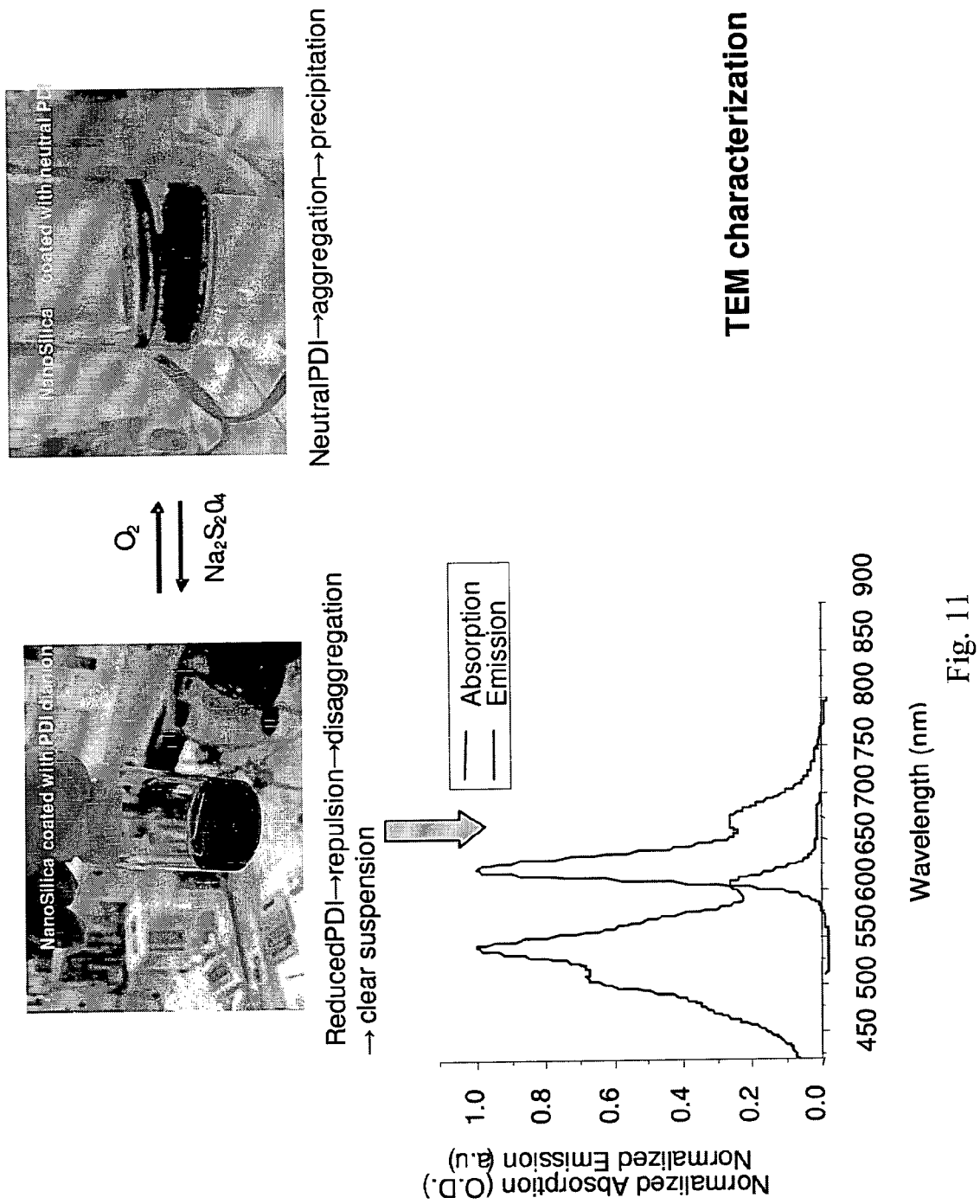
FIG. 11 depicts a soluble dianion PDI adsorbed on silica nanoparticles as opposed to precipitation of neutral PDI adsorbed on silica nanoparticles. UV-vis absorption and Fluoresence emission of the solubilized absorbed nanoparticles.

In one embodiment the compounds of this invention are assembled on nanoparticles and may control the properties of said nanoparticles. In another embodiment, the assembly of doubly reduced compounds results in disaggregation of the nanoparticles to a homogeneous solution due to anionic repulsive interactions. In another embodiment, a homogeneous solution of doubly reduced compounds assembled on nanoparticles is presented in FIG. 11. In another embodiment, the assembly of neutral compounds of this invention on nanoparticles results in nanoparticle aggregation and precipitation due to $\pi$-$\pi$ interactions. In another embodiment, the precipitation of neutral assemblies is presented in FIG. 11.

In one embodiment, the compounds of this invention are adsorbed to the surface of via hydrogen bonding. In another embodiment, the compounds of this invention are adsorbed to the surface via hydrophobic interaction. In another embodiment, the compounds of this invention are adsorbed to the surface via covalent interaction. In another embodiment, the compounds of this invention are adsorbed to the surface via ionic interactions. In another embodiment the covalent bond, hydrophobic interaction, ionic bond or hydrogen bond is between a functional group of the compound and the surface. In another embodiment, the functional group is carboxylic acid, trichloro silane or trimethoxysilane.

In one embodiment, the compounds of this invention are adsorbed on the solid surface by spin coating. In another embodiment, the compounds of this invention are adsorbed on the solid surface by self assembly. In another embodiment, the compounds of this invention are adsorbed on the solid surface by drop casting. In another embodiment, the compounds of this invention are adsorbed on the solid surface by chemical deposition. In another embodiment, the compounds of this invention are adsorbed on the solid surface by suspension deposition. In another embodiment, the compounds of this invention are adsorbed on the solid surface by spray coating. In another embodiment, the compounds of this invention are adsorbed on the solid surface by MOCVD (metal organic chemical vapor deposition.

Spin coating is a procedure used to apply uniform thin films to flat substrates. An excess amount of a solution is placed on the solid surface, which is then rotated at high speed in order to spread the fluid by centrifugal force. Rotation is continued while the fluid spins off the edges of the substrate, until the desired thickness of the film is achieved.

Drop Casting films are obtained by placement of a droplet of a solution of the compounds on a solid surface and subsequent solvent evaporation.

MOCVD is method of creating controllable epi-taxial layered structures by atomic deposition over a substrate material. A substrate wafer is placed on graphite and heated in a reaction vessel. The compounds are grown in a hydrogen-rich atmosphere and subsequently form epi-taxial layers on the substrate.

Wet chemical deposition includes the use of a liquid as a carrier for the compounds of this invention, in which the surface is immersed for a period of time to allow physisorbed or chemisorbed adsorption.

Spray coating which includes the use of pressure device able to distribute the compounds of this invention on a surface, using a liquid or a gas as a carrier material or combination thereof, in which the substrate is immersed for a period of time to allow physisorption or chemisorption.

In another embodiment, compounds I-III, VIa and VIb are adsorbed on solid surface and the compounds are reduced with dithionite to obtain doubly reduced compounds. In another embodiment, compounds I-III, VIa and VIb are adsorbed on solid surface and the compounds are reduced with hydrazine and Pt catalyst to obtain doubly reduced compounds. In another embodiment, compounds I-III, VIa and VIb are adsorbed on solid surface and the compounds are reduced electrochemically to obtain doubly reduced compounds. In another embodiment, the doubly reduced compounds of this invention are adsorbed directly onto the solid surface. In another embodiment, the doubly reduced adsorbed compounds yield a high electron rich surface. In another embodiment, the doubly reduced adsorbed compounds on nanoparticles yield a high electron rich nanoparticles. In another embodiment, electron rich nanoparticles characterized by UV-vis absorption and Fluoresence emission as presented in FIG. 11.

In one embodiment, the compounds of this invention absorb visible light and reach highly energetic excited states, allowing access to high energy electron transfer reactions.

In one embodiment, this invention provides a use of compounds of this invention in organic electronic devices.

In one embodiment, the compounds of this invention possess plurality of conjugated groups, and can be generally advantageously employed in the electroluminescence field, particularly for light-emitting diodes (OLEDs), more particularly blue-light OLEDs and OLEDs emitting from the triplet state, as electron transporting materials in OLEDs as well as in other applications, as molecular switching components, for non linear optics, in molecular-based computational systems, in field-effect transistors (FET), In negative differential resistance (NDR) semiconductors. Just for the presence of many conjugated groups, the compounds of the invention allow the easy transfer of more electrons with respect to similar compounds, thus allowing to obtain anionic species usable as molecular magnets. The compounds according to the invention can be applied in form of thin film or coating upon a proper substrate (metallic or non metallic) according to techniques (for example chemical, physical-chemical, physical) known to those skilled in the art. The devices carry at least an active layer including at least one compound of the invention, applied on said substrate.

In another embodiment, the organic electronic device is preferably organic and polymeric light emitting diodes (OLEDs, PLEDs), organic field-effect transistors (O-FETs), organic thin film transistors (O-TFTs), organic light emitting transistors (O-LETs), organic integrated circuits (O-ICs), organic solar cells (O-SCs), organic field quench devices (O-FQDs) or organic laser diodes (O-Laser). Particularly preferred are organic or polymeric light emitting diodes.

In another embodiment, the compounds of this invention can be applied on the substrate of the organic electronic device by sublimation. The compounds can further be applied on the substrate of the organic electronic device by the OVPD (organic vapour phase deposition) process or by means of a train sublimation. The compounds can further be applied on the substrate of the organic electronic device from solution, e.g. by spin-coating, or by a printing method, such as offset-printing, or preferably by LITI (light induced thermal imaging) or by ink-jet printing.

In another embodiment, said organic electronic devices are organic field-effect transistors for use in switching devices, flexible displays or smart cards.

OFET applications using low-cost production and large area coverage such as radio frequency IDs, smart tags, textile integrated electronics, etc. are known In one embodiment, this invention provides a use of the doubly reduced compounds of this invention for pigmented systems.

In another embodiment, said pigmented systems are paints, inks, paper or macromolecular materials.

In another embodiment, said paints are physically drying lacquers, oxidatively drying lacquers, staving enamels, reactive paints, two component paints, solvent-based paints, water-based paints, emulsion paints or distempers.

In another embodiment, said inks are suitable for use in paper, textile or tinplate printing.

In another embodiment, said macromolecular materials are natural materials such as rubber; chemically modified materials such as acetyl cellulose, cellulose butyrate or viscose; or synthetic materials such as polymers, polyaddition products or polycondensates.

In another embodiment, synthetic materials include plastic materials, such as polyvinyl chloride, polyvinyl acetate, and polyvinyl propionate; polyolefins, such as polyethylene and polypropylene; high molecular weight 5 polyamides; polymers and copolymers of acrylates, methacrylates, acrylonitrile, acrylamide, butadiene, or styrene; polyurethanes; polyynes; and polycarbonates.

In another embodiment, the materials pigmented with the perylene pigment compositions of the present invention can have any desired shape or form.

In another embodiment, said pigmented formulations are pastes with organic liquids, pastes with water, dispersions with water, dispersants or preservatives.

In one embodiment, this invention provides a use of the compounds of this invention for a sensor system. In another embodiment, sensing of said sensor system is based on the change in magnetic and polarity (dielectric constant) properties. In another embodiment, said sensor system detects electron poor species. In another embodiment, said sensor system responds with changes in absorption of the dianions component. In another embodiment, said sensor system responds with changes in emission of the dianions component. In another embodiment, said sensor system responds with reversible changes in absorption of the dianions component. In another embodiment, said sensor system responds with reversible changes in emission of the dianions component. In another embodiment, said sensor system is an electron reservoir. In another embodiment, said sensor system is an electron reservoir having reducing properties (i.e donating electrons). In another embodiment, said sensor system is useful for ground state chemical reductions. In another embodiment, said sensor system is useful for photoinduced chemical reductions. In one embodiment, this invention provides a use of the doubly reduced compounds of this invention for use in energy storage devices. In another embodiment, said energy storage devices are supercapacitors. In another embodiment, said energy storage devices are batteries. In another embodiment said sensor device is in water.

The following examples are presented in order to more fully illustrate the preferred embodiments of the invention. They should in no way be construed, however, as limiting the broad scope of the invention.

EXAMPLES

General Methods

All procedures with air and moisture-sensitive compounds were performed in a glove box (MBraun, LABmaster) under a dry nitrogen atmosphere or on a high vacuum line using Schlenk techniques. Unless otherwise indicated, all starting materials were obtained from commercial suppliers and were used without further purification. All organic solvents were purchased in the purest form available, degassed by purging with argon and kept over molecular sieves in the glove box.

$^1$H, $^{13}$C and $^{19}$F NMR spectra were recorded at 20° C. on 400 MHz NMR spectrometer (Bruker). $^1$H, $^{13}$C{$^1$H} and $^{19}$F NMR chemical shifts are reported in parts per million (ppm) downfield from tetramethylsilane (δ scale). $^1$H NMR chemical shifts were referenced to the residual hydrogen signal of CDCl$_3$ (7.26 ppm). In $^{13}$C{$^1$H} NMR measurements, the signal of CDCl$_3$ (77.16 ppm) was used as a reference. In $^{19}$F NMR measurements, the signal of C$_6$F$_6$ in CDCl$_3$ (−163 ppm) was used as a reference. Coupling constants (J) are reported in Hertz (Hz), and splitting patterns are designated as s (singlet), d (doublet), t (triplet), q (quartet), m (multiplet), b (broad).

UV-vis absorption measurements were carried out on a Cary-5000 spectrometer (Varian). Steady state fluorescence measurements were performed on a Cary Eclipse fluorimeter (Varian) with excitation/emission geometry at right angles. Fluorescence quantum yields were determined using a standard procedure.[1] Sulforodamine 101 solution in ethanol ($\lambda_{abs}$=576 nm; $\lambda_{em}$=592 nm, Φ=0.9) was used as a fluorescence reference. Quantum yield measurements were made using four excitation wavelengths (450, 475, 505, 560 nm), the quantum yields were averaged over 20 measurements, and the errors were estimated to be less than 5%. Electrochemical measurements were performed with a CH Instruments electrochemical workstation, model 660C. The solvents were methylene chloride, DMF, methanol and water. When measurements were performed in organic solvents, 0.1 M solution of tetra-n-butylammonium hexafluorophosphate (TBAPF$_6$) electrolyte was used. A platinum disk electrode (2.0 mm diameter) was employed as a working electrode, and platinum wires as counter and auxiliary electrodes. Ferrocene/ferrocenium (Fc/Fc+, 0.475 V in CH$_2$Cl$_2$, 0.45 V in DMF and 0.42 V in MeOH vs. SCE) was used as an internal reference for all measurements. For measurements in water, 0.1M KCl solution was used and saturated calomel electrode was employed as reference. All electrochemical measurements were performed in a nitrogen filled glove box. In order to obtain absorption spectrum of the FIG. 1 compound in water during electrochemical reduction, solution of the FIG. 1 compound (0.1 M KCl) was loaded into a spectroelectrochemical cell (BAS Inc.) and sealed under N$_2$. Potential difference of −0.8 V was applied and the absorption spectrum was continuously scanned. During the reduction process the cell compartment was kept under argon.

Figure 7:
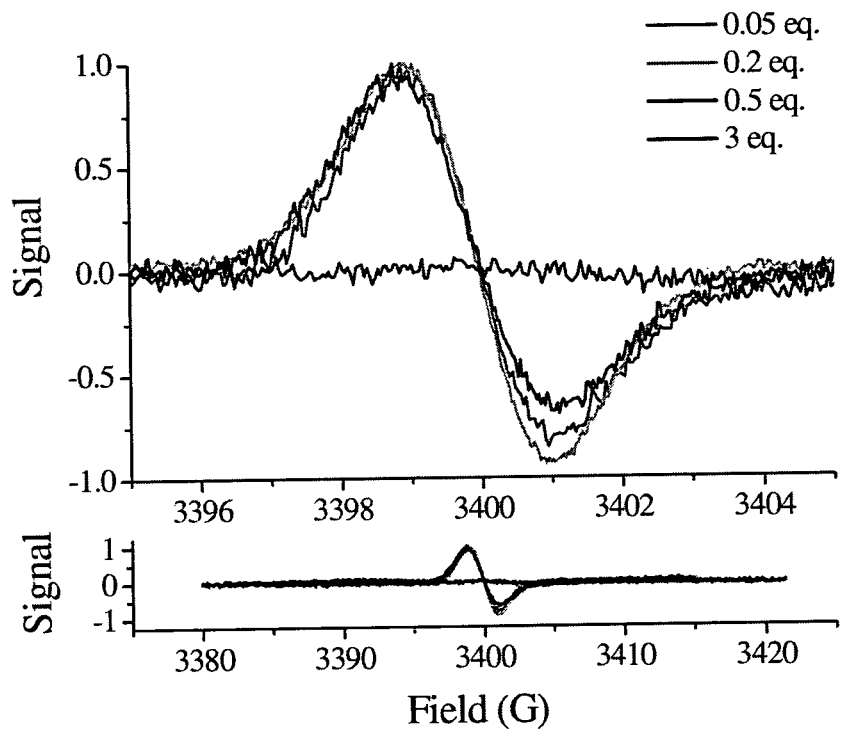
FIG. 7 depicts an EPR spectra observed for titration of compound of formula III compound with sodium dithionite.

EPR spectra were acquired with a Bruker E-580 spectrometer, fitted with an EN801 resonator. Temperatures were maintained at 290 K. For example samples of the FIG. 1 compound (10$^{-4}$ M in deoxygenated water) that reacted with sodium dithionite, were loaded in 2 mm quartz tubes in a nitrogen filled glove box and sealed with grease and parafilm before the EPR measurements. The EPR spectra of the FIG. 1 compound are featureless, with g=2.0028-2.0029, as typical of aggregated PDI systems (FIG. 7).

Figure 8:
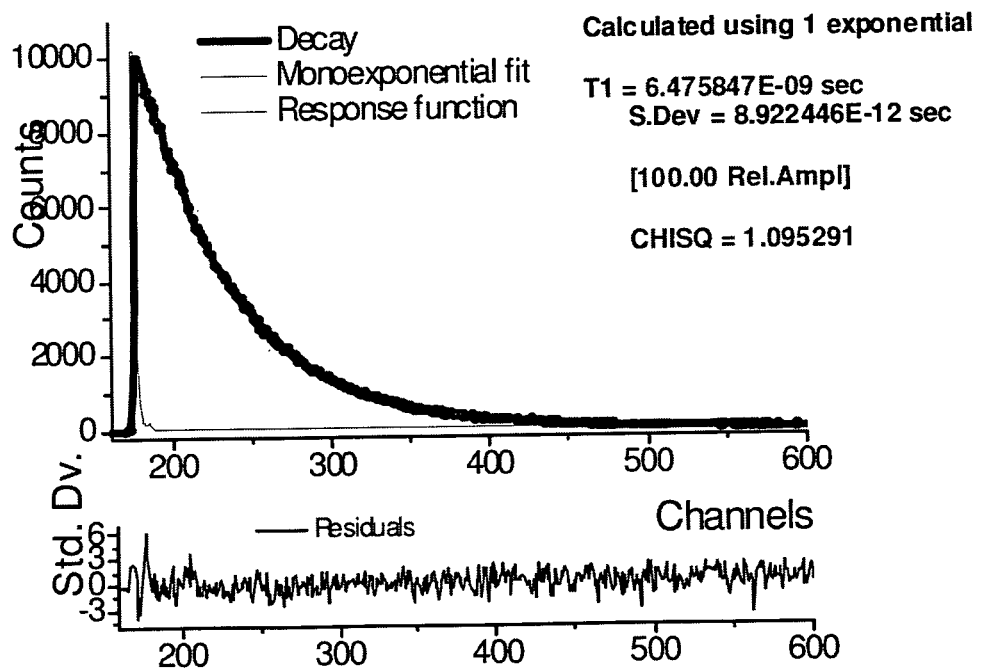
FIG. 8 depicts an emission lifetime measurement for compound of formula III. Excitation at 466 nm, detection at 620 nm.

Fluorescence lifetime measurements were performed by the time correlated single photon counting technique using FluoroCube (HORIBA Jobin Yvon) station equipped with TBX-04 detection module of less than 180 ps typical timing jitter and less than 100 ps overall time resolution. The instrument response function was obtained by measuring scattering from a standard sample (Ludox) with the monochromator set for detection at or close to the excitation source wavelength and remaining all other parameters unchanged. The excitation of samples was performed using a laser diode (NanoLED 470L) that generated 200 ps pulses of 466 nm light. The samples were excited with 1 MHz repetition rate and 10000 counts in the peak channel were collected. Lifetime decays were deconvoluted and fitted using Das6 decay analysis software. Fluorescence decays at different wavelengths were measured resulting in identical decay profiles. For example, a representative graph for the FIG. 1 compound corresponding to excitation at 466 nm and detection at 620 nm is provided (FIG. 8).

Femtosecond transient absorption spectroscopy was performed on a system based on a modelocked Ti:sapphire oscillator (Spectra Physics Tsunami) pumped by a CW diode pumped Nd:YVO4 laser (Millennia X). The oscillator produces a train of <100 fs pulses (bandwidth ~10 nm FWHM), with a peak wavelength at around 815 nm, typically of 850 mW, corresponding to ~10 nJ per pulse. The weak oscillator pulses are amplified by a chirped pulse regenerative amplifier (CPA) (Spectra Physics Spitfire). The pulses are first stretched to about 200 ps, then regeneratively amplified in a Ti:sapphire cavity, pumped by a pulsed Nd:YLF laser (Spectra Physics Evolution-15) operating at 1 kHz. After the pulse has been amplified and recompressed, its energy is about 1.0 mJ in a train of 1-kHz pulses. An independent pump pulse is obtained by pumping an optical parametric amplifier (Spectra Physics OPA-800CF) that produces 120-fs pulses tunable from 300 nm to 3 um.

The output power of the OPA is between a few micro joules to tens of micro joules (depending on the chosen wavelength) at 1 kHz. The probe beam is mechanically chopped at half the amplifier repetition rate. The chopper (C-995 TTI) is synchronized to the Spitfire amplifier. Normally a few thousand pulse pairs (pump on/pump off) are averaged to produce a transient absorption spectrum with a noise level below 0.3 mOD.

A small portion of the remaining amplified pulse was used to generate a white light continuum as a probe pulse. To this end, the Ti:sapphire beam was focused onto a 3-mm thick sapphire disk by a 10-cm focal length lens, and the numerical aperture of the beam is controlled by an iris placed in front of the lens, which helped in obtaining a stable and smooth white light continuum. The resulting beam is passed through a short pass filter to remove the remains of the amplified fundamental beam from the probe white light continuum.

The pump and probe pulses were crossed in the sample at a small angle, while maintaining a magic angle between the pump and probe polarizations. The remains of the pump pulse were removed by an iris, and the probe light is imaged onto an optical fiber that brings it into an imaging interface, which focuses the light onto the entrance slit of a Jobin Yvon Triax 180 spectrograph. The light was normally dispersed by a 300 gr/mm grating onto a fast CCD camera (Andor Newton DU-970N-UV, operating at 1,000 spectra per second using "crop mode"). The whole setup was controlled by National Instruments LabView software.

A variable neutral-density filter was employed to adjust the pump power. The pump power intensities were measured using Ophir thermal head powermeter in proximity to the sample. The excitation densities were estimated for a laser spot of 300 μm diameter on the sample. This diameter was measured by placing beamprofiler (Ophir Beamstar FX33) at the sample position and determining the 4-sigma (95% of the power) parameter. In the reported experiments the pump was turned to 525 nm and the optical densities of the samples, filled in 4 mm optical path length cuvettes, were kept between 0.2 and 0.4 at the excitation wavelength.

The instrument response function (300 fs) was recorded by repetition of the experiments with sample replaced by pure solvent and keeping all other parameters unchanged. Spectral corrections and analysis were performed using Surface Xplorer Pro (Ultrafast Systems) and Origin 7.5 (OriginLab) software.

MALDI-TOF mass spectrometry was carried out using a REFLEX™ reflector time-of-flight instrument with SCOUT™ multiprobe (384) inlet.

ESI mass spectrometry was performed using a Miromass Platform instrument. Chloroform was the solvent for all samples analyzed by mass spectrometry.

Electrochemical experiments were carried out using a CH Instruments electrochemical workstation (model 666C). The measurements were performed in methylene chloride containing 0.1 M tetra-n-butylammonium hexafluorophosphate (TBAPF6), and the ferrocene/ferrocenium redox couple (Fc/Fc$^+$, 0.475 V vs. SCE in $CH_2Cl_2$) was used as an internal reference. Sample concentrations were 1 mM. All electrochemical measurements were performed under dried nitrogen atmosphere.

EPR experiments were performed using a Bruker E-580 spectrometer fitted with an EN801 resonator. The temperature was kept at 25° C. Samples were filled into flat cell EPR tubes under nitrogen atmosphere in the glovebox and the tubes were sealed with Parafilm.

Gel permeation chromatography was carried out using a Varian PrepStar 218 HPLC pump, Varian ProStar Model 325 UV-vis detector, and a Varian/Polymer labortories PLgel Olexis 7.5×300 mm column with THF as the eluent. The temperature was set to 40° C. Polystyrene standards were used for calibration.

Rheological studies were performed using a cone and plate geometry (RotoVisco1 Rheometer, Thermo Haake, Germany) at (25±1)° C. The measuring process was controlled via PC through an interface whereby the viscosities of the samples at different shear rates were automatically recorded. For each set of measurements, an "up" shear-rate cycle was recorded immediately after the sample was transferred onto the sample plate in order to avoid drying.

Cryo-TEM was performed using a Tecnai F20 transmission electron microscope operating at 200 kV and using a Gatan 626 cooling holder and transfer station with a TVIPS F415 CCD digital camera. For sample-preparation 4 μL of the sample was applied to a 300-mesh copper grid coated with lacey carbon (SPI supplies). Samples were blotted in an environment at 25° C. and 100% relative humidity, and subsequently plunged into liquid ethane using a CEVS plunger. Specimens were equilibrated at ~178° C. in the microscope prior to imaging. The images were analyzed using AnalySIS 5.0 (2004, Soft Imaging System GmbH). Presented lengths measurements include the arithmetic mean and standard deviation of at least 20 exemplars.

Cryo-SEM sample preparation involved the high pressure freezing (HPF) technique/For this purpose, 3 μL, of the gel was applied to a regular TEM grid (200 mesh) and sandwiched between two aluminum planchettes (size=3.0×0.5 mm, inner cavity=2.0×0.15 mm). HPF was carried out using a Bal-Tec HPM 010. Subsequently, the sandwich was transferred into a Bal-Tech BAF 060 freeze etching system where it was opened with a pre-cooled razorblade and solvent was allowed to sublime (−105° C., 20 min). Subsequently, it was coated with Ta/W employing double axis rotary shadowing (DARS). Using a quartz crystal for measurement, the metal layer was determined to be 1.5 nm thick. According to model calculations, the measured thickness has to be corrected to $\frac{1}{5}^{th}$ of its original value for vertical planes and to $\frac{2}{3}^{rd}$ for horizontal planes. Therefore, vertical metal layers are 0.3 nm thick, whereas horizontal metal layers are 1.0 nm thick. Images of the gel were taken using a Zeiss Ultra 55 cryogenic scanning electron microscope operated at 1 kV with an aperture size set to 10 μm. The images were analyzed using AnalySIS 5.0 (2004, Soft Imaging System GmbH). Presented lengths measurements include the arithmetic mean and standard deviation of at least 20 exemplars.

Polarized Light Microscopy was carried out using a Nikon Eclipse E600 POL microscope. A glass cuvette with ~100 μm path length was used to create a thin layer of gel that was studied in the microscope.

Reductions of the FIG. 1 compound were performed in a nitrogen filled glove box. Solutions of the FIG. 1 compound in deoxygenated water were treated with sodium dithionite using weighted powder or stock solutions in deoxygenated water.

For further example, samples of supramolecular structures of compounds of formulas XI-XV were prepared by dissolving compounds of formulas XI-XV in THF and addition of the THF solution to water until 9:1 volume ratio was achieved, followed by sonication for 1 hour and aging for 1 day at room temperature. Clear homogeneous solutions were obtained. Longer aging do not result in significant change in samples appearance and morphologies as evidenced by cryo-TEM. Unless otherwise specified, all studies on self-assembled compounds of formulas XI-XIV were performed on $2 \cdot 10^{-4}$ M solutions in water/THF (9:1, v/v) mixtures.

Computational Methods. All theoretical calculations were done using Density Functional Theory with the Gaussian 03 Revision C.01 quantum chemistry program package. All calculations were carried out at the B3LYP/6-31++G level of theory. The B3LYP hybrid-generalized gradient approximation (GGA) exchange-correlation functional is Becke's three-parameter hybrid density functional method with the Becke88 exchange functional and the Lee-Yang-Parr correlation functional. The 6-31++G is Pople's double-ζ augmented and polarized basis set. PDI and the dianion have $D_{2h}$ symmetry, which was used throughout, except for the NICS (vide infra) calculations where Gaussian cannot use symmetry due to the presence of a "dummy" atom. Molecular orbitals were visualized using GaussView.

Charges presented are Natural Population Analysis (NPA) charges calculated during a Natural Bond Order (NBO) analysis. They were calculated both in the gas phase and in water using a polarizable continuum model (PCM), specifically the integral equation formalism model (IEF-PCM). Also presented from the NBO analysis are the Wiberg bond indices.

The optimized geometries obtained from these calculations were used for time dependent density functional theory (TDDFT) single point energy calculations. In the TDDFT calculations, bulk solvent (water) effects were approximated the IEF-PCM model. The default three singlet excitations were considered. Preliminary tests using Zerner's Intermediate Neglect of Differential Overlap (ZINDO/S) with additional singlet and triplet excitations confirmed that we were considering in our TDDFT calculations all the significant excitations.

Aromaticity and electron delocalization were evaluated using two independent methods. The first is the nucleus-independent chemical shifts (NICS) method of Schleyer et al. For this method, the NMR chemical shifts and magnetic susceptibility tensors (χ) were calculated using the Gauge-Independent Atomic Orbital (GIAO) method with the "dummy" atom suspended 1.0 Å above the center of each ring. The second method is the Anisotropy of the Induced Current Density (AICD) plots of Herges and co-workers. This method employs the Continuous Set of Gauge Transformations (CSGT) method to calculate the current densities. The AICD results were plotted using POVRAY 3.6.1 for Windows with the aid of POVCHEM 1.0.

Example 1

Synthesis of N'-Bis(PEG$_{17}$)perylene-3,4:9,10-tetracarboxylic diimide (Compound III)

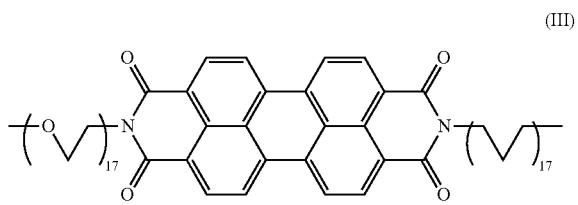

(III)

PEG$_{17}$-N$_3$ (856 mg, 1.06 mmol) and 10 mg of Pd/C (5% wt) were stirred in 15 ml of absolute MeOH at room temperature for 72 h, in a round bottomed flask, under H$_2$ atmosphere. The reaction mixture was filtered through filter paper to separate the Pd/C, and the solvent was evaporated resulting in transparent colorless oil. Further purification of the product was carried out by precipitation from dichloromethane/ether mixture at 0° C. The product was filtered and dried in vacuum to give an off-white-pink solid (579 mg, 55%). $^1$H NMR (250 MHz, CDCl$_3$, ppm): 7.62 (bs, 2H, NH$_2$), 3.90 (t, 2H, J$_{HH}$=4.8 Hz, —O—CH$_2$—CH$_2$—N$_3$), 3.64 (m, 64H, CH$_2$), 3.36 (s, 3H, CH$_3$), 3.14 (t, 2H, J$_{HH}$=4.8 Hz, —CH$_2$—NH$_2$). $^{13}$C NMR (250 NMR, CDCl$_3$, ppm): 71.60 (s), 70.23 (m, unresolved PEG methylene carbons), 66.43 (s, —O—CH$_2$—CH$_2$—NH$_2$), 58.71 (s, CH$_3$), 40.13 (s, —CH$_2$—NH$_2$). Assignment was confirmed by $^{13}$C DEPT. MS-ESI (m/z): calculated for C$_{35}$H$_{73}$O$_{17}$N 780; found 781 [M+H]$^+$.

Figure 9:
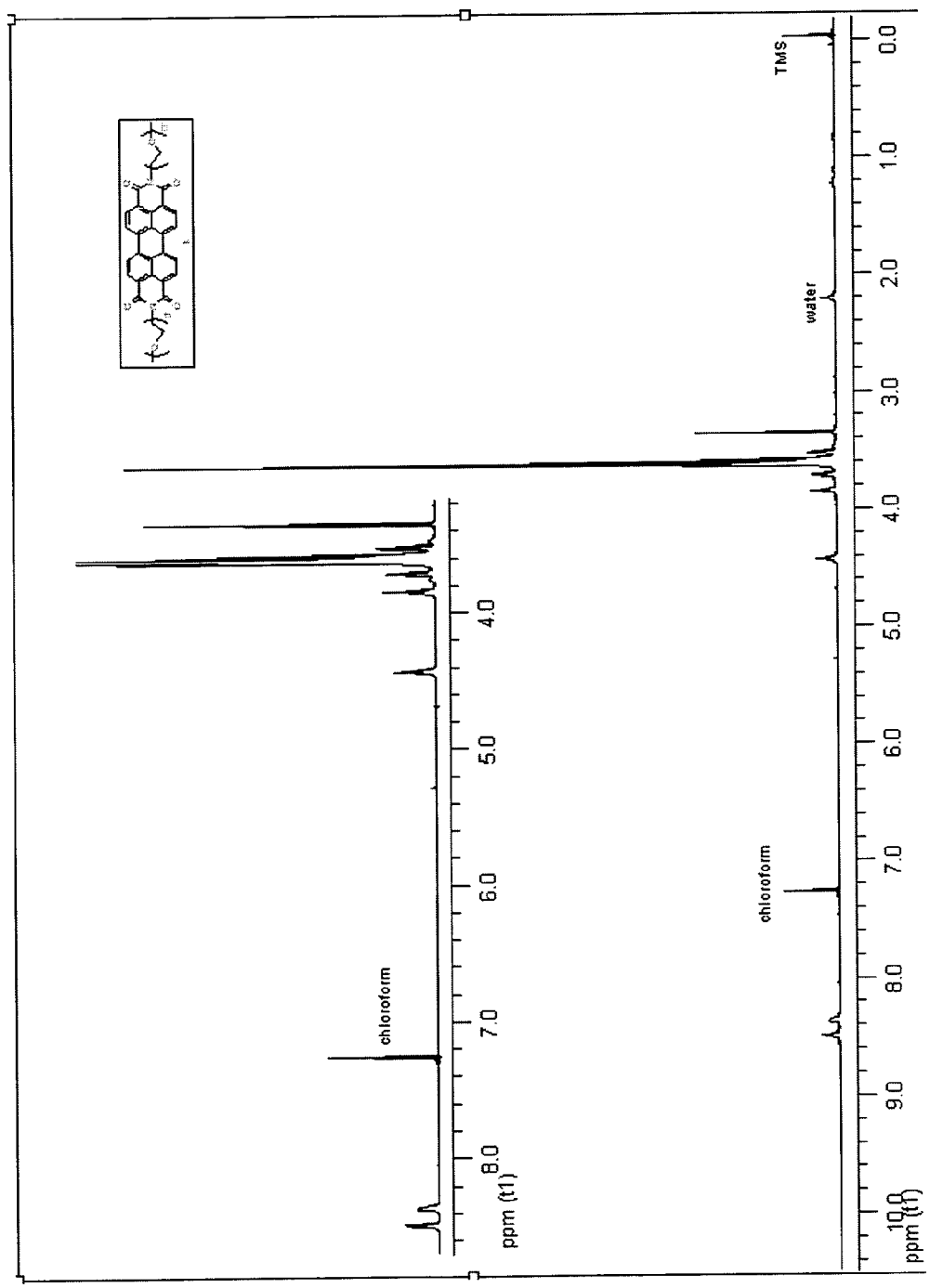
FIG. 9 depicts a $^1H$ NMR spectrum of compound of formula III in $CDCl_3$.
Figure 10:
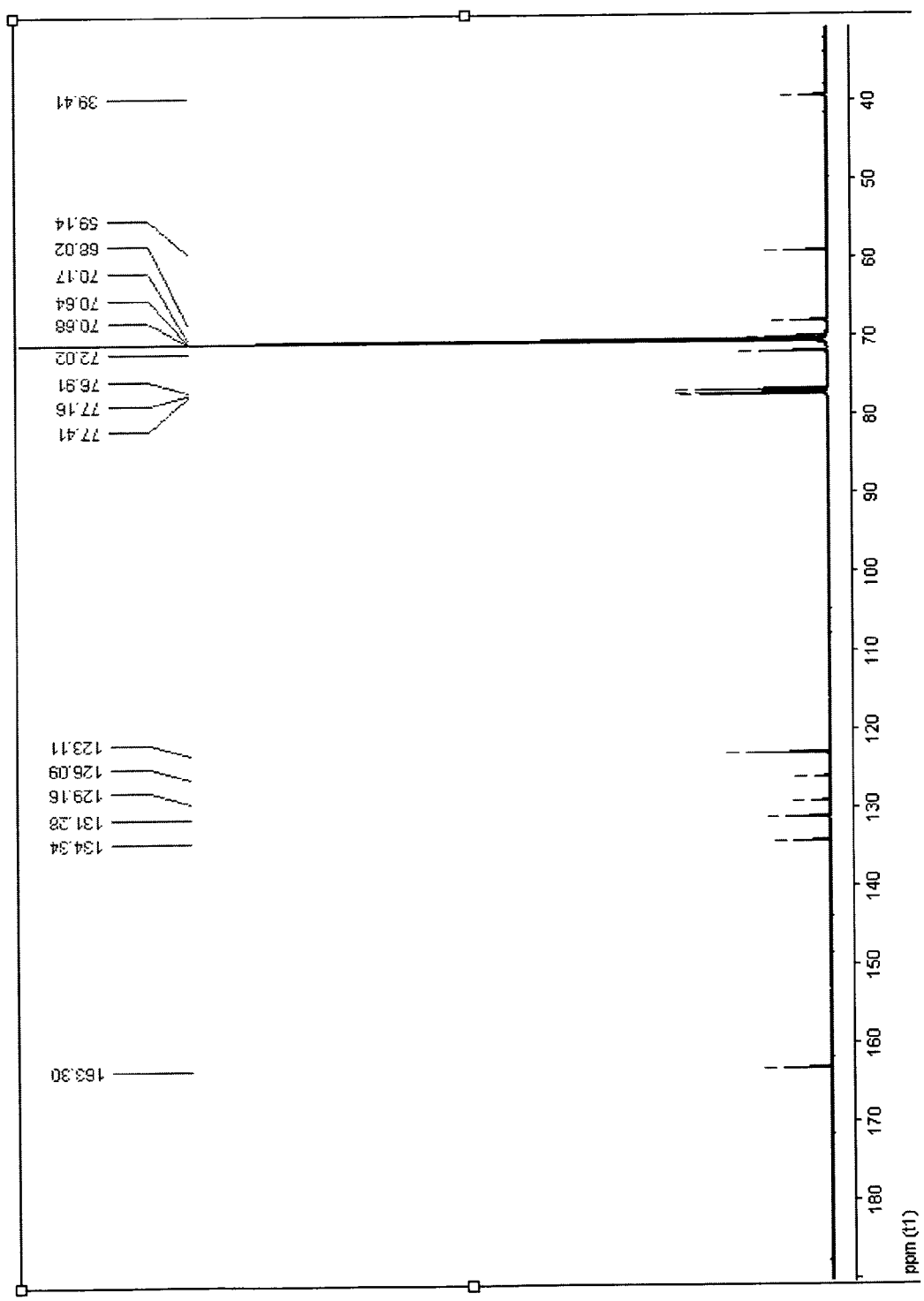
FIG. 10 depicts a $^{13}C\{^1H\}$ NMR spectrum of compound of formula III in $CDCl_3$.

PEG$_{17}$-NH$_2$ (780 mg, 1.0 mmol), 3,4,9,10-perylene-tetracaroxylic anhydride (120 mg, 0.306, mmol), and imidazole (1.20 g, 17.6 mmol), were mixed in a pressure flask under N$_2$ atmosphere. The mixture was heated to 140° C. for 3 days. After cooling to room temperature, 100 ml of dichloromethane was added. The organic phase was washed with 1 M aqueous solution of HCl, and then with water. The solvent was evaporated, and the residue was purified by column chromatography using CHCl$_3$/MeOH (17:1, v/v) as an eluent to yield 488 mg (83%) of III as a dark orange solid, which was further purified by precipitation from diethyl ether to give 320 mg (56%) of III. $^1$H NMR (500 MHz, CDCl$_3$, ppm): 8.50 (d, 4H, J$_{HH}$=5.0 Hz, ArH), 8.37 (d, 4H, ArH), 4.44 (t, 4H, J$_{HH}$=5.1 Hz, CH$_2$), 3.86 (t, 4H, CH$_2$), 3.64 (m, 128H, CH$_2$), 3.36 (s, 6H, CH$_3$). $^{13}$C {$^1$H} NMR (500 NMR, CDCl$_3$, ppm): 163.30 (s, carbonyl), 134.34 (s), 131.29 (s), 129.16 (s), 126.09 (s), 123.11 (s, two overlapped aromatic signals), 72.02 (s), 70.64 (m, unresolved signals of PEG), 70.17 (s), 68.02 (s), 59.14 (s, CH$_3$), 39.41 (s, CH$_2$—N). The $^{13}$C NMR assignments were confirmed by $^{13}$C DEPT. $^1$H and $^{13}$C NMR spectra of the product are given in FIG. 9 and FIG. 10. MS-ESI (m/z): calculated for C$_{94}$H$_{150}$N$_2$O$_{38}$ 1,916; found 1,939 [M+Na]$^+$; MS MALDI-TOF (m/z) 1,916 [M]$^+$.

Example 2

Reduction of N,N'-Bis(PEG$_{17}$)perylene-3,4:9,10-tetracarboxylic diimide (Preparation of Compound 3)

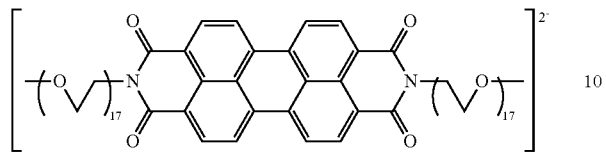

(3)

Figure 3:
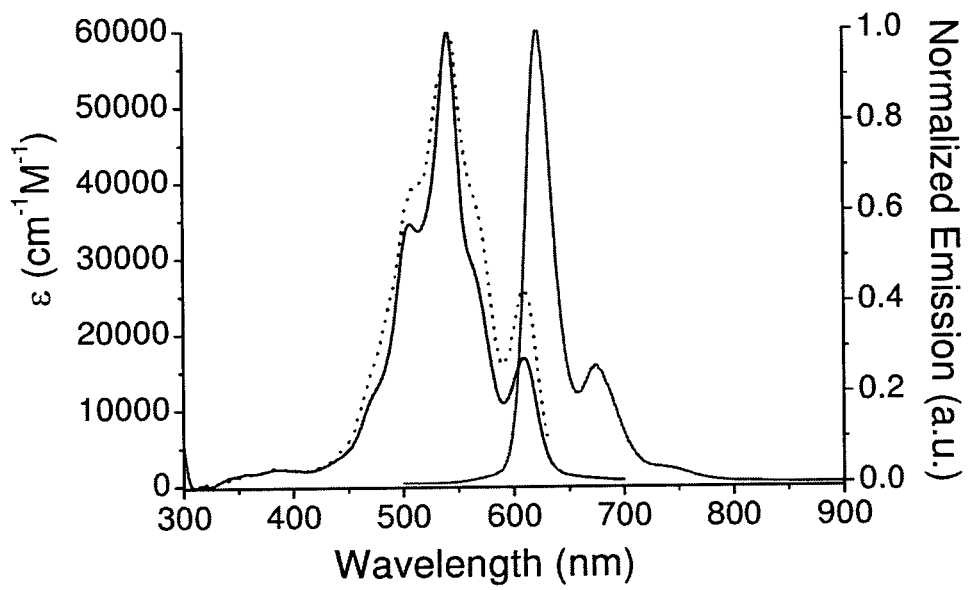
FIG. 3 depicts an absorption (black line), emission (red line), and excitation (dotted line) spectra of the doubly reduced compound of formula 3 in water.
Figure 4:
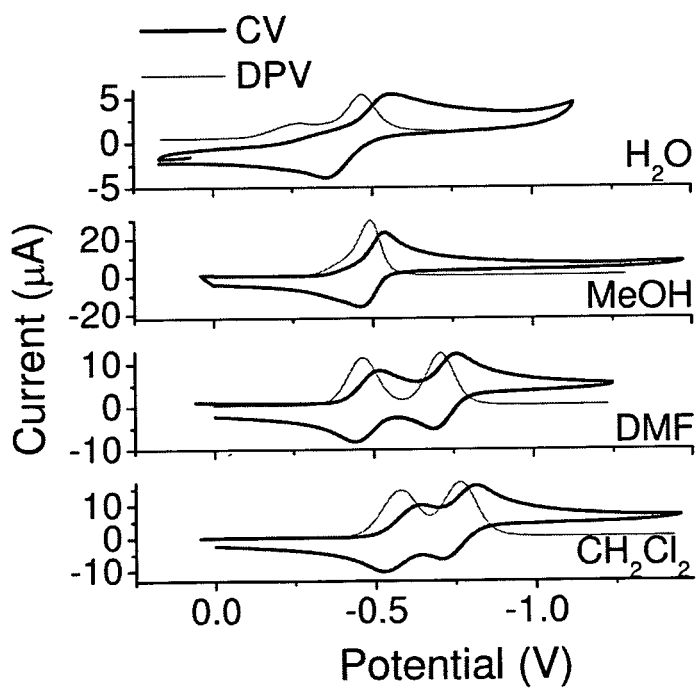
FIG. 4 depicts a cyclic and differential pulse voltammograms for the compound of formula III in various solvents.
Figure 5:
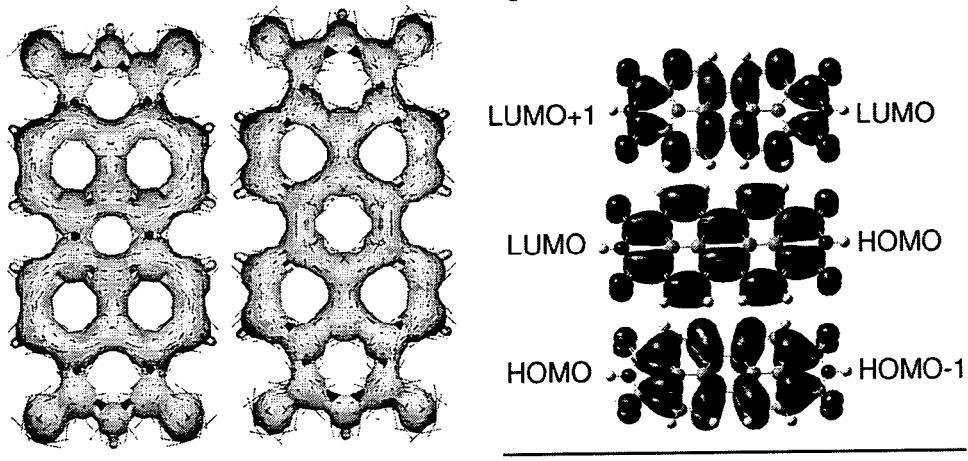
FIG. 5 depicts an AICD (Anisotropy of the Induced Current Density) plots and orbital diagrams of PDI and $PDI^{2-}$ model systems.
Figure 6:
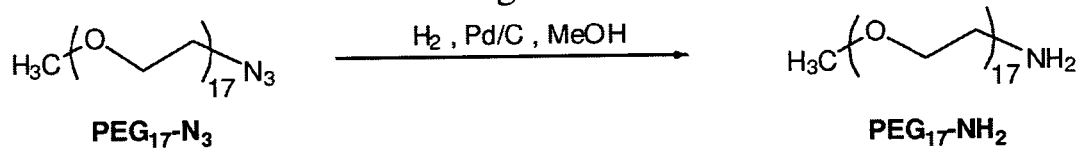
FIG. 6 depicts a synthetic scheme for the preparation of the compound of formula III.
Figure 6:
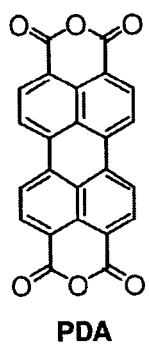
Figure 6:
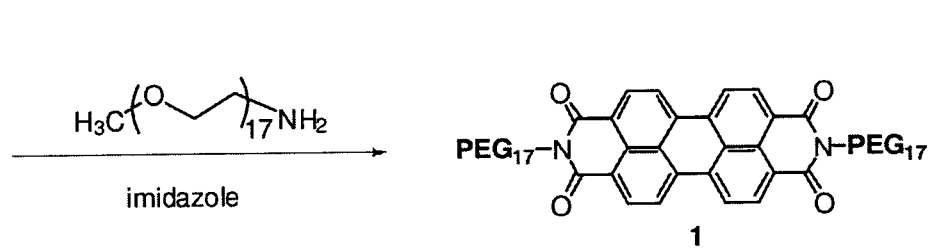

Reductions of the FIG. 1 compound (compound III) were performed in a nitrogen filled glove box. Solutions of the FIG. 1 compound in deoxygenated water were treated with sodium dithionite using weighted powder or stock solutions in deoxygenated water. $^1$H NMR (500 MHz, D$_2$O, ppm): 8.05 (d, 4H-1, $J_{HH}$=10.0 Hz, ArH), 7.95 (d, 4H, ArH) 3.09-3.90 (m, 160H, PEG). Broadening at concentrations above 10$^{-4}$ M precluded acquisition of $^{13}$C NMR spectra. Absorption: ∈ (541 nm)=59700 M$^{-1}$cm$^{-1}$, ∈ (609 nm)=16800 M$^{-1}$cm$^{-1}$; Emission: $\lambda_{max}$=622 nm, Φ=0.1 (FIG. 3).

Example 3

Formation of Acetylene-Bridged Perylene Dimers

As illustrated in FIG. 12, 2 e.q of PEG-PDIBr (obtained in a reaction of equimolar amounts of 1,7-PDIBr$_2$, PEGOH and NaH in THF, purified by SiO$_2$ column, yield 79%) was mixed with 1 eq of ditin derivative in toluene or THF at r.t. overnight in the presence of Pd catalyst. The product was separated using column chromatography (SiO$_2$, chloroform/MeOH as an eluent). Yield 90%.

Example 4

Formation of Diethynylbenzene-Bridged Perylene Dimers

As illustrated in FIG. 13, 2 eq. of PEG-PDIBr (obtained in a reaction of equimolar amounts of 1,7-PDIBr$_2$, PEGOH and NaH in THF, purified by SiO$_2$ column, yield 79%) was mixed with 1 eq. of diethynyl benzene in diisopropyl amine at room temperature overnight in the presence of Pd catalyst. The product was separated using column chromatography (SiO2, chloroform/MeOH as an eluent). Yield 90%.

Example 5

Synthesis of 1,2-bis(N,N'-bis(1-ethylpropyl)-3,4,9,10-tetracarboxylic diimide-7-(polyethylene glygol)-perylen-1-yl)ethyne (Compound IX)

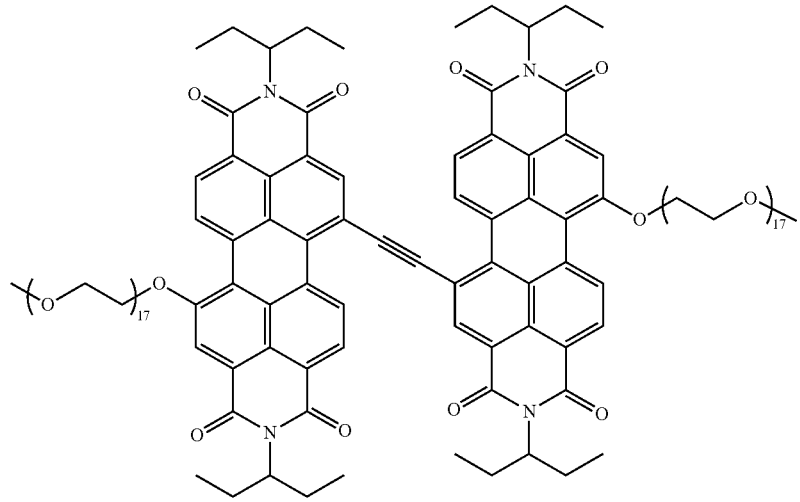

(IX)

As illustrated in FIG. 12 Compound IX was prepared as follows: A mixture of PEG-PDI-Br (50 mg, 0.036 mmol) and Bis-(tributylstannyl)acetylene (11 mg, 0.018 mmol) was dissolved in toluene (1 ml) and stirred for 10 min. Di-Palladium-tri-Dibenzylideneacetone (1.65 mg, 1.8 μmol) and tri-(t-Butyl)phosphine (0.727 mg, 3.6 μmol) were dissolved in toluene (1 ml) and stirred for 10 min in a separate vial. Then the mixtures were combined and stirred at r.t. for 6 h. accompanied by color change from red to deep purple. Then the reaction mixture was washed with brine and purified by column chromatography (silica 60-200 micron, eluted with acetone/methanol (1:1)) to afford 43 mg of 1 as a dark purple solid. Yield 90%.

GPC showed polydispersity of 1.06. $^1$H NMR (CDCl$_3$): δ=10.12 (d, 2H, $J_{HH}$=8.4, perylene-H), 9.76 (d, 2H, $J_{HH}$=8.4 Hz, perylene-H), 8.97 (s, 2H, perylene-H), 8.72 (d, 2H, perylene-H), 8.54 (d, 2H, $J_{HH}$=8.0 Hz, perylene-H), 8.52 (s, 2H, perylene-H), 5.07 (m, 4H, N(CH(CH$_2$CH$_3$)$_2$), 4.69 (m, 4H, PEG), 4.13 (m, 4H, PEG), 3.88 (m, 4H, PEG), 3.80 (m, 4H, PEG), 3.64 (bs, 88H, PEG), 3.37 (m, 6H, PEG-OCH$_3$), 2.27 (m, 8H, N(CH(CH$_2$CH$_3$)$_2$), 1.93 (m, 8H, N(CH (CH$_2$CH$_3$)$_2$), 0.93 (m, 24H, N(CH(CH$_2$CH$_3$)$_2$). $^{13}$C NMR (CDCl$_3$): 157.6, 135.62, 133.39, 129.21, 128.92, 128.4, 128.16, 127.62, 124.09, 120.8, 117.81, 97.69 (PDI-C≡C-PDI), 71.93, 71.08, 70.87, 70.74, 70.57, 69.48, 69.42, 59.04, 57.71, 25.02, 11.39, 11.35. MS-MALDI-TOF calcd for C$_{140}$H$_{198}$N$_4$O$_{44}$: 2639.34, found 2639 [M$_+$]. UV/vis (CHCl3): $\lambda_{max}$/nm (∈/M$_{-1}$ cm$_{-1}$)=412.4 (12704), 461.25 (13798), 537.9 (29425), 573.5 (28482), Fluorescence: $\lambda_{max}$=693 nm, quantum yield Φ$_f$=0.06.

Figure 15:
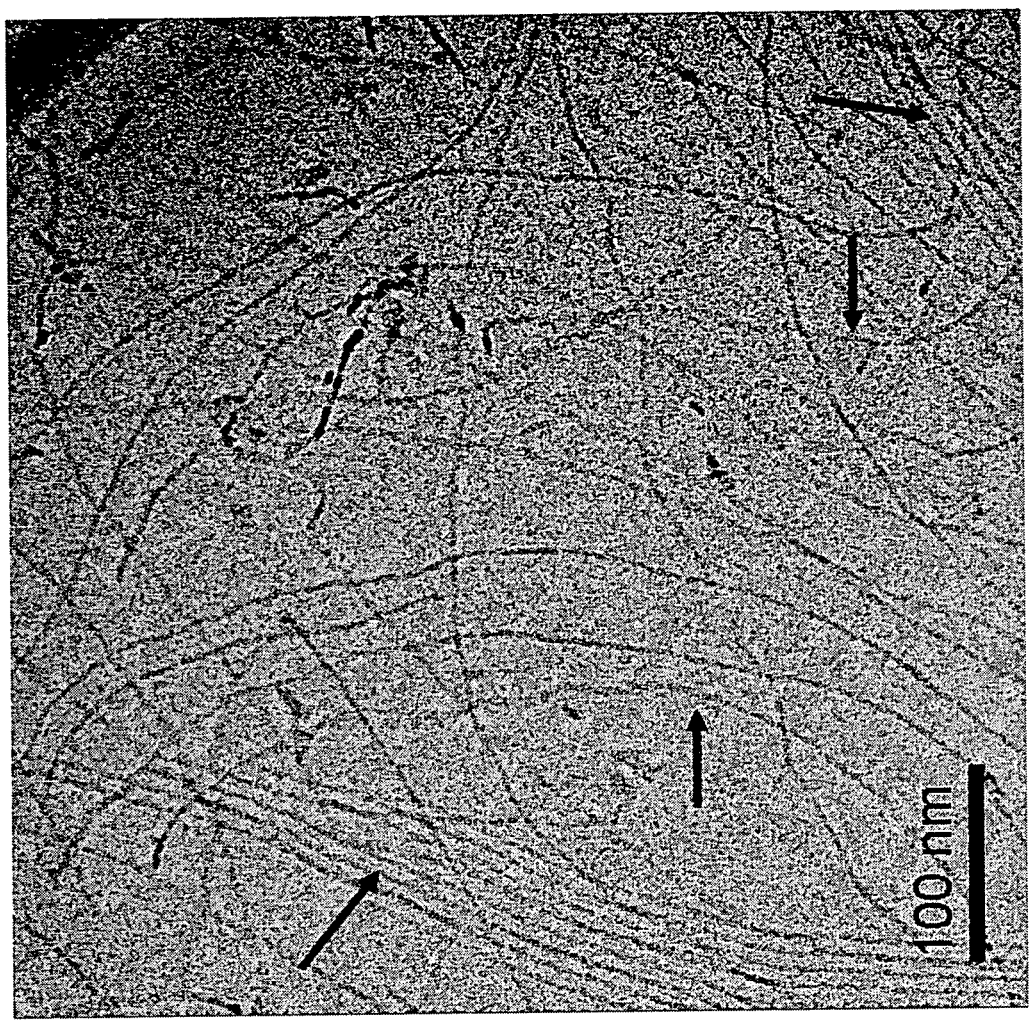
FIG. 15 depicts a cryo-TEM image of a supramolecular polymer formed by Compound IX in water/THF (4:1 v/v, $1\times10^{-3}$ M).
Figure 16:
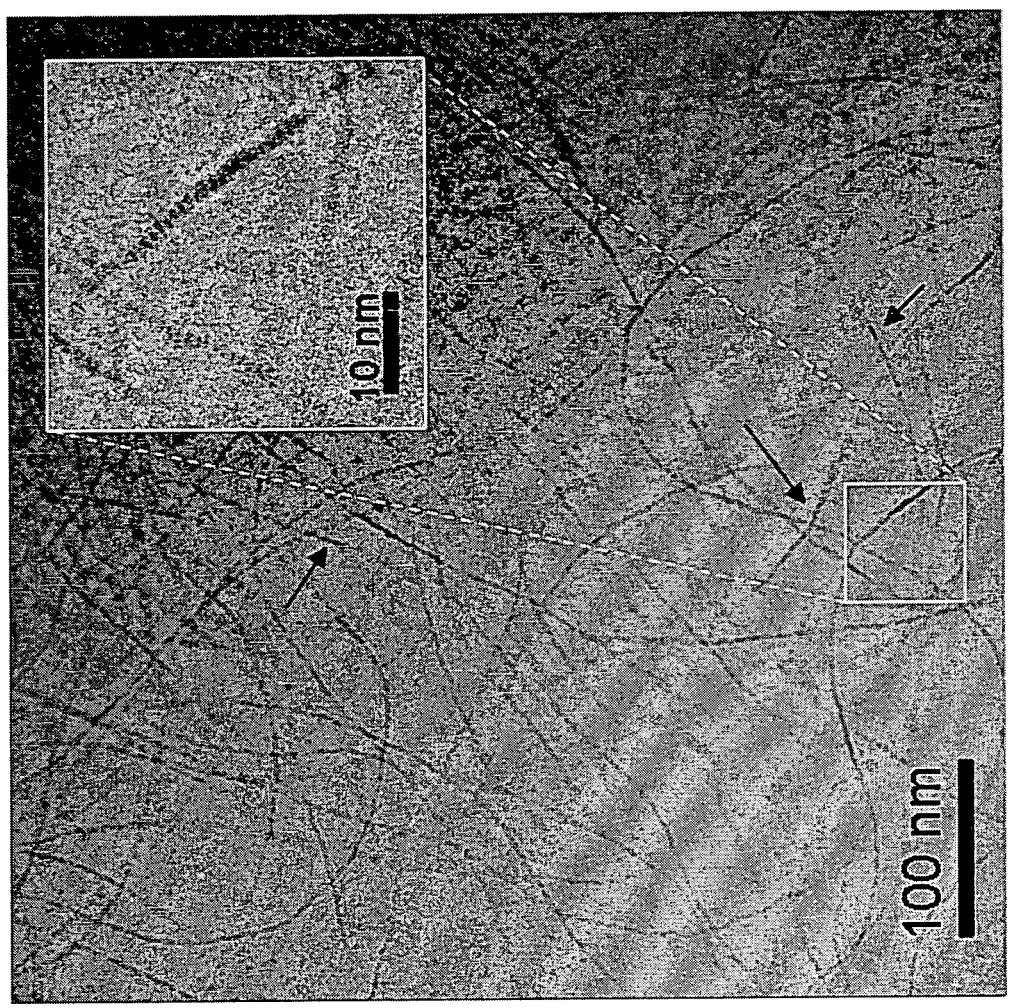
FIG. 16 depicts the system shown in FIG. 15 after reduction, followed by oxidation in air.

In water/THF mixture (4:1, v/v) compound IX self-assembles into long fibers as evidenced by cryogenic transmission electron microscopy (cryo-TEM), see FIG. 15. The fibers show a ribbon-like structure, and the fiber twisting from a narrow high-contrast edge (3.1±0.4 nm) to a wider low-contrast face (8.8±1.1 nm) is observed (FIG. 15, black arrows). The length of the fibers reaches several microns. Occasional tightly packed domains of aligned fibers show fiber-to-fiber spacings of 9.7±0.7 nm, which correspond to a high contrast ordered aromatic core (responsible for fiber images in cryo-TEM) and low contrast solvated PEGs (inter-fiber area). Individual fibers show segmented, "necklace" structure (FIG. 16). Such hierarchical structures with segmented core are rare, and may occur due to kinetic trapping. Notably, the 1.8-nm segment periodicity (segment height of 1.2 nm and the low contrast inter-segment spacing of 0.6 nm) is almost identical throughout all structures and corresponds well to the PDI dimensions.

To corroborate cryo-TEM results, solution-phase small angle X-ray scattering (SAXS) studies were performed on the self-assembled fibers of compound IX using a high-flux synchrotron source. SAXS shows a pattern typical for rod-like structures, and analysis of SAXS data gives radius of gyration $R_g$=113 nm, cross-section diameter of 8.2 nm, persistence length of 27 nm, and contour length of 1.5 μm, in agreement with cryo-TEM.

Figure 17:
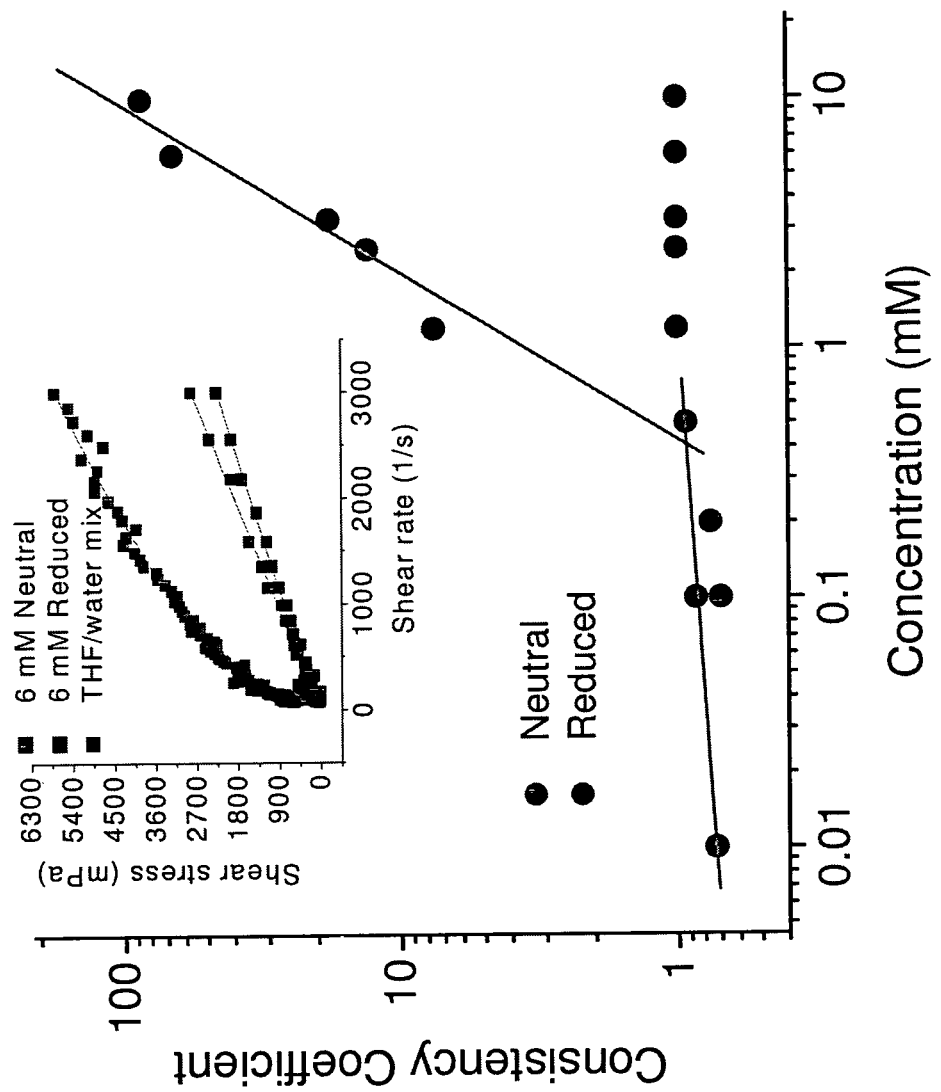
FIG. 17 depicts the concentration dependence of viscosity of Compound IX in water/THF (4:1 v/v) (left) and the normalized UV-vis spectra of disaggregated Compound IX in chloroform and self-assembled Compound IX in water/THF (4:1 v/v) (right).
Figure 17:
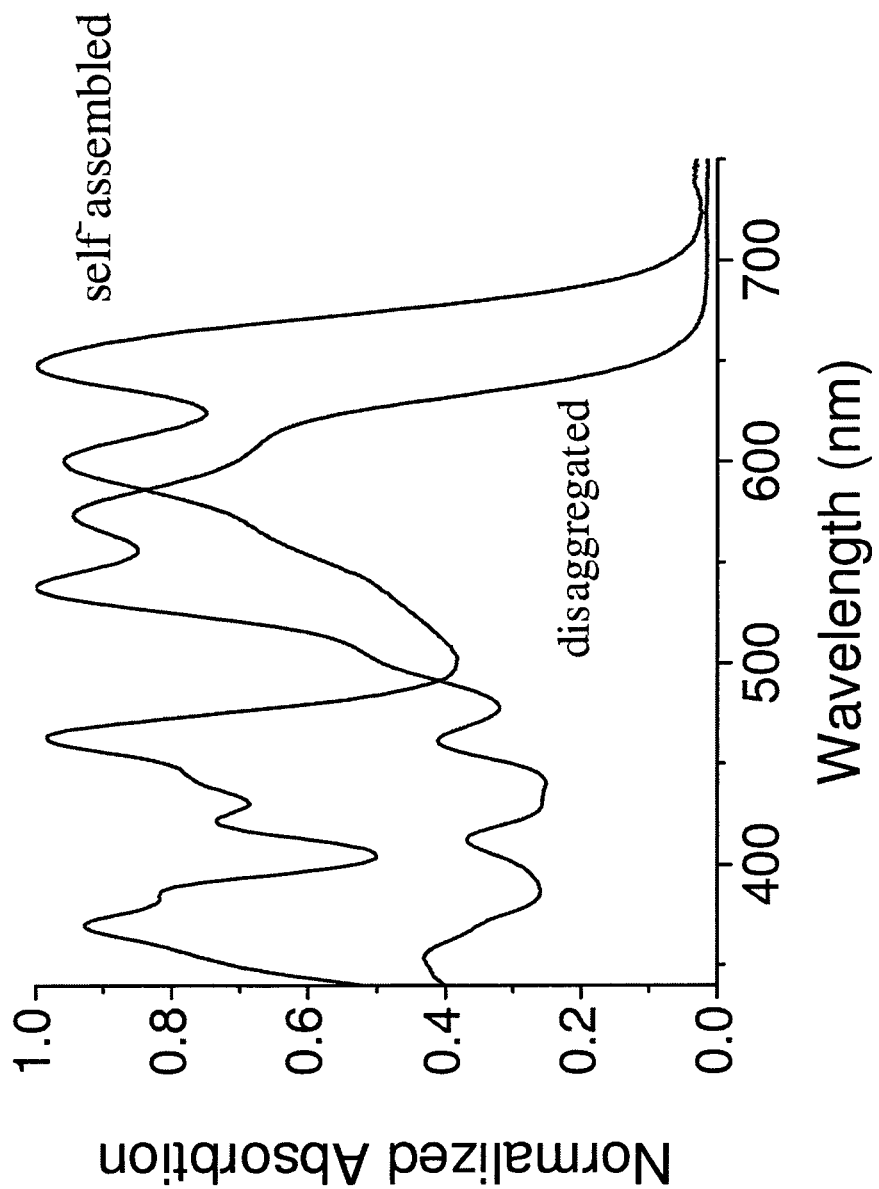

Rheological measurements of compound IX in water/THF solution reveal shear thinning behavior, characteristic of linear polymers and worm-like micelles whose, chains become untangled and oriented by flow. Furthermore, distinctive switching of viscosity regimes upon increase in concentration (FIG. 17) indicates the entanglement onset at ~$10^{-3}$ M. UV-vis spectra of compound IX in water/THF solution show a significant red shift in the PDI absorption in comparison to compound IX in disaggregated state (FIG. 17), indicative of slipped stack formation (J-aggregates).

Reduction of compound IX in water/THF solution (8:2, v/v) with 10 eq. of sodium dithionite results in color change from green to blue, accompanied by a dramatic viscosity drop (FIG. 17), indicating polymer fission. The fission is evidenced by cryo-TEM, revealing formation of spherical micelles, 8.3±1.7 nm in diameter. The reduced system was not sufficiently stable for SAXS studies. The reduced compound of formula 10 gives rise to a broad absorption peak (450-700 nm) in UV-vis spectra, while EPR shows the presence of paramagnetic species. Electrochemistry of compound 10 in water/THF solution reveals four one-electron reductions (−0.39, −0.52, −0.77, and −1.52 V vs SCE), as expected for accommodation of two electrons by each PDI unit. The reduced Compound 10 is stable for days when kept under inert atmosphere and protected from light. Upon exposure to air the reduced system is oxidized to neutral compound IX within 1 h, restoring the supramolecular polymeric fibers as evidenced by cryo-TEM and UV-vis (identical to the neutral system). The fibers retain ribbon-like segmented structure, with high contrast width of 3.1±0.3 nm, and lower contrast width of 9.1±1.1 nm. The cycle can be repeated at least three times.

Example 6

Synthesis of 4'-(4-((N,N'-bis(1-ethylpropyl)-3,4,9,10-tetracarboxylic diimide-7-(polyethylene glygol)-perylen-1-yl)ethynyl)phenyl)-2,2':6',2"-Terpyridine (Compound XI)

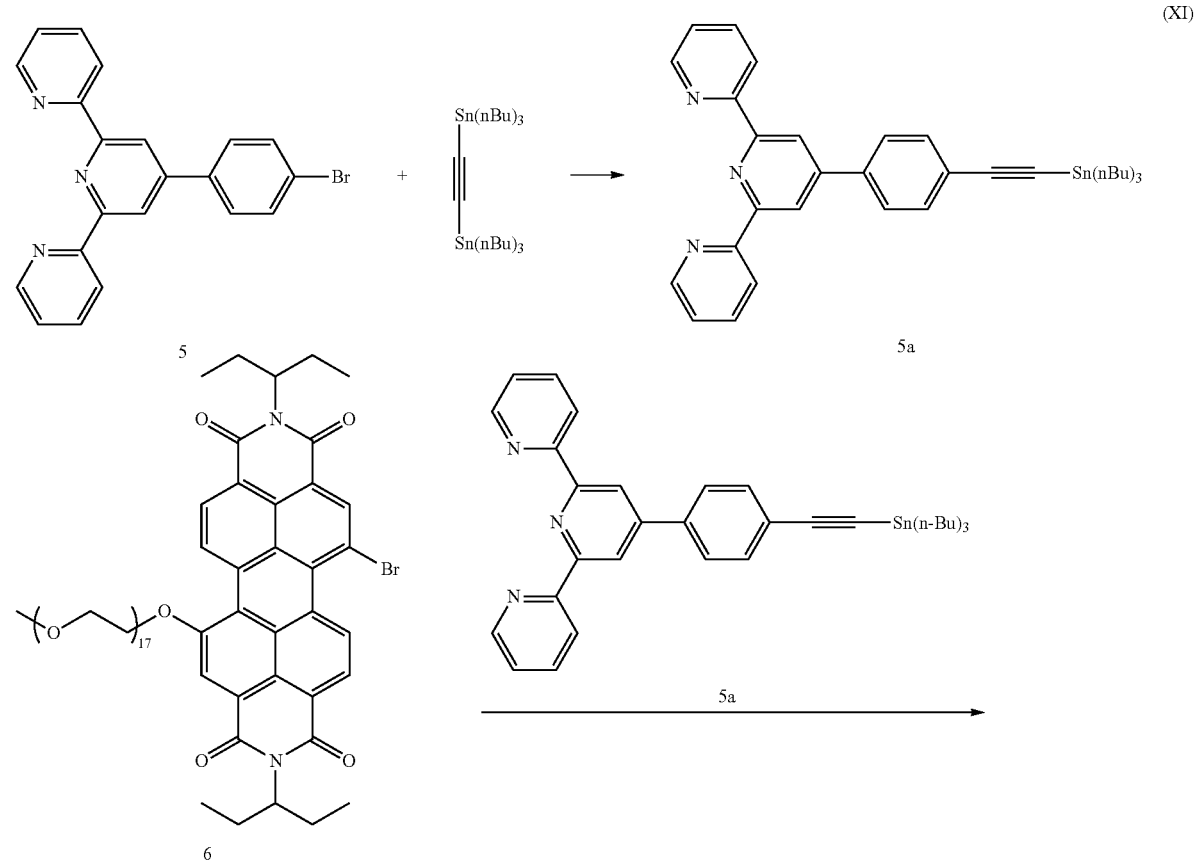

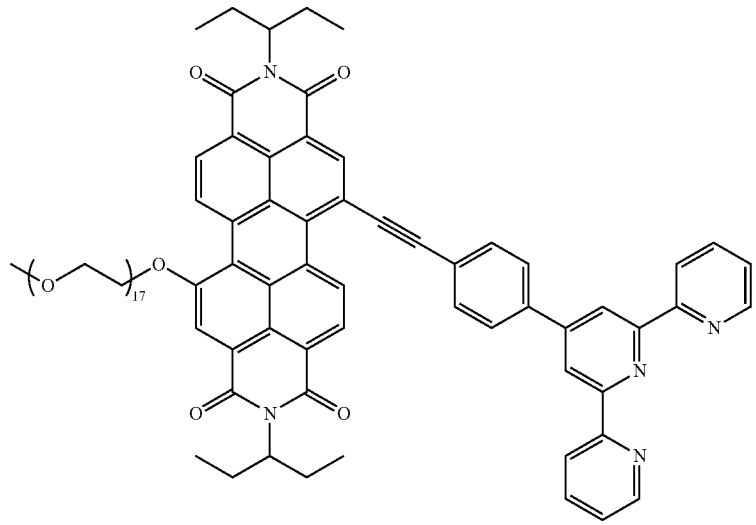

1

In a glove box, compound 5 (56 mg, 0.144 mmol), Pd$_2$(DBA)$_3$ (6.6 mg, 0.0072 mmol), P($^t$Bu)$_3$ (3.2 mg, 0.014 mmol), and 5 ml of toluene were stirred for 5 min at r.t. and then added dropwise to the toluene solution (5 ml) of bis-(tributylstannyl)acetylene (91 µl, 0.173 mmol). The mixture was stirred overnight at room temperature. Then the reaction mixture (compound 5a obtained in situ) was filtered through a 0.2 µm teflon filter. Compound 6[3] (200 mg, 0.144 mmol), Pd$_2$(DBA)$_3$ (6.6 mg, 0.0072 mmol) and 10 ml of toluene were mixed in vial. The mixture was stirred for 5 min and then added dropwise to the solution of 5a prepared as described above. The reaction was allowed to stir overnight at room temperature followed by solvent removal under vacuum. The solid was dissolved in minimal amount of methylene chloride and precipitated with hexane. The precipitate was washed with hexane, dissolved in the minimal amount of methylene chloride and precipitated with diethyl ether. The resulting precipitate was dissolved in chloroform and subjected to silica gel chromatography using chloroform/methanol (97:3, v/v) mixture as an eluent to yield 129 mg of 1 (Compound XI) as a purple solid. Yield 55%.

$^1$H NMR (400 MHz, CDCl$_3$): δ 0.92 (t, JHH=7.4, CH$_3$, 6H), 0.93 (t, JHH=7.4, CH$_3$, 6H), 1.88-1.99 (m, CH$_2$, 4H), 2.32-2.34 (m, CH$_2$, 4H), 3.35 (s, CH$_3$, 3H), 3.51-3.70 (m, CH$_2$, 60H), 3.76-3.78 (m, CH$_2$, 2H), 3.84-3.86 (m, CH$_2$, 2H), 4.09 (t, JHH=4.4, CH$_2$, 2H), 4.64 (t, JHH=4.4, CH$_2$, 2H) 5.08 (m, CH, 2H) 7.34-7.37 (td, JHH=1.0, JHH=7.7 ArH, 2H), 7.77 (d, JHH=8.3 Hz, ArH, 2H), 7.85-7.90 (td, JHH=1.7, JHH=4.8, ArH, 2H), 7.99 (d, JHH=8.2, ArH, 2H), 8.46 (s, PDI, 1H), 8.66 (d, JHH=7.9, Ar—H, 4H), 8.73 (d, JHH=3.6, ArH, 2H), 8.77 (s, ArH, 2H), 8.91 (s, PDI, 1H), 9.70 (d, JHH=8.4, PDI, 1H); 10.13 (d, JHH=8.2, PDI, 1H); $^{13}$C {$^1$H} NMR (400 NMR, CDCl$_3$): 157.33, 156.12, 156.01, 149.17, 149.06, 139.38, 136.87, 134.90, 134.11, 133.76, 132.34, 129.05, 129.01, 128.06, 127.78, 127.69, 124.03, 123.09, 121.31, 120.95, 118.81, 118.70, 96.76, 92.55, 71.9, 70.75 (m, unresolved signals of PEG), 69.46, 69.33, 59.02, 57.60, 25.06, 11.32.

MS-MALDI (m/z): [M+Na$^+$], calcd. for C$_{92}$H$_{113}$N$_5$NaO$_{22}$, 1663.79; found 1663.49; GPC: Mw/Mn=1.1; UV-vis (CH$_2$Cl$_2$): λabs/nm (∈/M$^{-1}$cm$^{-1}$)=575 (30000), 537 (21800), 460 (5900), 410 (7200). Fluorescence (CH2Cl2): λmax/nm=603; Φf=0.82. Electrochemistry: Redox potentials (V vs SCE): Ered1=−0.67; Ered2=−0.81; Ered3=−1.37; Eox=1.43

Figure 18A:
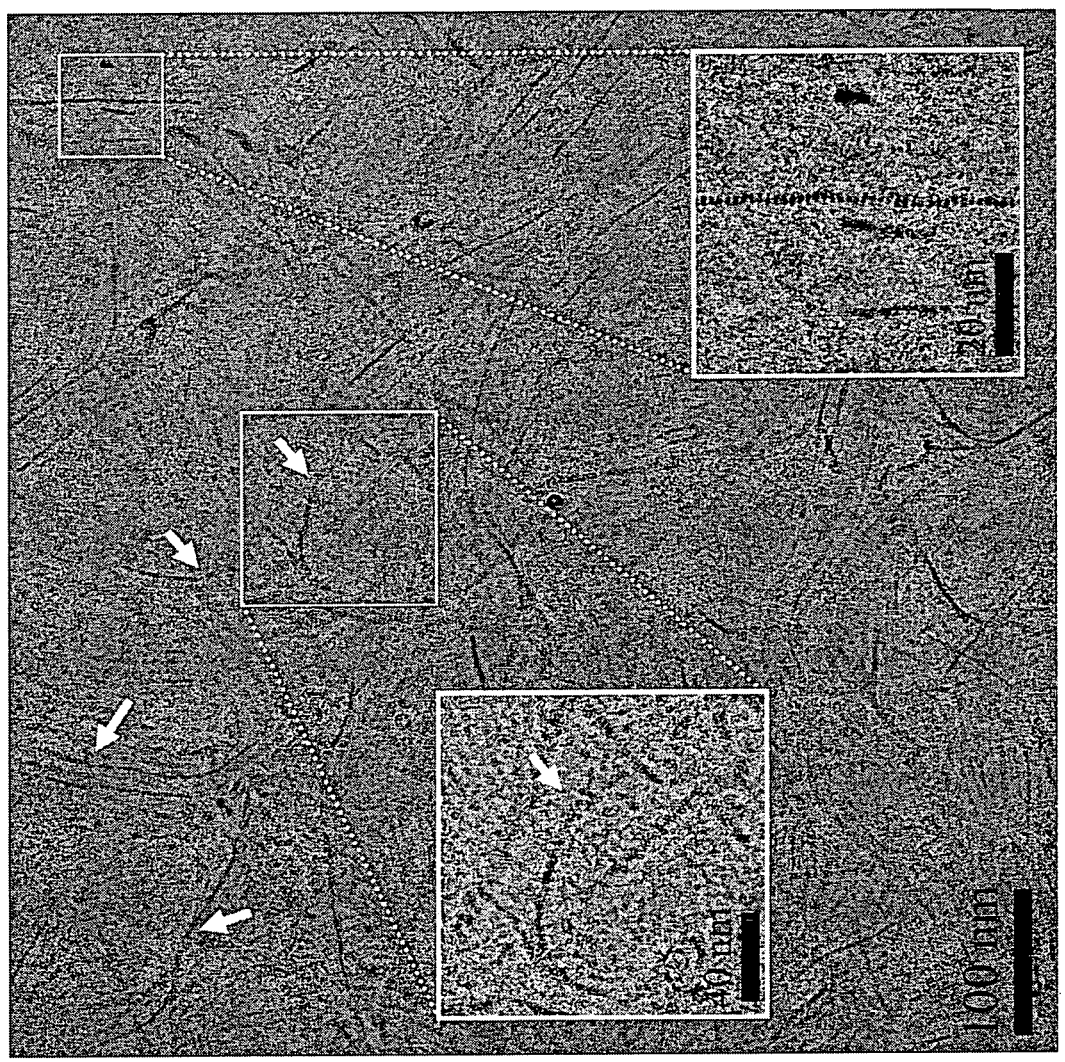
FIG. 18A depicts a cryo-TEM image of a supramolecular polymer formed by Compound XI in water/THF (9:1 v/v, $2\times10^{-4}$ M). The right inset shows an enlarged image of a segmented fiber (scale bar 40 nm). The left inset shows an enlarged image of a fiber twist (scale bar 20 nm). The white arrows point at twisting regions (from the narrow edge to the wider face) of ribbon-like fibers.
Figure 18B:
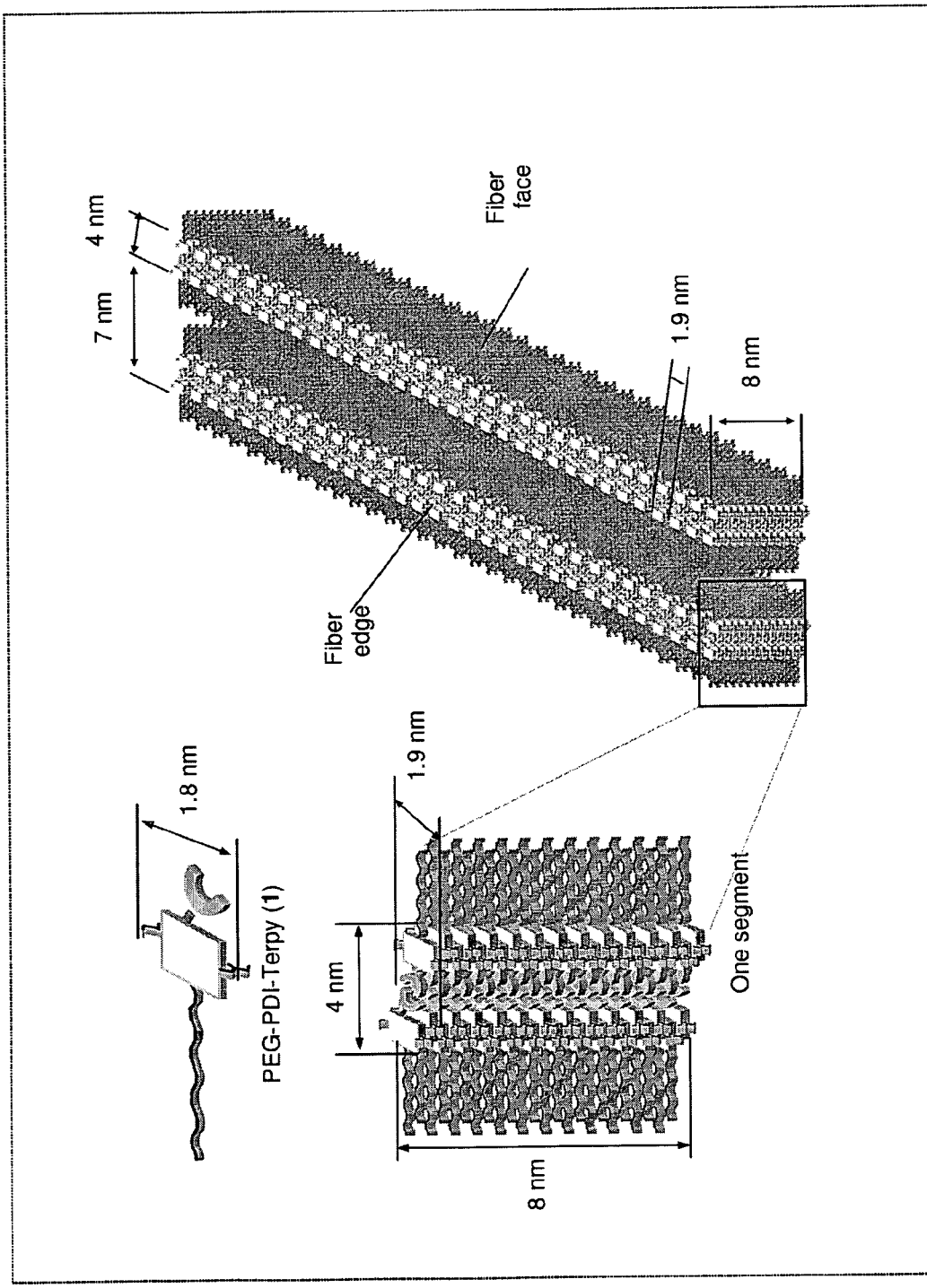
FIG. 18B depicts a possible structure for the supramolecular polymer depicted in FIG. 18A.
Figure 18C:
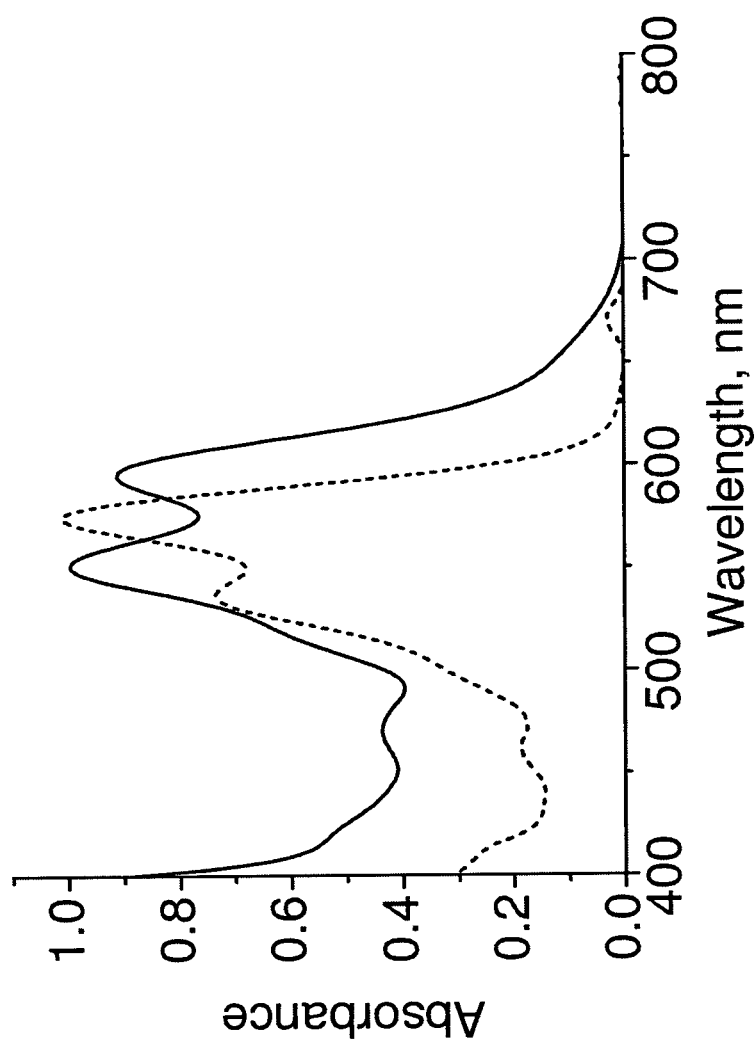
FIG. 18C depicts normalized UV-vis spectra of a solution of Compound XI in dichloromethane (disassembled, dotted line) and in water/THF (9:1, v/v) solution (solid line).

In water/THF mixture (9:1, v/v) compound XI self-assembles into long fibers (FIG. 18A) as evidenced by cryogenic transmission electron microscopy (cryo-TEM). The fibers show a ribbon-like structure, and an occasional twisting of the ribbons from their narrower, high-contrast edges (4±0.6 nm) to their wider low-contrast faces (7.9±1.3 nm) is observed (FIG. 18A, white arrows). Most of the fibers appear to extend over the entire cryo-TEM image, probably reaching several microns in length. The aligned, tightly packed fibers exhibit fiber-to-fiber spacing of 7.1±0.8 nm, corresponding to a high contrast ordered aromatic core (responsible for fiber images in cryo-TEM) and low contrast solvated PEGs (inter-fiber area). Individual fibers show segmented structure. The 1.9 nm segment periodicity is almost identical throughout all structures and corresponds well to the PDI dimensions. Possible structure of the fibers is presented in FIG. 18B (all schematic structures are based on molecular modeling). Comparison between the UV-vis spectra of the assembled and disassembled compound XI (FIG. 18C) shows that self-assembly causes change in the 0→0 and 0→1 transition intensities and substantial broadening of the spectrum. The complete inversion of 0→0 and 0→1 transition intensities is typical for face-to-face stacking (H-aggregation) of PDIs. Lesser degree of inversion in the case for compound XI may be due to a less significant overlap of PDI aromatic systems or structural in-homogeneity in the fibers.

Example 7

Synthesis of Palladium chloro(4'-(4-((N,N'-bis(1-ethylpropyl)-3,4,9,10-tetracarboxylic diimide-7-(polyethylene glygol)-perylen-1-yl)ethynyl)phenyl)-2,2':6',2"-Terpyridine) triflate (Compound XII)

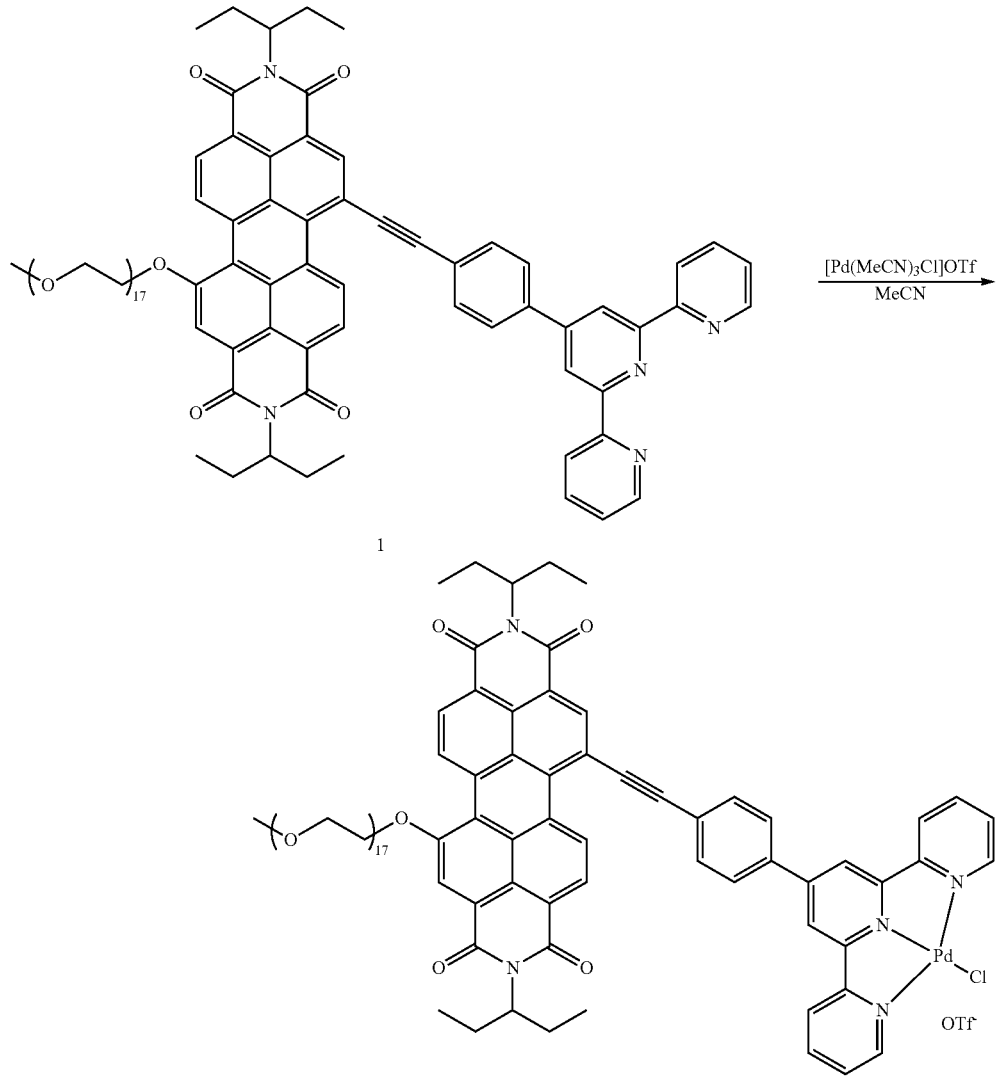

Bis(benzonitrile)palladium dichloride (25 mg, 0.0652 mmol) and silver triflate (17 mg, 0.066 mmol) were dissolved in 10 ml of acetonitrile and inserted into a pressure flask equipped with a magnetic stirrer. The pressure flask was heated at 85° C. upon stirring for 15 h resulting in formation of precipitate (silver chloride).

The solution was filtered using 0.2 μm PTFE filter to remove silver chloride, and 2 ml of the filtrate (containing 0.013 mmol of [Pd(MeCN)$_3$Cl]OTf) were inserted into a pressure flask, to which compound 1 (20 mg, 0.012 mmol) dissolved in 10 ml of toluene/acetonitrile (1:1, v/v) was added. The pressure flask was heated overnight at 85° C. upon stirring. Then it was cooled to room temperature and the reaction mixture was evaporated to dryness, dissolved in a minimal amount of methylene chloride and precipitated with diethyl ether to yield 20 mg (92%) of 2 (Compound XII) as a purple solid.

$^1$H NMR (400 MHz, CDCl$_3$): δ 0.98 (overlapping t, JHH=7.5, CH$_3$, 12H), 1.99 (m, CH$_2$, 4H), 2.28 (m, CH$_2$, 4H), 3.35 (s, CH$_3$, 3H), 3.52 (m, CH$_2$, 2H), 3.62 (m, CH$_2$, 52H), 3.67 (m, CH$_2$, 2H), 3.71 (m, CH$_2$, 2H), 3.80 (m, CH$_2$, 2H), 3.89 (m, CH$_2$, 2H), 4.15 (unresolved t, CH$_2$, 2H), 4.69 (unresolved t, CH$_2$, 2H) 5.06 (m, CH, 2H), 7.23 (unresolved t, ArH, 2H), 7.39 (d, ArH, 2H), 8.09 (d, ArH, 2H), 8.14 (unresolved t, ArH, 4H), 8.25 (d, ArH, 1H), 8.29 (s, PDI, 1H), 8.47 (s, PDI, 1H), 8.62 (s, ArH, 2H), 8.64 (d, JHH=8.3, Ar—H, 1H), 8.84 (d, JHH=7.7, ArH, 2H), 9.71 (d, JHH=8.5, PDI, 1H); 9.83 (d, JHH=8.0, PDI, 1H). $^{13}$C NMR (400 NMR, CDCl$_3$): 157.55, 157.42, 154.17, 152.10, 152.08, 142.22, 134.96, 133.97, 133.26, 132.39, 129.14, 128.95, 128.63, 128.57, 128.11, 127.94, 127.29, 126.22, 125.13, 123.76, 122.34, 121.43, 121.38, 120.71, 119.16, 117.51, 115.98, 71.71, 70.41 (m, unresolved signals of PEG), 69.44, 58.97, 57.89, 25.03, 11.48. $^{19}$F NMR (500 MHz, CDCl$_3$): δ −78.91;

MS-MALDI (m/z): [M$^+$]. calcd. for C$_{92}$H$_{113}$ClN$_5$O$_{22}$Pd: 1782.77; found 1782.66; UV-vis (CH$_2$Cl$_2$): λabs/nm (∈/M$^{-1}$ cm$^{-1}$)=575 (31900), 538 (25500), 412 (24600); Fluorescence (CH$_2$Cl$_2$): λmax/nm=605; Φf=0.20. Electrochemistry: Redox potentials (V vs SCE): Ered1=−0.54; Ered2=−0.72; Ered3=−0.94; Eox=1.44.

Figure 19A:
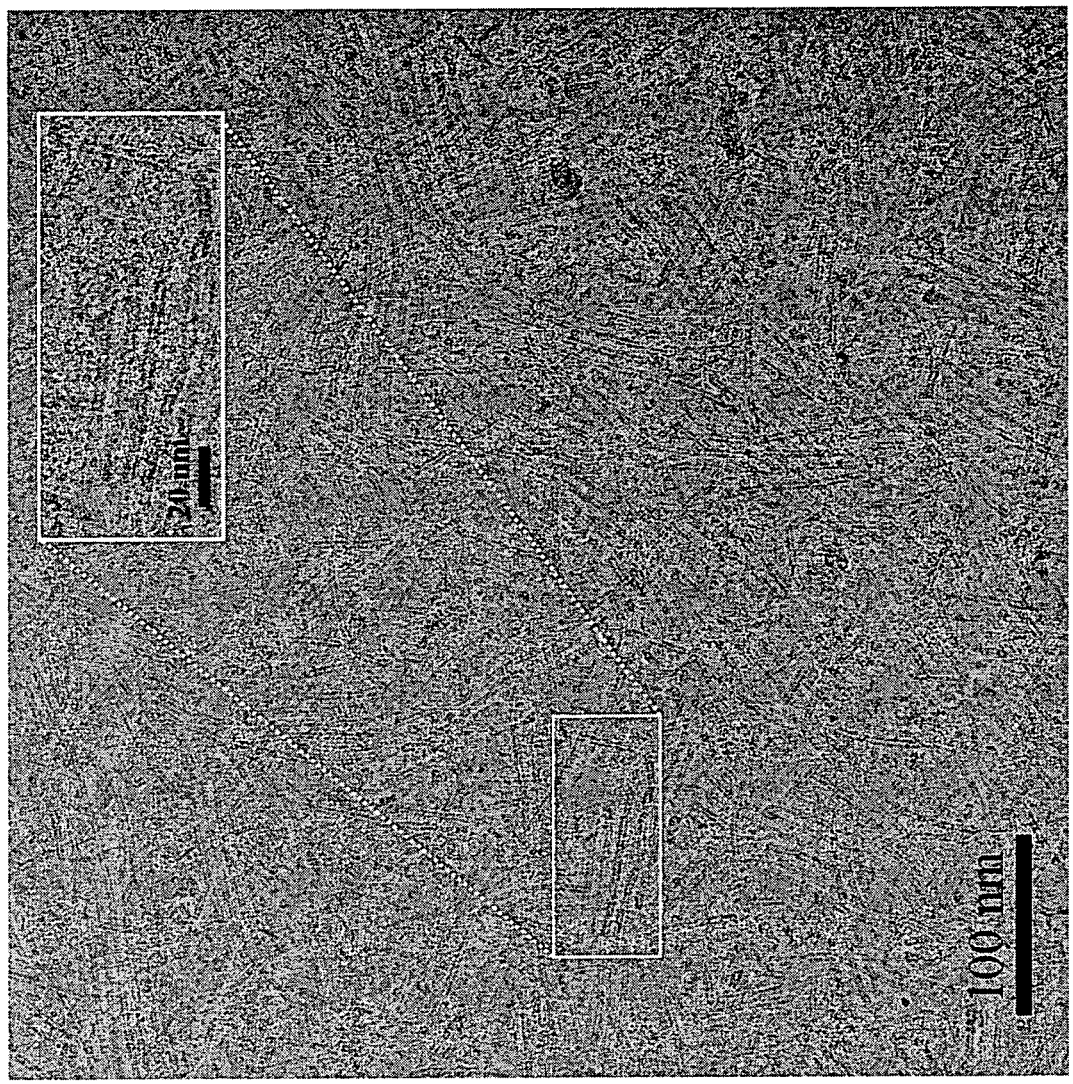
FIG. 19A depicts a cryo-TEM image of a supramolecular polymer formed by Compound XII in water/THF (9:1 v/v, $2 \times 10^{-4}$ M). The inset shows an enlarged image of a nanotube (scale bar 40 nm).
Figure 19B:
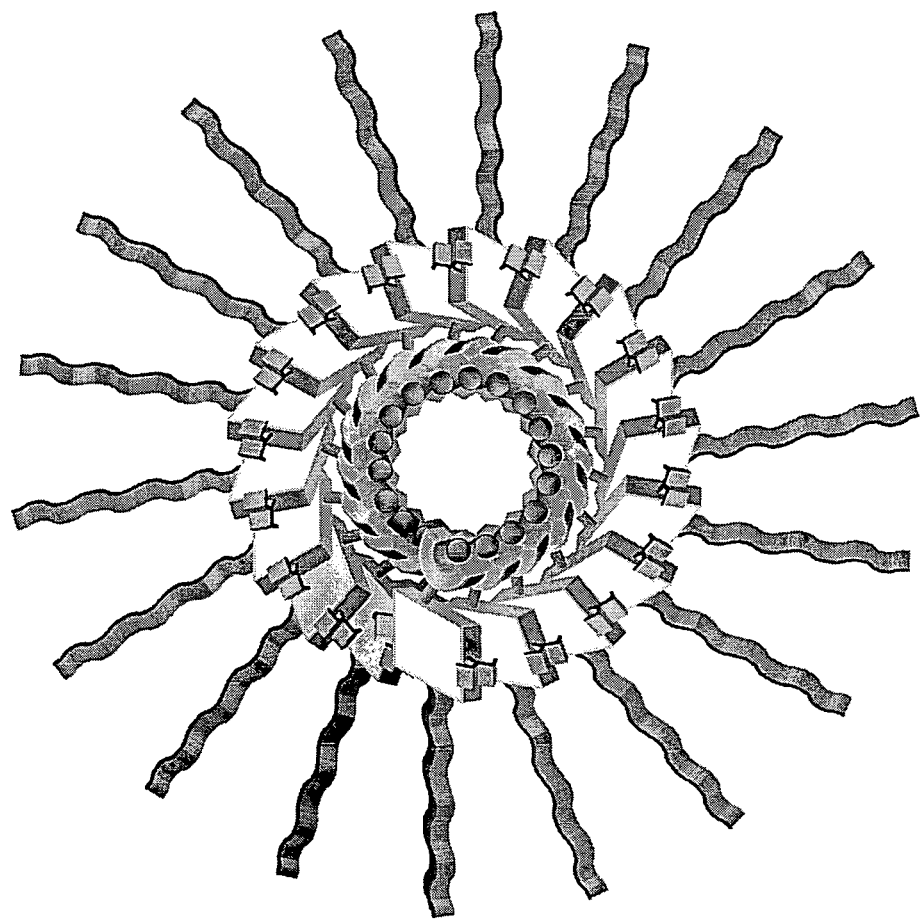
FIG. 19B depicts a possible structure for the supramolecular polymer nanotubes depicted in FIG. 19A.
Figure 19C:
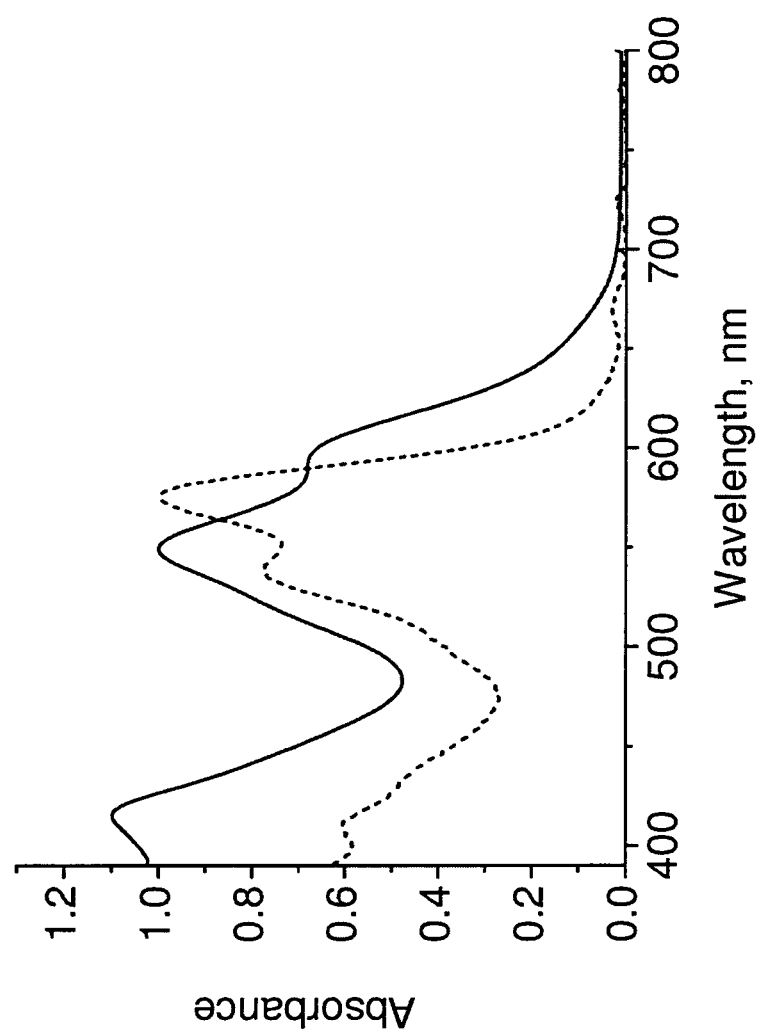
FIG. 19C depicts normalized UV-vis spectra of a solution of Compound XII in dichloromethane (disassembled, dotted line) and in water/THF (9:1, v/v) solution (solid line).

In water/THF mixture (9:1 v/v) Compound XII self-assembles into fiber-like structures as evidenced by cryo-TEM (FIG. 19A). The different contrast of the periphery and center of these structures is characteristic of the projection images of tubular aggregates (hollow cylinders). The nanotubes show uniform diameter of 4.7±0.4 nm. The internal diameter and the wall thickness are 1.1±0.2 nm and 1.8±0.2 nm respectively. The length of the nanotubes is difficult to estimate, while most of them appear to extend over the entire cryo-TEM image, probably reaching several microns in length. Comparison between UV-vis spectra of the aggregated and the disaggregated XII (FIG. 19C) reveals a swap in 0→0 and 0→1 transition intensities and significant broadening, typical of extended PDI assemblies with predominant face-to-face stacking (H-aggregation). The possible structure of the tube is presented in FIG. 19B. In this model PEG groups are located at the periphery of the tube and cationic Pd centers cover the inner part.

Example 8

Synthesis of Platinum chloro(4'-(4-((N,N'-bis(1-ethylpropyl)-3,4,9,10-tetracarboxylic diimide-7-(polyethylene glygol)-perylen-1-yl)ethynyl)phenyl)-2,2': 6',2"-Terpyridine)triflate (Compound XIII)

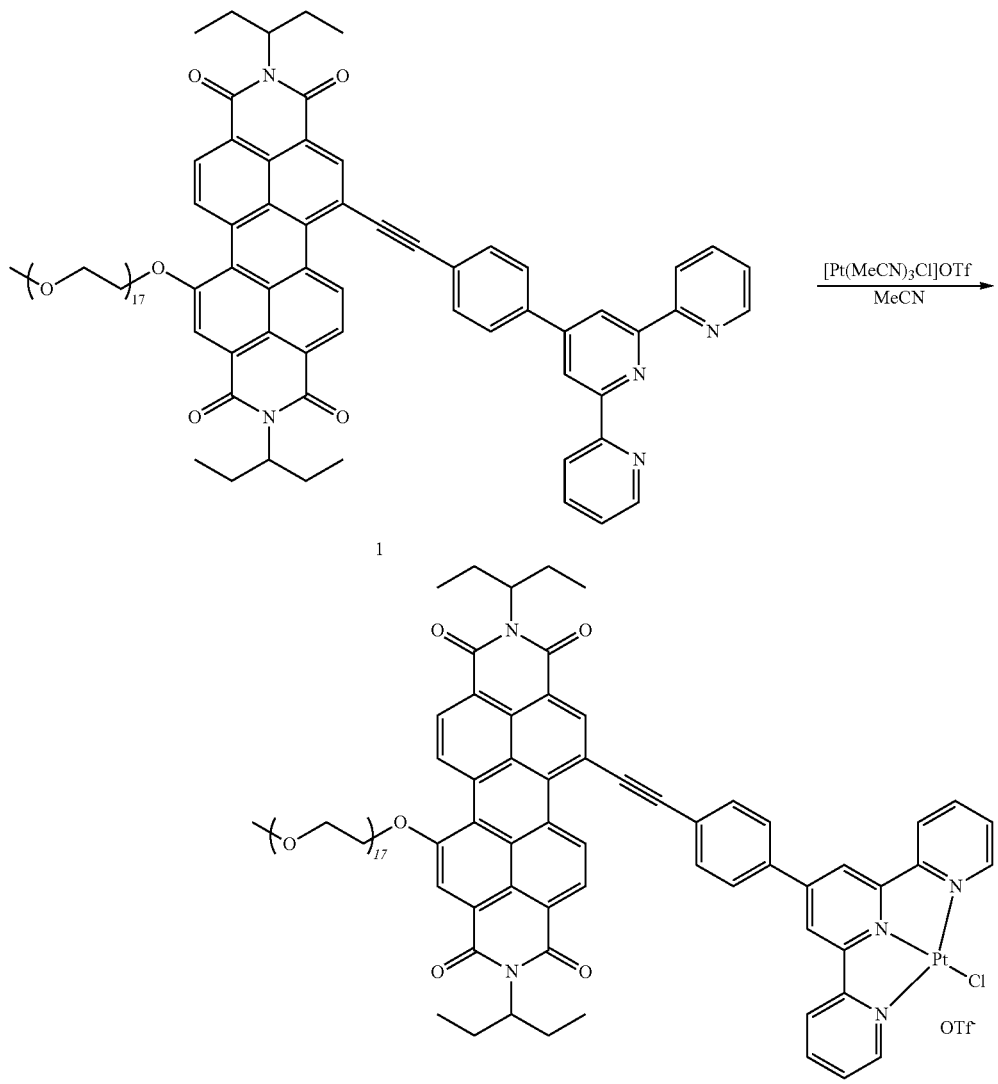

In a glove box, bis(benzonitrile)platinum dichloride (3 mg, 0.0635 mmol) and silver triflate (16.5 mg, 0.064 mmol) were dissolved in 10 ml of acetonitrile and inserted into a pressure flask equipped with a magnetic stirrer. The pressure flask was heated at 85° C. upon stirring for 15 h resulting in formation of precipitate (silver chloride).

The solution was filtered with 0.2 μm filter to remove silver chloride and 2 ml of the filtrate (containing 0.013 mmol of [Pt(MeCN)$_3$Cl]OTf) was inserted into a pressure flask, to which compound 1 (20 mg, 0.012 mmol) in 10 ml of toluene/acetonitrile (1:1, v/v) was added. The pressure flask was heated overnight at 85° C. upon stirring. Then it was cooled to room temperature, the solvent was stripped, and the residue was subjected to silica gel chromatography using chloroform/methanol (95:5, v/v) as an eluent to yield 17 mg (75%) as a purple solid.

$^1$H NMR (400 MHz, CDCl$_3$): δ 0.98 (overlapping t, JHH=7.5, CH$_3$, 12H), 1.99 (m, CH$_2$, 4H), 2.27 (m, CH$_2$, 4H), 3.35 (s, CH$_3$, 3H), 3.52-3.72 (m, CH$_2$, 60H), 3.80 (m, CH$_2$, 2H), 3.88 (m, CH$_2$, 2H), 4.15 (t, CH$_2$, 2H), 4.67 (t, CH$_2$, 2H) 5.04 (m, CH, 2H) 7.34 (t, ArH, 4H), 8.12-8.25 (m, ArH, 6H), 8.36 (s, ArH, 2H), 8.44 (s, PDI, 1H), 8.60 (s, Ar—H, 2H), 8.61 (s, PDI, 1H), 8.82 (d, JHH=8.5, ArH, 2H), 9.66 (d, JHH=8.8, PDI, 1H); 9.79 (d, JHH=8.2, PDI, 1H). $^{13}$C {$^1$H} NMR (400 NMR, CDCl$_3$): 158.02, 157.33, 153.85, 151.18, 142.15, 132.30, 128.80, 128.40, 127.96, 127.90, 123.87, 123.69, 123.65, 121.35, 117.53, 71.89, 70.70 (m, unresolved signals of PEG), 69.45, 59.00, 57.71, 25.00, 11.54. $^{19}$F NMR (500 MHz, CDCl$_3$, ppm): δ −78.88; MS-MALDI (m/z): [M+2Na$^+$], calcd for C$_{92}$H$_{113}$ClN$_5$Na$_2$O$_{22}$Pt: 1917.41; found 1919.27; UV-vis (CH2Cl2): λabs/nm (∈/M$^{-1}$cm$^{-1}$)=575 (28300), 538 (22000), 412 (23100); Fluorescence (CH2Cl2): λmax/nm=604; Φf=0.37. Electrochemistry: Redox potentials (V vs SCE): Ered1=−0.46; Ered2=−0.89; Ered3=−1.36; Eox=1.49.

Figure 20A:
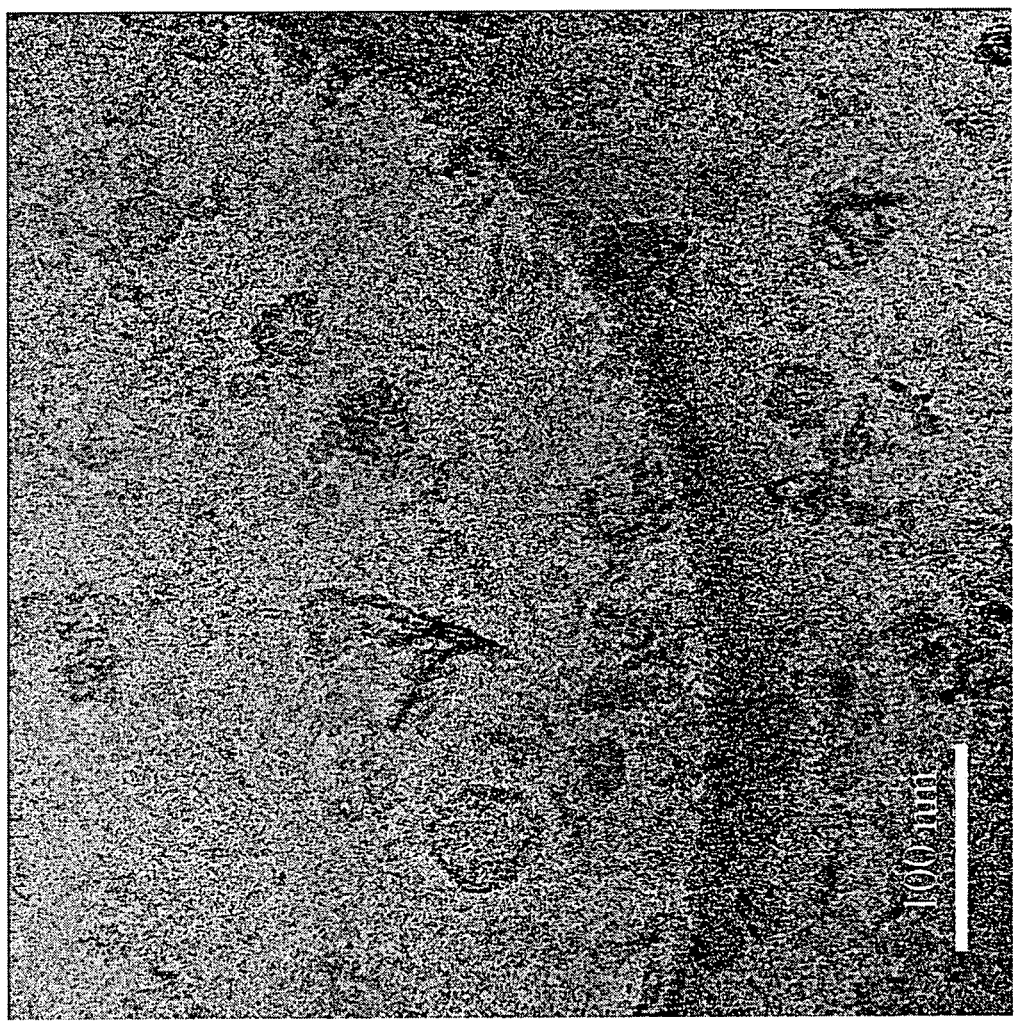
FIG. 20A depicts a cryo-TEM image of a supramolecular polymer formed by Compound XIII in water/THF (9:1 v/v, $2 \times 10^{-4}$ M).

Cryo-TEM images of Compound XIII, in water/THF mixture (9:1 v/v) show mostly vesicular aggregates (FIG. 20A). The average diameter of the vesicles is 26±9 nm. The largest one has a diameter of 72 nm. As vesicles are formed from bilayers that are closed on themselves, Compound XIII is characterized by a self-assembly motif very different from that of isoelectronic Pd complex Compound XII.

Figure 20B:
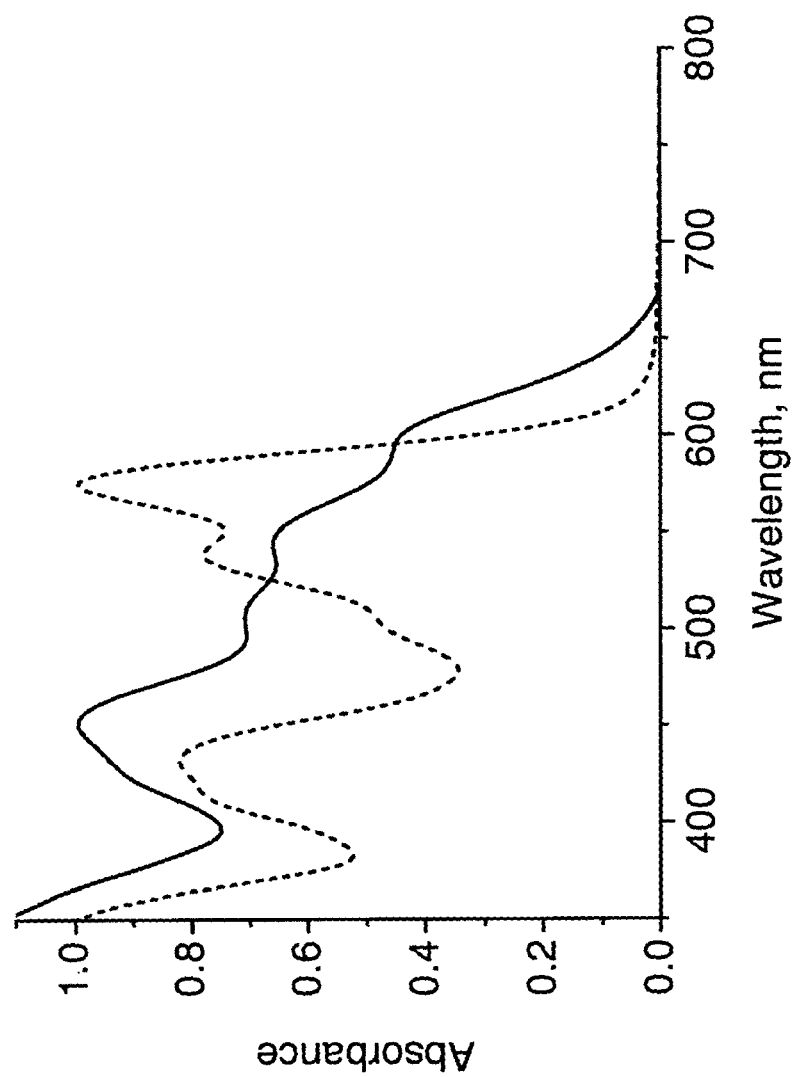
FIG. 20B depicts normalized UV-vis spectra of a solution of Compound XIII in dichloromethane (disassembled, dotted line) and in water/THF (9:1, v/v) solution (solid line).

Comparison between UV-vis spectra of the aggregated and the disaggregated Compound XIII (FIG. 20B) reveals a very, significant broadening, change in the vibronic bands intensity of PDI peaks, and a red shift of terpyridine platinum complex (TerpyPt) band, indicating that besides strong interactions between PDIs, electronic coupling between TerpyPt units is substantial. This is consistent with the known propensity of TerpyPt complexes to interact via Pt—Pt interactions in solution and solid state, which may be a reason for a difference in the self-assembly patterns of Compounds XII and XIII Example 9

Synthesis of Silver aqua(4'-(4-((N,N-bis(1-ethylpropyl)-3,4,9,10-tetracarboxylic diimide-7-(polyethylene glygol)-perylen-1-yl)ethynyl)phenyl)-2,2':6',2"-Terpyridine)triflate (Compound XIV)

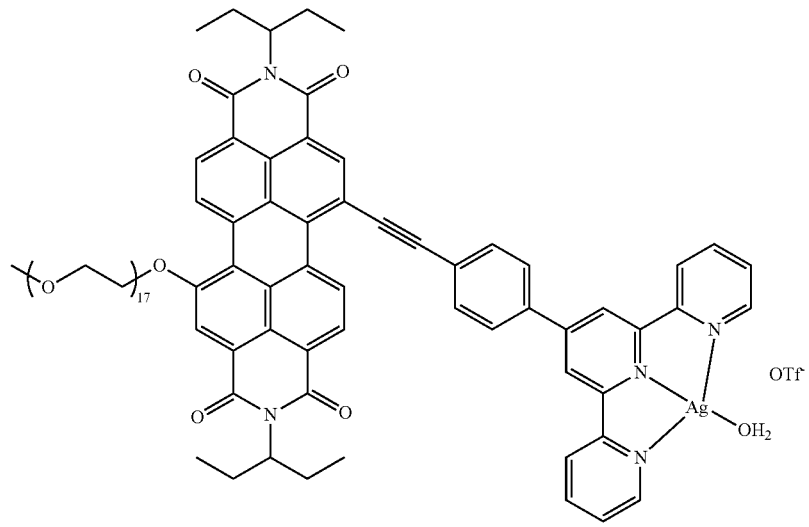

(XIV)

In a 20 mL vial equipped with a magnetic stir bar compound 1 (20.8 mg, 12.9 nmol) was dissolved in 5.0 mL of dichloromethane, to which silver triflate (14 nmol) in 2 ml of tetrahydrofurane was added. The mixture was stirred for 14 h at room temperature. The solvent was removed under vacuum, and the resultant purple solid was dissolved in methylene chloride, filtered through a 0.45 μm PTFE syringe filter and evaporated to yield 22 mg (93%) of Compound XIV as a purple solid. Compound XIV was not stable enough for MS-ESI and MS-MALDI-TOF. A sample for the mass spectroscopy was prepared in the presence of one equivalent of 4-methylpyridine (4-picoline) as a stabilizing ligand.

$^1$H NMR (500 MHz, CDCl$_3$): δ 0.95 (overlapping t, JHH=7.4, CH$_3$, 12H), 1.96 (m, CH$_2$, 4H), 2.29 (m, CH$_2$, 4H), 3.37 (s, CH$_3$, 3H), 3.63 (m, CH$_2$, 2H), 3.64 (m, CH$_2$, 52H), 3.67 (m, CH$_2$, 2H), 3.71 (m, CH$_2$, 2H), 3.79 (m, CH$_2$, 2H), 3.87 (m, CH$_2$, 2H), 4.12 (unresolved t, CH$_2$, 2H), 4.68 (unresolved t, CH$_2$, 2H) 5.10 (m, CH, 2H), 7.36 (t, JHH=6.4, ArH, 2H), 7.83 (d, ArH, 2H), 7.93 (d, ArH, 2H), 7.99 (t, JHH=8.0, ArH, 2H), 8.25 (d, JHH=8.0 ArH, 2H), 8.30 (s, ArH, 2H), 8.45 (unresolved d, Ar—H, 2H), 8.49 (s, PDI, 1H), 8.66 (t, JHH=9.7, ArH, 2H), 8.90 (s, PDI, 1H), 9.72 (d, JHH=8.0, PDI, 1H); 10.09 (d, JHH=8.0, PDI, 1H); $^{13}$C NMR (500 NMR, CDCl$_3$): 157.44, 154.13, 152.64, 151.60, 142.15, 139.03, 137.26, 135.20, 134.10, 133.62, 132.79, 129.11, 129.04, 128.97, 128.54, 128.33, 128.15, 128.01, 127.90, 127.80, 125.74, 124.58, 124.39, 124.01, 123.85, 123.47, 121.79, 120.82, 119.80, 119.34, 118.34, 95.79, 93.54, 71.82, 71.04, 70.79, 70.67, 70.34 (m, unresolved signals of PEG), 69.46, 69.38, 59.02, 57.83, 57.67, 25.06, 25.01, 11.37. $^{19}$F NMR (500 MHz, CDCl$_3$): δ −78.64. MS-ESI (m/z): [M+4-picoline]$^+$. calcd. for C$_{98}$H$_{120}$AgN$_6$O$_{22}$: 1840.75; found 1840.94; UV-vis (CH2Cl2): λabs/nm (∈/M$^{-1}$cm$^{-1}$)=574 (10600), 536 (8200), 407 (4600); Fluorescence (CH$_2$Cl$_2$): λmax/nm=602; Φf=0.56. Electrochemistry: Redox potentials (V vs SCE): Ered1=−0.68; Ered2=−0.86; Eox(Ag)=0.71, Eox(PDI)=1.47.

Figure 21A:
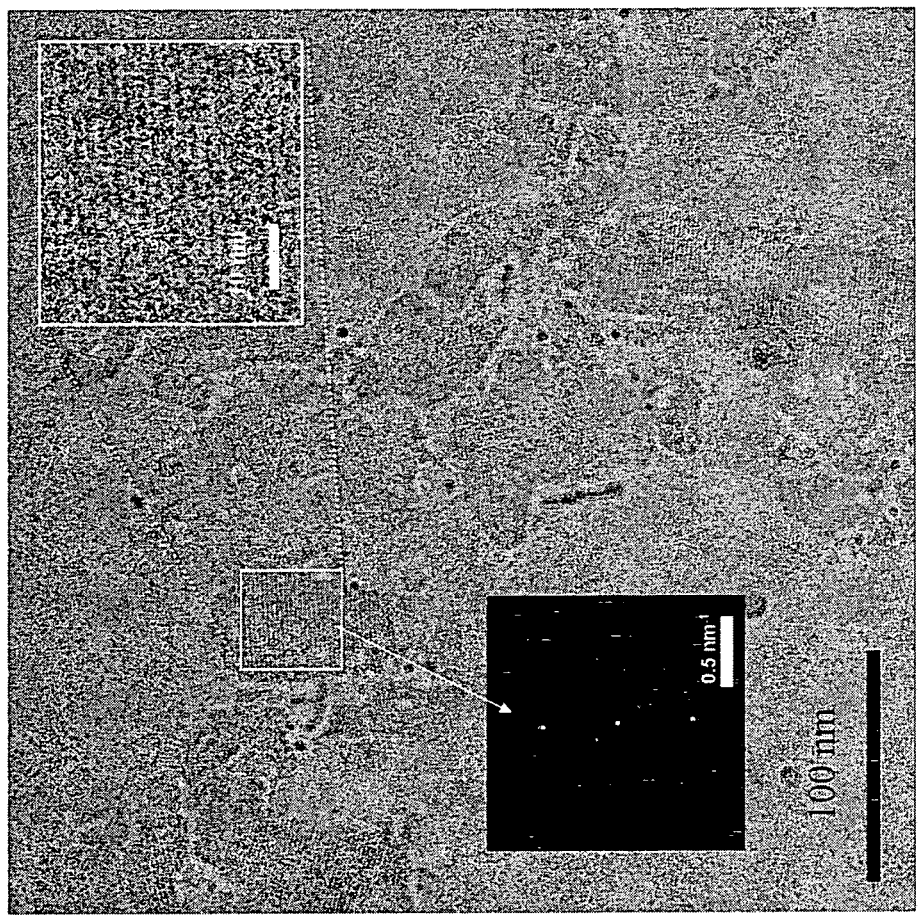
FIG. 21A depicts a cryo-TEM image of a supramolecular polymer formed by Compound XIV in water/THF (9:1 v/v, $2 \times 10-4$ M). The inset surrounded by a white frame shows an enlarged image of a nanoplatelet (scale bar 10 nm). The inset in the black square (scale bar 0.5 $nm^{-1}$) shows a fast Fourier transform image (performed on the region in the white frame), which shows high crystallinity with the pattern that corresponds to 1.85 nm spacing.
Figure 21B:
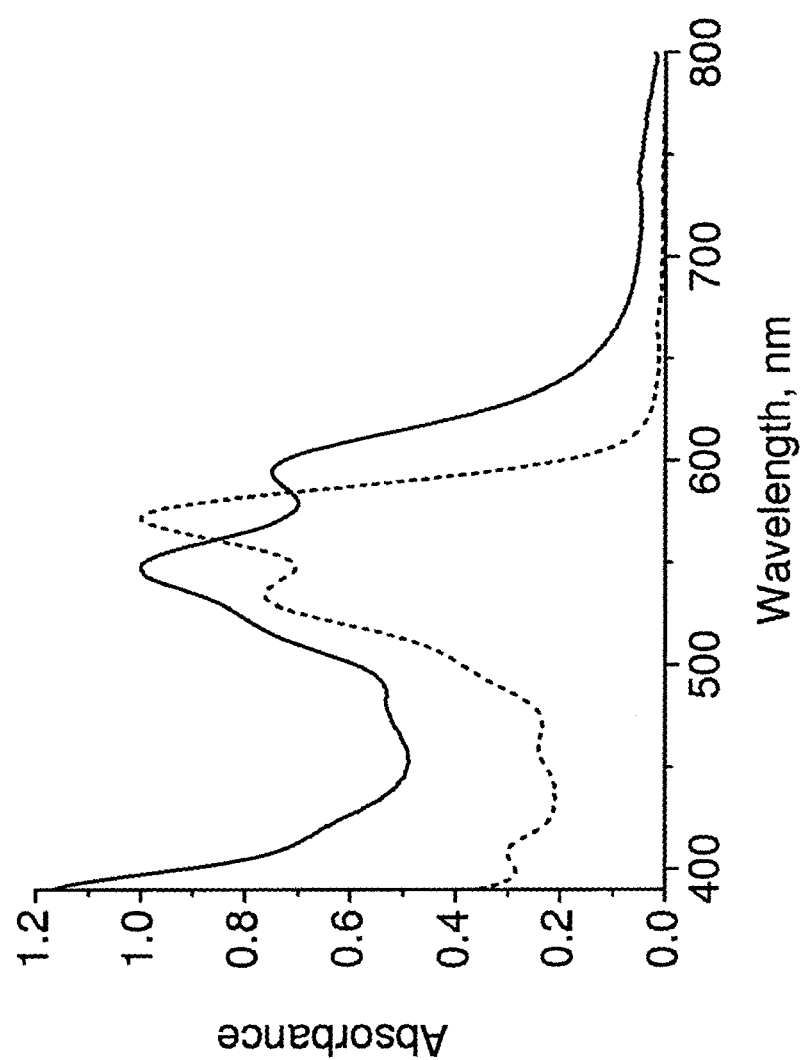
FIG. 21B depicts normalized UV-vis spectra of a solution of Compound XIV in dichloromethane (disassembled, dotted line) and in water/THF (9:1, v/v) solution (solid line).
Figure 21C:
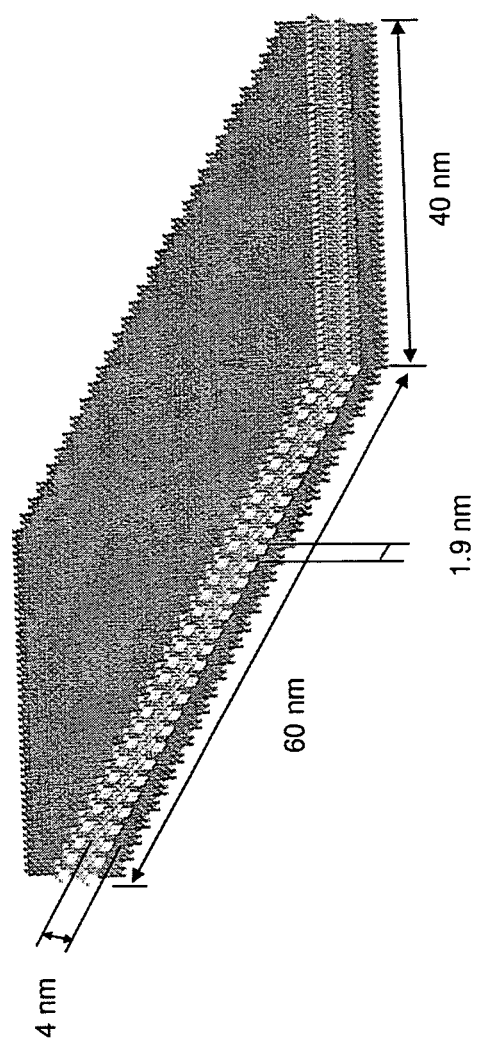
FIG. 21C depicts a model of the bilayer formed by Compound XIV.

Compound XIV in water/THF mixture (9:1 v/v) self-assembles into nano-platelets (FIG. 21A). The average dimensions the nano-platelets are 60×40 nm. Fine structure of the platelets reveals ordered "striped" pattern, which shows periodicity of 1.85±0.05 nm. UV-vis spectrum of the assembled Compound XIV shows a swap in 0→0 and 0→1 transition intensities and significant broadening, consistent with the formation of extended structures with face-to-face stacking (H-aggregation) motif (FIG. 21B). A possible model is presented in FIG. 21C. Molecular models suggest that hydrogen bonding between coordinated water molecules may contribute to the directionality and strength of the assembly, resulting in lower curvature of Compound XIV (to give a more rigid assembly motif) in comparison to Compounds XII and XIII.

Example 10

Femtosecond Transient Absorption Studies on Compounds XI, XII and XIII

Femtosecond transient absorption studies were conducted on the nanostructures self-assembled from Compounds XI, XII and XIII. The results are presented in Table 1.

TABLE 1

Time constants for the $^1$*PDI decay (probed at 735 nm) at various pump fluences in water/THF (9:1, v/v) solution (relative amplitudes are given in parentheses).

| | | Pump fluences | | |
|---|---|---|---|---|
| | | 2.26 mJ/cm$^2$ | 1.70 mJ/cm$^2$ | 1.10 mJ/cm$^2$ |
| XI | τ$_1$/ps | 1.6 (0.46) | 1.8 (0.41) | 2 (0.37) |
| | τ$_2$/ps | 45 (0.44) | 45 (0.41) | 45 (0.31) |
| | τ$_3$/ps | 1160 (0.10) | 1160 (0.16) | 1160 (0.33) |
| XII | τ$_1$/ps | 4 (0.36) | 4 (0.30) | 4 (0.22) |
| | τ$_2$/ps | 80 (0.55) | 80 (0.55) | 80 (0.49) |
| | τ$_3$/ps | 1600 (0.09) | 1600 (0.15) | 1600 (0.29) |
| XIII | τ$_1$/ps | 1 (0.30) | 1 (0.18) | 1 (0.14) |
| | τ$_2$/ps | 20 (0.38) | 20 (0.36) | 20 (0.28) |
| | τ$_3$/ps | 1400 (0.32) | 1400 (0.46) | 1400 (0.58) |

As can be seen for Table 1, the PDI excited state feature demonstrated multiexponential decay. The contribution of the fast processes in the nanostructures is dependent on the laser power (in all cases τ$_1$ and τ$_2$ relative amplitudes decrease with decreasing laser power, see Table 1). This indicated that exciton annihilation took place, typical of chromophore aggregates where a high photon flux of a laser pulse results in multiple excitations enabling exciton annihilation processes. Accordingly, disaggregated Compounds XI, XII and XIII (in chloroform solution) did not show power-dependent behavior. The presence of two power-dependent components may be attributed to the annihilation processes of delocalized (faster time) and localized excitons, as well as complex high order multiexciton processes, complicating the elucidation of energy transfer patterns. Employing a widely used approximation, site-to-site exciton hopping time constant, τ$_{hop}$, could be estimated from the annihilation time constant, τ$_{an}$ (corresponding to τ$_1$ and τ$_2$), using an "exciton random walk"

model that has been shown to give satisfactory results for both natural and artificial chromophore aggregates. According to this model, $\tau_{an}=(\pi^{-1}N \ln N+0.2N-0.12)\tau_{hop}$, where N is the number of hopping sites. The photon flux (the highest energy pulse) corresponds to one photon per six molecular units, which gave τ$_{hop}$ of 360 fs, 890 fs, and 220 fs (corresponding to τ$_1$) and 10 ps, 18 ps, and 4 ps (corresponding to T$_2$) for Compounds XI, XII and XIII, respectively. For comparison, the hopping time constant observed for PDI aggregates in organic medium was 5 ps. Overall, good exciton mobility in the assemblies of Compounds XI, XII and XIII was observed.

Example 11

Synthesis of 5,5'-Bis(1-PEG-PDI-7-ethynyl)-2,2'-bipyridine (Compound X)

Synthesis of 5,5'-dibromo-2,2'-bipyridine (3)

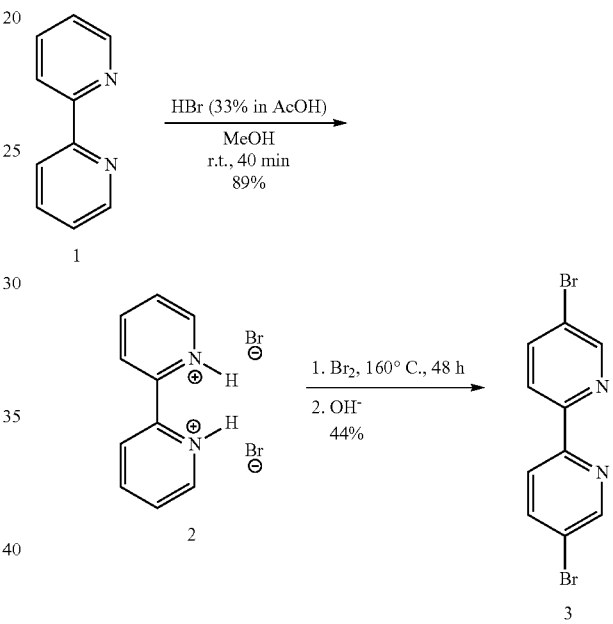

A solution of HBr in acetic acid (5 ml, 33 wt %) was added dropwise to a solution of 1 (0.992 g, 6.35 mmol) in MeOH (2 ml). The instantly forming precipitate was filtered and dried to yield 1.80 g (5.66 mmol, 89%) of 2 as a crude salt. Subsequently, a mixture of 2 (0.975 g, 3.07 mmol) and bromine (981 mg, 6.14 mmol) was heated in a pressure flask to 160° C. for 48 hours with stirring. The reaction was stopped and the hard solid was powdered using mortar and pestle. In order to remove unreacted bromine, a concentrated aqueous solution of Na$_2$S$_2$O$_3$ (60 ml) was added to the brown powder and the mixture was stirred for 10 minutes. Subsequently, it was treated with 1 N NaOH (10 ml) and the product was extracted with CH$_2$Cl$_2$ (6×40 ml). The combined organic phases were concentrated under reduced pressure. This lead to partial precipitation of 3 together with unreacted 1. The precipitate was filtered and the two compounds were separated by flash column chromatography on silica gel, using CH$_2$Cl$_2$ as an eluent. The mother liquor contained 3, mono-brominated bipyridine, and other products of bromination. 3 was separated from the side products by silica flash column chromatography of the mother liquor using CH$_2$Cl$_2$ as an eluent. A total amount of 420 mg (1.34 mmol, 44%) of pure 3 as a white solid was obtained. $^1$H NMR (CDCl$_3$, 250 MHz): δ=8.70 (dd, 2H, J$_{HH}$=0.6 Hz, 2.4 Hz), 8.28 (dd, 2H, J$_{HH}$=0.6 Hz, 8.5 Hz), 7.93 (dd, 2H, J$_{HH}$=2.3 Hz, 8.5 Hz).

Synthesis of 5,5'-Bis((trimethylsilyl)ethynyl)-2,2'-bipyridine (4)

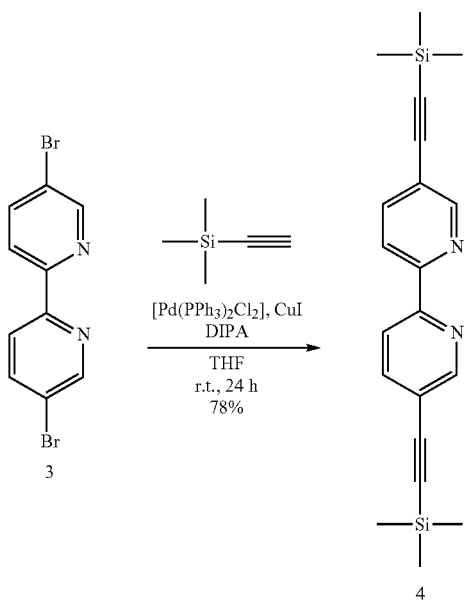

Under dry nitrogen atmosphere, successively trimethylsilyl-acetylene (619 mg, 6.30 mmol), [Pd(PPh$_3$)$_2$Cl$_2$] (112 mg, 159 µmol), CuI (54.5 mg, 286 µmol) and DIPA (4 ml) were added to a stirred suspension of 3 (500 mg, 1.59 mmol) in 30 ml THF. While the mixture was stirred for 24 hours at room temperature, its color turned black. It was stirred together with activated carbon for 20 minutes and filtered over celite. Then the solvent was removed under reduced pressure, the residue was resuspended in hexane, sonicated for 15 minutes and filtered over celite again yielding an orange solution. The solvent was removed under reduced pressure and the residue was purified by flash column chromatography on silica (eluent: CH$_2$Cl$_2$) to yield 430 mg (1.23 mmol, 78%) of pure 4 as an off-white solid. $^1$H NMR (CDCl$_3$, 250 MHz): δ=8.71 (s, 2H, bpy-H), 8.33 (d, 2H, J$_{HH}$=8.3 Hz, bpy-H), 7.85 (d, 2H, J$_{HH}$=7.8 Hz, bpy-H), 0.27 (s, 18H, Si(CH$_3$)$_3$).

Synthesis of 5,5'-diethynyl-2,2'-bipyridine (5)

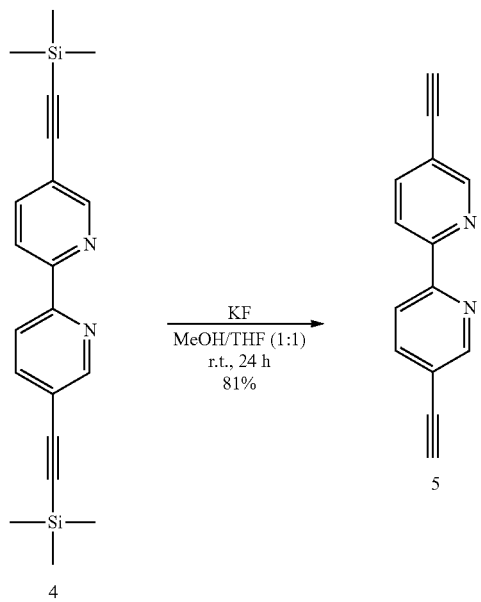

4 (390 mg, 1.12 mmol) was dissolved in a mixture of 40 ml MeOH and 10 ml THF; then KF powder (400 mg, 6.88 mmol) was added and the solution was stirred at room temperature overnight. Subsequently, the solvents were removed under reduced pressure. The residue was redissolved in 200 ml CH$_2$Cl$_2$ and washed four times with 100 ml H$_2$O each, in order to remove inorganic salts. The organic phase was dried over Na$_2$SO$_4$, concentrated under reduced pressure and purified by silica flash column chromatography (eluent: CH$_2$Cl$_2$) to yield a colorless powder of 204 mg (1.0 mmol, 81%) pure 5. $^1$H NMR (CDCl$_3$, 250 MHz): δ=8.76 (d, 2H, J$_{HH}$=1.0 Hz, bpy-H), 8.39 (d, 2H, J$_{HH}$=6.0 Hz, bpy-H), 7.90 (dd, 2H, J$_{HH}$=1.1 Hz, 5.1 Hz, bpy-H), 3.31 (s, 2H, bpy-CCH).

Synthesis of 1-Br-7-PEG-N,N'-Bis(ethylpropyl) perylene-3,4:9,10-tetracarboxylic diimide (7)

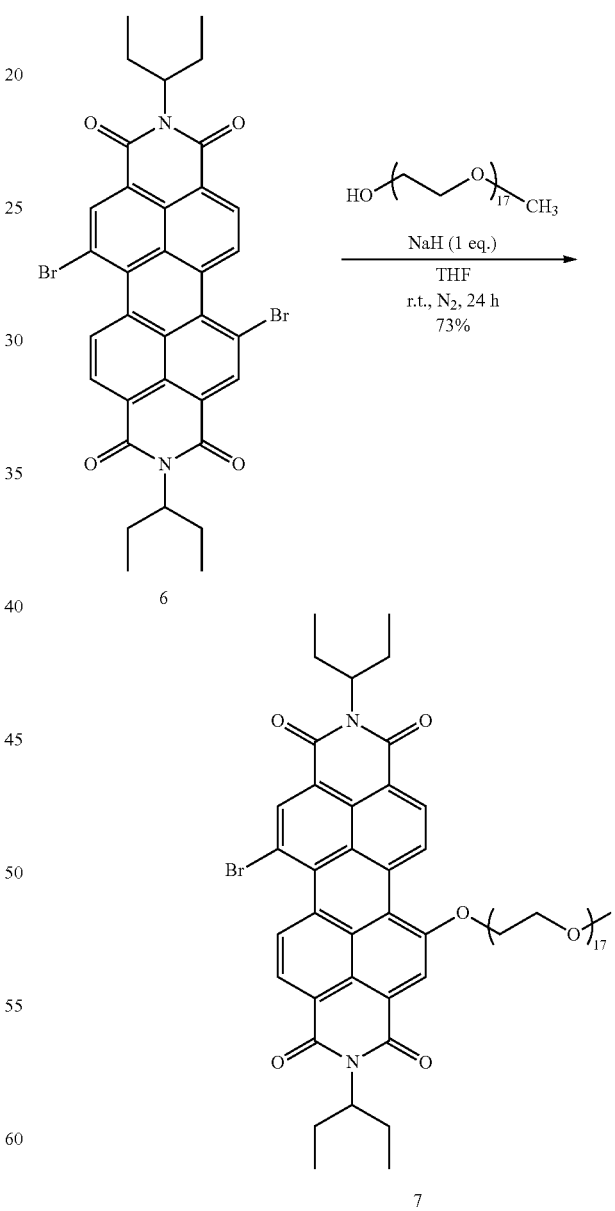

Under dry nitrogen atmosphere, 6 (255.7 mg, 372.7 µmol) was dissolved in 30 ml THF in a 100 ml round bottom flask equipped with a magnetic stirrer. Subsequently, dry PEG (371.2 mg, ~485 µmol) was added to the stirring solution, followed by NaH (60 wt %, 20 mg, 500 µmol). Instantly, the color turned darker and after a short time a dark red precipitate formed. The reaction was stopped after 24 hours and the solvent was evaporated under reduced pressure. In order to remove inorganic salts and an excess of PEG, the mixture was treated with 30 ml of water, a few drops of HCl (1N), and 7 was extracted with $CH_2Cl_2$ (3×30 ml). The combined organic extracts were washed with brine (3×30 ml). The solvent was removed under reduced pressure and the resulting dark purple solid was purified by silica gel flash column chromatography. Initially, $CHCl_3$ was used as an eluent, followed by $CHCl_3$/ methanol mixtures with a content of methanol rising gradually from 1 to 6 percent. The second band collected contained a red solid yielding 370 mg (269 µmol, 73%) of pure 7. $^1$H NMR (CDCl$_3$, 250 MHz): δ=9.58 (d, 2H, $J_{HH}$=8.3 Hz, perylene-H), 8.91 (s, 1H, perylene-H), 8.65 (d, 1H, $J_{HH}$=8.5 Hz, perylene-H), 8.57 (d, 1H, $J_{HH}$=8.0, perylene-H), 8.45 (s, 1H, perylene-H), 5.05 (m, 2H, N(CH(CH$_2$CH$_3$)$_2$). 4.63 (m, 2H, PEG), 4.07 (m, 2H, PEG), 3.82 (m, 2H, PEG), 3.78 (m, 2H, PEG) 3.70-3.50 (m, 56H, PEG), 3.37 (s, 3H, PEG-OCH$_3$), 2.24 (m, 4H, N(CH(CH$_2$CH$_3$)$_2$), 1.92 (m, 4H, N(CH(CH$_2$CH$_3$)$_2$), 0.90 (m, 12H, N(CH(CH$_2$CH$_3$)$_2$).

Synthesis of 5,5'-Bis(1-PEG-PDI-7-ethynyl)-2,2'-bipyridine (8)

(X)

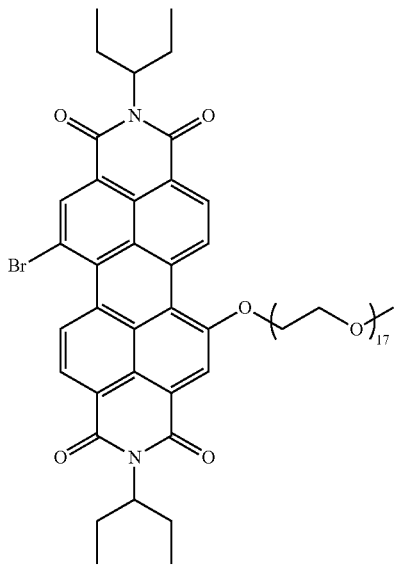

7

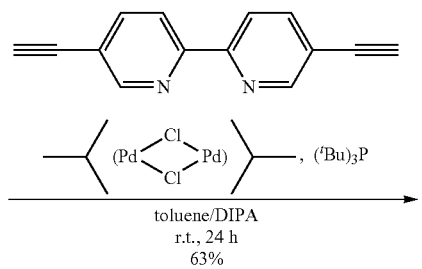

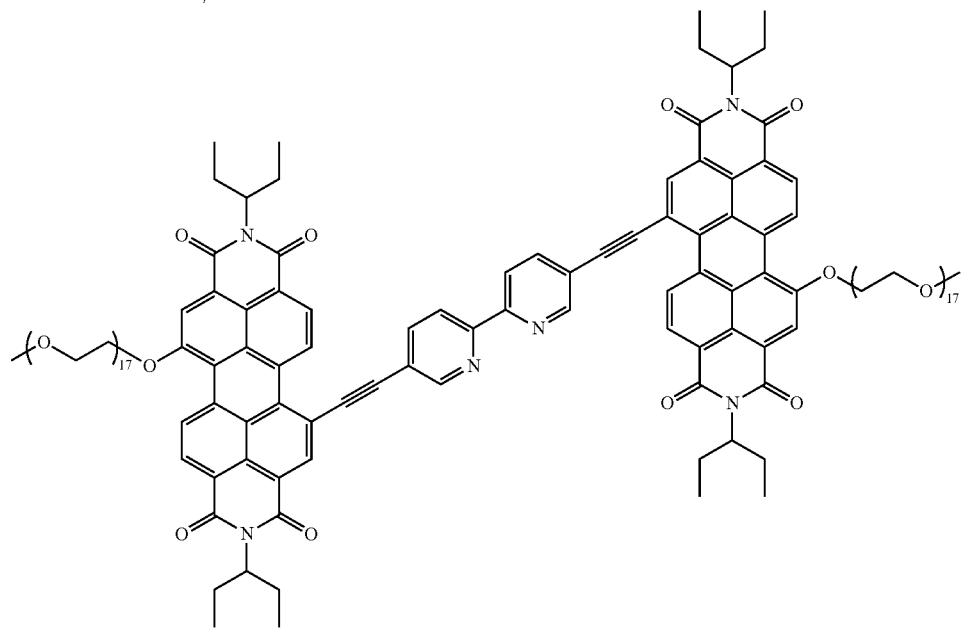

8

A modified Sonogashira cross-coupling reaction was carried out under nitrogen atmosphere. In contrast to typical Sonogashira reactions, no copper iodide was used as a co-catalyst, in order to prevent coordination of the bpy units to copper ions. To a stirred solution of 7 (315.3 mg, 227 µmol) in 50 ml of dry toluene was added successively a mixture of allyl palladium chloride (6.76 mg, 17.2 μmol) and tris(tert-butyl) phosphine (6.93 mg, 34.3 μmol) in 5 ml toluene, 5,5'-diethynyl-2,2'-bipyridine 5 (20.7 mg, 101 μmol), and 20 ml of DTPA. After stirring for 24 hours at room temperature, the solvents were evaporated and the crude product was dried in high vacuum for several hours. It was purified using silica gel flash column chromatography with $CHCl_3$/MeOH mixtures as an eluent, starting from pure $CHCl_3$, and subsequently raising the MeOH content to 6%. A red solid was obtained from the second band, yielding 179.2 mg (64 μmol, 63%) of pure 8 (Compound X).

$^1$H NMR ($CDCl_3$, 500 MHz): δ=10.08 (d, 2H, $J_{HH}$=8.5 Hz, perylene-H), 9.73 (d, 2H, $J_{HH}$=8.5 Hz, perylene-H), 8.97 (s, 2H, bpy-H), 8.94 (s, 2H, perylene-H), 8.68 (dd, 4H, $J_{HH}$=8.5 Hz, 8.0 Hz, perylene-H, bpy-H), 8.62 (d, 2H, $J_{HH}$=8.0 Hz, perylene-H), 8.51 (s, 2H, perylene-H), 8.10 (d, 2H, $J_{HH}$=8.0 Hz, bpy-H), 5.09 (m, 4H, $N(CH(CH_2CH_3)_2)_2$), 4.67 (m, 4H, PEG), 4.11 (m, 4H, PEG), 3.50-3.75 (m, 120H, PEG), 3.37 (s, 6H, PEG-$OCH_3$), 2.29 (m, 8H, $N(CH(CH_2CH_3)_2)_2$), 1.96 (m, 8H, $N(CH(CH_2CH_3)_2)_2$), 0.94 (m, 24H, $N(CH(CH_2CH_3)_2)_2$). $^{13}$C {$^1$H} NMR ($CDCl_3$, 125 MHz): δ=164 (br., carbonyl), 157.65, 154.88, 152.05, 139.64, 137.57 (br.) 135.47, 134.34, 133.73, 132.11 (br. s), 129.30, 129.17, 128.5 (br.), 128.41, 128.22, 124.4 (br.), 124.21, 123.6 (br.), 122.1 (br.), 121.29, 121.01, 120.12, 118.24, 95.64 (ethynyl), 93.70 (ethynyl), 72.09 (PEG), 71.23 (PEG), 71.02-70.05 (PEG), 69.63 (PEG), 69.56 (PEG), 59.20 (PEG-O—$CH_3$), 57.98, 57.83 ($NCH(CH_2CH_3)_2$), 25.20 ($N(CH(CH_2CH_3)_2)$), 11.51 ($NCH(CH_2CH_3)_2$).

MALDI-TOF-MS m/z calc. for $C_{148}H_{196}N_6O_{42}$: 1730.3. found: 1754.7 [M+Na$^+$]. UV/Vis ($CHCl_3$): $\lambda_{max}$/nm (∈/M$^{-1}$ cm$^{-1}$) 577.8 (42,700), 539.3 (33,400), 386.4 (39800). Fluorescence ($CHCl_3$): $\lambda_{max}$/nm: 604.0, fluorescence quantum yield, $\Phi_f$ 0.58. GPC: Polydispersity 1.15, molecular weight≈3000 Da. Redox potentials (E vs. SCE): +1.49 V (M$^+$+e$^-$ ⇌ M), −0.68 V (M+e$^-$ ⇌ M$^-$), −0.88 V (M$^-$+e$^-$ ⇌ M$^{2-}$).

The large and rigid aromatic core of compound X containing PDI, bipyridyl, and acetylene moieties, is highly hydrophobic, whereas the two PEG tails are hydrophilic. This amphiphilicity allows a bottom-up approach for the design of supramolecular structures. The hydrophobic moieties guarantee aggregation driven by π-π interactions and the hydrophobic effect, whereas the hydrophilic PEG tails are dissolved well in aqueous medium preventing precipitation.

Addition of water to a solution of Compound X in THF induces self-assembly, as evidenced by electron microscopy (see below) and UV/Vis and fluorescence spectroscopy (FIGS. 22A and 22B.) In pure THF the UV/Vis absorption bands of Compound X are intensive and sharp, showing peaks at 572 and 535 nm attributed to the 0-0 and 0-1 electronic transitions of the PDI-chromophore, respectively. Moreover, an absorption band at 384 nm is observed, that is due to the absorption of the bis(ethynyl)bipyridyl moiety. With increasing water content, these bands lose intensity, broaden, and show a slight red-shift. Also, the relative intensities of the transitions in the PDI chromophore change. With increasing water content, the 0-0 transition becomes less intensive than the 0-1 transition. Simultaneously, a shoulder at ~517 nm rises, being attributed to the 0-2 transition of PDI.

The emission spectrum shows intensive fluorescence of Compound X in THF (FIG. 21B). Addition of water leads to a drastic quenching of fluorescence and below 20 vol % THF content the original fluorescence is quenched quantitatively, thus indicating the high efficiency of aggregation. At the same time, a weak, red-shifted emission band at 685 nm appears. This emission band is attributed to excimer fluorescence of closely packed molecules within the aggregates.

In order to investigate the morphologies of the self-assembled supramolecular structures of Compound X, a dilute solution (10$^{-4}$ M) in water/THF mixture (80:20, v/v) was studied using cryogenic transmission electron microscopy (cryo-TEM). Fibrous structures are identified as the dominant morphology, and a few vesicles are also observed as well (FIG. 23A). The width of the fibres is 3.3±0.4 nm, while their lengths reach at least one micron. The fibers tend to align, as manifested by observation of alternating high-contrast regions separated by regular spacings of 4.2±0.4 nm. The high-contrast regions represent tightly stacked aromatic systems that possess high electron density. The spacings with low contrast represent a shell of hydrophilic PEG tails that is swollen by the aqueous medium, resulting in their low contrast. The total diameter of a fiber (inner aromatic core region and outer PEG shell) is 7.5±0.8 nm. The periodic arrangement of the fibers leads to mesoscopically well ordered regions with liquid crystalline character (see below).

Both freshly prepared samples and samples aged for more than 8 months likewise contain these fibers as the clearly dominating morphology. The fibers generally show a low number of defects, such as junctions or end-caps.

The sample was filtered through a 0.20 μm Teflon syringe filter, by which a colorless solvent mixture was obtained (FIG. 23B). This demonstrates the great mechanical stability of the fibrous aggregates. Considering the fibers' extraordinary length, their abundance, their low number of defects as well as their mechanical strength, the molecules inside the fibers are likely held together by very strong intermolecular forces, such as hydrophobic effect and π-π interactions.

Figures 24A, 24B, 24C:
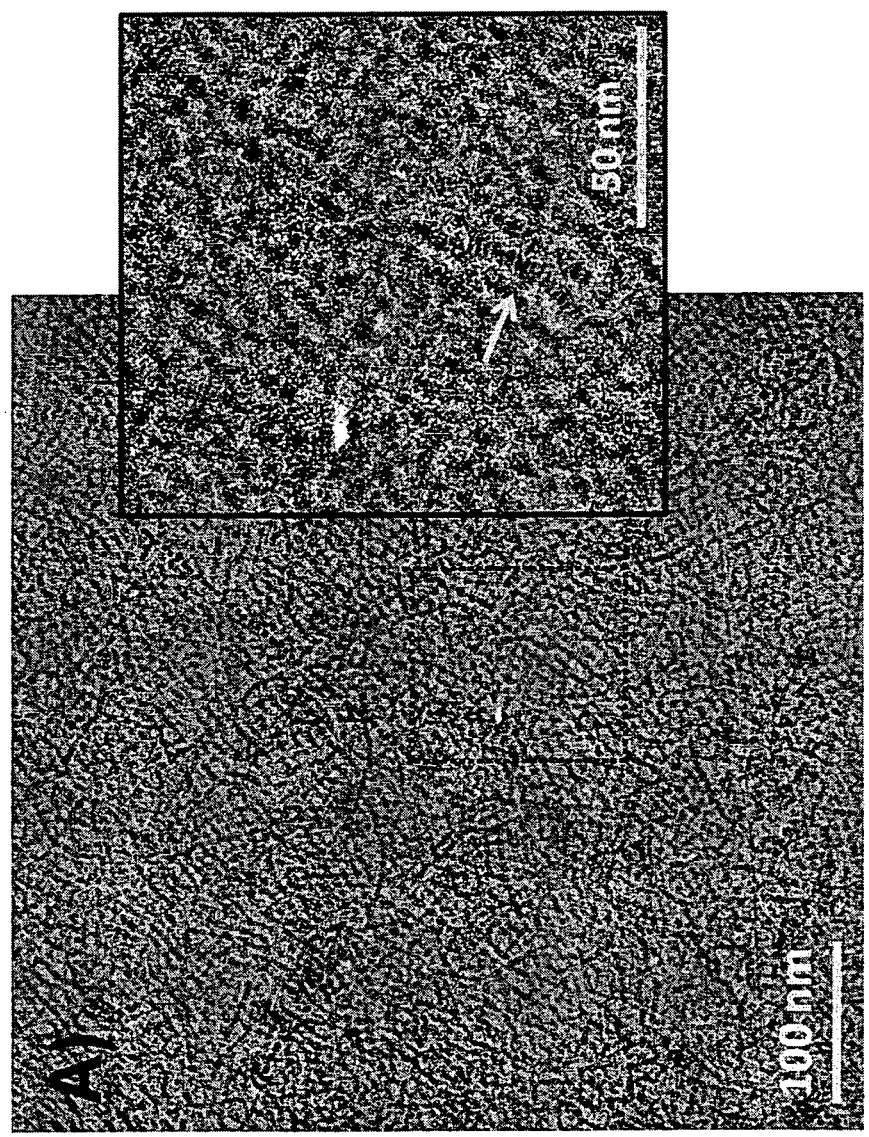
FIG. 24 depicts (A) a cryo-TEM image of a viscous solution of Compound X ($3.3 \times 10^{-4}$ M) in water/THF mixture (83.3:16.7, v/v), revealing fibrous structures, which, in certain cases, show segmentation within the fibers (arrow in inset), (B) a schematic representation of a segmented fiber showing the width and height of the segments, and (C) the optimized geometry of the molecular structure of Compound X, as shown by a space filling representation (for simplification only four PEG units are considered).

Similar morphologies were observed at higher concentrations (viscous solution, 3.3×10$^{-4}$ M, water/THF (83.3:16.7, v/v), FIG. 24A). Fiber widths were measured to be 3.8±0.7 nm, which corresponds well to the value in dilute solution. No morphological change of the fibers was observed in comparison with the dilute sample. The fibers appear to be highly entangled in the higher concentrated sample. A number of fibers were observed to consist of distinct segments of 2.0±0.3 nm height (FIG. 24B).

In order to relate the dimensions of supramolecular features to the molecular dimensions of Compound X, computational geometry optimization using the PM3 semi-empirical method were employed. Several local minimum energy conformations were found with quasi-coplanar PDI and bpy units as a common feature. According to the calculations, in the most stable conformation the PDI units wereoriented in parallel and quasi-coplanar to the bipyridyl-moiety, in which the N-atoms were in trans position to each other (FIG. 24C).

Figure 25:
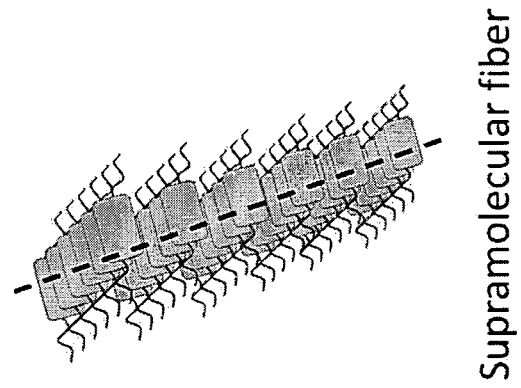
FIG. 25 depicts a schematic drawing of the suggested aggregation of Compound X into supramolecular fibers. The dashed line indicates the direction of propagation of the fiber.
Figure 25:
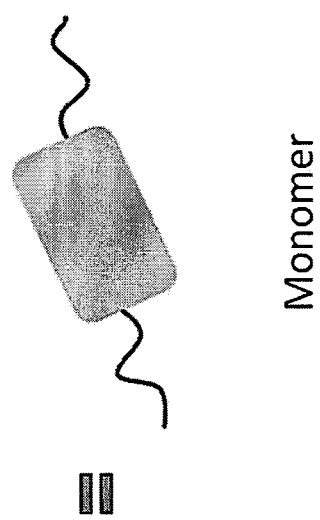

The segments in the fibers (~2 nm high and ~3.8 nm wide) cannot be attributed to single units of Compound X, since the segment height far exceeds the typical π-π stacking distance of 3.5 Å. Additionally, its width is significantly larger than the 2.6 nm length of the conjugated π-systems along their major axis. Rather, the segment height of 2 nm fits to the length of Compound X along the long axis of the two PDI units (1.9 nm). This suggests that the molecules are aligned edge-to-edge along the direction of fiber propagation, whereas stacking of the aromatic systems takes place in the direction perpendicular to the fiber propagation (FIG. 25). Therefore, there were two different forces causing the formation of segmented fibers in this model. Firstly, aromatic stacking leads to the formation of rodlike aggregates of 3 to 4 nm corresponding to 8 to 12 monomer units. Secondly, the hydrophobic effect causes the aggregation along the two hydrophobic edges of the rods to form segmented fibers.

Supramolecular Gels of Compound X

Above a critical concentration, Compound X was observed to gel in water/THF mixtures. In a typical experiment, Compound X (10 mg, 3.6 µmol) in a 1.5 ml vial was dissolved in THF (120 µL). Subsequently, water (660 µL) was added dropwise in small portions, each portion followed by vigorous shaking of the vial. While adding water, the viscosity of the solution increased until a gel formed, as evidenced by a vial-inversion test. If no flow of the mixture was observed within several minutes following inversion, the substance was considered a gel. The gel thus produced, consists of 1.3 wt % Compound X in water/THF mixture (84.6:15.4, v/v).

Figure 26A:
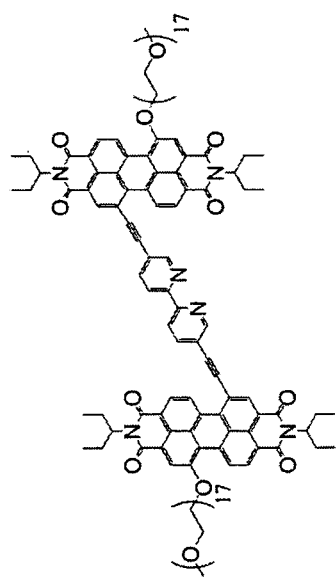
FIG. 26 depicts the gel inversion test of a freshly prepared sample of Compound X ($8 \times 10^{-3}$ M) in water/THF (80:20, v/v) (A) and a diagram showing the observed phases in samples containing different concentrations of Compound X in various water/THF ratios (B). Solution, gel, and inhomogeneous regions in the phase diagram can be distinguished.

The occurrence of gelation was found to depend on two major factors: the concentration of Compound X and the ratio between water and THF in the solvent mixture. In order to investigate the sol-gel phase boundaries a number of samples were prepared, varying in both their concentration and water/THF ratios. Gels and solutions were distinguished by the vial-inversion test (FIG. 26A). Three phase regions could be distinguished: solution, gel, and a phase separated mixture of Compound X and solvent (FIG. 26B). Solutions containing supramolecular fibers are observed in aqueous mixtures containing THF at volume ratios >20% even at high concentrations of Compound X. In aqueous mixtures containing THF volumes between 14 and 20%, Compound X, gels the solvent mixture above a critical concentration. At lower concentrations more or less viscous solutions are observed. For mixtures containing less than 14 vol % THF, precipitation of Compound X takes place and an almost clear solution can be decanted from the vial, leaving the precipitate on the bottom.

The gel of Compound X is stable at room temperature in the presence of air and can be stored under these conditions over a period of several months without showing any visible change. Furthermore, it can be sonicated for an hour without any visible change. Commonly, gel-sol phase transitions are observed above a certain temperature in organogels and hydrogels likewise. In contrast, heating the gel of Compound X up to 60° C. does not lead to gel-sol phase transition, but rather to a phase separation creating a heterogeneous mixture of a clear water/THF solution and a dark precipitate of Compound X. Without wishing to be bound by theory, one reason for the unexpected phase separation at elevated temperatures might be the complex effect of temperature change on the spontaneous curvature of aggregates formed from amphiphilic molecules. The spontaneous curvature of micellar aggregates determines the morphology. A rise in temperature can lead to desolvation of PEG, resulting in deswelling of the PEG shell and therefore causing a decrease of the spontaneous curvature, triggering a change in morphology and leading to precipitation.

Supramolecular Structure of Compound X

In order to investigate the three-dimensional structure of the gel, a sample of Compound X ($8\times10^{-4}$ M) in water/THF mixture (80:20, v/v) was prepared and studied by cryogenic scanning electron microscopy (cryo-SEM). Sample preparation involved vitrification of the gel at cryogenic temperature, followed by sublimation of some vitrified water/THF, thus exposing the supramolecular structure of the gel. Subsequently, the gel structure was covered with a conductive metal layer (Ta/W).

Figure 26A:
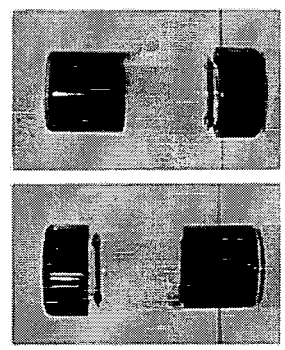
Figure 26B:
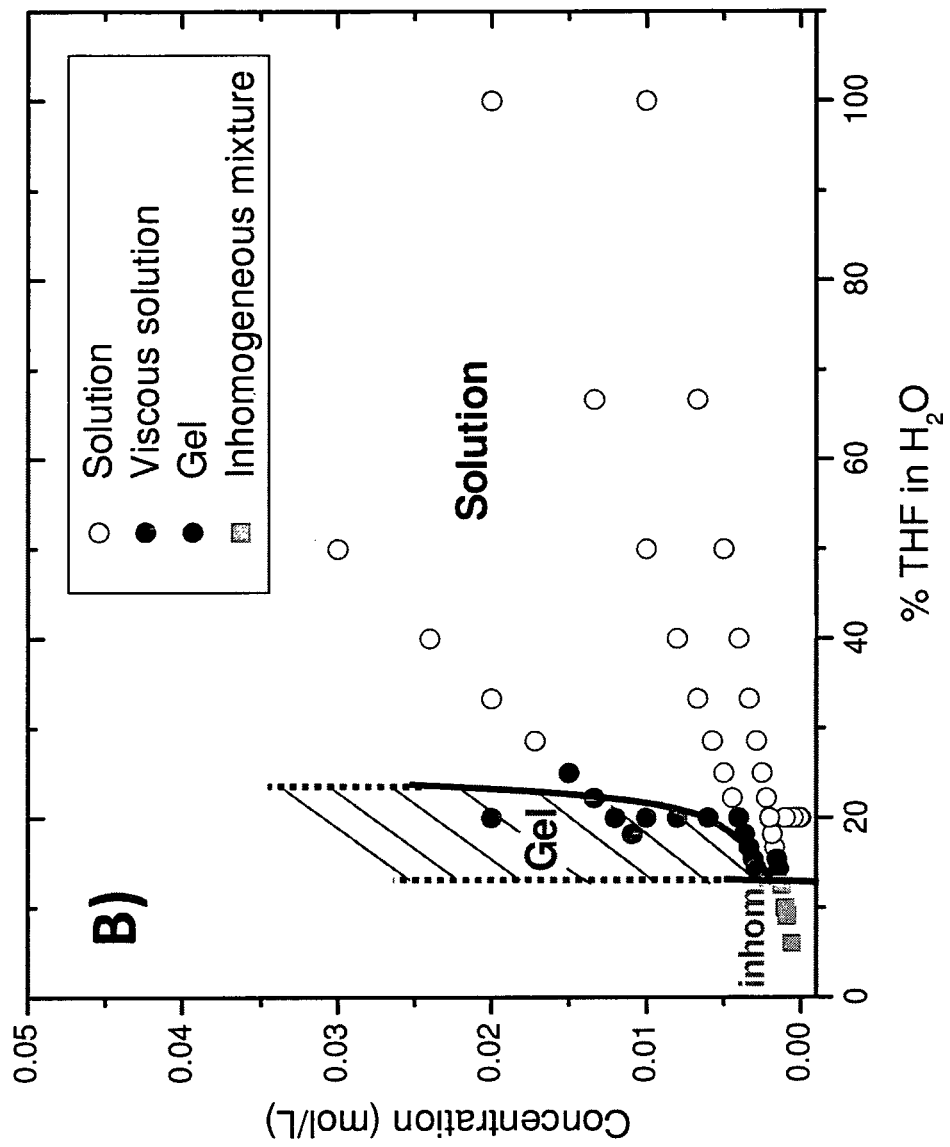
Figure 27:
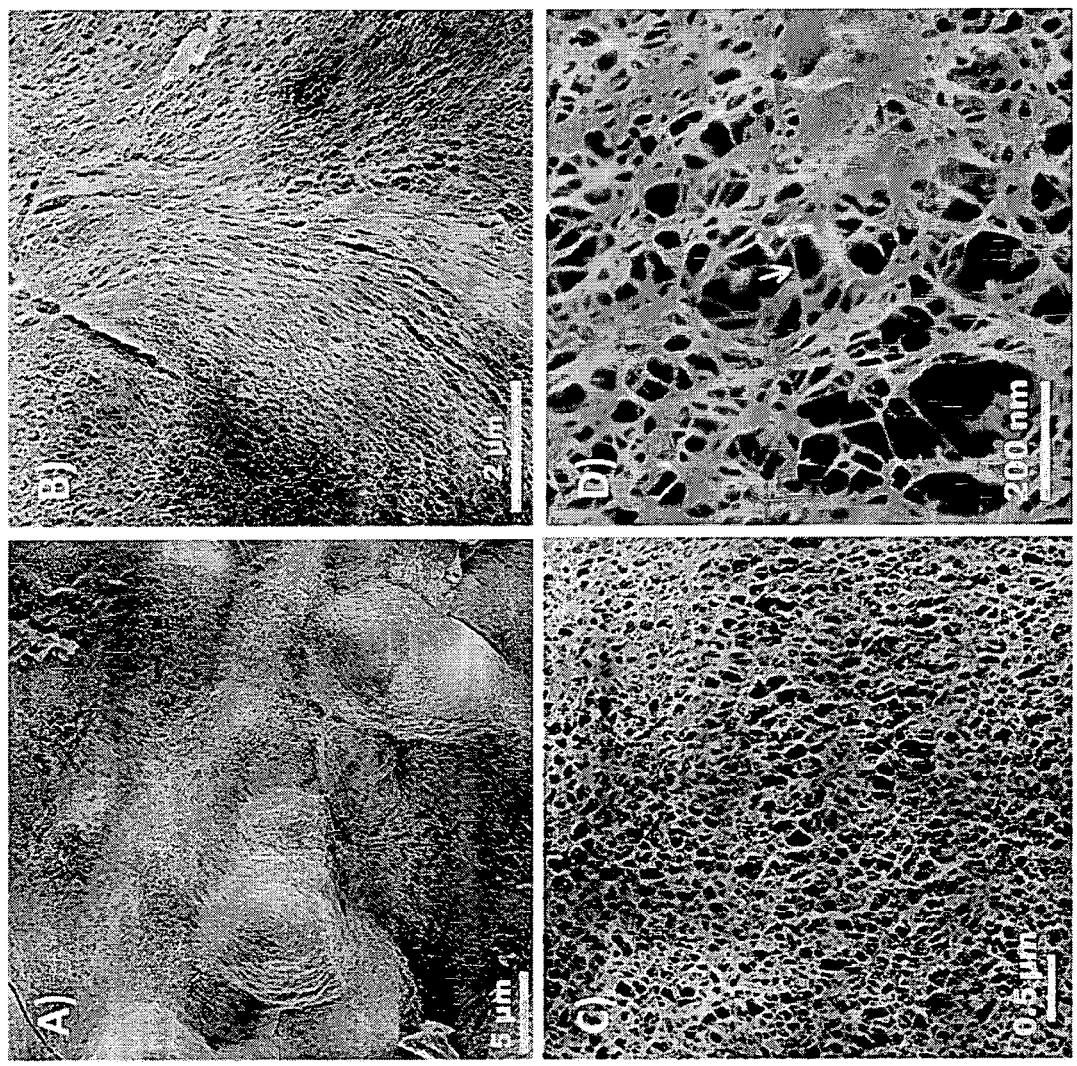
FIG. 27 depicts cryo-SEM images of a gel of Compound X ($8 \times 10^{-3}$ M in water/THF mixtures (80:20)) at different magnifications: (A) whirls with diameters of 10-15 μm, (B) directive arrangement of fibers within a "microstream" of gel, (C) nanoporous structure of the three-dimensional network, and (D) tiny, interconnected fibers spanning the network. Single fibers are 6.1±1.1 nm in diameter (see arrow in D).

The electron microscopic images of the vitrified gel are shown in FIG. 26. At low magnifications, the presence of whirls and streams consisting of fibers is visible. These locally constricted spatial anisotropies are of several microns in size and demonstrate the ability of the gel to maintain a long-range order of the supramolecular fibers (FIGS. 27A and 27B). At higher magnification, a porous three dimensional nanostructure is visible (FIG. 27C). Even higher magnification reveals tiny fibers that are interconnected to each other, thus spanning the three dimensional network (FIG. 27D). The smallest fibers have widths measured to be $6.1\pm1.1$ nm. Subtracting the thickness of the metal layer covering the fiber, its real diameter is approximately 5.5 nm. Thicker fibers up to 20 nm in diameter were also observed, frequently branching out into smaller fibers.

The gel sample studied by cryo-SEM differs from the solution sample investigated above only in its concentration. THF content, sonification time and other conditions are identical. The UV/Vis absoption spectrum of the gel is the same as that of the dilute and viscous solution indicating that the stacking geometry of the aromatic systems of Compound X is identical in gel, dilute and viscous solution systems.

Figure 28A:
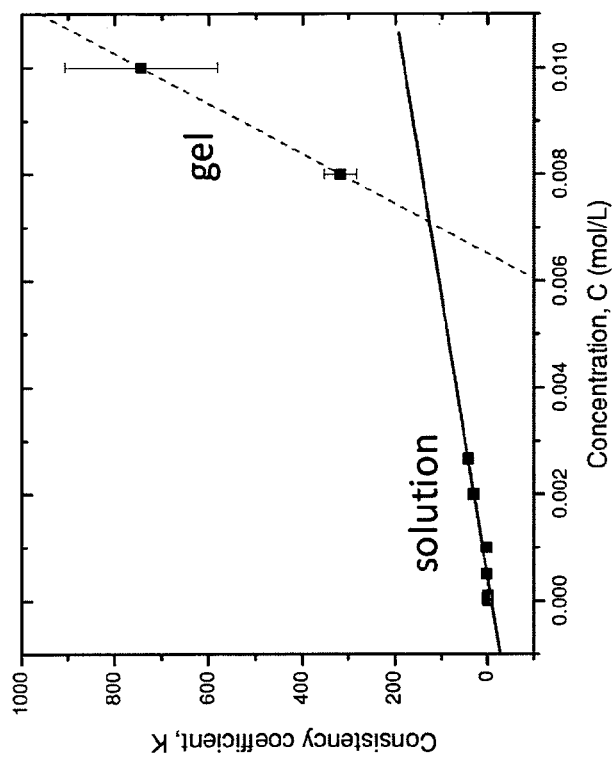
FIG. 28 depicts (A) a plot of shear stress vs. shear rate of samples of Compound X ($10^{-5}$ M to $10^{-2}$ M) in water/THF (80:20, v/v) (the data points were fitted using the Herschel-Bulkley model) and (B) a plot of consistency coefficients as a function of concentration. The intersection of linear fits of solution and gel samples represents the approximate onset of gelation.

In order to correlate the supramolecular structure with the bulk properties, rheological measurements were performed at different concentrations of Compound X: 10 M (dilute solution) to $10^{-2}$ M (gel) in water/THF mixture (80:20, v/v). All samples show shear-thinning behavior (FIG. 28A). This is typical for linear aggregates, which are oriented by the shear forces during the measurement. The data points of the solution samples can be well fitted using the standard power law $\sigma=K\dot\gamma^n$ (where $\sigma$=shear stress, $\dot\gamma$=shear rate, K=consistency coefficient, and 0<n<1). In contrary, the data points of the gel samples could only be fitted by adding an additional yield stress, $\sigma_0$ to the term, leading to the Herschel-Bulkley model $(\sigma=K\dot\gamma^n+\sigma_o)$.[34] $\sigma_o$ represents a finite shear stress even at infinitesimal shear rate, which is expected for gels, since flux of the gel only occurs above a critical mechanical force. The data plots of the gel samples show an anomaly at a shear rate of ~250 $s^{-1}$. This may be due to the fact, that the shear forces cause disruption, reorganization or other structural changes in the gel.

Figure 28B:
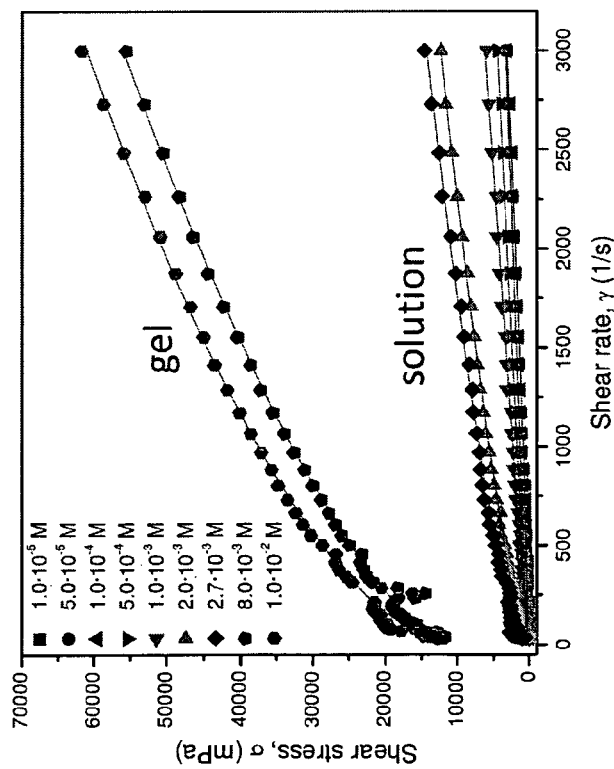

The consistency coefficient K, which is a measure of viscosity, was plotted against the concentration (FIG. 28B). Values obtained from solution samples are well fitted linearly, whereas those obtained from the gel samples deviate significantly from the fitted line to higher viscosities. This deviation indicates that above a certain concentration, fluidity is strongly hindered by complete interconnection of the gel fibers, forming a continuous three-dimensional network. The onset of gelation can be roughly estimated from the intersection of the line fitted to solution samples and a line through the gel samples. The value obtained ($\sim7\sim10^{-3}$ M) is in good agreement with the phase diagram depicted in FIG. 26B.

Figure 29:
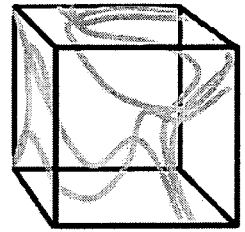
FIG. 29 depicts a schematic illustration showing the hierarchy of gelation of Compound X in water/THF mixtures (80:20, v/v). Hydrophobic effect and π-π interactions cause formation of small rodlike aggregates of 8-12 face-to-face stacked monomer units. These aggregates assemble into segmented fibers, driven by the hydrophobic effect. The fibers align to form bundles. In turn, the bundles branch out into smaller fibers, thus forming junctions.
Figure 29:
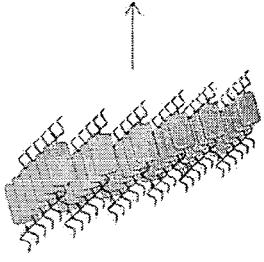
Figure 29:
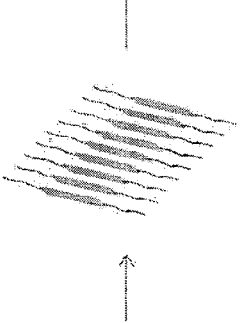
Figure 29:
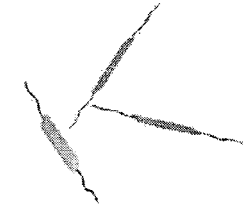
Figure 29:
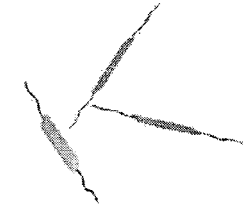

Based on the structural characteristics observed in solution and in gel, a hierarchy of gel-assembly may be proposed (FIG. 29). It involves hydrophobic and π-π interactions that cause single molecules to self-assemble into small rodlike aggregates of 8 to 12 monomer units in length. Then, the hydrophobic effect leads to further assembly into fibers, each rodlike aggregate representing a segment in a fiber. In a third step, the fibers assemble weakly into bundles driven by interaction and entanglement between the PEG tails. The formation of bundles is crucial for gelation in this case, since branching out of these bundles into smaller bundles or individual fibers provides the mechanism for the creation of junctions. Above a critical concentration of Compound X, the density of fiber bundles and junctions is sufficiently high to cause complete interconnection of the fibers, resulting in the macroscopically homogeneous and uniform network structure.

Effects of Structural Anisotropy

The observation that fibers or bundles of fibers can be oriented anisotropically into certain directions on the microscopic scale demonstrates long range order within the supramolecular gel. This structural anisotropy can cause optical anisotropy, which, makes the gel potentially applicable in the area of active optical devices.

In order to investigate optical anisotropy, a thin layer of gel of Compound X was studied in the polarized light microscope (PLM). Images of intensively red colored gel with rather homogeneous color intensity distribution are observed when plane polarized light is used, whereas the same area appears to consist of domains of intensive red and dark color when using cross polarized light. When the sample is rotated in the plane perpendicular to the path length of the light, red domains turn dark and dark domains turn red in alternating order. The phenomenon described above indicates birefringence. The birefringence corresponds to the physical net alignment of fibers in distinct directions within each of the small domains that appear alternately in red and dark color when rotating the sample in cross-polarized light. The observed anisotropies do not change within one hour. This stability over time can be attributed to the restricted movement of the fibers within the gel, trapping them in their orientation.

Time-Resolved Photophysics

Understanding the nature of excited states created by absorption of visible light is crucial for the development of artificial light harvesting and solar energy converting systems. Designed as a functional building block for such systems, Compound X shows strong absorption of visible light ($\in_{max}$=42,700$M^{-1}cm^{-1}$ in $CHCl_3$). Furthermore, good electronic communication between the densely stacked chromophore moieties of Compound X is expected to take place within the supramolecular fibers in gel and solution.

In order to investigate the dynamics of excited states in the supramolecular gel of Compound X, femtosecond transient absorption (fsTA) studies were performed. The decay of the transient signal was fitted to triexponential decay, the time constants being $\tau_1$~1.5 ps, $\tau_2$~25 ps, and $\tau_3$~500 ps. Remarkably, this decay shows strong dependence on the laser power (FIG. 30A). At low pump fluence, the contribution of the fast component $\tau_1$ is very low, whereas at high pump fluence it is the major component of the excited state decay. Similar to this but much less pronounced rises $\tau_2$. At the same time, the contribution of the slow component, $\tau_3$ decreases drastically with increasing pump fluence (FIG. 30B).

The observed phenomenon of power dependence indicates exciton-exciton annihilation, which is typical for extended chromophore arrays where high laser fluences can create multiple excitons. In $CHCl_3$ solution, where Compound X is disaggregated, power dependence was not observed. The process necessitates a certain mobility of the excitons within the gel-fibers. This mobility is important for artificial light harvesting systems, in which excitation energies need to be funneled efficiently to electron acceptors, donors or to catalytic reaction centers.

The presence of two decay components rising with the pump power might indicate that two different annihilation processes taking place. One process might be due to exciton annihilation within a fiber, whereas the other is due to annihilation of excitons from different fibers within the same bundle. Alternatively, more complex processes such as high order multiexcitation annihilation might be involved.

Reduction of Compound X

Photoinduced electron transfer in a light harvesting and solar energy converting system based on Compound X involves temporarily reduced organic species within the supramolecular fibers. The molecular and supramolecular structure of the gel is therefore required to be sufficiently stable towards reduction. In order to investigate the effect of reduction and the nature of reduced species within the gel, samples of Compound X (2.24 mg, 0.8 μmol) in deuterated THF (20 μL) were mixed with $D_2O$ (110 μL) containing different concentrations of sodium dithionite as a reducing agent (0.1-4.0 equivalents in respect to Compound X). Rapid mixing of the THF with the water solution causes self-assembly and reduction simultaneously.

Reduction has a notable effect on the viscosity of the mixture. The sample containing only 0.1 eq. of $Na_2S_2O_4$ retains a similar viscosity to the unreduced gel, whereas samples containing 0.5 eq. and above are fluid solutions. The substantial loss of viscosity upon reduction above a critical concentration of reducing agent is explained by mutual electrostatic repulsion of the reduced π-systems, which prevents stacking.

UV/Vis spectroscopy of the samples reduced with ≥0.5 eq. $Na_2S_2O_4$ reveal four additional peaks at 747, 841, 894, and 1008 nm wavelength, which are characteristic for the radical anion of PDI. Interestingly, the gel containing 0.1 eq. $Na_2S_2O_4$ does not show these radical anion peaks. A possible reason for this difference is electron delocalization along several π-stacked aromatic systems within the supramolecular fibers of the gel. However, no additional charge transfer bands were found in the near IR region that could be attributed to such delocalized electrons.

All reduced species are EPR-active, whereas the unreduced gel is EPR-silent. The signal intensity is the same in the samples containing 2 eq. and 4 eq. dithionite and the signal shape is similar as well, indicating that no further reduction takes place between 2 and 4 equivalents. In respect to the peak-to-peak width ($\Delta B_{PP}$) of the liquid samples containing 2.0 and 4.0 eq. dithionite ($\Delta B_{PP}$=0.5 G), the peak of the gel with only 0.1 eq. $Na_2S_2O_4$ is significantly broadened ($\Delta B_{PP}$=1.9 G) and shows strong asymmetry. Both findings suggest that the radical anions $8^{*-}$ in the gel containing only 0.1 eq. reductant are not dissociated in solution, but associated anisotropically within the supramolecular fibers of the gel. The reduction of Compound X is reversible by exposing the samples to air. This way, the unreduced gel is recovered and multiple reduction experiments can be performed with the same sample without deterioration. The studies indicate stability of the molecular structure of Compound X towards reduction in aqueous media and reversibility of this process. The supramolecular structure of the gel is broken by addition of sodium dithionite when using 0.5 equivalents or more. However, small amounts of this reductant (0.1 eq.) do not destroy the supramolecular structure. Reduced species in this system are located within the supramolecular fibers. This molecular and supramolecular stability towards partial reduction makes possible electron transport within the fibers of the gel without deterioration of the organic building blocks, which is crucial for a light harvesting system based on the gel of Compound X.

Hybrid Gel

In order to modify the gel towards a functional system capable of photoinduced electron transfer and light harvesting, a hybrid gel based on Compound X was created containing MPA-stabilized quantum dots.

Figure 31:
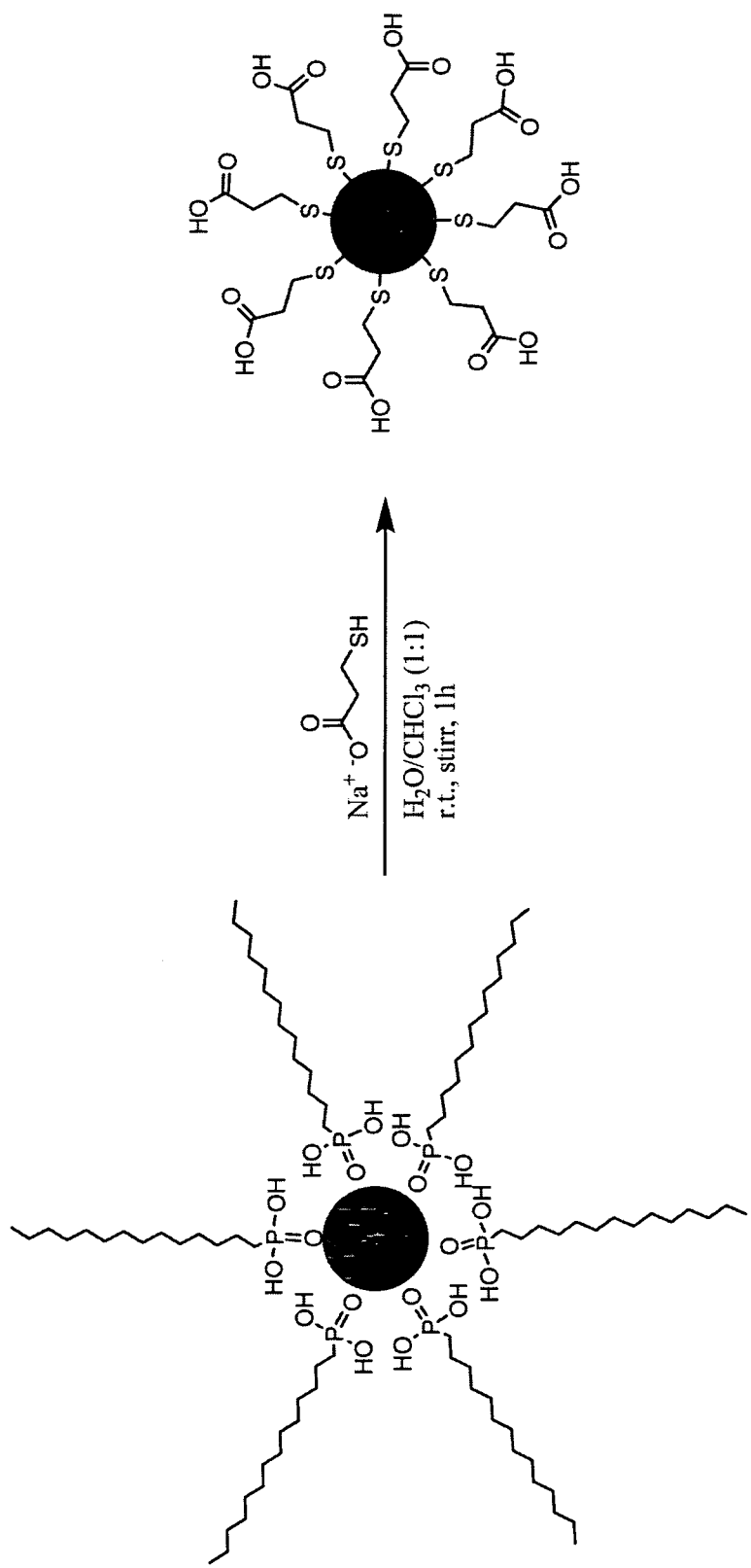
FIG. 31 depicts the formation of water-soluble CdTe quantum dots, prepared by modification of tetradecanephosphonic acid (TDPA) stabilized CdTe quantum dots.

Water-soluble CdTe quantum dots were prepared by modification of tetradecanephosphonic acid (TDPA)-stabilized CdTe quantum dots under argon atmosphere. See FIG. 31. An aqueous solution of sodium mercaptopropionate (0.1 mmol/L, 0.7 ml) was added to a solution of I (1 mg) in $CH_2Cl_2$ (0.7 ml). The two-phase mixture was stirred vigorously for 1 hour and complete transfer of red color from the organic to the aqueous phase was observed. The aqueous phase containing highly luminescent CdTe quantum dots (II) showed good stability against air and heat (60° C.).

The quantum dots can function as electron donors, provided that they interact with the fibers of the gel. In turn, the fibrous photoactive network of the gel can function as an electron acceptor. Photoinduced charge transfer from the quantum dots to the gel-fibers is expected to take place if both donor and acceptor are sufficiently close to each other. The linear arrangement of aromatic π-systems within the gel fibers provides a potential mechanism of secondary electron transport along the fibers, thus leading to a large spacial separation of positive and negative charges on microscopic scale. Similar to natural photosynthesis, this spacial charge separation can make it sufficiently long-lived for following catalytic reactions that eventually convert the energy of visible light into chemical energy.

In a typical experiment for the production of the hybrid gel, Compound X (0.84 mg, 0.3 μmol) was dissolved in THF (25 μL) in a 500 μL Eppendorf tube and subsequently gelation was induced adding small portions of a solution of MPA-stabilized quantum dots (II) in H$_2$O (140 μL) followed by vigorous shaking after addition of each portion. The hybrid gel thus obtained contains homogeneously dispersed quantum dots within its fibrous network. Two control samples were prepared as well, one containing only Compound X and the other containing only MPA-stabilized quantum dots (II), at the same concentrations as in the hybrid system and in the same water/THF mixture, respectively.

Figure 32:
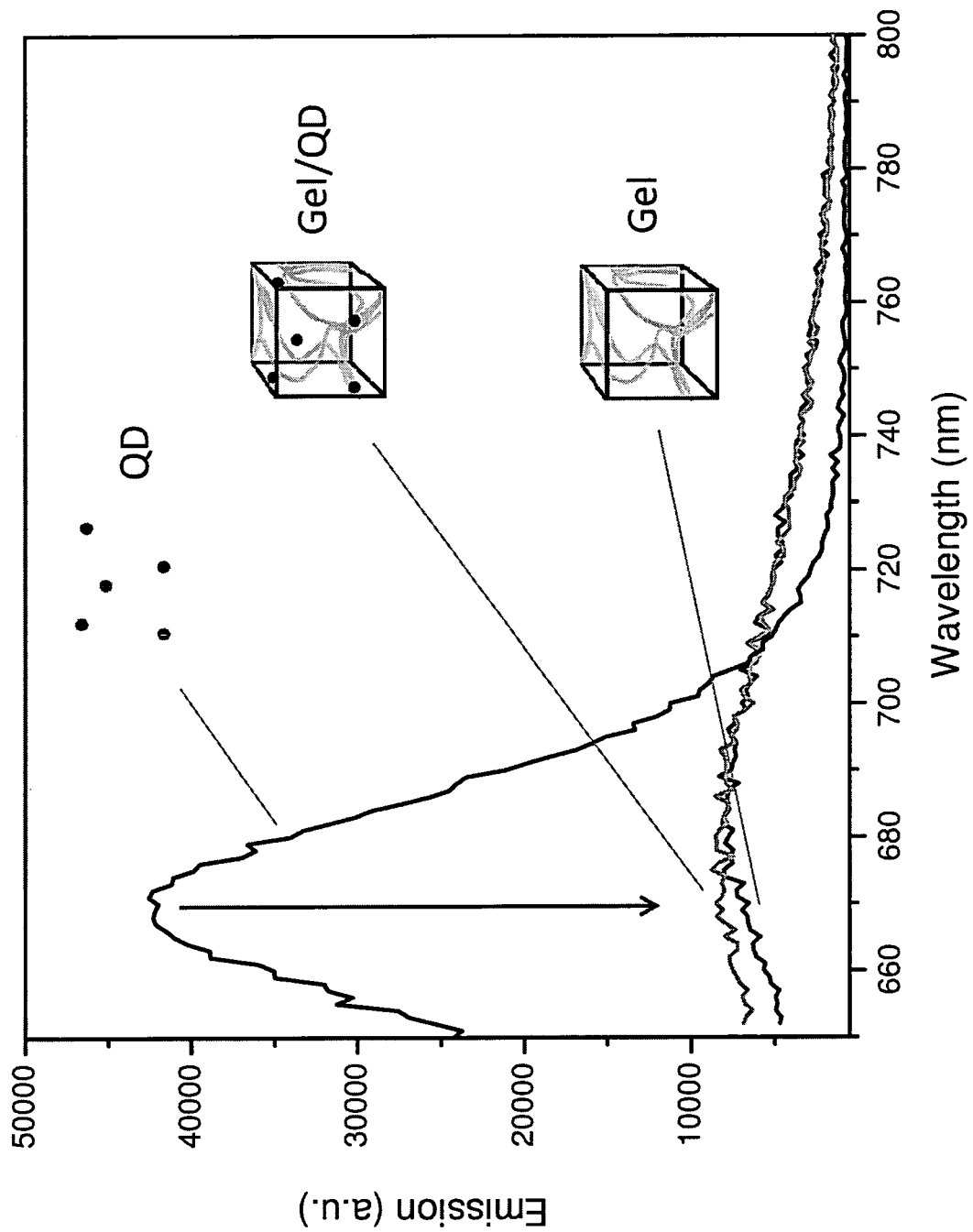
FIG. 32 depicts luminescence spectra of CdTe/MPA quantum dots, the gel of Compound X, and the hybrid system containing the same amount of both components. Luminescence of the quantum dots is quenched efficiently in the hybrid system. $\lambda_{ex.}=630$ nm.

Luminescence spectroscopy of the hybrid system and the control samples reveals efficient quenching of quantum dot luminescence (FIG. 32). This quenching suggests the presence of fast radiationless processes, such as photoinduced electron or energy transfer. Preliminary femtosecond transient absorption spectroscopy (fsTA) corroborates this conclusion. Whereas the excited state decay of the gel of Compound X can be fitted to triexponential decay, the decay of the hybrid gel has four components, including an additional sub-picosecond process (τ≈0.5 ps). This fast process possibly indicates photoinduced electron transfer Example 12

Synthesis of [PtCl$_2$(5,5'-Bis(1-PEG-PDI-7-ethynyl)-2,2'-bipyridine)]

(XV)

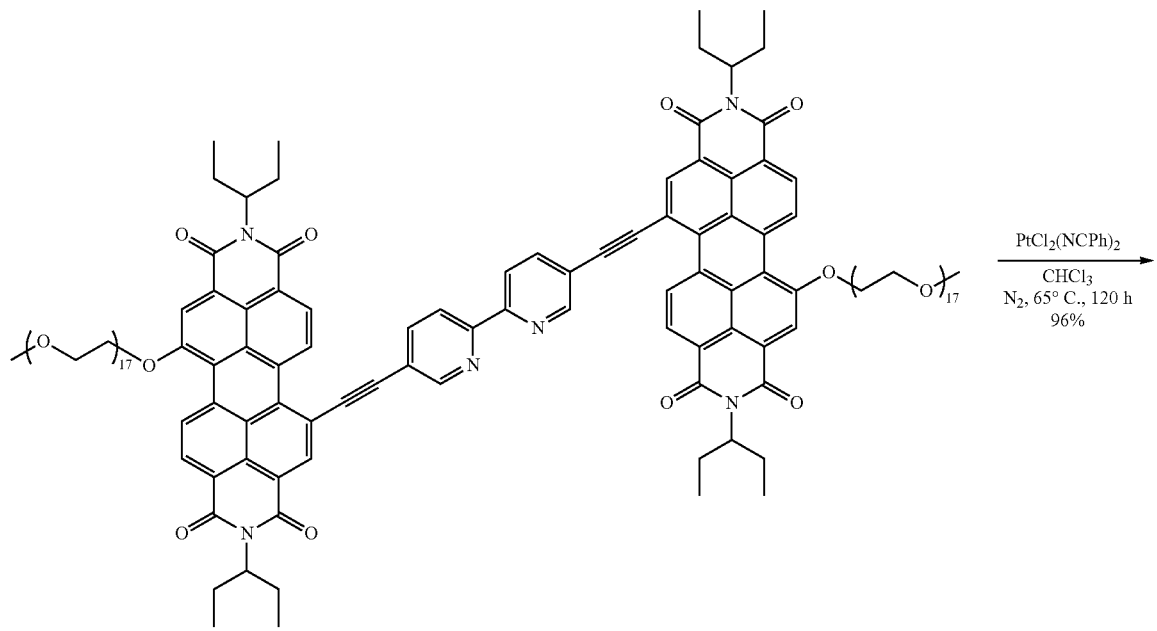

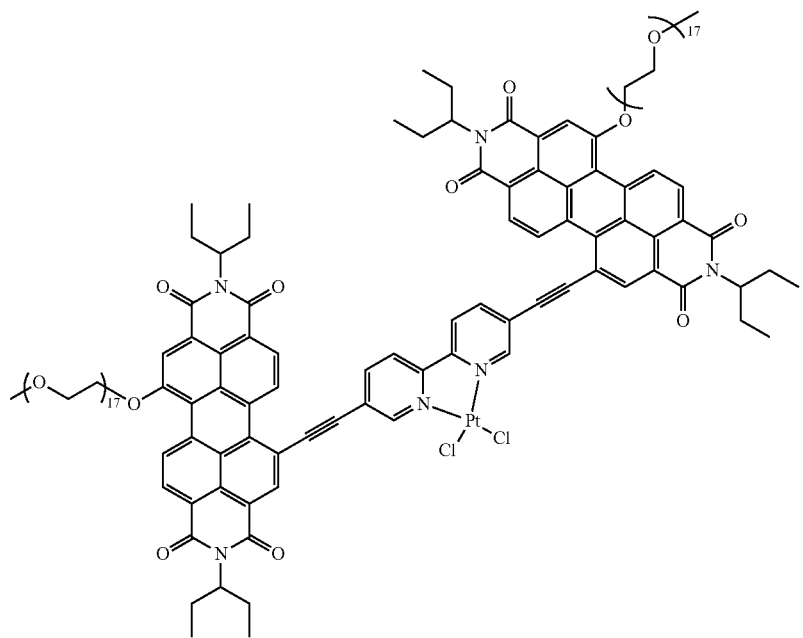

The bipyridyl group in Compound X allows for easy modification of its optical, electronic, and geometric properties by chelation to transition metals, thus producing new functional building blocks for supramolecular chemistry. Furthermore, a solar energy converting system necessitates a catalytic reaction center for the production of high energy chemical species.

Compound XV was prepared by reaction of Compound X with bis(benzonitrile)dichloro platinum(II) in high yield. The platinum complex is stable towards heat (65° C.), air, and water.

Under a dry nitrogen atmosphere, a solution of $PtCl_2(NCPh)_2$ (6.6 mg, 13.9 μmol) in $CHCl_3$ (0.5 ml) was added to a solution of 8 (30 mg, 10.7 μmol) in $CHCl_3$ (2.5 ml). The mixture was heated to 65° C. for 120 h during which time the color became darker. Subsequently, the solvent was evaporated and crude Compound XV was purified by repeated precipitation from chloroform solution (1 ml) with n-hexane (3 ml) to yield 31 mg (10.3 μmol, 96%).

$^1$H NMR ($CDCl_3$, 400 MHz): δ=9.69 (br., 4H, aryl-H), 9.09 (br. s, 2H, aryl-H), 8.8-8.0 (br., 12H, aryl-H), 7.74 (br. s, 2H, aryl-H), 4.95 (br., 4H, $N(CH(CH_2CH_3)_2)$, 4.35 (br., 4H, PEG), 4.11 (br, 4H, PEG), 4.0-3.5 (br., 130H, PEG), 3.37 (s, 6H, PEG-$OCH_3$), 2.26 (br., 8H, $N(CH(CH_2CH_3)_2)$, 2.08 (br., 8H, $N(CH(CH_2CH_3)_2)$, 1.06 (br., 24H, $N(CH(CH_2CH_3)_2)$.

MALDI-TOF-MS m/z calc. for $C_{150}H_{200}Cl_2N_6O_{43}Pt$: 3041. found: 3065 [M+Na$^+$]. UV/Vis ($CHCl_3$): $\lambda_{max}$/nm ($\in$/M$^{-1}$cm$^{-1}$) 580.0 (34,000), 547.8 (32,900), 412.3 (33,000), 331.1 (33,700). Redox potentials (E vs. SCE): +1.56 V (M$^+$+e$^-$ ⇌ M), −0.61 V (M+e$^-$ ⇌ M$^-$), −0.80 V (M$^-$+e$^-$ ⇌ M$^{2-}$), −1.14 V (M$^-$+e$^-$ ⇌ M$^{2-}$).

The red color of Compound XV is much darker than that of the free ligand (Compound X), which may be ascribed to the quantitative quenching of PDI-fluorescence upon coordination. The UV/Vis absorption spectrum of Compound XV shows some interesting differences when compared to Compound X: the absorption bands appear broadened, the 0-0 and 0-1 electronic transitions have almost equal intensity, which is untypical for disaggregated PDI molecules in solution, and the absorption band corresponding to bpy is significantly red-shifted from 387 to 413 nm. The optical gap of the bpy group is decreased in Compound XV, demonstrating the influence of metal coordination on the electronic structure of Compound X.

Figure 33:
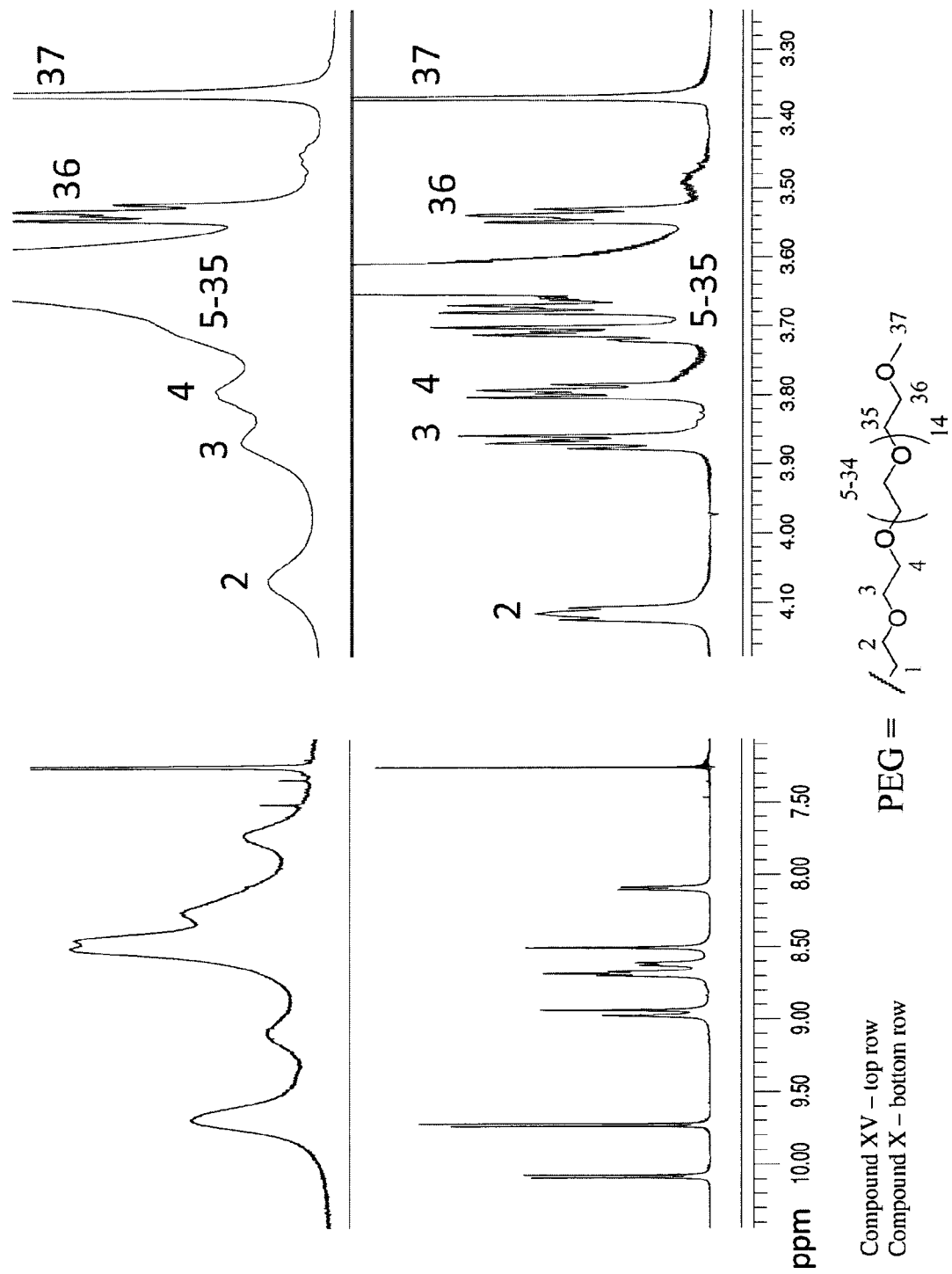
FIG. 33 depicts $^1$H-NMR spectra of Compound XV and Compound X in $CDCl_3$, showing peaks corresponding to aromatic hydrogen atoms and PEG hydrogen atoms.

The quenching of fluorescence, together with the absorption band broadening and the change in the relative intensities of the 0-0 and 0-1 transitions in UV/Vis are strong indications for aggregation. This notion is corroborated by $^1$H-NMR spectroscopy (FIG. 33). Spectra of the free ligand (Compound X) in $CDCl_3$ exhibit sharp peaks in both the aromatic and aliphatic area, whereas most of the peaks of Compound XV in the same solvent are strongly broadened, as is common for aggregated species.

Compound XV shows similar solubility as Compound X in organic solvents and is soluble in chloroform, dichloromethane, THF, methanol, and DMSO. However, aggregation is observed in all of these solvents. The aggregation could not be broken in mixtures of these solvents, or by sonication or variations in temperature. The strong aggregation of Compound XV in organic solvents driven by π-π interactions is ascribed to an enhanced planarity and rigidity of the large aromatic π-system resulting from the coordination of platinum. Compound X can rotate freely around the single bond in the bpy-group, whereas the bpy-group in Compound XV is forced into a coplanar conformation.

Figure 34A:
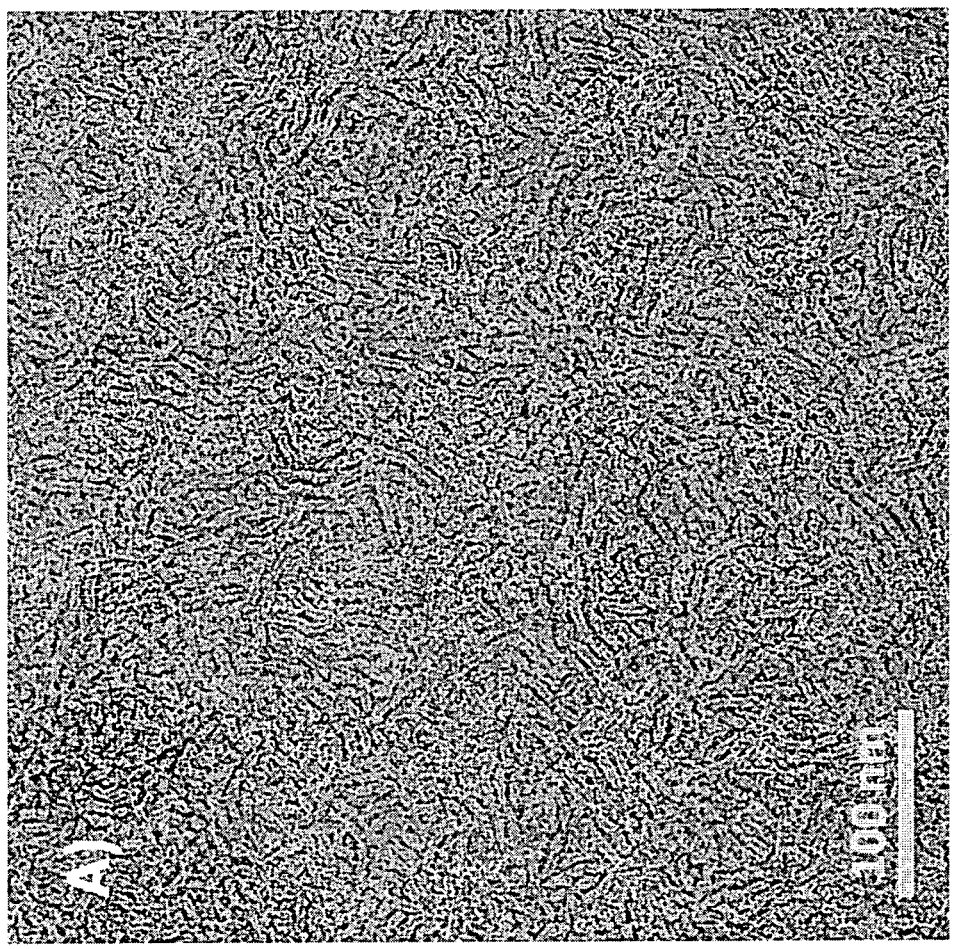
FIG. 34 depicts (A) a TEM image of Compound XV ($10^{-4}$ M) in water/THF mixture (70:30, v/v) showing fibrous aggregates with 5.4±0.7 nm in diameter (negative staining with $UO_2(OAc)_2$), and (B) a cryo-TEM image of Compound XV ($10^{-4}$ M) in water/THF mixture (60:40, v/v) showing similar fibers, partially aligned.
Figure 34B:
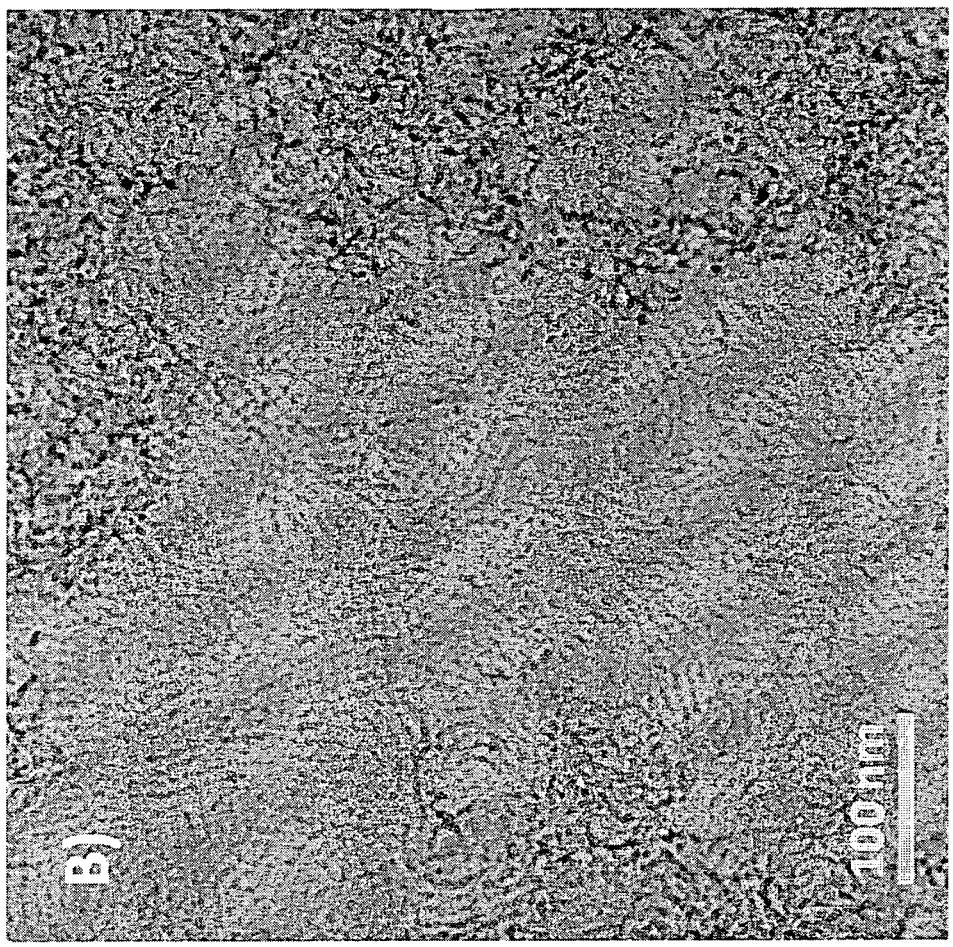

Compound XV self assembles predominantly into supramolecular fibers in water/THF mixtures, as evidenced by TEM of a dried sample (FIG. 34A) and cryo-TEM of the vitrified solution (FIG. 34B). The total diameter of the fibers observed in TEM is 5.4±0.7 nm, whereas those imaged by cryo-TEM are 6.8±0.7 nm in width. The latter value coincides with the width of the supramolecular fibers of ligand Compound X (7.5±0.8), whereas the former one is somewhat smaller, as it is expected for dried samples, due to shrinkage of the solvent-containing hydrophilic PEG-shell during drying. As shown in FIG. 34B, the fibers appear aligned to each other in some areas, whereas less ordered fibers are observed in other areas. Altogether, the observed supramolecular morphologies of Compound XV in water/THF mixtures are very similar to those of ligand Compound X, suggesting an analogous supramolecular architecture.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. A doubly reduced perylene-diimide compound represented by the structure of formula 7a or 7b:

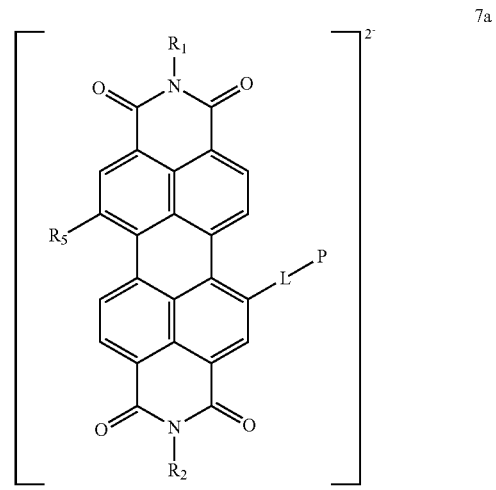

-continued

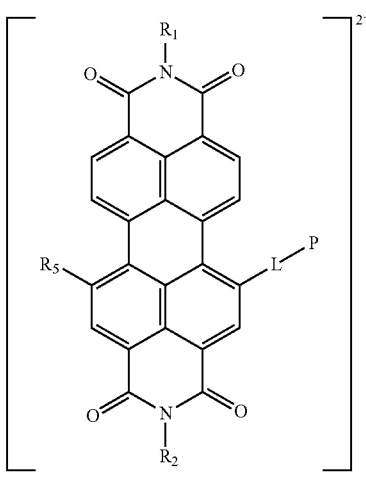

7b wherein said compound is a dianion;
wherein $R_1$ is $[(CH_2)_nO]_oCH_3$, $[(CH_2)_nC(O)O]_oCH_3$, $[(CH_2)_nC(O)NH]_oCH_3$, $[(CH_2)_nCH=CH_2]_oCH_3$, $[(CH_2)_nCH\equiv CH]_oCH_3$, $[(CH_2)_nNH]_oCH_3$, $(C_1-C_{32})$alkyl, $(C_3-C_8)$cycloalkyl, aryl, heteroaryl, $(C_1-C_{32})$alkyl-COOH, $(C_1-C_{32})$alkyl-Si-A, or $[C(O)CHR_3NH]_pH$ wherein said aryl or heteroaryl groups are optionally substituted by 1-3 substituents selected from halide, CN, $CO_2H$, OH, SH, $NH_2$, $CO_2$—$(C_1-C_6$ alkyl), and O—$(C_1-C_6$ alkyl); wherein A comprises three same or different of the following substituents Cl, Br, I, $O(C_1-C_8)$alkyl or $(C_1-C_8)$ alkyl; and wherein $R_3$ in said $[C(O)CHR_3NH]_pH$ is independently the same or different when p is larger than 1;

$R_2$ is $[(CH_2)_qO]_rCH_3$, $[(CH_2)_qC(O)O]_rCH_3$, $[(CH_2)_qC(O)NH]_rCH_3$, $[(CH_2)_qCH=CH_2]_rCH_3$, $[(CH_2)_qCH\equiv CH]_rCH_3$, $[(CH_2)_qNH]_rCH_3$, $(C_1-C_{32})$alkyl, $(C_3-C_8)$cycloalkyl, aryl, heteroaryl, $(C_1-C_{32})$alkyl-COOH, $(C_1-C_{32})$alkyl-Si-A, or $[C(O)CHR_4NH]_sH$ wherein said aryl or heteroaryl groups are optionally substituted by 1-3 substituents selected from halide, CN, $CO_2H$, OH, SH, $NH_2$, $CO_2$—$(C_1-C_6$ alkyl), and O—$(C_1-C_6$ alkyl); wherein A comprises three same or different of the following substituents Cl, Br, I, $O(C_1-C_8)$alkyl or $(C_1-C_8)$ alkyl; and wherein $R_4$ in said $[C(O)CHR_4NH]_sH$ is independently the same or different when s is larger than 1;

$R_5$ is —$OR_x$ where $R_x$ is $C_1-C_6$ alkyl or $[(CH_2)_nO]_oCH_3$, aryl, heteroaryl, $C\equiv C$—$R_7$, $CH=CR_8R_9$, $NR_{10}R_{11}$ or a saturated carbocyclic or heterocyclic ring wherein said saturated heterocyclic ring or heteroaryl contains at least one nitrogen atom and $R_5$ is connected via the nitrogen atom and wherein said saturated carbocyclic ring, heterocyclic ring, aryl and heteroaryl groups are optionally substituted by 1-3 substituents selected from halide, aryl, heteroaryl, CN, $CO_2H$, OH, SH, $NH_2$, $CO_2$—$(C_1-C_6$ alkyl), and O—$(C_1-C_6$ alkyl);

$R_7$ is H, halo, $(C_1-C_{32})$alkyl, aryl, heteroaryl, Si(H)$_3$ or Si[$(C_1-C_8)$alkyl]$_3$ wherein said aryl or heteroaryl groups are optionally substituted by 1-3 substituents selected from halide, CN, $CO_2H$, OH, SH, $NH_2$, $CO_2$—$(C_1-C_6$ alkyl), and er O—$(C_1-C_6$ alkyl);

$R_8$, $R_9$, $R_{10}$ and $R_{11}$ are independently H, $(C_1-C_{32})$alkyl, aryl or heteroaryl wherein said aryl or heteroaryl groups are optionally substituted by 1-3 substituents selected from halide, CN, $CO_2H$, OH, SH, $NH_2$, $CO_2$—$(C_1-C_6$ alkyl), and O—$(C_1-C_6$ alkyl);

L is an ethynyl group or a diethynylbenzene group;

P is a perylene-diimide group represented by the structure of formula Va or Vb:

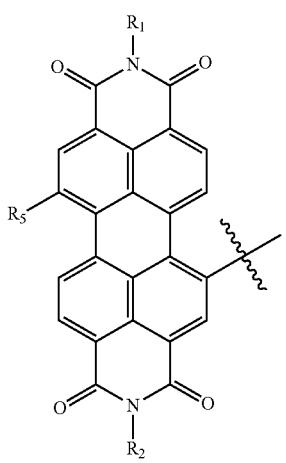

Va

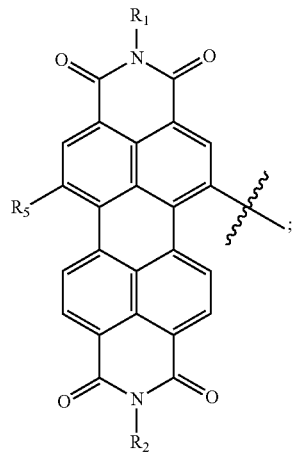

Vb n is an integer from 1-5;

is an integer from 1-100;

p is an integer from 1-100;

q is an integer from 2-5;

r is an integer from 1-100; and s is an integer from 1-100;

or metal complex thereof.

2. The compound of claim 1, wherein $R^1$ and $R^2$ are both $(C_1-C_{32})$alkyl; $R^5$ is —$OR^x$ where $R^x$ is $C_1-C_6$ alkyl or $[(CH_2)_nO]_oCH_3$; n is 2 or 3 and o is an integer from 1-100.

3. The compound of claim 1, selected from:

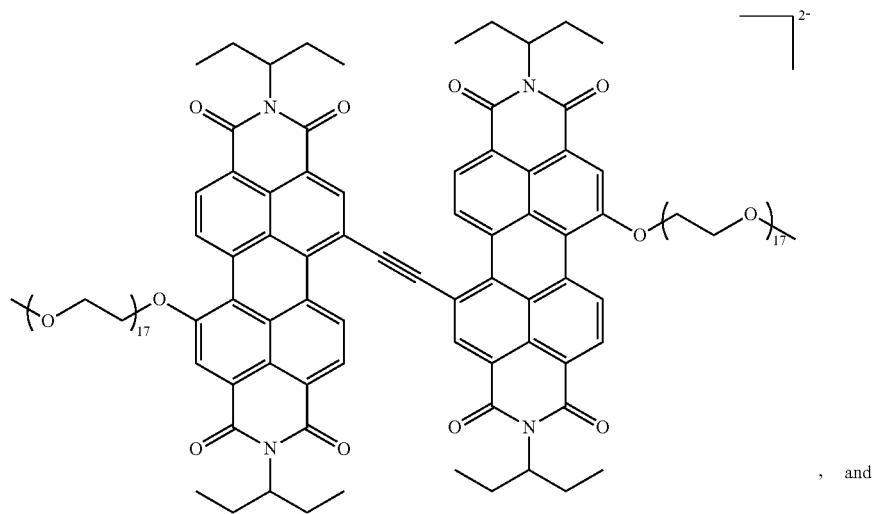

(8)

, and

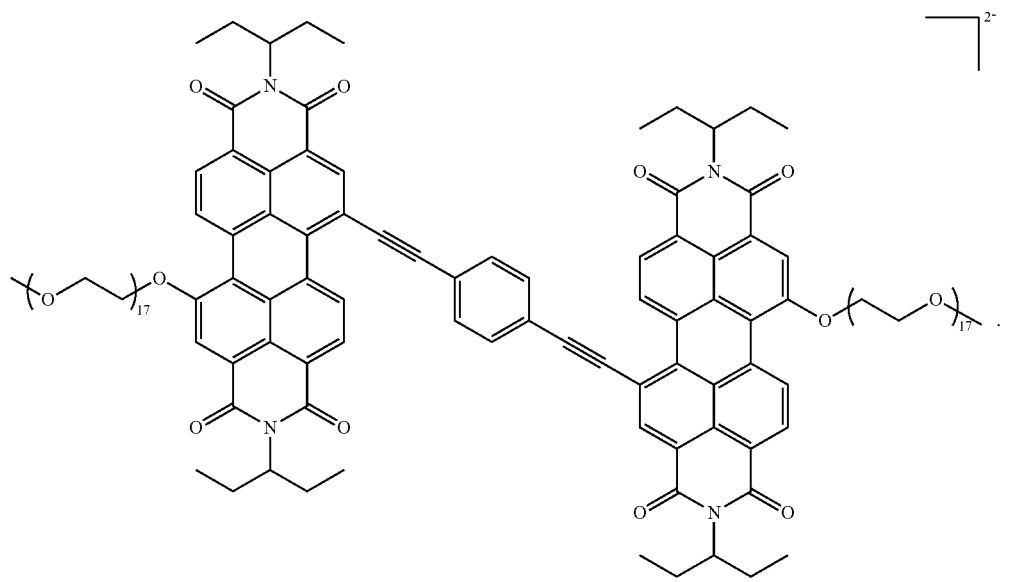

(9)

4. Nanoparticles comprising silica or titanium coated by a reduced perylene-diimide compound of claim 1.

5. A light emitting diode comprising a reduced perylene-diimide compound of claim 1.

6. A supramolecular polymer structure comprising a monomer unit represented by formula VIa or VIb wherein the monomer unit forms a supramolecular polymer structure by non-covalent interactions:

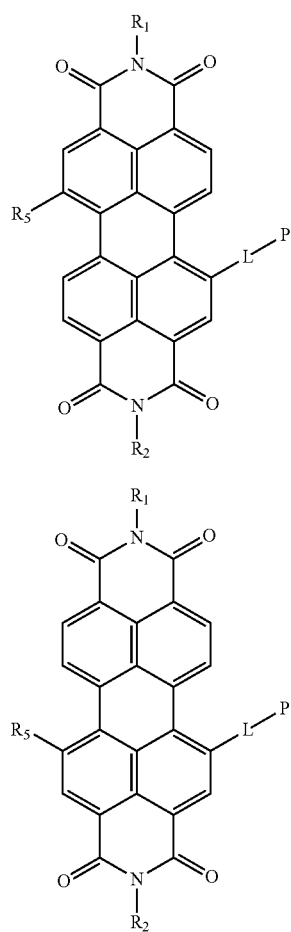

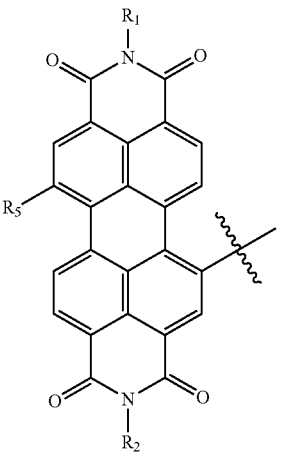

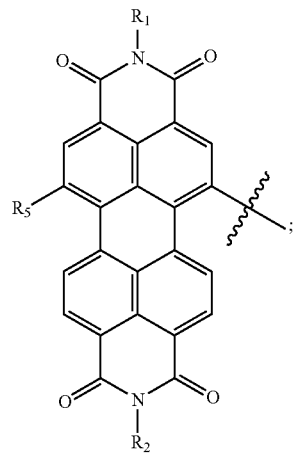

wherein $R_1$ is $[(CH_2)_nO]_oCH_3$, $[(CH_2)_nC(O)O]_oCH_3$, $[(CH_2)_nC(O)NH]_oCH_3$, $[(CH_2)_nCH=CH_2]_oCH_3$, $[(CH_2)_nCH=CH]_oCH_3$, $[(CH_2)_nNH]_oCH_3$, $(C_1-C_{32})$alkyl, $(C_3-C_8)$cycloalkyl, aryl, heteroaryl, $(C_1-C_{32})$alkyl-COOH, $(C_1-C_{32})$alkyl-Si-A, or $[C(O)CHR_3NH]_pH$ wherein said aryl or heteroaryl groups are optionally substituted by 1-3 substituents selected from halide, CN, $CO_2H$, OH, SH, $NH_2$, $CO_2$—$(C_1-C_6$ alkyl), and O—$(C_1-C_6$ alkyl); wherein A comprises three same or different of the following substituents Cl, Br, I, O$(C_1-C_8)$alkyl or $(C_1-C_8)$alkyl; and wherein $R_3$ in said $[C(O)CHR_3NH]_pH$ is independently the same or different when p is larger than 1;

$R_2$ is $[(CH_2)_qO]_rCH_3$, $[(CH_2)_qC(O)O]_rCH_3$, $[(CH_2)_qC(O)NH]_rCH_3$, $[(CH_2)_qCH=CH_2]_rCH_3$, $[(CH_2)_qCH=CH]_rCH_3$, $[(CH_2)_qNH]_rCH_3$, $(C_1-C_{32})$alkyl, $(C_3-C_8)$cycloalkyl, aryl, heteroaryl, $(C_1-C_{32})$alkyl-COOH, $(C_1-C_{32})$alkyl-Si-A, or $[C(O)CHR_4NH]_sH$ wherein said aryl or heteroaryl groups are optionally substituted by substituents selected from halide, CN, $CO_2H$, OH, SH, $NH_2$, $CO_2$—$(C_1-C_6$ alkyl), and O—$(C_1-C_6$ alkyl); wherein A comprises three same or different of the following substituents Cl, Br, I, O$(C_1-C_8)$alkyl or $(C_1-C_8)$alkyl; and wherein $R_4$ in said $[C(O)CHR_4NH]_sH$ is independently the same or different when s is larger than 1;

$R_5$ is —$OR_x$ where $R_x$ is $C_1-C_6$ alkyl or $[(CH_2)_nO]_oCH_3$, aryl, heteroaryl, C≡C—$R_7$, CH=$CR_8R_9$, $NR_{10}R_{11}$ or a saturated carbocyclic or heterocyclic ring wherein said saturated heterocyclic ring or heteroaryl contains at least one nitrogen atom and $R_5$ is connected via the nitrogen atom and wherein said saturated carbocyclic ring, heterocyclic ring, aryl and heteroaryl groups are optionally substituted by 1-3 substituents selected from halide, aryl, heteroaryl, CN, $CO_2H$, OH, SH, $NH_2$, $CO_2$—$(C_1-C_6$ alkyl), and O—$(C_1-C_6$ alkyl);

$R_7$ is H, halo, $(C_1-C_{32})$alkyl, aryl, heteroaryl, $Si(H)_3$ or $Si[(C_1-C_8)$alkyl$]_3$ wherein said aryl or heteroaryl groups are optionally substituted by 1-3 substituents selected from halide, CN, $CO_2H$, OH, SH, $NH_2$, $CO_2$—$(C_1-C_6$ alkyl), and O—$(C_1-C_6$ alkyl);

$R_8$, $R_9$, $R_{10}$ and $R_{11}$ are independently H, $(C_1-C_{32})$alkyl, aryl or heteroaryl wherein said aryl or heteroaryl groups are optionally substituted by 1-3 substituents selected from halide, CN, $CO_2H$, OH, SH, $NH_2$, $CO_2$—$(C_1-C_6$ alkyl), and O—$(C_1-C_6$ alkyl);

L is an ethynyl group or a diethynylbenzene group;

P is a perylene-diimide group represented by the structure of formula Va or Vb:

n is an integer from 1-5;
o is an integer from 1-100;
p is an integer from 1-100;
q is an integer from 2-5;

r is an integer from 1-100; and
s is an integer from 1-100;
or a metal complex thereof.

7. The supramolecular polymer of claim 6, wherein $R^1$ and $R^2$ are both $(C_1-C_{32})$alkyl, $R_5$ is $-OR^x$ where $R^x$ is $(C_1-C_6)$ alkyl or $[(CH_2)_nO]_oCH_3$ and n is 2 or 3 and o is an integer from 1-100.

8. The supramolecular polymer of claim 6, comprising a monomer selected from:

9. The supramolecular polymer of claim 6, wherein the monomer unit is in the form of a metal complex.

10. The supramolecular polymer of claim 9, wherein the metal complex is a platinum, palladium or silver complex.

11. A doubly reduced perylene-diimide compound represented by the structure of formula 7a or 7b:

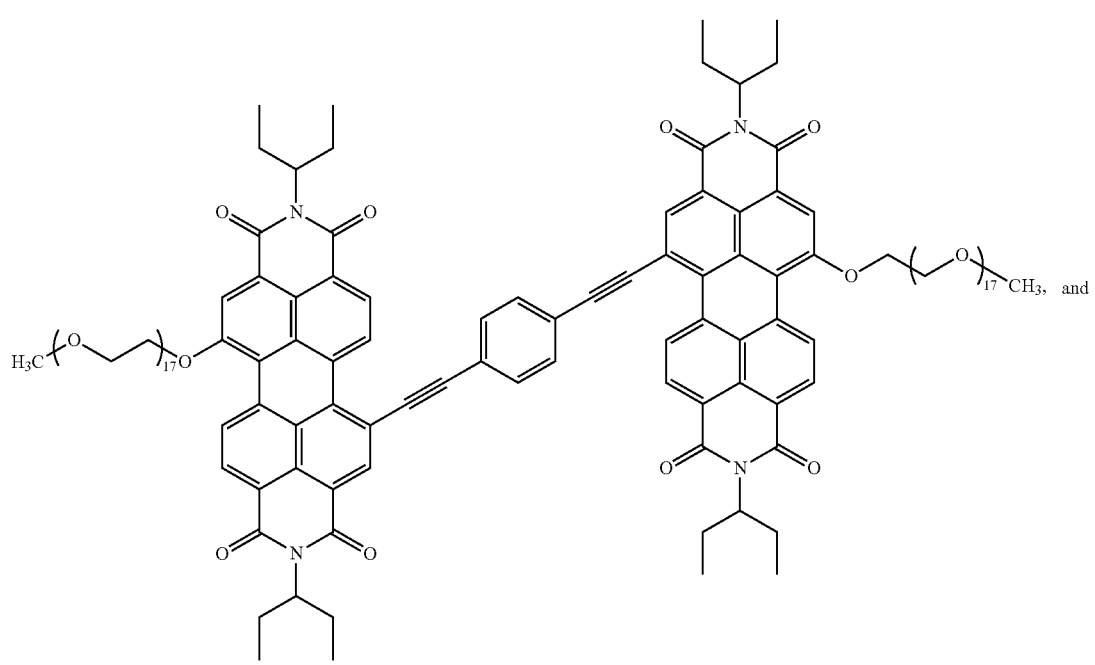

(VIII)

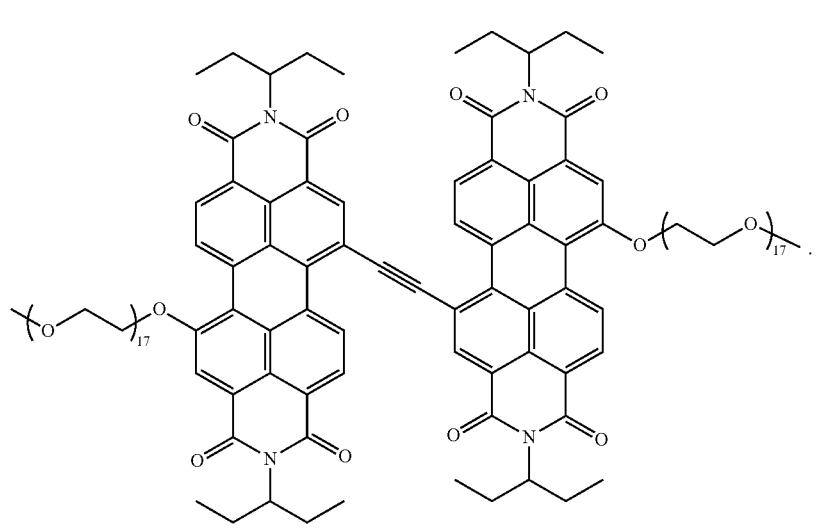

(IX)

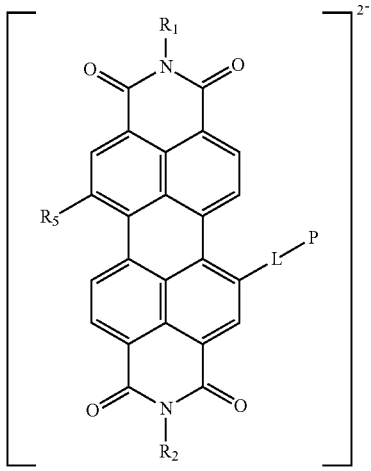

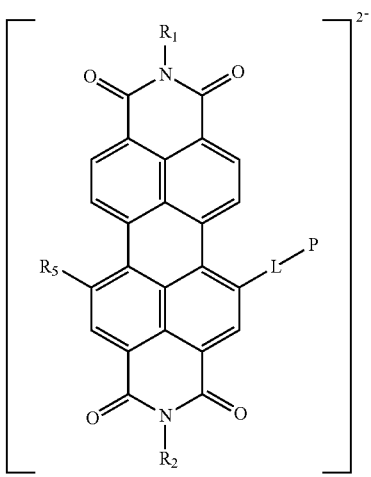

wherein said compound is a dianion;
wherein $R_1$ is $[(CH_2)_nO]_oCH_3$, $[(CH_2)_nC(O)O]_oCH_3$, $[(CH_2)_nC(O)NH]_oCH_3$, $[(CH_2)_nCH_2=CH_2]_oCH_3$, $[(CH_2)_nCH=CH]_oCH_3$, $[(CH_2)_nNH]_oCH_3$, $(C_1-C_{32})$alkyl, $(C_3-C_8)$cycloalkyl, aryl, heteroaryl, $(C_1-C_{32})$alkyl-COOH, $(C_1-C_{32})$alkyl-Si-A, or $[C(O)CHR_3NH]_pH$ wherein said aryl or heteroaryl groups are optionally substituted by 1-3 substituents selected from halide, CN, $CO_2H$, OH, SH, $NH_2$, $CO_2-(C_1-C_6$ alkyl), and $O-(C_1-C_6$ alkyl); wherein A comprises three same or different of the following substituents Cl, Br, I, $O(C_1-C_8)$alkyl or $(C_1-C_8)$alkyl; and wherein $R_3$ in said $[C(O)CHR_3NH]_pH$ is independently the same or different when p is larger than 1;

$R_2$ is $[(CH_2)_qO]_rCH_3$, $[(CH_2)_qC(O)O]_rCH_3$, $[(CH_2)_qC(O)NH]_rCH_3$, $[(CH_2)_qCH_2=CH_2]_rCH_3$, $[(CH_2)_qCH=CH]_rCH_3$, $[(CH_2)_qNH]_rCH_3$, $(C_1-C_{32})$alkyl, $(C_3-C_8)$cycloalkyl, aryl, heteroaryl, $(C_1-C_{32})$alkyl-COOH, $(C_1-C_{32})$alkyl-Si-A, or $[C(O)CHR_4NH]_sH$ wherein said aryl or heteroaryl groups are optionally substituted by 1-3 substituents selected from halide, CN, $CO_2H$, OH, SH, $NH_2$, $CO_2-(C_1-C_6$ alkyl), and $O-(C_1-C_6$ alkyl); wherein A comprises three same or different of the following substituents Cl, Br, I, $O(C_1-C_8)$alkyl or $(C_1-C_8)$alkyl; and wherein $R_4$ in said $[C(O)CHR_4NH]_sH$ is independently the same or different when s is larger than 1;

$R_5$ is $-OR_x$ where $R_x$ is $C_1-C_6$ alkyl or $[(CH_2)_nO]_oCH_3$, aryl, heteroaryl, $C\equiv C-R_7$, $CH=CR_8R_9$, $NR_{10}R_{11}$ or a saturated carbocyclic or heterocyclic ring wherein said saturated heterocyclic ring or heteroaryl contains at least one nitrogen atom and $R_5$ is connected via the nitrogen atom and wherein said saturated carbocyclic ring, heterocyclic ring, aryl and heteroaryl groups are optionally substituted by 1-3 substituents selected from halide, aryl, heteroaryl, CN, $CO_2H$, OH, SH, $NH_2$, $CO_2-(C_1-C_6$ alkyl), and $O-(C_1-C_6$ alkyl);

$R_7$ is H, halo, $(C_1-C_{32})$alkyl, aryl, heteroaryl, $Si(H)_3$ or $Si[(C_1-C_8)$alkyl$]_3$ wherein said aryl or heteroaryl groups are optionally substituted by 1-3 substituents selected from halide, CN, $CO_2H$, OH, SH, $NH_2$, $CO_2-(C_1-C_6$ alkyl) or $O-(C_1-C_6$ alkyl);

$R_8$, $R_9$, $R_{10}$ and $R_{11}$ are independently H, $(C_1-C_{32})$alkyl, aryl or heteroaryl wherein said aryl or heteroaryl groups are optionally substituted by 1-3 substituents selected from halide, CN, $CO_2H$, OH, SH, $NH_2$, $CO_2-(C_1-C_6$ alkyl), and $O-(C_1-C_6$ alkyl);

L is a diethynyldipyridine group;

P is a perylene-diimide group represented by the structure of formula Va or Vb:

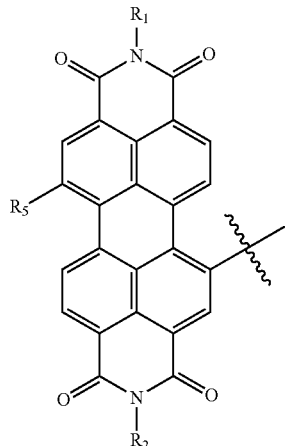

Va

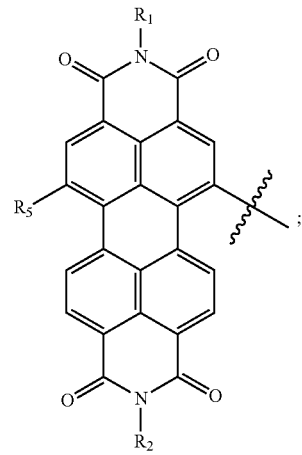

Vb n is an integer from 1-5;
o is an integer from 1-100;
p is an integer from 1-100;
q is an integer from 2-5;
r is an integer from 1-100; and
s is an integer from 1-100;
or metal complex thereof.

12. The compound of claim 11, wherein $R_5$ is $-OR_x$ where $R_x$ is $C_1-C_6$ alkyl or $[(CH_2)_nO]_oCH_3$.

13. The compound of claim 11, wherein $R^1$ and $R^2$ are both $(C_1-C_{32})$alkyl; $R_5$ is $-OR^x$ wherein $R^x$ is $C_1-C_6$ alkyl or $[(CH_2)_nO]_oCH_3$; n is 2 or 3 and o is an integer from 1-100.

14. The compound of claim 11, wherein said compound is

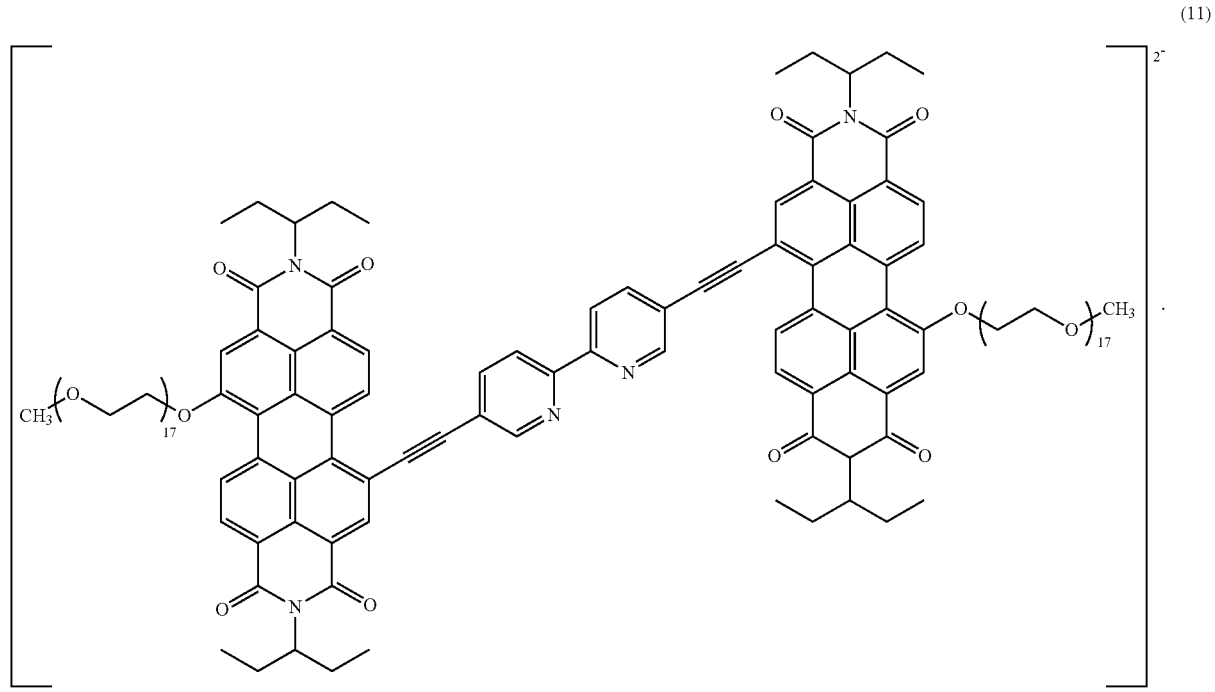

(11)

15. Nanoparticles comprising silica or titanium coated by a reduced perylene-diimide compound of claim 11.

16. A light emitting diode comprising a reduced perylene-diimide compound of claim 11.

17. The compound of claim 11, wherein $R_5$ is —$OR_x$ where $R_x$ is $C_1$-$C_6$ alkyl or $[(CH_2)_nO]_oCH_3$.

18. A supramolecular polymer structure comprising a monomer unit represented by formula VIa or VIb wherein the monomer unit forms a supramolecular polymer structure by non-covalent interactions:

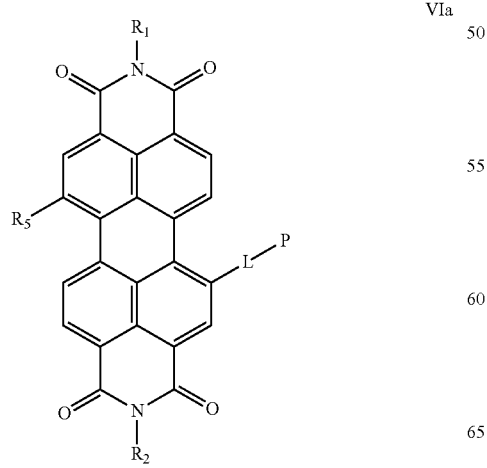

VIa

-continued

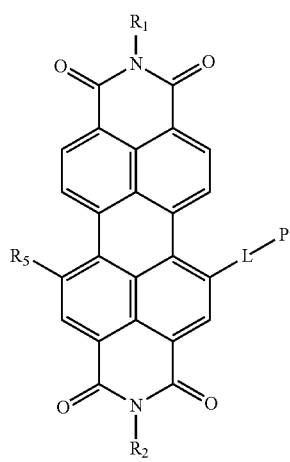

VIb wherein $R_1$ is $[(CH_2)_nO]_oCH_3$, $[(CH_2)_nC(O)O]_oCH_3$, $[(CH_2)_nC(O)NH]_oCH_3$, $[(CH_2)_nCH_2{=}CH_2]_oCH_3$, $[(CH_2)_n$ CH≡CH]$_o$CH$_3$, [(CH$_2$)$_n$NH]$_o$CH$_3$, (C$_1$-C$_{32}$)alkyl, (C$_3$-C$_8$)cycloalkyl, aryl, heteroaryl, (C$_1$-C$_{32}$)alkyl-COOH, (C$_1$-C$_{32}$)alkyl-Si-A, or [C(O)CHR$_3$NH]$_p$H wherein said aryl or heteroaryl groups are optionally substituted by 1-3 substituents selected from halide, CN, CO$_2$H, OH, SH, NH$_2$, CO$_2$—(C$_1$-C$_6$ alkyl), and O—(C$_1$-C$_6$ alkyl); wherein A comprises three same or different of the following substituents Cl, Br, I, O(C$_1$-C$_8$)alkyl or (C$_1$-C$_8$) alkyl; and wherein R$_3$ in said [C(O)CHR$_3$NH]$_p$H is independently the same or different when p is larger than 1;

R$_2$ is [(CH$_2$)$_q$O]$_r$CH$_3$, [(CH$_2$)$_q$C(O)O]$_r$CH$_3$, [(CH$_2$)$_q$C(O)NH]$_r$CH$_3$, [(CH$_2$)$_q$CH=CH$_2$]$_r$CH$_3$, [(CH$_2$)$_q$CH≡CH]$_r$CH$_3$, [(CH$_2$)$_q$NH]$_r$CH$_3$, (C$_1$-C$_{32}$)alkyl, (C$_3$-C$_8$)cycloalkyl, aryl, heteroaryl, (C$_1$-C$_{32}$)alkyl-COOH, (C$_1$-C$_{32}$)alkyl-Si-A, or [C(O)CHR$_4$NH]$_s$H wherein said aryl or heteroaryl groups are optionally substituted by 1-3 substituents selected from halide, CN, CO$_2$H, OH, SH, NH$_2$, CO$_2$—(C$_1$-C$_6$ alkyl), and O—(C$_1$-C$_6$ alkyl); wherein A comprises three same or different of the following substituents Cl, Br, I, O(C$_1$-C$_8$)alkyl or (C$_1$-C$_8$) alkyl; and wherein R$_4$ in said [C(O)CHR$_4$NH]$_s$H is independently the same or different when s is larger than 1;

R$_5$ is —OR$_x$ where R$_x$ is C$_1$-C$_6$ alkyl or [(CH$_2$)$_n$O]$_o$CH$_3$, aryl, heteroaryl, C≡C—R$_7$, CH=CR$_8$R$_9$, NR$_{10}$R$_{11}$ or a saturated carbocyclic or heterocyclic ring wherein said saturated heterocyclic ring or heteroaryl contains at least one nitrogen atom and R$_5$ is connected via the nitrogen atom and wherein said saturated carbocyclic ring, heterocyclic ring, aryl and heteroaryl groups are optionally substituted by 1-3 substituents selected from halide, aryl, heteroaryl, CN, CO$_2$H, OH, SH, NH$_2$, CO$_2$—(C$_1$-C$_6$ alkyl), and O—(C$_1$-C$_6$ alkyl);

R$_7$ is H, halo, (C$_1$-C$_{32}$)alkyl, aryl, heteroaryl, Si(H)$_3$ or Si[(C$_1$-C$_8$)alkyl]$_3$ wherein said aryl or heteroaryl groups are optionally substituted by 1-3 substituents selected from halide, CN, CO$_2$H, OH, SH, NH$_2$, CO$_2$—(C$_1$-C$_6$ alkyl), and O—(C$_1$-C$_6$ alkyl);

R$_8$, R$_9$, R$_{10}$ and R$_{11}$ are independently H, (C$_1$-C$_{32}$)alkyl, aryl or heteroaryl wherein said aryl or heteroaryl groups are optionally substituted by 1-3 substituents selected from halide, CN, CO$_2$H, OH, SH, NH$_2$, CO$_2$—(C$_1$-C$_6$ alkyl), and O—(C$_1$-C$_6$ alkyl);

L is a diethynyldipyridine group;

P is a perylene-diimide group represented by the structure of formula Va or Vb:

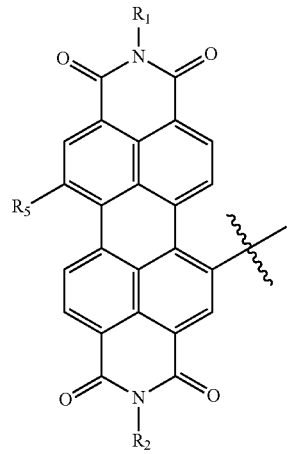

Va

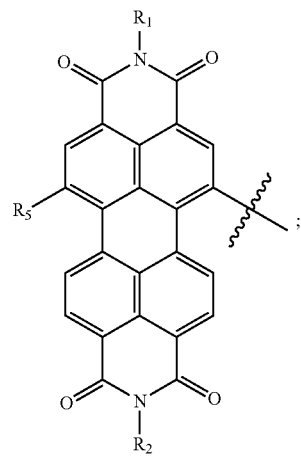

Vb n is an integer from 1-5;
o is an integer from 1-100;
p is an integer from 1-100;
q is an integer from 2-5;
r is an integer from 1-100; and
s is an integer from 1-100;
or a metal complex thereof.

19. The supramolecular polymer of claim 18, wherein R$_5$ is —OR$_x$ where R$_x$ is C$_1$-C$_6$ alkyl or [(CH$_2$)$_n$O]$_o$CH$_3$.

20. The supramolecular polymer of claim 18, wherein R$^1$ and R$^2$ are both (C$_1$-C$_{32}$)alkyl, R$_5$ is —OR$^x$ wherein R$^x$ is (C$_1$-C$_6$)alkyl or [(CH$_2$)$_n$O]$_o$CH$_3$ and n is 2 or 3 and o is an integer from 1-100.

21. The supramolecular polymer of claim 18, comprising a monomer:

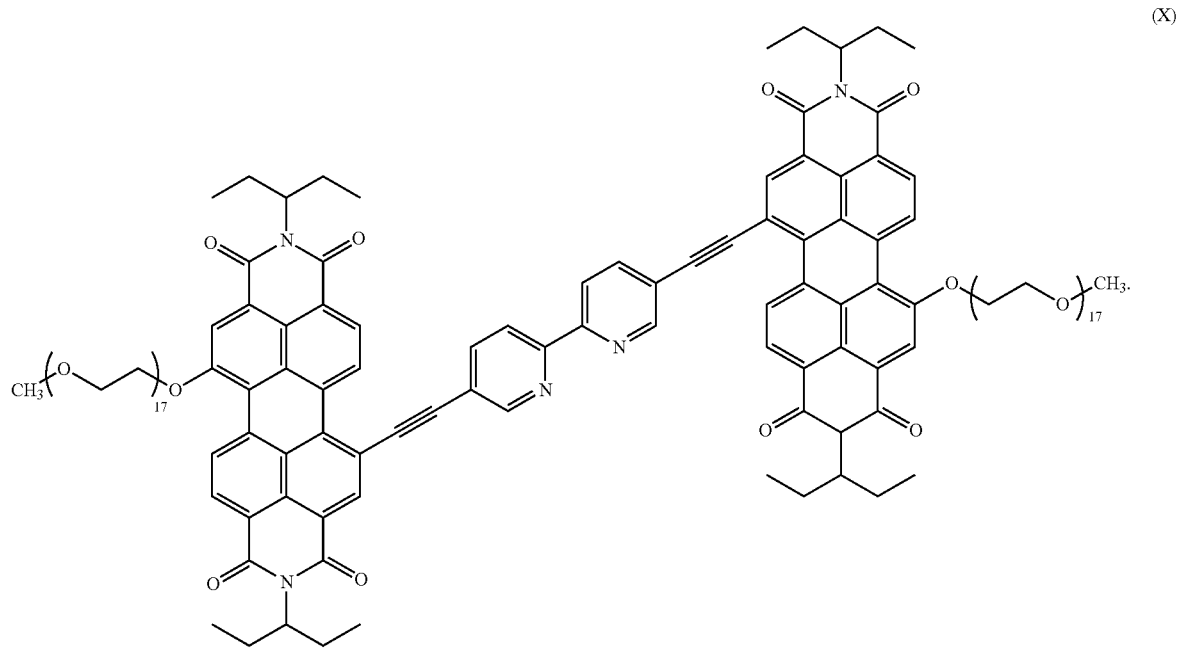

(X)

22. The supramolecular polymer of claim 18, wherein the monomer unit is in the form of a metal complex.

23. The supramolecular polymer of claim 22, wherein the metal complex is a platinum, palladium or silver complex.

24. The supramolecular polymer of claim 22, comprising a monomer unit selected from

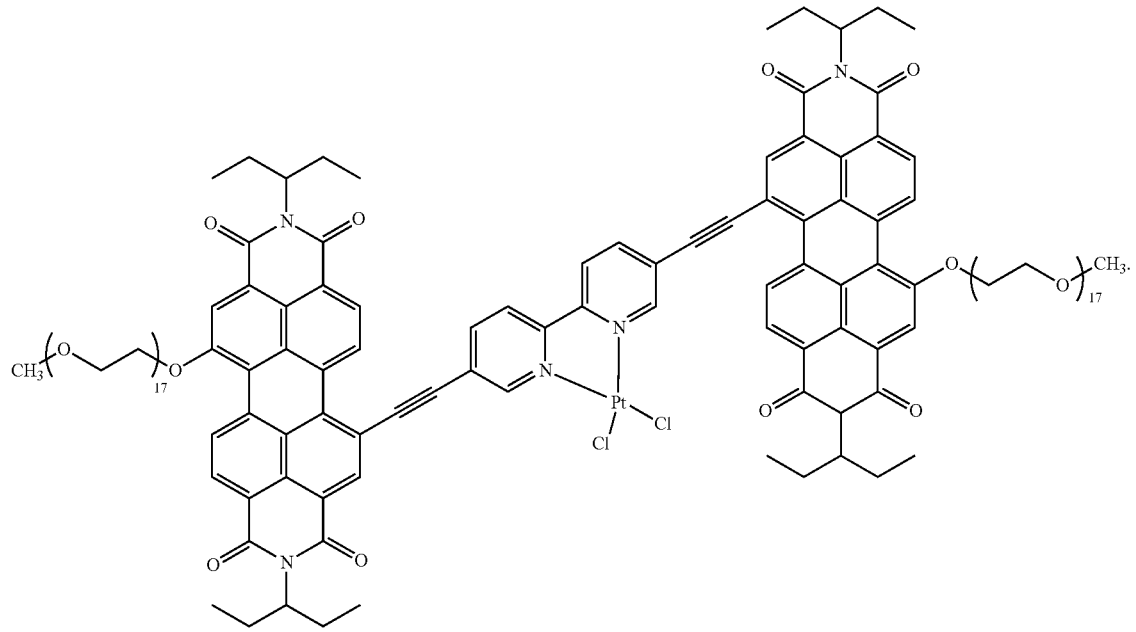

25. The supramolecular polymer of claim 20, wherein $R_5$ is —$OR_x$ where $R_x$ is $C_1$-$C_6$ alkyl or $[(CH_2)_nO]_oCH_3$.